US012544506B2

(12) United States Patent
Lanigan

(10) Patent No.: US 12,544,506 B2
(45) Date of Patent: Feb. 10, 2026

(54) INFUSION SET AND INSERTER ASSEMBLY SYSTEMS AND METHODS

(71) Applicant: DEKA Products Limited Partnership, Manchester, NH (US)

(72) Inventor: Richard J. Lanigan, Concord, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 19/176,585

(22) Filed: Apr. 11, 2025

(65) Prior Publication Data

US 2025/0235612 A1 Jul. 24, 2025

Related U.S. Application Data

(63) Continuation of application No. 18/784,148, filed on Jul. 25, 2024, which is a continuation of application (Continued)

(51) Int. Cl.

*A61M 5/158* (2006.01)

*A61M 5/142* (2006.01)

(52) U.S. Cl.

CPC ........ *A61M 5/158* (2013.01); *A61M 5/14248* (2013.01); *A61M 2005/1585* (2013.01); *A61M 2005/1586* (2013.01)

(58) Field of Classification Search

CPC .......... A61M 5/158; A61M 2005/1585; A61M 2005/1581; A61M 2005/1587;

(Continued)

(56) References Cited

U.S. PATENT DOCUMENTS

| | | |
|---|---|---|
| 2,512,568 A | 6/1950 | Saffir |
| 3,856,009 A | 12/1974 | Winnie |

(Continued)

FOREIGN PATENT DOCUMENTS

| | | |
|---|---|---|
| CA | 225208 | 10/2023 |
| CA | 219028 | 1/2025 |

(Continued)

OTHER PUBLICATIONS

MiniMed Mio Advance Infusion Set, announced in YouTube on May 7, 2019 [Online]. [Retrieved on Aug. 2, 2023], Available from the internet URL:https://www.youtube.com/watch?v=2For6SAvxRQ (Year: 2022).

(Continued)

*Primary Examiner* — Scott J Medway

(74) *Attorney, Agent, or Firm* — Toohey Law Group, LLC; Kevin D. Mandro

(57) ABSTRACT

An inserter assembly comprising a first unit including a skin contacting face which surrounds an opening and a second unit housed within the first unit. The second unit comprises an infusion set base disposed within the opening and having a bottom face which is substantially level with the skin contacting face and covered at least partially with adhesive and further comprising a spring biased insertion assembly. The second unit further comprising a cannula sub assembly carried by an insertion sharp of the insertion assembly. The spring biased insertion assembly and a cannula of the cannula sub assembly are driven into skin and the cannula sub assembly is coupled into the infusion set base by an insertion spring which is released from an energy storing state after the skin has been tugged upward beyond a certain distance by the adhesive as the inserter assembly is withdrawn from the body.

20 Claims, 82 Drawing Sheets

Related U.S. Application Data

No. 17/883,063, filed on Aug. 8, 2022, which is a continuation of application No. 16/797,624, filed on Feb. 21, 2020, now Pat. No. 11,446,434.

(60) Provisional application No. 62/809,248, filed on Feb. 22, 2019.

(58) Field of Classification Search
CPC ...... A61M 2005/14252; A61M 5/3287; A61M 2005/1586; A61M 5/1413; A61M 2005/14268; A61M 5/14244; A61M 5/142; A61M 25/02; A61M 5/3243; A61M 25/0668; A61M 2025/0675
See application file for complete search history.

(56) References Cited

U.S. PATENT DOCUMENTS 4,755,173 A * 7/1988 Konopka .......... A61M 25/0606 604/122
5,176,662 A 1/1993 Bartholomew et al.
5,257,980 A 11/1993 Van Antwerp et al.
D363,542 S 10/1995 Parris et al.
5,522,803 A 6/1996 Teissen-Simony
5,743,891 A 4/1998 Tolkoff et al.
D395,501 S 6/1998 Erskine et al.
D403,398 S 12/1998 Guala et al.
D405,882 S 2/1999 Yale
D416,086 S 11/1999 Parris et al.
5,980,506 A 11/1999 Mathiasen
D417,733 S 12/1999 Howell et al.
6,017,328 A 1/2000 Fischell et al.
6,056,718 A 5/2000 Funderburk et al.
6,086,575 A 7/2000 Mejslov
6,123,690 A 9/2000 Mejslov
6,261,272 B1 7/2001 Gross et al.
6,302,866 B1 10/2001 Marggi
6,379,339 B1 4/2002 Klitgaard et al.
6,461,329 B1 10/2002 Van Antwerp et al.
D465,845 S 11/2002 Swenson
D465,846 S 11/2002 Hwang
D472,630 S 4/2003 Douglas et al.
D476,418 S 6/2003 Sprieck et al.
6,579,267 B2 6/2003 Lynch et al.
6,582,403 B1 6/2003 Bierman et al.
6,589,229 B1 7/2003 Connelly et al.
D484,242 S 12/2003 Wilkinson
D484,976 S 1/2004 Wilkinson
6,685,674 B2 2/2004 Douglas et al.
6,699,218 B2 3/2004 Flaherty et al.
D488,230 S 4/2004 Ignotz et al.
6,736,797 B1 5/2004 Larsen et al.
6,749,589 B1 6/2004 Douglas et al.
6,887,417 B1 5/2005 Gawreluk et al.
D507,833 S 7/2005 Coss
6,923,791 B2 8/2005 Douglas
6,949,084 B2 9/2005 Marggi et al.
7,070,580 B2 7/2006 Nielsen
7,083,597 B2 8/2006 Lynch et al.
7,214,207 B2 5/2007 Lynch et al.
D547,859 S 7/2007 Choi
D554,253 S 10/2007 Kornerup
7,303,543 B1 12/2007 Maule et al.
7,303,544 B2 12/2007 Bütikofer et al.
7,309,326 B2 12/2007 Fangrow, Jr.
7,338,465 B2 3/2008 Patton
D576,267 S 9/2008 Mogensen et al.
7,431,876 B2 10/2008 Mejlhede et al.
7,481,794 B2 1/2009 Jensen
7,494,481 B2 2/2009 Moberg et al.
7,520,867 B2 4/2009 Bowman et al.
7,524,309 B2 4/2009 McConnell et al.
7,569,034 B2 8/2009 Lynch et al.
7,594,902 B2 9/2009 Horisberger et al.
D604,836 S 11/2009 Crawford et al.
D604,837 S 11/2009 Crawford et al.
D604,838 S 11/2009 Crawford et al.
D604,839 S 11/2009 Crawford et al.
7,621,395 B2 11/2009 Mogensen et al.
D605,287 S 12/2009 Crawford et al.
D609,804 S 2/2010 Uchida et al.
D609,806 S 2/2010 Uchida et al.
7,678,079 B2 3/2010 Shermer et al.
7,699,808 B2 4/2010 Marrs et al.
D616,094 S 5/2010 Boone, III et al.
7,766,867 B2 8/2010 Lynch et al.
7,766,874 B2 8/2010 Liniger
D627,459 S 11/2010 Uchida et al.
7,850,658 B2 12/2010 Faust et al.
7,887,737 B2 2/2011 Mejlhede et al.
7,892,216 B2 2/2011 Fangrow, Jr.
7,931,615 B2 4/2011 Fangrow, Jr.
7,935,104 B2 5/2011 Yodfat et al.
7,946,984 B2 5/2011 Brister et al.
7,951,080 B2 5/2011 Taub
7,951,122 B2 5/2011 Shekalim
7,955,297 B2 6/2011 Radmer et al.
7,993,306 B2 8/2011 Marrs et al.
8,025,658 B2 9/2011 Chong et al.
8,062,250 B2 11/2011 Mogensen et al.
8,062,253 B2 11/2011 Nielsen et al.
8,157,773 B2 4/2012 Tashjian
8,172,805 B2 5/2012 Mogensen et al.
8,226,614 B2 7/2012 Turner et al.
8,292,849 B2 10/2012 Bobroff et al.
8,298,172 B2 10/2012 Nielsen et al.
8,303,549 B2 11/2012 Mejlhede et al.
8,317,759 B2 11/2012 Moberg et al.
8,343,115 B2 1/2013 Lynch et al.
8,529,515 B2 9/2013 Woehr et al.
8,551,047 B2 10/2013 Burns et al.
8,571,624 B2 10/2013 Stafford
8,579,863 B2 11/2013 Scherr
8,628,498 B2 1/2014 Safabash et al.
8,641,674 B2 2/2014 Bobroff et al.
8,734,391 B2 5/2014 Yodfat et al.
D709,186 S 7/2014 Boaz et al.
8,790,311 B2 7/2014 Gryn
D713,957 S 9/2014 Woehr et al.
D720,466 S 12/2014 Edding
8,920,381 B2 12/2014 Ejlersen
8,945,050 B2 2/2015 Wei
8,956,330 B2 2/2015 Fangrow, Jr.
8,961,469 B2 2/2015 Sonderegger et al.
9,220,833 B2 12/2015 Robert et al.
D747,456 S 1/2016 Sonderegger et al.
D747,459 S 1/2016 Sonderegger et al.
D747,472 S 1/2016 Bradley et al.
9,238,123 B2 1/2016 Weadock et al.
9,254,373 B2 2/2016 Hørdum
9,265,881 B2 2/2016 Montalvo et al.
D754,842 S 4/2016 Sonderegger et al.
D754,843 S 4/2016 Sonderegger et al.
9,308,354 B2 * 4/2016 Farrell ................ A61M 5/3204
D756,504 S 5/2016 Sonderegger et al.
9,327,098 B2 5/2016 Kelvered et al.
9,375,537 B2 6/2016 Montalvo et al.
9,545,477 B2 1/2017 Chong et al.
9,610,401 B2 4/2017 Antonio et al.
D790,691 S 6/2017 Davis et al.
9,675,750 B2 6/2017 Grant et al.
9,731,069 B2 8/2017 Bené et al.
9,744,295 B2 8/2017 Wyss et al.
D801,522 S 10/2017 Shalom
9,789,250 B2 10/2017 Hwang
9,795,777 B2 10/2017 Sonderegger et al.
9,872,642 B2 1/2018 Deck
D812,223 S 3/2018 Evans et al.
D817,482 S 5/2018 Howell et al.
9,968,742 B2 5/2018 Van Antwerp et al.
9,987,476 B2 6/2018 Montalvo et al.
10,071,209 B2 9/2018 Solomon et al.
10,076,356 B2 9/2018 Hadvary et al.
10,080,582 B2 * 9/2018 Hadvary ............ A61B 17/3403

(56) References Cited

U.S. PATENT DOCUMENTS

| | | | | |
|---|---|---|---|---|
| 10,130,761 | B2 | 11/2018 | Searle et al. | |
| D839,423 | S | 1/2019 | Großer et al. | |
| D842,464 | S | 3/2019 | Davis et al. | |
| D863,546 | S | 10/2019 | Converse et al. | |
| D883,474 | S | 5/2020 | Tipsmark | |
| D884,160 | S | 5/2020 | Adams | |
| 10,646,643 | B2 | 5/2020 | Cabiri et al. | |
| D893,707 | S | 8/2020 | Burkholz et al. | |
| D900,308 | S | 10/2020 | Burkholz et al. | |
| D913,487 | S | 3/2021 | Orofino | |
| 10,933,191 | B2 | 3/2021 | Lawrence et al. | |
| D961,782 | S | 8/2022 | Locke et al. | |
| D975,845 | S | 1/2023 | Kobayashi et al. | |
| D1,008,452 | S | 12/2023 | Lanigan | |
| D1,013,864 | S | 2/2024 | Lanigan | |
| D1,043,975 | S | 9/2024 | Cox et al. | |
| D1,043,976 | S | 9/2024 | Cannan et al. | |
| D1,057,941 | S | 1/2025 | Cannan et al. | |
| D1,064,312 | S | 2/2025 | Chae | |
| D1,077,238 | S | 5/2025 | Filgate et al. | |
| D1,090,862 | S | 8/2025 | Furtado et al. | |
| 2002/0055711 | A1 | 5/2002 | Lavi et al. | |
| 2002/0072720 | A1 | 6/2002 | Hague et al. | |
| 2004/0116866 | A1 | 6/2004 | Gorman et al. | |
| 2005/0107743 | A1 | 5/2005 | Fangrow, Jr. | |
| 2005/0273076 | A1 | 12/2005 | Beasley et al. | |
| 2006/0247574 | A1 | 11/2006 | Maule et al. | |
| 2007/0088254 | A1 | 4/2007 | DeStefano | |
| 2007/0191773 | A1 | 8/2007 | Wojcik | |
| 2008/0154205 | A1 | 6/2008 | Wojcik | |
| 2009/0012473 | A1 | 1/2009 | Stettler et al. | |
| 2009/0076451 | A1 | 3/2009 | Teisen-Simony et al. | |
| 2009/0198190 | A1 | 8/2009 | Jensen et al. | |
| 2009/0204077 | A1 | 8/2009 | Hasted et al. | |
| 2009/0218243 | A1 | 9/2009 | Gyrn et al. | |
| 2009/0326472 | A1 | 12/2009 | Carter et al. | |
| 2010/0036323 | A1* | 2/2010 | Smith | A61B 17/3498 604/167.01 |
| 2010/0137695 | A1 | 6/2010 | Yodfat et al. | |
| 2010/0160851 | A1 | 6/2010 | Dimalanta et al. | |
| 2010/0198157 | A1 | 8/2010 | Gyrn et al. | |
| 2011/0009703 | A1* | 1/2011 | Smith | A61B 17/3421 600/203 |
| 2011/0034883 | A1 | 2/2011 | Gyrn et al. | |
| 2011/0087159 | A1* | 4/2011 | Parihar | A61B 17/3462 604/167.03 |
| 2011/0098652 | A1 | 4/2011 | Hasted et al. | |
| 2012/0046533 | A1 | 2/2012 | Voskanyan et al. | |
| 2012/0265166 | A1 | 10/2012 | Yodfat | |
| 2012/0283646 | A1 | 11/2012 | Kouyoumijian | |
| 2013/0197439 | A1* | 8/2013 | Melvin | A61B 17/3417 604/117 |
| 2013/0338594 | A1 | 12/2013 | De Ros et al. | |
| 2014/0039453 | A1 | 2/2014 | Sonderegger | |
| 2014/0074028 | A1 | 3/2014 | Sonderegger et al. | |
| 2014/0155679 | A1 | 6/2014 | Pesach et al. | |
| 2014/0155819 | A1 | 6/2014 | Amirouche et al. | |
| 2014/0296782 | A1 | 10/2014 | Ulrich et al. | |
| 2015/0051583 | A1 | 2/2015 | Horvath et al. | |
| 2015/0238705 | A1 | 8/2015 | Gravesen et al. | |
| 2016/0015303 | A1 | 1/2016 | Bernstein et al. | |
| 2017/0281863 | A1 | 10/2017 | Kamen et al. | |
| 2019/0009019 | A1* | 1/2019 | Shor | A61M 5/1456 |
| 2019/0060562 | A1 | 2/2019 | Olivas et al. | |
| 2021/0268179 | A1 | 9/2021 | Schøndorff et al. | |
| 2022/0125346 | A1 | 4/2022 | Stafford | |
| 2022/0202366 | A1 | 6/2022 | Mitchell et al. | |
| 2023/0062738 | A1 | 3/2023 | Lanigan et al. | |
| 2025/0082271 | A1 | 3/2025 | Oakes | |
| 2025/0107939 | A1 | 4/2025 | Gardner et al. | |

FOREIGN PATENT DOCUMENTS

| | | | |
|---|---|---|---|
| DE | 29905072 | U1 | 9/1999 |
| IL | 71109 | | 7/2023 |
| JP | 2014510574 | A | 5/2014 |
| JP | D2021-01054 | | 7/2022 |
| WO | WO2004020035 | A1 | 3/2004 |
| WO | WO2012134588 | A1 | 10/2012 |
| WO | WO2013070715 | A1 | 5/2013 |

OTHER PUBLICATIONS

Neria Guard Infusion Set, announced in You Tube on May 17, 2022 [Online]. [Retrieved on Aug. 2, 2003], Available from the internet URL:https://www.youtube.com/watch?v=VUoLi-_gcyE (Year: 2023).

Autosoft XC Infusion Set. Product Support Page[Online]. Tandemdiabetes.com 2023. [Retrieved on Aug. 2, 2023]. Retrieved from the Internet: URL:https://support.tandemdiabetes.com/hc/en-us/articles/360039015054/ (Year: 2023).

Tapecon. using Adhesive Constructions to Improve Chain of Custody Sleep Apnea Tests. No Publication Date. Retrieved Feb. 19, 2025. https://www.tapecon.com/blog/adhesive-constructions-chain-of-custody-sleep-apnea-tests.

Medical Design & Outsourcing. new 3M Durapore Advanced Surgical Tape Offers Adhesive Innovation. Oct. 25, 2018. https://www.medicaldesignandoutsourcing.com/new-3m-durapore-advanced-surgical-tape-offers-adhesive-innovation/.

* cited by examiner

INFUSION SET AND INSERTER ASSEMBLY SYSTEMS AND METHODS

CROSS-REFERENCE TO RELATED APPLICATIONS

The present application is a Continuation of U.S. patent application Ser. No. 18/784,148, filed on Jul. 25, 2024, now US2024-0382674, published Nov. 21, 2024, and entitled Infusion Set and Inserter Assembly Systems and Methods which is a Continuation of U.S. Ser. No. 17/883,063, filed on Aug. 8, 2022, now US2022-0379019, published Dec. 1, 2022, and entitled Infusion Set and Inserter Assembly Systems and Methods which is a Continuation of U.S. patent application Ser. No. 16/797,624, filed on Feb. 21, 2020, now U.S. Pat. No. 11,446,434, Issued Sep. 20, 2022, and entitled Infusion Set and Inserter Assembly Systems and Methods which claims the benefit of U.S. Provisional Application Ser. No. 62/809,248 filed Feb. 22, 2019 and entitled Infusion Set and Inserter Assembly Systems and Methods, each of which being hereby incorporated herein by reference in their entireties.

BACKGROUND

Field of Disclosure

This application relates generally to infusion sets and inserter assemblies for infusion sets, and more particularly, to infusion sets and inserter assemblies as well as methods for the use thereof.

Description of Related Art

Many potentially valuable medicines or compounds, including biologicals, are not orally active due to poor absorption, hepatic metabolism or other pharmacokinetic factors. Additionally, some therapeutic compounds, although they can be orally administered, are sometimes required to be taken so often that it is difficult for a patient to maintain the desired schedule. In these cases, parenteral delivery is often employed or could be employed.

Effective parenteral delivery routes of drugs, other fluid, and compounds such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compound over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight, and cost of these devices is also an ongoing challenge. Additionally, these devices often apply to the skin and pose the challenge of frequent relocation for application.

SUMMARY

In accordance with an embodiment of the present disclosure an inserter assembly may comprise a casing. The inserter assembly may further comprise a body including a cavity disposed within the casing. The inserter assembly may further comprise a sharp holder affixed to an insertion sharp. The sharp holder may be at least partially disposed within the cavity. The inserter assembly may further comprise a bias member within the cavity. The bias member may be positioned between the sharp holder and a wall of the cavity. The inserter assembly may further comprise a trigger having a first state in which the bias member is maintained in an energy storing state and a second state in which the bias member is released from the energy storing state. The bias member may be configured to propel the sharp holder to displace the insertion sharp out of the casing when released from the energy storing state. The inserter assembly may further comprise an infusion set base in retaining engagement with the body. The infusion set base may have an adhesive included on a bottom face thereof. The inserter assembly may further comprise a trigger actuation projection extending from the casing and arranged to actuate the trigger from the first to the second state as the casing is displaced away from a body once the adhesive is stuck to skin and the skin has been tugged a distance away from the body.

In some embodiments, the casing may include a housing and a retaining base coupled to the housing so as to move together as a unit with the housing. In some embodiments, the trigger actuation projection may be included on the retaining base. In some embodiments, the trigger may include a latch. In some embodiments the latch may include a catch disposed on the body which engages a ledge formed on a cantilevered arm of the sharp holder. In some embodiments, the bottom face of the infusion set base may be substantially level with a skin contacting face of the casing prior to application of the inserter assembly to the skin. In some embodiments, the inserter assembly may further comprise a cannula sub assembly through which the insertion sharp extends. In some embodiments, the cannula sub assembly may be separate from the infusion set base when the trigger is in the first state. In some embodiments, the cannula sub assembly may include a cannula which is integral with a septum housing. In some embodiments, the cannula sub assembly and infusion set base may include cooperating coupling features which interface to join the cannula sub assembly and infusion set base when the cannula sub assembly is displaced into the infusion set base. In some embodiments, the energy storing state of the first bias member is a compressed state. In some embodiments, the inserter assembly may further comprise a second bias member. In some embodiments, the second bias member may be configured to be released from an energy storing state of the second bias member due to displacement of the insertion sharp out of the casing. In some embodiments, the second bias member may propel the sharp holder and insertion sharp to a retracted position within the casing when released from its energy storing state.

In accordance with another embodiment of the present disclosure an inserter assembly may comprise a first unit including a deflector member and a trigger actuation projection. The inserter assembly may further comprise a second unit housed within the first unit. The second unit may comprise a body including a cavity and an arm having a resiliency. The arm may be aligned with the deflector member. The second unit may further comprise a sharp holder having an insertion sharp thereon. The sharp holder may be at least partially disposed in the cavity. The second unit may further comprise a bias member held in an energy storing state by a trigger. The second unit may further comprise an insertion set base. The insertion set base may include an adhesive. The insertion set base may be releasably coupled to the body. When the adhesive is stuck to skin and the inserter assembly is withdrawn from body, the first and second unit may move together tugging the skin away from the body until a force exerted by the elasticity of the skin overcomes the resiliency of the arm by pressing the arm into the deflector in a first stage of actuation. In a second stage of actuation, the trigger may be displaced and energy stored in the bias member may be released to propel the sharp holder toward the skin.

In some embodiments, the first unit may include an exterior housing and a retainer base which is coupled to the exterior housing. In some embodiments, the deflector member and trigger actuation projection may be included on the retainer base. In some embodiments, the trigger actuation projection includes a finger including a fin. The fin may extend from a portion of the retainer base into the second unit. In some embodiments, the trigger may include a catch of the body which engages with a ledge included on a deflectable member of the sharp holder. In some embodiments, the first unit may include a second deflector member. In some embodiments, the body of the second unit may include a second arm having a second arm resiliency. In some embodiments, the second arm may be aligned with the second deflector member. In some embodiments, the infusion set base may be arranged to be decoupled from the body as the sharp holder is propelled toward the skin. In some embodiments, the bias member may be a compression spring. In some embodiments, the deflector member may include an angled deflector face disposed in opposition to an angled arm face include on the arm. In some embodiments, the infusion set base may be releasably coupled to the body by a set of cantilevered arms. In some embodiments, the cantilevered arms may be configured for displacement to a splayed apart state to release the infusion set base by ears of a cannula sub assembly carried with the insertion sharp as the sharp holder is propelled by the bias member. In some embodiments, the inserter assembly may further comprise a cannula sub assembly carried by the insertion sharp and spaced from the infusion set base during the first stage of actuation. In some embodiments, the cannula sub assembly may be coupled into the base during the second stage of actuation.

In accordance with another embodiment of the present disclosure, an inserter assembly may comprise a casing including a skin contacting face. The skin contacting face may surround an opening in the casing. The inserter assembly may further comprise a sharp holder including an insertion sharp. The inserter assembly may further comprise a cannula sub assembly carried by the insertion sharp. The insertion sharp and a cannula of the cannula sub assembly each may have a skin penetrating end disposed above the skin contacting surface. The inserter assembly may further comprise an infusion set base disposed within the opening in the casing and having a bottom face substantially level with the skin contacting surface. The infusion set base may include a cannula sub assembly receiving void sized to receive the cannula sub assembly and prevent finger ingress. The inserter assembly may further comprise an insertion bias member. The sharp holder may be configured for displacement by a transition of the insertion bias member from an insertion energy storing state to a relaxed state to drive the insertion sharp and cannula at least partially out of the casing and couple the cannula sub assembly to the infusion set base.

In some embodiments, the inserter assembly may further comprise a plurality of standoffs which position the infusion set base level with the skin contacting face prior to actuation.

In some embodiments, the cannula sub assembly may include the cannula, a septum, a septum retainer, and a septum housing. In some embodiments, the septum housing and the cannula are formed as a continuous, monolithic, or unitary part. In some embodiments, the cannula sub assembly receiving void and cannula sub assembly include cooperating coupling features which interact to join the infusion set base and cannula sub assembly to one another when the cannula sub assembly is advanced into the cannula sub assembly receiving void. In some embodiments, the cooperating coupling features may include a cantilevered arm having a protuberance on the infusion set base and a receiving notch to accept the protuberance on the cannula sub assembly. In some embodiments, the inserter assembly may further comprise a sharp retractor and a retractor bias member configured to be released from a retraction energy storing state in response to a projection on the cannula sub assembly disengaging a latch as the sharp holder is displaced by the transition of the insertion bias member. In some embodiments, the retractor bias member may be configured to displace the sharp retractor away from the skin contacting surface as the retractor bias member transitions from the retraction energy storing state to a relaxed state. In some embodiments, the sharp holder may include at least one ledge and the sharp retractor includes a least one stop. There may be a dwell distance between the at least one ledge and the stop when the retractor bias member is released from the retraction energy storing state.

In accordance with another embodiment of the present disclosure an inserter assembly may comprise a casing. The inserter assembly may further comprise a sharp holder having an insertion sharp coupled thereto and a cantilevered arm having a protuberance defining a ledge. The inserter assembly may further comprise a sharp retractor having a cavity at least partially containing the sharp holder and having a stop therein configured to engage the ledge. The sharp retractor may additionally have a catch configured to engage the ledge and hold an insertion spring in a biased state. The inserter assembly may further comprise a cannula sub assembly carried by the insertion sharp. The inserter assembly may further comprise an infusion set base releasably coupled to the sharp retractor and holding a retraction spring in a biased state while releasably coupled to the sharp retractor. The insertion spring may be configured to drive the sharp holder along an insertion path upon disengagement of the ledge from the catch. The infusion set base may be uncoupled from the sharp retractor, the cannula sub assembly may be coupled to the infusion set base, and the ledge may be spaced from the stop by a dwell distance when the sharp holder transits to the end of the insertion path. The retraction spring may be configured to displace the sharp retractor into the casing along with the sharp holder after the sharp retractor transits the dwell distance and engages the stop with the ledge.

In some embodiments, the infusion set base may be releasably coupled to the sharp retractor by a set of cantilevered arms extending from the sharp retractor. In some embodiments, the cannula sub assembly may include a pair of ears configured to splay the set of arms apart releasing the infusion set base when the sharp holder transits to the end of the insertion path. In some embodiments, the sharp holder may include a second cantilevered arm having a second protuberance defining a second ledge. In some embodiments, the cavity may include a second stop therein configured to engage the second ledge. In some embodiments, the cannula sub assembly may include a notch. The notch may be configured to couple to a protuberance included in the infusion set base when the sharp holder transits to the end of the insertion path. In some embodiments, the cannula sub assembly includes a salient which is configured to couple to a protuberance included in the infusion set base when the sharp holder transits to the end of the insertion path. In some embodiments, a cannula and septum housing of the cannula sub assembly may be formed together as a monolithic part in a straight pull mold. In some embodiments, the casing may include an exterior housing and a retainer base. The infusion set base may be disposed within an opening in the retainer base and level with a skin contacting surface of the retainer base prior to actuation of the inserter assembly. In some embodiments, the infusion set base may include an adhesive on a bottom face thereof and the ledge may be disengaged from the catch by lifting of the inserter assembly from a patch of skin to which it has been applied.

In accordance with another embodiment of the present disclosure an inserter assembly may comprise a first unit including a skin contacting face which surrounds an opening. The inserter assembly may further comprise a second unit housed within the first unit. The second unit may comprise an infusion set base disposed within the opening and having a bottom face which is substantially level with the skin contacting face and covered at least partially with adhesive. The second unit may further comprise a spring biased insertion assembly. The second unit may further comprise a cannula sub assembly carried by an insertion sharp of the insertion assembly. The spring biased insertion assembly and a cannula of the cannula sub assembly may be configured to be driven into skin and the cannula sub assembly may be configured to be coupled into the infusion set base by an insertion spring which may be configured to be released from an energy storing state after the skin has been tugged upward beyond a certain distance by the adhesive as the inserter assembly is withdrawn.

In some embodiments, the inserter assembly may further comprise a sharp retractor and a retractor spring which may be configured to retract the sharp retractor along with the insertion assembly away from the skin contacting face. In some embodiments, the inserter assembly may include at least one latch configured to maintain the retractor spring in an energy storing state. The latch may be disengaged upon displacement of the cannula sub assembly into coupling engagement with the infusion set base. In some embodiments, the at least one latch may include a set of cantilevered arms included on the sharp retractor. In some embodiments, the cantilevered arms may each include a ledge which engages a respective projection on the infusion set base. In some embodiments, the respective projection on the infusion set base may be a portion of a guide for a portion of a tubing set connector. In some embodiments, the infusion set base may include a cannula sub assembly receiving void extending therethrough and sized to accept the cannula sub assembly but prevent finger ingress. In some embodiments, the cannula sub assembly and cannula sub assembly receiving void include cooperating coupling features which interact to couple the infusion set base and cannula sub assembly to one another.

In accordance with another embodiment of the present disclosure an inserter assembly may comprise a first unit. The first unit may comprise an infusion set base including an adhesive on a bottom face thereof. The first unit may further comprise an insertion sharp drive assembly releasably coupled to the infusion set base and including an insertion sharp, a drive spring, a resilient member, and a latch arrangement configured to, in an engaged state, retain the drive spring in an energy storing state. The inserter assembly may further comprise a casing. The infusion set base may be disposed within an opening in the casing. Displacement of the inserter assembly away from the body when the adhesive is in an adhering relationship to skin, in a first stage, tugs the skin from underlying structures. In a second stage where a force exerted by elasticity of the skin overcomes a resiliency of the resilient member displaces the casing relative to the first unit and disengages the latch arrangement. The drive spring may be arranged to displace the insertion sharp out of the casing upon transition to a relaxed state.

In accordance with another embodiment of the present disclosure an inserter assembly for placing an infusion set on an infusion site of a body may comprise a casing having an actuation projection. The inserter assembly may further comprise a first unit within the casing moveable relative to the casing. The first unit may comprise an infusion set base having an adhesive. The first unit may further comprise a sharp holder including an insertion sharp. The first unit may further comprise a body including a cavity in which a drive spring and the sharp holder are a least partially disposed. The sharp holder may be displaceable by the drive spring from a raised state to a forward state. The first unit may further comprise a drive spring release latch arrangement. The actuation projection may be configured to disengage the drive spring release latch arrangement after a magnitude of relative displacement between the casing and first unit exceeds a threshold. The adhesive may be configured to anchor the first unit against the body while casing is pulled away from the body and the magnitude of relative displacement between the casing and first unit increases.

In some embodiments, the first unit may further comprise a resilient member. In some embodiments, the resilient member may be aligned with a deflector on the casing. In some embodiments, the resilient member may be configured to abut a portion of the casing to inhibit relative displacement of the casing and first unit until a force threshold is exceeded. In some embodiments, the portion of the casing may be a deflector member and the resilient member may be a resilient arm included on the body. In some embodiments, the force threshold may be selected such that, as the casing is pulled away from the body, skin of the body is lifted due to adhesion of the adhesive at least a certain distance from underlying body structures before the magnitude of relative displacement exceeds the threshold. In some embodiments, the force threshold may be selected such that, as the casing is pulled away from the body, skin of the body is lifted due to adhesion of the adhesive at least a certain distance from underlying body structures before relative displacement of the casing and first unit begins. In some embodiments, the force threshold may be selected such that, as the casing is pulled away from the body, skin of the body is lifted due to adhesion of the adhesive at least a certain distance from underlying body structures. In some embodiments, the infusion set base may be releasably coupled to the body. In some embodiments, the infusion set base may be arranged to be released from the body upon displacement of the sharp holder to the forward state. In some embodiments, the inserter assembly may further comprise a retraction spring. The sharp holder may be displaceable by the retraction spring from the forward state to a retracted state. In some embodiments, the inserter assembly may further comprise a retraction spring release latch arrangement configured to disengage upon displacement of the sharp holder to the forward state via the drive spring. In some embodiments, the retraction spring release latch arrangement may releasably couple the infusion set base to the body. The infusion set base may be released from the body when the spring release latch arrangement is disengaged. In some embodiments, a cannula sub assembly may be carried on the insertion sharp.

In accordance with an embodiment of the present disclosure a cannula sub assembly for an infusion set may comprise a continuous monolithic body including a cannula and a septum housing. The septum housing may have a septum receptacle with a raised region at a bottom thereof. A lumen of the cannula may be continuous with a sharp guide included in raised region. The cannula sub assembly may further comprise a septum including a septum recess having a centering wall section formed as a negative version of the raised region. The cannula sub assembly may further comprise a septum retainer including a body having latch arms extending through the septum housing and each including a latching surface which in an engaged state catches a cooperating feature of the septum housing to capture the septum within the septum housing.

In some embodiments, the septum housing may include a salient arranged to engage a latch of an infusion set base to retain the cannula sub assembly within the infusion set base. In some embodiments, a top face of a wall of the septum receptacle may include slots recessed therein. In some embodiments, the slots may include two slots which are disposed opposite one another. In some embodiments, the septum retainer may further comprise a set of projections. In some embodiments, the set of projections are sized to be received within slots recessed into a top face of a wall defining the septum receptacle. In some embodiments, the set of projections obstructs only a top portion of the slot when received therein so as to leave a bottom segment of the slot open and exposing a side wall of the septum at a location even with at least a portion of the septum recess. In some embodiments, the raised section of the septum receptacle has a frusto-conic outer wall. In some embodiments, the septum housing may include a notch in a side wall thereof configured to engage a latch of an infusion set base to retain the cannula sub assembly within the infusion set base. In some embodiments, the monolithic body may be formed via straight pull molding. In some embodiments, the monolithic body may be devoid of undercut features. In some embodiments, the monolithic body may be polypropylene. In some embodiments, the monolithic body may be PTFE. In some embodiments, the body of the septum retainer may include a channel extending therethrough and sized to receive a nub on a face of the septum. In some embodiments, the sharp guide may be encompassed by a substantially flat peripheral edge at an uppermost part of the raised section.

In accordance with another embodiment of the present disclosure a cannulated housing for an infusion set may comprise a continuous monolithic body. The continuous monolithic body may comprise a cannula. The continuous monolithic body may further comprise a septum housing having septum receptacle defined by a side wall and bottom wall. The septum housing may include a raised region, a lumen of the cannula being a continuous surface with raised region. The side wall may have at least one guide extending the length of the septum receptacle and aligned with an aperture extending through a bottom of the septum housing.

In some embodiments, the septum housing may include a salient on the exterior face of the side wall arranged to engage a latch of an infusion set base to retain the cannulated housing within the infusion set base. In some embodiments, a top face of a wall of the septum receptacle may have slots recessed therein. In some embodiments, the slots may include two slots which may be disposed opposite one another. In some embodiments, the slots may be configured to accept a set of projection included in a septum retainer so as to leave a bottom segment of each of the slots open and providing a path the volume of the septum receptacle. In some embodiments, the raised section of the septum receptacle may have a frusto-conic outer wall. In some embodiments, the septum housing may include a notch in an exterior face of the side wall configured to engage a latch of an infusion set base to retain the cannulated housing assembly within the infusion set base. In some embodiments, the monolithic body may be formed via straight pull molding. In some embodiments, the monolithic body may be devoid of undercut features. In some embodiments, the monolithic body may be polypropylene. In some embodiments, the monolithic body may be PTFE. In some embodiments, the cannula may include a sharp guide encompassed by a substantially flat peripheral edge at an uppermost part of the raised section. In some embodiments, a ledge may be positioned adjacent the aperture on an exterior face of the bottom wall. In some embodiments, a wall of the aperture may form a catch configured to engage a protuberance of a projection of a portion of a septum retainer. In some embodiments, the guides may be recessed into the side wall.

In accordance with an embodiment of the present disclosure a method of placing an infusion set on a body of a user may comprise adhering an infusion set base releasably coupled to an inserter assembly to the body. The method may further comprise pulling the inserter assembly away from the body. The method may further comprise lifting skin, via adhesion of the infusion set, from underlying structures of the body as the inserter assembly is pulled away from the body. The method may further comprise displacing a trigger actuator into a trigger of the inserter assembly after the skin has been lifted at least a certain distance. The method may further comprise driving an insertion sharp through the skin.

In some embodiments, the method may further comprise releasing a bias member from an energy storing state to drive the insertion sharp through the skin. In some embodiments, the method may further comprise releasing the infusion set base from the inserter assembly. In some embodiments, the method may further comprise removing a lock member from the inserter assembly and removing an adhesive backing from the infusion set base. In some embodiments, the method may further comprise releasing a retraction prevention latch and driving the insertion sharp in a direction away from the skin. In some embodiments, method may further comprise driving a cannula sub assembly of carried by the insertion sharp into the infusion set base. In some embodiments, driving the cannula sub assembly into the infusion set base may comprise driving a cannula of the cannula sub assembly through the skin. In some embodiments, the method may further comprise inhibiting relative movement between a casing of the inserter assembly and the rest of the inserter assembly at least when the skin begins being lifted.

In accordance with another embodiment of the present disclosure a method of placing an infusion set on a body of a user may comprise adhering an infusion set base which is releasably coupled to an inserter assembly to the body. The method may further comprise pulling the inserter assembly away from the body. The method may further comprise displacing skin, via adhesion of the infusion set, from its resting position as the inserter assembly is pulled away from the body. The method may further comprise prohibiting actuation of a trigger until the skin has been displaced to a point at which the elasticity of the skin exerts more than a threshold force against the infusion set base. The method may further comprise displacing a trigger actuator into a trigger of the inserter assembly. The method may further comprise driving an insertion sharp through the skin.

In some embodiments, the method may further comprise freeing a bias member from an energy storing state to drive the insertion sharp through the skin. In some embodiments, the method may further comprise decoupling the infusion set base from the inserter assembly. In some embodiments, the method may further comprise removing a lock member from the inserter assembly and removing an adhesive backing from the infusion set base. In some embodiments, the method may further comprise driving a cannula sub assembly along with the insertion sharp toward the skin such that the cannula sub assembly is driven into a retraction prevention latch. The method may further comprise driving the insertion sharp in a direction away from the skin. In some embodiments, the method may further comprise driving a cannula sub assembly of carried by the insertion sharp into the infusion set base. In some embodiments, driving the cannula sub assembly into the infusion set base may comprise driving a cannula of the cannula sub assembly through the skin. In some embodiments, prohibiting actuation of the trigger may comprise inhibiting relative movement between a casing of the inserter assembly and the rest of the inserter assembly at least when the skin begins being displaced.

In accordance with another embodiment of the present disclosure an inserter assembly may comprise a first unit comprising a casing. The inserter assembly may further comprise a second unit comprising an infusion set base having an adhesive. The second unit may further comprise a sharp holder including an insertion sharp. The second unit may further comprise a trigger. The second unit may further comprise a body including a cavity in which a drive spring and the sharp holder are a least partially disposed. The sharp holder may be displaceable by the drive spring from a raised state to a forward state upon actuation of the trigger from a first state to a second state. The adhesive may be configured to anchor the second unit against the body while casing is pulled away from the body. The trigger may be precluded from being actuated until a magnitude of relative displacement between the casing and second unit reaches a threshold.

In some embodiments, the second unit may further comprise a resilient member aligned with a deflector on the casing. In some embodiments, the second unit may further comprise a resilient member configured to abut a portion of the casing to inhibit relative displacement of the casing and second unit until a force threshold is exceeded. In some embodiments, the portion of the casing may be a deflector member and the resilient member may be a resilient arm included on the body. In some embodiments, the force threshold may be selected such that, as the casing is pulled away from the body, skin of the body may be lifted due to adhesion of the adhesive at least a certain distance from its resting position before the magnitude of relative displacement exceeds the threshold. In some embodiments, the force threshold may be selected such that, as the casing is pulled away from the body, skin of the body may be lifted due to adhesion of the adhesive at least a certain distance from its resting position before relative displacement of the casing and first unit begins. In some embodiments, the force threshold may be selected such that, as the casing is pulled away from the body, skin of the body may be lifted due to adhesion of the adhesive at least a certain distance from its resting position. In some embodiments, the infusion set base may be releasably coupled to the body. In some embodiments, the infusion set base may be arranged to be released from the body upon displacement of the sharp holder to the forward state.

In some embodiments, the inserter assembly may further comprise a retraction spring. The sharp holder may be displaceable by the retraction spring from the forward state to a retracted state. In some embodiments, the sharp holder may be in a different location in the retracted state than it is in the raised state. In some embodiments, the inserter assembly may further comprise a retraction spring release latch arrangement configured to disengage upon displacement of the sharp holder to the forward state. In some embodiments, the retraction spring release latch arrangement releasably couples the infusion set base to the body. The infusion set base may be released from the body when the spring release latch arrangement is disengaged. In some embodiments, a cannula sub assembly may be carried on the insertion sharp.

In accordance with another embodiment of the present disclosure a cartridge for a reusable inserter assembly may comprise an exterior housing. The cartridge may further comprise an interior housing releasably coupled to the exterior housing. The cartridge may further comprise an infusion set base retainer having an infusion set base retained thereon. The cartridge may further comprise a sharp holder having an insertion sharp coupled thereto. The cartridge may further comprise a cannula subassembly mounted on the insertion sharp such that an insertion end of the insertion sharp extends out of an outlet end of a cannula of the cannula subassembly. The insertion end of the insertion sharp may be within the interior housing.

In some embodiments, the cartridge may further comprise a removable barrier member. In some embodiments, the barrier member may be permeable to a sterilization agent. In some embodiments, the exterior housing may be shaped as a cup. In some embodiments, the exterior housing may include at least one receptacle and the interior housing may include at least one displaceable projection. In some embodiments, the interior housing may be releasably coupled to the exterior housing via engagement of each of the at least one projection with a respective one of the at least one receptacle. In some embodiments, each of the at least one projection may be included on an unsupported end of a cantilevered arm. In some embodiments, each cantilevered arm may include a ramped projection at the unsupported end thereof. The ramped projection may be configured to interact with a deflector member on the reusable inserter assembly such that the deflector member deflects the cantilevered arm and displaces the associated projection out of engagement with a receptacle of the at least one receptacle upon coupling of the cartridge to the reusable inserter assembly. In some embodiments, the cartridge may further comprise a set of mating pins. In some embodiments, the mating pins may be configured to be received in retention shoes of the reusable inserter assembly when the cartridge is coupled to the reusable inserter assembly. In some embodiments, the sharp holder may include a terminal flange which extend out of the interior housing. In some embodiments, the terminal flange may have an obround cross sectional shape. In some embodiments, the infusion set base may include adhesive on a face thereof. The adhesive being covered by a liner or backing. In some embodiments, the interior housing may include an indention providing a recess within which pull tabs of the liner are positioned. In some embodiments, the infusion set base retainer may include a cavity within which a majority of the insertion sharp holder is disposed. In some embodiments, the cavity may include guides and the insertion sharp holder may include rails which cooperate with the guides to constrain displacement of the insertion sharp holder within the cavity to a prescribed path.

In accordance with an embodiment of the present disclosure a cartridge for a reusable inserter assembly may comprise a container. The cartridge may further comprise a housing releasably coupled within the container. The housing may include a bay. The cartridge may further comprise an infusion set base disposed within the bay. The cartridge may further comprise a retainer body including a set of cantilevered arms and a cavity. The infusion set base may be releasably coupled to the retainer body via the set of cantilevered arms. The cartridge may further comprise a sharp holder having an insertion sharp coupled thereto. The sharp holder may be configured for displacement along guides included in the cavity. The cartridge may further comprise a cannula subassembly mounted on the insertion sharp such that an end of the cannula subassembly is adjacent a first end of the sharp holder.

In some embodiments, the cartridge further comprises a barrier member which, together with the container, may enclose the housing. In some embodiments, the cartridge may further comprise a set of mating pins. In some embodiments, the mating pins may be configured to be received in retention shoes of the reusable inserter assembly when the cartridge is coupled to the reusable inserter assembly. In some embodiments, the sharp holder may include a terminal flange which extends out of the housing. In some embodiments, the terminal flange may have an obround cross-sectional shape. In some embodiments, the bay may include at least one notch and the infusion set base may include at least one tube retainer. Each tube retainer of the infusion set base may be disposed within one of the notches of the bay. In some embodiments, the cannula subassembly may include a salient arranged to engage a latch of the infusion set base to retain the cannula sub assembly within the infusion set base when the cannula sub assembly is displaced into a receiving void in the infusion set base. In some embodiments, the cannula subassembly may include a notch arranged to engage a latch of the infusion set base to retain the cannula subassembly within the infusion set base when the cannula sub assembly is displaced into a receiving void in the infusion set base. In some embodiments, the retainer body may be coupled to the housing via a snap fit engagement. In some embodiments, the cantilevered arms may be configured for displacement to a splayed apart state to release the infusion set base by ears of the cannula subassembly when the cannula subassembly is displaced toward the infusion set base. In some embodiments, the housing may include an indention within which pull tabs of an adhesive backing covering adhesive on the infusion set base are disposed. In some embodiments, the housing may include at least one set of stop surfaces.

In accordance with another embodiment of the present disclosure a cartridge for a reusable inserter assembly may comprise a container. The cartridge may further comprise a housing including a spring loaded tab. The housing may be coupled within the container with the spring loaded tab in a first state and freed from the container with the spring loaded tab deflected from the first state to a deflected state. The cartridge may further comprise a retainer body including a cavity, a set of retainer arms, and an end plate having mating pins projecting therefrom. The cartridge may further comprise a medical device. At least a portion of the medical device may be retained by the retainer arms. The cartridge may further comprise an insertion sharp. The cartridge may further comprise a sharp holder configured to displace along guides included in the cavity. The insertion sharp may be coupled to the sharp holder.

In some embodiments, the spring loaded tab may be included on a resilient cantilevered arm. In some embodiments, the cartridge further may comprise a second spring loaded tab opposite the spring loaded tab. In some embodiments, the medical device may be an analyte sensor. In some embodiments, the medical device may be a physiological monitor. In some embodiments, the medical device may be an infusion set. The infusion set may include an infusion set base and a cannula subassembly. In some embodiments, the infusion set base may be retained by the retainer arms and the cannula subassembly may be disposed on the insertion sharp and may be separated from the infusion set base. In some embodiments, the cannula subassembly may include a set of ears. The retainer arms may be configured for displacement to a splayed apart state to release the infusion set base by the ears of the cannula subassembly when the sharp holder is displaced toward the infusion set base. In some embodiments, the infusion set base may include an aperture therethrough. In some embodiments, the infusion set base may have an adhesive coupled thereto. The adhesive may be covered by an adhesive backing. At least one of the adhesive and the adhesive backing may extend across and cover the aperture. In some embodiments, the sharp holder may include a terminal flange configured to mate to an insertion driver of the reusable inserter assembly. In some embodiments, the mating pins may be configured to mate with retention shoes included in the inserter assembly. In some embodiments, the cartridge may further comprise an adhesive backing covering adhesive on a portion of the medical device. The housing may include an indention in which pull tabs of the adhesive backing are disposed. In some embodiments, the housing may include a set of stop surfaces configured to interact with lock members of the inserter assembly to lock the housing from rotational displacement once the inserter assembly and housing are coupled. In some embodiments, the container may be configured to displace the lock members when pressed against the inserter assembly to unlock rotational displacement of the housing. In some embodiments, the spring loaded tab may be configured to displace to the deflected state upon coupling of the cartridge to the inserter assembly. In some embodiments, the medical device may include an adhesive patch coupled thereto. The adhesive patch may be covered by a release liner.

In accordance with another embodiment of the present disclosure an inserter assembly may comprise a first unit. The inserter assembly may further comprise a second unit. The first unit may be displaceable relative to the second unit. The inserter assembly may further comprise an insertion bias member configured to transition to a stressed state when the first unit is pressed against the second unit. The inserter assembly may further comprise a retainer configured engage a first latch maintaining the insertion bias member in the stressed state when the first unit is displaced toward the second unit beyond a first threshold distance. The inserter assembly may further comprise an insertion driver included in the second unit and displaceable from a first position to an extended position. The inserter assembly may further comprise a release finger included on the first unit. The release finger may be configured to dislodge the insertion driver from an insertion driver latch releasing the insertion bias member from the stressed state when the first unit is pulled back away from the second unit beyond a second threshold distance. The insertion bias member may propel the insertion driver from the first position to the extended position when released from the stressed state. The insertion driver may disengage the first latch when displaced to the extended position.

In some embodiments, the inserter assembly may be needle free. In some embodiments, the inserter assembly may not include an insertion sharp. In some embodiments, the inserter assembly may further comprise at least one retraction bias member. In some embodiments, the at least one retraction bias member may be configured to transition to a stressed state when the first unit is pressed against the second unit. In some embodiments, the at least one retraction bias member may be maintained in the stressed state when the retainer is engaged with the first latch. In some embodiments, the at least one retraction bias member may be released from the stressed state when the first latch is disengaged as the inserter driver is propelled to the extended position. In some embodiments, the insertion driver may be displaced to the first position as the at least one retraction bias member transitions from the stressed state to a relaxed state. In some embodiments, the release finger may include a paddle body having a first side and a second side. The first side may be more medial to a longitudinal axis of the inserter assembly. In some embodiments, the second unit may include a director wedge projecting into a displacement path followed by the release finger as the first unit is displaced relative to the second unit. In some embodiments, the first and second side of the paddle body may include sloped portions. At least one of the sloped portions may be configured to contact the director wedge and deflect the release finger away from the insertion driver latch as the first unit is pressed toward the second unit. In some embodiments, the first and second side of the paddle body may include sloped portions and at least one of the sloped portions may be configured to contact the director wedge and deflect the release finger into the insertion driver latch as the first unit is pulled away from the second unit. In some embodiments, the insertion driver may include a port configured to mate with an insertion sharp holder. In some embodiments, the second unit may include a receptacle body coupled thereto. The receptacle body may be disposed on an end of the second unit. In some embodiments, the receptacle body may include at least one retention interface configured to couple with a mating projection of a disposable cartridge. In some embodiments, the first latch may include a pair of arms each having a latching ledge. The pair of arms may be cantilevered from a main portion of a latch body. In some embodiments, the inserter driver latch may include a projection which extends into a notch in a cantilevered arm extending from a main body of the insertion driver. In some embodiments, the second threshold distance may be measured from a location of the first unit after the first unit has been displaced the first threshold distance. In some embodiments, the second unit may include a receptacle body which is configured to mate with any of an infusion set cartridge, a sensor cartridge, and a lancet cartridge.

In accordance with an embodiment of the present disclosure an inserter assembly may comprise an exterior housing and a cap coupled to an end thereof. The inserter assembly may further comprise an interior housing. The exterior housing and cap may be displaceable relative to the interior housing. The inserter assembly may further comprise an insertion driver included in the interior housing and displaceable from a stowed position to an extended position. The inserter assembly may further comprise an insertion bias member housed in a portion of the insertion driver and configured to transition to a stressed state when the exterior housing and cap are displaced toward the interior housing. The inserter assembly may further comprise a retainer configured engage a first latch maintaining the insertion bias member in the stressed state when the exterior hosing and cap are displaced toward the interior housing to a ready position. The inserter assembly may further comprise a release finger projecting from the cap configured to dislodge the insertion driver from an insertion driver latch releasing the insertion bias member from the stressed state when the exterior housing and cap are pulled from the ready position more than a threshold distance. The insertion bias member may propel the insertion driver from the first position to the extended position when released from the stressed state. The insertion driver may disengage the first latch when displaced to the extended position.

In some embodiments, the inserter assembly may not include an insertion sharp. In some embodiments, the inserter assembly may be needle free. In some embodiments, the inserter assembly may further comprise at least one retraction bias member. In some embodiments, the at least one retraction bias member may be configured to transition to a stressed state when the exterior housing and cap are pressed against the interior housing. In some embodiments, the at least one retraction bias member may be maintained in the stressed state when the retainer is engaged with the first latch. In some embodiments, the at least one retraction bias member may be released from the stressed state when the first latch is disengaged. In some embodiments, the insertion driver may be displaced to the stowed position as the at least one retraction bias member transitions from the stressed state to a relaxed state. In some embodiments, the release finger may include a paddle body having a first side and a second side. The first side may be more medial to a longitudinal axis of the inserter assembly. In some embodiments, the interior housing may include a director wedge projecting into a displacement path followed by the release finger as the exterior housing and cap are displaced relative to the interior housing. In some embodiments, the first and second side of the paddle body may include ramped portions. At least one of the ramped portions may be configured to contact the director wedge and deflect the release finger away from the insertion driver latch as the exterior housing and cap are pressed toward the interior housing. In some embodiments, the first and second side of the paddle body may include ramped portions. At least one of the ramped portions may be configured to contact the director wedge and deflect the release finger into the insertion driver latch as the exterior housing and cap are pulled away from the interior housing. In some embodiments, the insertion driver may include a port configured to mate with an insertion sharp holder. In some embodiments, the interior housing may include a receptacle body coupled thereto. The receptacle body may be disposed on an end of the interior housing. In some embodiments, the receptacle body may include at least one retention interface configured to couple with a mating projection of a disposable cartridge. In some embodiments, the receptacle body may include at least one retention shoe configured to couple with a mating pin of a disposable cartridge. In some embodiments, the first latch may include a pair of arms each having a latching ledge, the arms being cantilevered from a main portion of a latch body. In some embodiments, the inserter driver latch includes a projection which extends into a notch in a cantilevered arm extending from a main body of the insertion driver.

In accordance with an embodiment of the present disclosure an inserter assembly may comprise a first portion. The inserter assembly may further comprise a second portion.

The first portion may be displaceable relative to the second portion. The inserter assembly may further comprise an insertion driver included in the second portion. The inserter assembly may further comprise an insertion bias member included in the second portion configured to urge the insertion driver from a stowed state to an extended state when the insertion bias member is in a stressed state. The inserter assembly may further comprise a retainer included in the second portion. The inserter assembly may further comprise a first latch included in the second portion. The inserter assembly may further comprise an insertion driver latch included in the second portion. The insertion driver may releasably engage with the insertion driver latch. Displacement of the first portion toward the second portion and into a ready position may stress the insertion bias member and engage the retainer with the first latch to maintain the insertion bias member in the stressed state. Displacement of the first portion away from the ready position beyond a threshold distance may dislodge the insertion driver from the insertion driver latch and may release the insertion bias member from the stressed state.

In some embodiments, the first latch may include a set of cantilevered arms having catch ledges. In some embodiments, the inserter driver may include a body having a width greater than a separation distance between the arms of the set of cantilevered arms. The body may splay the arms apart when the insertion driver is in the extended position. In some embodiments, the insertion driver may include a body having a width greater than a separation distance between the arms of the set of cantilevered arms. The body may be configured to actuate the cantilevered arms out of engagement with the retainer when the insertion driver is in the extended position. In some embodiments, the insertion bias member may be housed within a portion of the inserter driver. In some embodiments, the insertion driver may include a port configured to mate with an insertion sharp holder from which an insertion sharp extends. In some embodiments, the insertion driver may include at least one cantilevered arm. The at least one cantilevered arm may include a notch. In some embodiments, the inserter assembly may be insertion sharp free. In some embodiments, the inserter assembly may not include an insertion sharp. In some embodiments, the insertion driver latch may be a projection extending from a housing of the second portion. The projection may extend into the notch. In some embodiments, the first portion may include a release finger and the second portion may include a deflector wedge. The deflector wedge may be configured to deflect the release finger into a portion of the insertion driver to dislodge the insertion driver from the insertion driver latch upon displacement of the first portion past the threshold distance. In some embodiments, the second portion may include a receptacle for one of a list consisting of a disposable infusion set cartridge, a disposable analyte sensor cartridge, and a lancet cartridge. In some embodiments, the second portion may include a receptacle including at least one mating interface for a mating projection of a disposable cartridge. In some embodiments, the insertion bias member may be in a relaxed state when the inserter assembly is in a storage state. In some embodiments, the insertion bias member may be a polymer spring. In some embodiments, the insertion bias member may be an injection molded spring. In some embodiments, the insertion bias member may be a compression spring. In some embodiments, the inserter assembly may further comprise at least one retraction bias member. In some embodiments, the at least one retraction bias member may be configured to transition to a stressed state as the first portion is displaced to the ready position. In some embodiments, the at least one retraction bias member may be maintained in the stressed state when the retainer is engaged with the first latch. In some embodiments, the at least one retraction bias member may be released from the stressed state when the first latch is disengaged. In some embodiments, the insertion driver may be displaced to the stowed state as the at least one retraction bias member transitions from the stressed state to a relaxed state.

In accordance with an embodiment of the present disclosure, a method of placing an infusion set may comprise coupling an infusion set cartridge to an inserter assembly. The method may further comprise adhering a portion of an infusion set contained within the infusion set cartridge to an infusion site. The method may further comprise latching an insertion bias member of the inserter assembly in a stressed state by displacing a first portion of the inserter assembly toward a second portion of the inserter assembly. The method may further comprise releasing the insertion bias member from the stressed state by displacing the first portion of the inserter assembly away from the second portion of the inserter assembly. The method may further comprise propelling an insertion driver and an insertion sharp of the infusion set cartridge coupled to the insertion driver toward the infusion site. The method may further comprise releasing the infusion set from the infusion set cartridge.

In some embodiments, latching the insertion bias member in the stressed state may comprise pressing the first portion of the inserter assembly against the second portion of the inserter assembly. In some embodiments, latching the insertion bias member in the stressed state may comprise pressing the first portion of the inserter assembly toward the infusion site. In some embodiments, displacing the first portion of the inserter assembly toward the second portion of the inserter assembly may stress the insertion bias member. In some embodiments, releasing the insertion bias member from the stressed state may comprise pulling the first portion of the inserter assembly away from the infusion site. In some embodiments, the method further may comprise lifting skin at the infusion site from underlying body structures before completing propelling an insertion driver and insertion sharp of the infusion set cartridge toward the infusion site. In some embodiments, propelling the insertion driver and the insertion sharp toward the infusion site may further comprise propelling a cannula subassembly toward the infusion site. In some embodiments, the method may further comprise coupling a cannula subassembly of the infusion set to a base of the infusion set. In some embodiments, adhering the portion of the infusion set to the infusion site may comprise adhering the base of the infusion set to the infusion site. In some embodiments, coupling the infusion set cartridge to the inserter assembly may comprise displacing mating projections included in the cartridge into retention interfaces on the inserter assembly. In some embodiments, coupling the infusion set cartridge to the inserter assembly may comprise removing an exterior housing of the infusion set cartridge. In some embodiments, the method may further comprise removing the infusion set cartridge from the inserter assembly and removing the infusion set cartridge from the inserter assembly may comprise recoupling the exterior housing to the infusion set cartridge. In some embodiments, the method further may comprise removing the infusion set cartridge from the inserter assembly once the infusion set cartridge has been used. In some embodiments, releasing the infusion set from the cartridge may comprise deflecting retainer arms of the infusion set cartridge out of engagement with a portion of the infusion set. In some embodiments, deflecting the retainer arms may comprise driving ears of a cannula subassembly of the infusion set into the retainer arms as the cannula subassembly is propelled into engagement with an infusion set base of the infusion set. In some embodiments, coupling the infusion set cartridge to the inserter assembly may comprise rotationally locking the infusion set cartridge in place on the inserter assembly. In some embodiments, the method may further comprise retracting the insertion driver and insertion sharp to a retracted state. In some embodiments, coupling the infusion set cartridge to the inserter assembly may comprise mating an insertion sharp holder of the infusion set cartridge into a port of the insertion driver. In some embodiments, displacing a first portion of the inserter assembly toward a second portion of the inserter assembly may stress at least one retraction spring. In some embodiments, the method may further comprise releasing the at least one retraction spring from a stressed state and propelling the insertion driver and the insertion sharp away from the infusion site. In some embodiments, releasing the at least one retraction spring from the stressed state may comprise propelling the insertion driver into a portion of a latch body to dislodge a latch.

In accordance with an embodiment of the present disclosure an inserter system may comprise an inserter assembly comprising a receptacle including a least one retention interface and an aperture therethrough. The inserter assembly may further comprise an insertion driver being displaceable through the aperture and being displaceable between a stowed position and an extended position. The inserter assembly may further comprise at least one spring biased lock member displaceable from a withdrawn position to an extended position. The system may further comprise a disposable cartridge comprising at least one mating projection, a medical device, and at least one set of stop surfaces. Each of the at least one mating projection configured to rotate into engagement with a respective one of the at least one retention interface. The at least one set of stop surfaces configured to flank the at least one lock member when the lock member is in the extended position inhibiting rotation of the disposable cartridge.

In some embodiments, the at least one lock member may be a resiliently cantilevered member. In some embodiments, the medical device may be an infusion set. In some embodiments, the infusion set may include an infusion set base and a cannula sub assembly. The cannula subassembly me be separate from the infusion set base. In some embodiments, the medical device may be a lancet. In some embodiments, the medical device may be an analyte sensor. In some embodiments, each of the at least one mating projection may be a mating pin having a head portion with a cross sectional area greater than a stem portion of the mating pin which couples the head portion to the cartridge. In some embodiments, the at least one retention interface may be a retention shoe. In some embodiments, each of the at least one retention interface may be configured to prevent translational displacement of a respective one of the at least one mating projection along a longitudinal axis of the inserter assembly when the respective mating projection is in engagement with that retention interface. In some embodiments, the cartridge may be configured to displace the at least one lock member to the withdrawn position when the at least one mating projection is out of engagement with the at least one retention interface and the cartridge is against the receptacle. In some embodiments, the cartridge may comprise an interior housing including tabs disposed on cantilevered portions of the interior housing. The housing may further comprise an exterior housing including receiving slots for the tabs. The interior housing may be coupled to the exterior housing when the tabs are disposed at least partially within the receiving slots. In some embodiments, the receptacle may include deflector members. In some embodiments, the deflector members may be configured to deflect the cantilevered portions of the interior housing when the mating projections are in engagement with the retention interfaces. The exterior housing being uncoupled from the interior housing when the cantilevered portions of the interior housing are in a deflected state. In some embodiments, the at least one set of stop surfaces may be defined by edge walls on either side of at least one of the cantilevered portions. In some embodiments, the insertion driver may include a port. In some embodiments, the cartridge may include a sharp holder coupled to an insertion sharp. The sharp holder may be configured to couple into the port when each of the at least one mating projection is in engagement with a respective one of the at least one retention interface. In some embodiments, the cartridge may include a sharp holder with a terminal flange having a shape which may be displaced into the port when the cartridge is in a first orientation on the receptacle and may not be displaced out of the port when the cartridge is in a position in which each of the at least one mating projection is in engagement with a respective one of the at least one retention interface. In some embodiments, the cartridge may include a sharp holder coupled to a sharp. In some embodiments, the cartridge may include at least one guide. At least a portion of the medical device may be configured to displace along the guide when the insertion driver is displaced from the stowed position to the extended position. In some embodiments, the cartridge may include a first housing and a second housing releasably coupled to the first housing. The second housing may displace the at least one lock member to the withdrawn state when the second housing is against the receptacle. In some embodiments, the inserter assembly may further comprise an insertion bias member and an insertion driver latch. The insertion bias member may be configured to urge the insertion driver to the extended position when the insertion driver is disengaged from the insertion driver latch.

In accordance with an embodiment of the present disclosure an infusion set base for an infusion set may comprise a platform portion having a first face and a second face on an opposing side thereof. The infusion set base may further comprise a set of connector finger receptacles extending from the second face of the platform portion. The infusion set base may further comprise a set of guides raised from the second face of the platform portion. Each of the guides may include a guide notch recessed into the guides from a face of the guides most distal to the second face of the platform portion. The infusion set base may further comprise a cannula subassembly receptacle defined by an aperture in the platform portion, a receptacle wall raised from the second face of the platform and by a portion of each guide which includes the guide notch. The infusion set base may further comprise a cantilevered arm included as a section of the receptacle wall, the cantilevered arm having a protuberance at an unsupported end thereof.

In some embodiments, the first face of the platform portion may include an adhesive attached thereto. In some embodiments, the adhesive may be covered by an adhesive backing. In some embodiments, the adhesive backing may extend across and cover the aperture. In some embodiments, the first face of the platform portion may include two annular ridges at the periphery of the first face and a plurality of radially arrayed ridges. In some embodiments, a substrate to which an adhesive is applied may be bonded to the annular ridges and the radially arrayed ridges. In some embodiments, the substrate may be welded to the annular ridges and the radially arrayed ridges. In some embodiments, the platform may include a plurality of passthroughs extending therethrough. In some embodiments, the platform portion may include at least one tubing retainer which extends from the periphery of the platform portion. In some embodiments, each of the connector receptacles may include a catch for engaging a projection on a connector finger of an infusion tubing connector. In some embodiments, at least one of the receptacle wall or the portions of the guides defining the receptacle may include a tapered portion at a section thereof most distal to the second face of the platform portion. In some embodiments, the cantilevered arm may be configured to deflect as a cannula subassembly is displaced into the cannula subassembly receptacle and resiliently restore to relaxed state when the cannula subassembly is in an installed orientation within the cannula subassembly receptacle such that the protuberance engages a ledge of a salient on the cannula subassembly. In some embodiments, the cantilevered arm may be configured to deflect as a cannula subassembly is displaced into the cannula subassembly receptacle and resiliently restore to relaxed state when the cannula subassembly is in an installed orientation within the cannula subassembly receptacle such that the protuberance engages a wall of a fenestration in a housing of the cannula subassembly. In some embodiments, the cantilevered arm may be configured to deflect as a cannula subassembly is displaced into the cannula subassembly receptacle and the resiliently restore to relaxed state when the cannula subassembly is in an installed orientation within the cannula subassembly receptacle such that the protuberance engages a wall of a cannula housing slot in a housing of the cannula subassembly. In some embodiments, each of the guides may define a ledge which has at least a portion which is parallel to the second face of the platform portion. In some embodiments, each ledge may be more proximal to the second face of the platform portion than the portion of each notch which is most proximal to the second face of the platform portion. In some embodiments, the cannula subassembly receptacle may be centrally disposed on the platform portion. In some embodiments, the aperture may include a salient receiving region for receiving a salient of a housing of a cannula subassembly. In some embodiments, each of the guides may include a first portion ledge and a second portion ledge each extending from a main portion of the respective guide. The first portion ledge may be substantially parallel to the second face of the platform portion and the second portion ledge may be disposed at an angle to the first portion ledge. In some embodiments, a surface of the second portion ledge most proximal to the second face of the platform portion increases in distance from the second face of the platform portion as the second portion ledge extends distally with respect to the first portion ledge. In some embodiments, the guides may extend parallel to one another and each may include a medial face and a lateral face. The medial faces may be more proximal to a midplane of the infusion set base than the lateral faces. In some embodiments, the guides may include a guide ledge disposed on the lateral face of each guide and an additional guide ledge on the medial face of each guide.

In accordance with an embodiment of the present disclosure a tubing connector for fluidically coupling a flow lumen of a run of infusion tubing to a cannula of an infusion set may comprise a flow hub having a channel therethrough. The run of infusion tubing may be coupled to a first end of the channel and a sharp may be coupled to a second opposing end of the channel. A sharp lumen of the sharp may be in fluid communication with the flow lumen. The tubing connector may further comprise a pair of alignment channels. One of the alignment channels may be recessed into a first side face of the flow hub. The other of the alignment channels may be recessed into a second opposing side face of the flow hub. The alignment channels may include a variable width segment proximal the second end of the channel and a constant width segment. The tubing connector may further comprise a pair of cantilevered connector fingers. A first connector finger of the pair of connector fingers may be coupled to the first side face via a first tubing connector body portion and a second connector finger of the pair of connector fingers coupled to the second opposing side face via a second tubing connector body portion. Each of the connector fingers may include a latch projection. The tubing connector may further comprise at least one sharp flanking projection extending from the flow hub parallel to an axis of the sharp.

In some embodiments, the at least one sharp flanking projection may include a centrally disposed flanking projection which extends from a top face of the flow hub over at least a portion of the sharp. In some embodiments, the at least one sharp flanking projection may include a set of sharp flanking projections disposed lateral to the sharp. In some embodiments, the at least one sharp flanking projection may include a first sharp flanking projection and a second sharp flanking projection disposed laterally to the sharp and in a plane along which the connector fingers extend. In some embodiments, the first sharp flanking projection may extend parallel to an axis of the sharp from the first tubing connector body portion and the second sharp flanking projection may extend parallel to the axis of the sharp from the second tubing connector body portion. In some embodiments, the first sharp flanking projection and second sharp flanking projection may each have a projection tip. The projection tips may be more distal to the flow hub than a terminal portion of each connector finger. In some embodiments, the first sharp flanking projection and the second sharp flanking projection may each include a curved end region. In some embodiments, the curved end regions may each have a curvature which swings an arc greater than 90°. In some embodiments, the radius of the curvature may be variable. In some embodiments, the curved end regions may each include a substantially straight expanse at a terminus thereof. In some embodiments, the curved end regions may curve in front of and around a terminal portion of a respective connector finger of the pair of connector fingers. In some embodiments, the first sharp flanking projection may extend parallel to an axis of the sharp from the first side face of the flow hub and the second sharp flanking projection may extend parallel to the axis of the sharp from the second side face of the flow hub. In some embodiments, each of the pair of alignment channels may be configured to ride along a guide ledge of an infusion set base. In some embodiments, the sharp may include a tip. The tip may be clocked to a prescribed rotational orientation during assembly of the tubing connector. In some embodiments, the tip may be magnetically clocked to the prescribed rotational orientation.

The details of one or more embodiments are set forth in the accompanying drawings and the description below. Other features and advantages will become apparent from the description, the drawings, and the claims.

BRIEF DESCRIPTION OF THE DRAWINGS

These and other aspects will become more apparent from the following detailed description of the various embodiments of the present disclosure with reference to the drawings wherein:

FIG. 88 depicts a cross sectional view taken at 88-88 of FIG. 87;

FIG. 89 depicts a cross sectional perspective view of an example inserter assembly;

FIG. 90 depicts a detailed view of the indicated region of FIG. 89;

FIG. 91 depicts a perspective view of an example interior housing of an example inserter assembly;

FIG. 92 depicts a cross sectional perspective view of an example inserter assembly;

FIG. 93 depicts a cross sectional view of a retainer cap of an example inserter assembly;

FIG. 94 depicts a detailed view of the indicated region of FIG. 93;

FIG. 95 depicts a cross sectional view of an example inserter assembly;

FIG. 96 depicts a cross sectional view of an example inserter assembly;

FIG. 97 depicts a cross sectional view of an example inserter assembly;

FIG. 98 depicts a cross sectional view of an example inserter assembly;

FIG. 99A depicts a cross sectional view of an example inserter assembly;

Figure 99A:
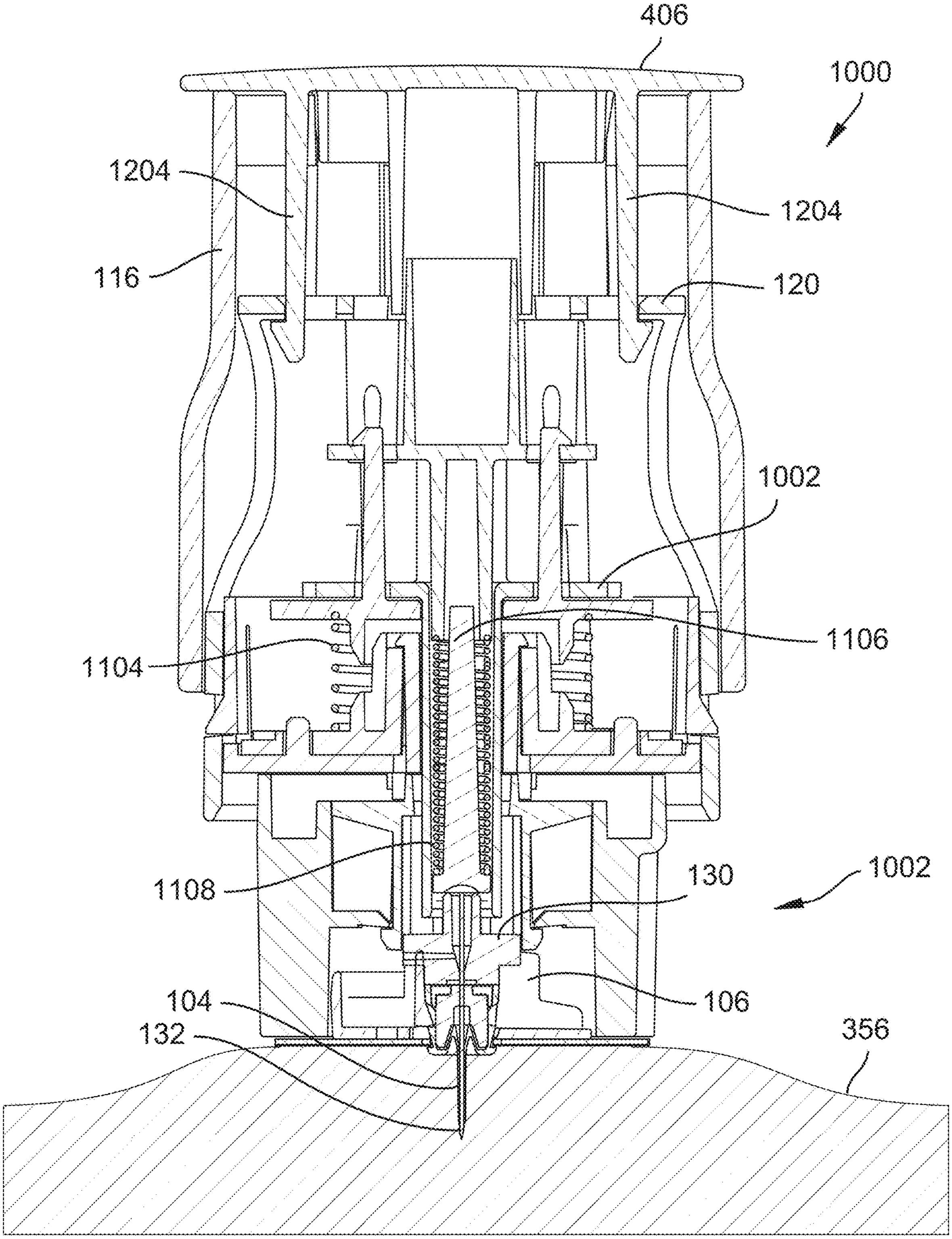
Figure 99B:
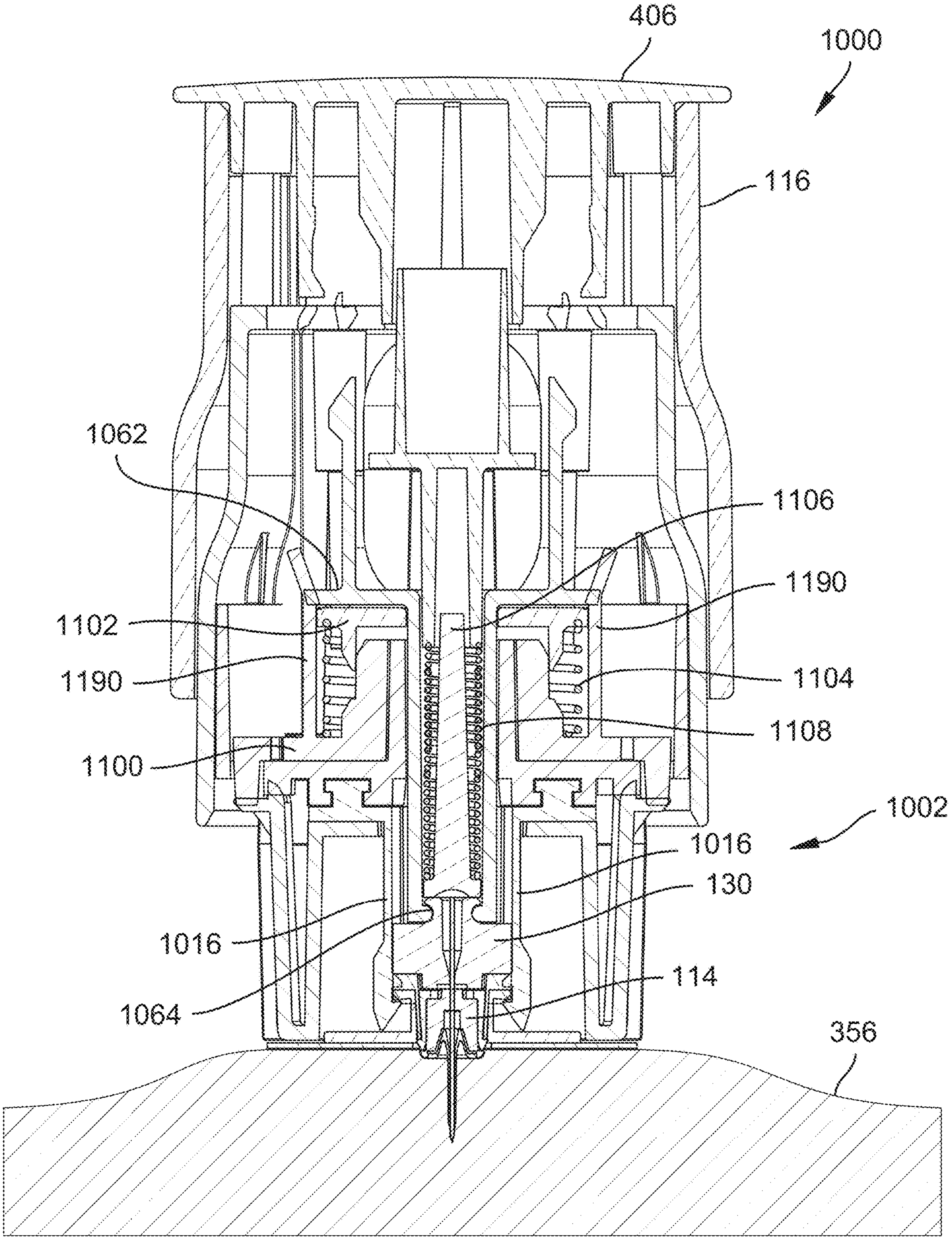
Figure 100:
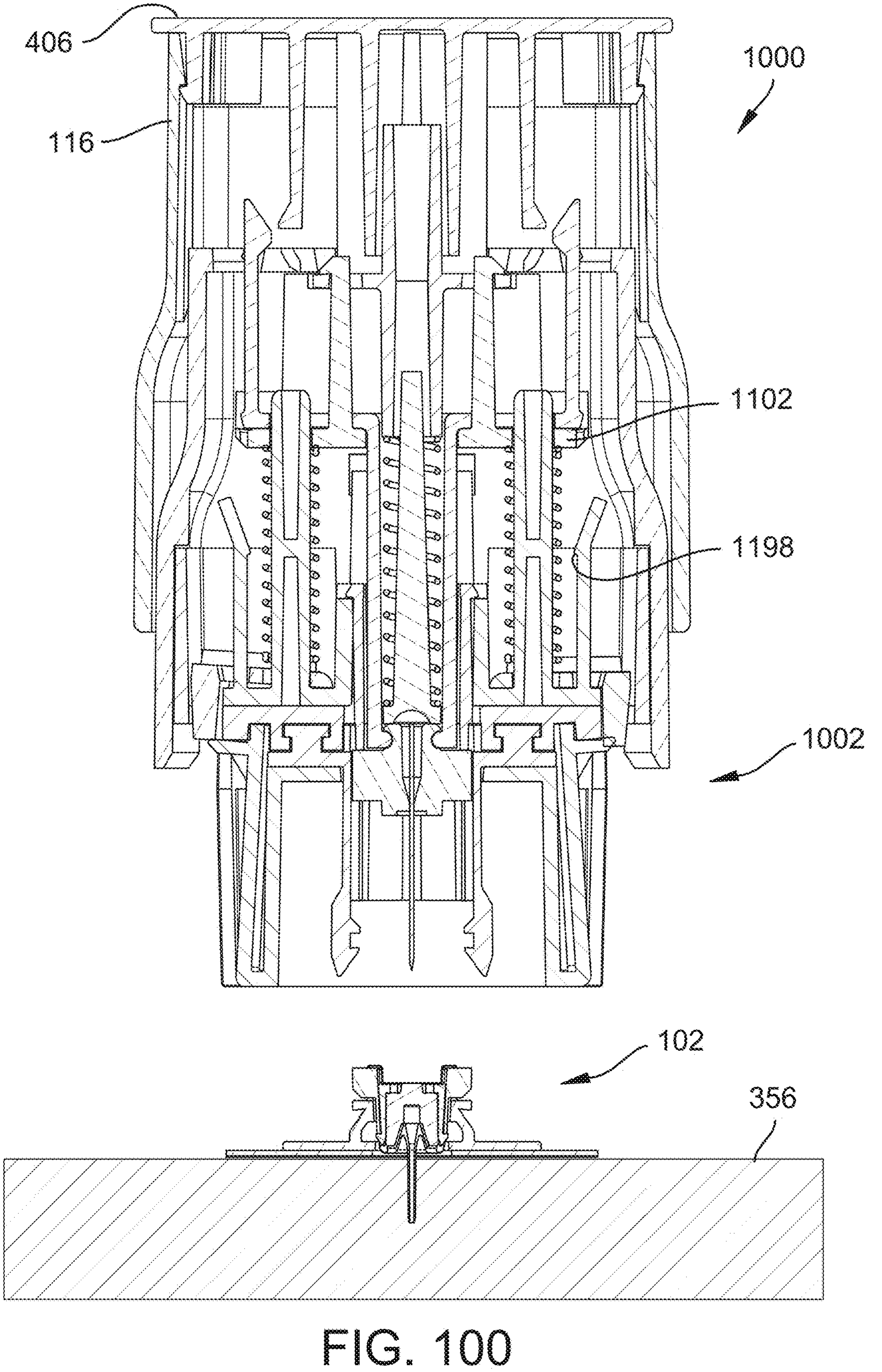
Figure 101:
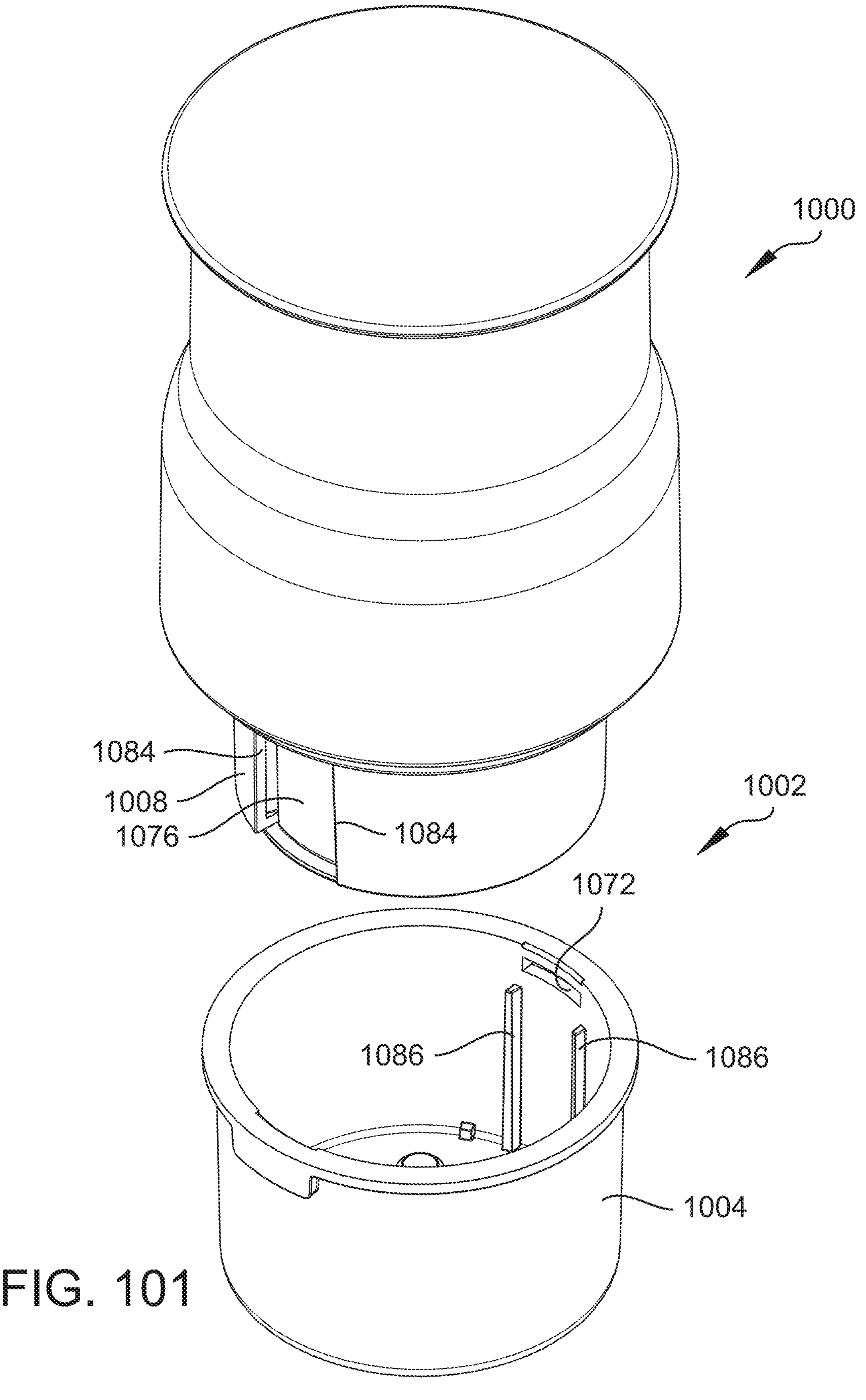
Figure 102:
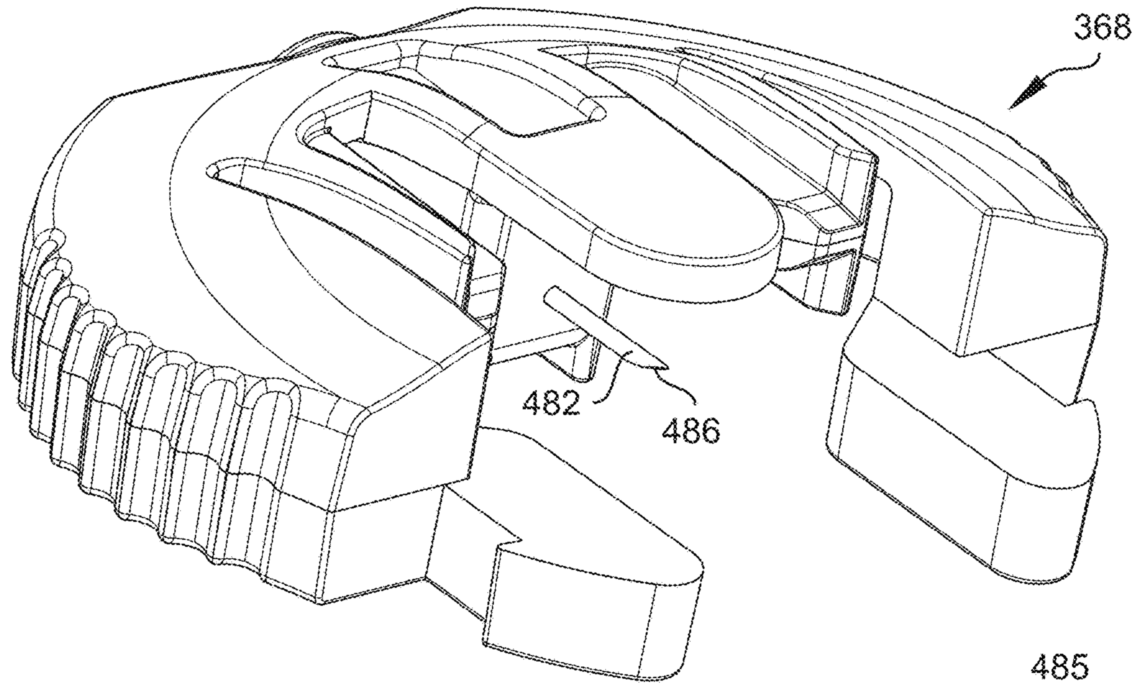
Figure 103B:
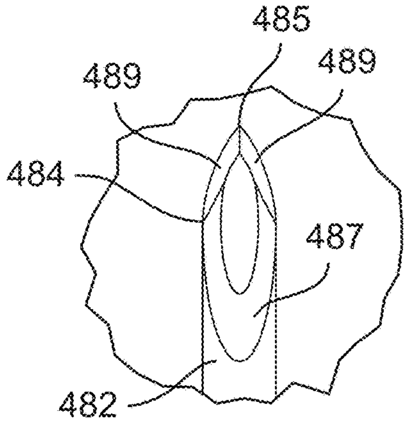
Figure 103A:
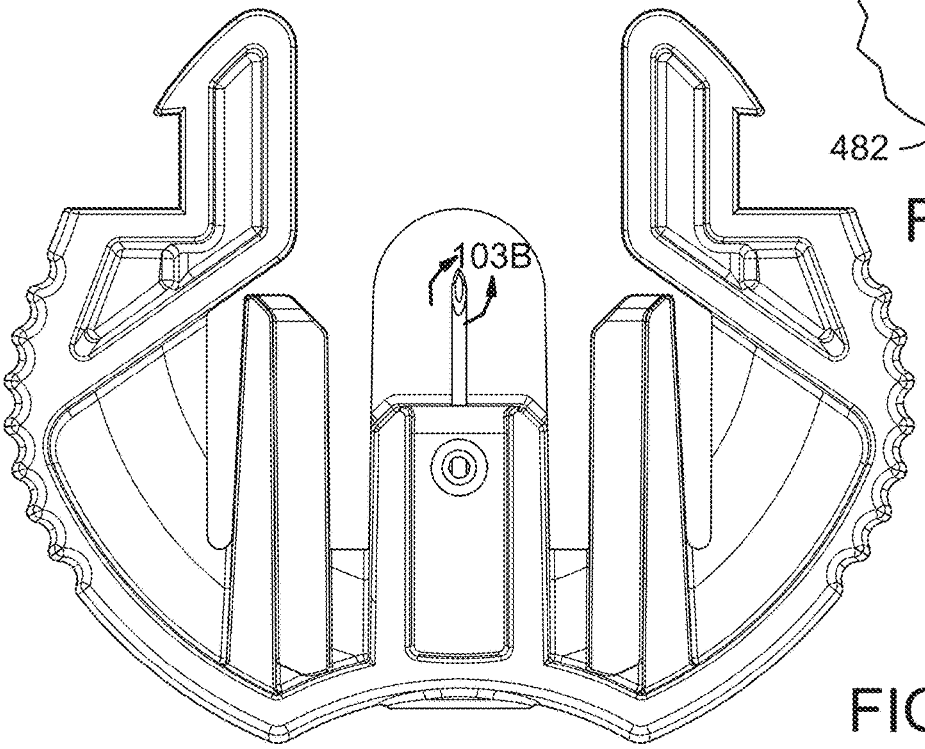
Figure 104:
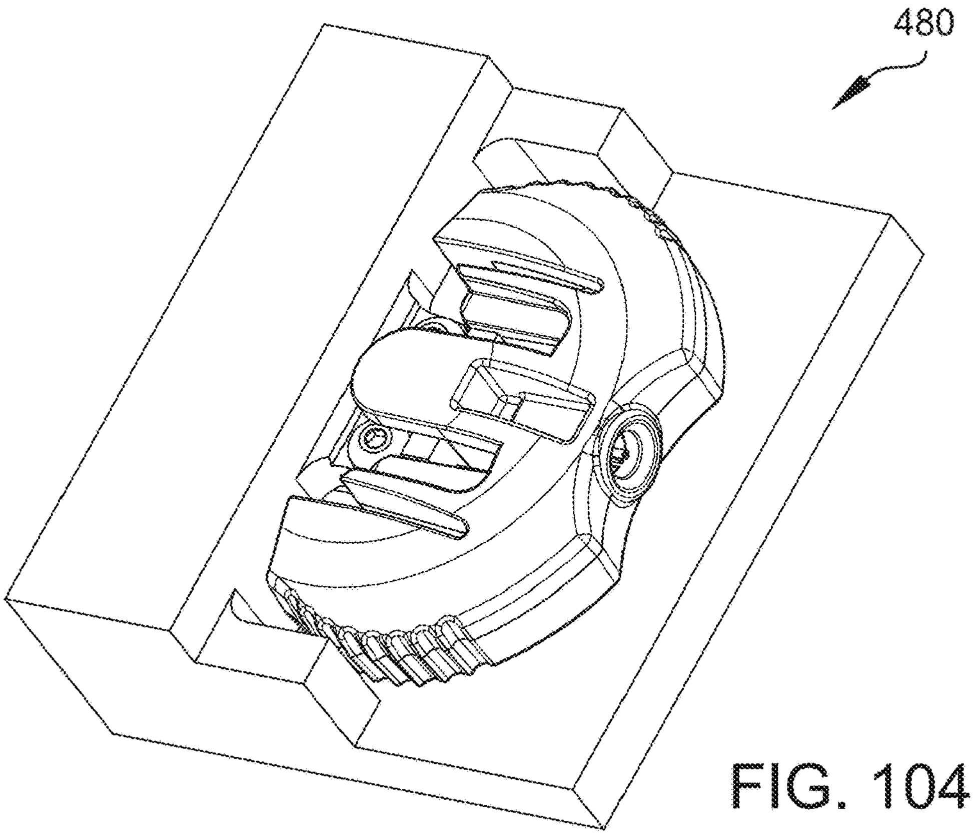
Figure 105:
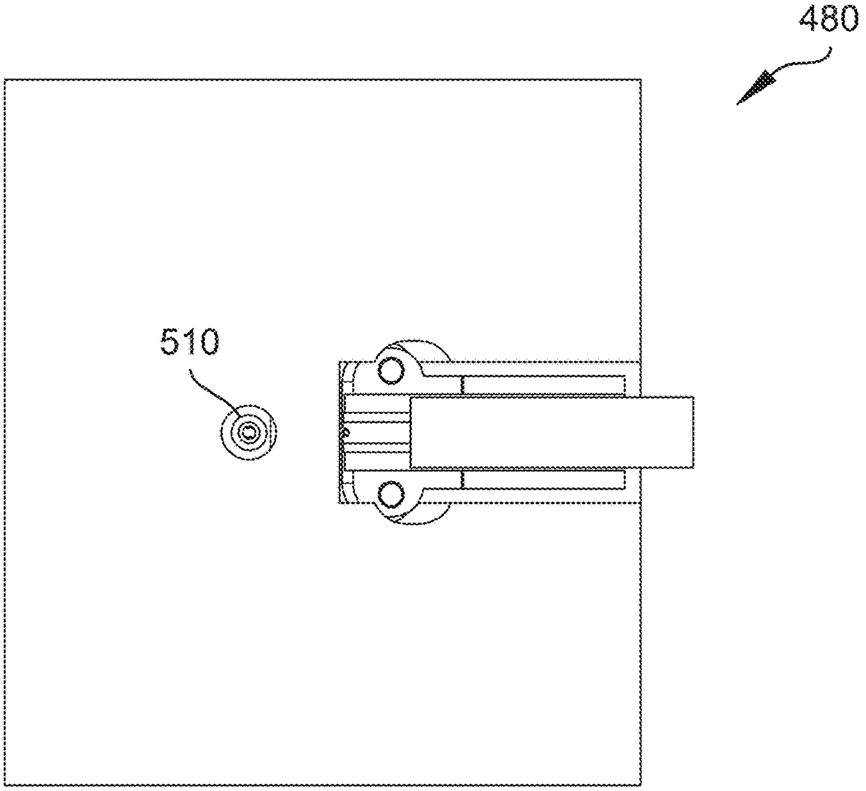
Figure 106:
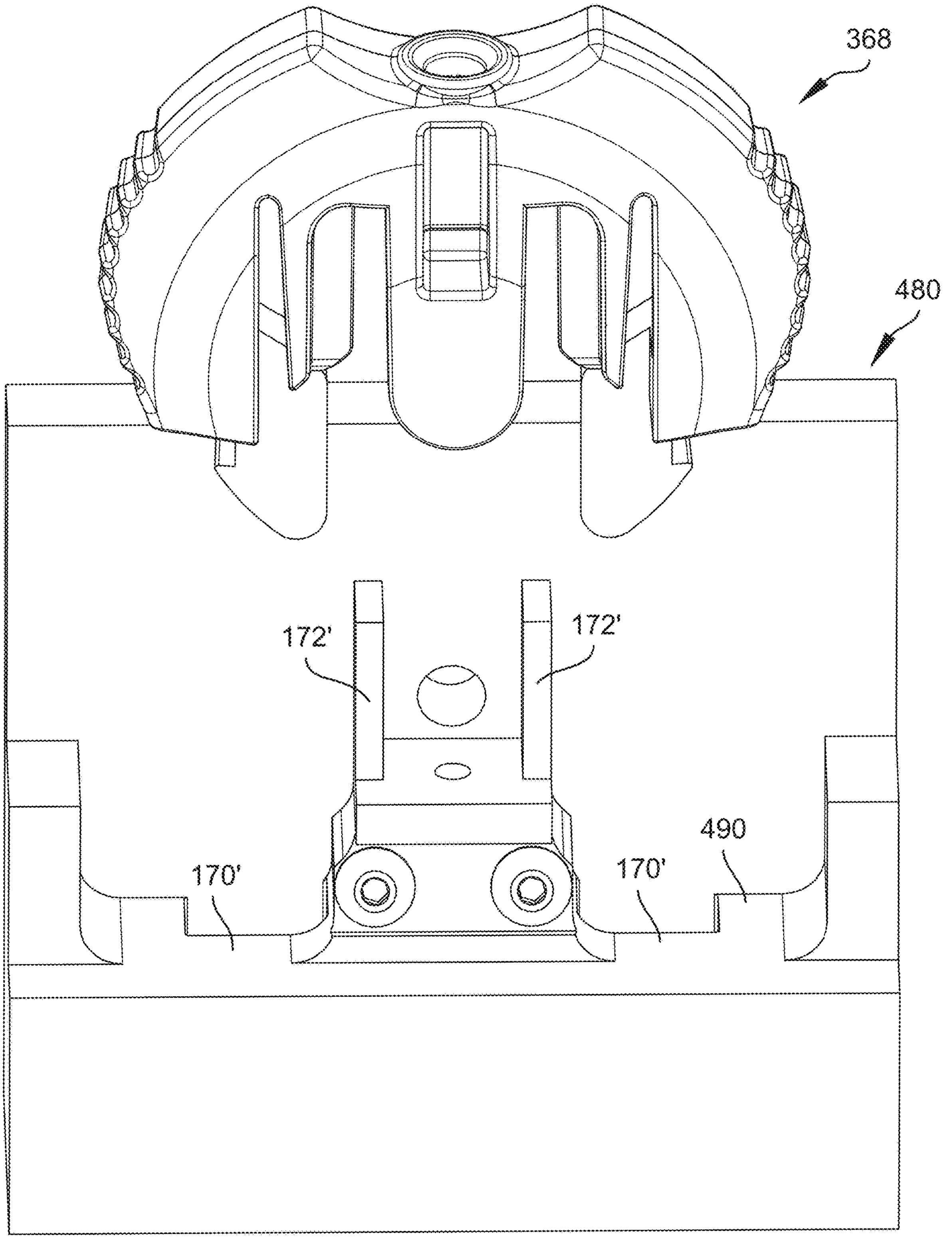
Figure 107:
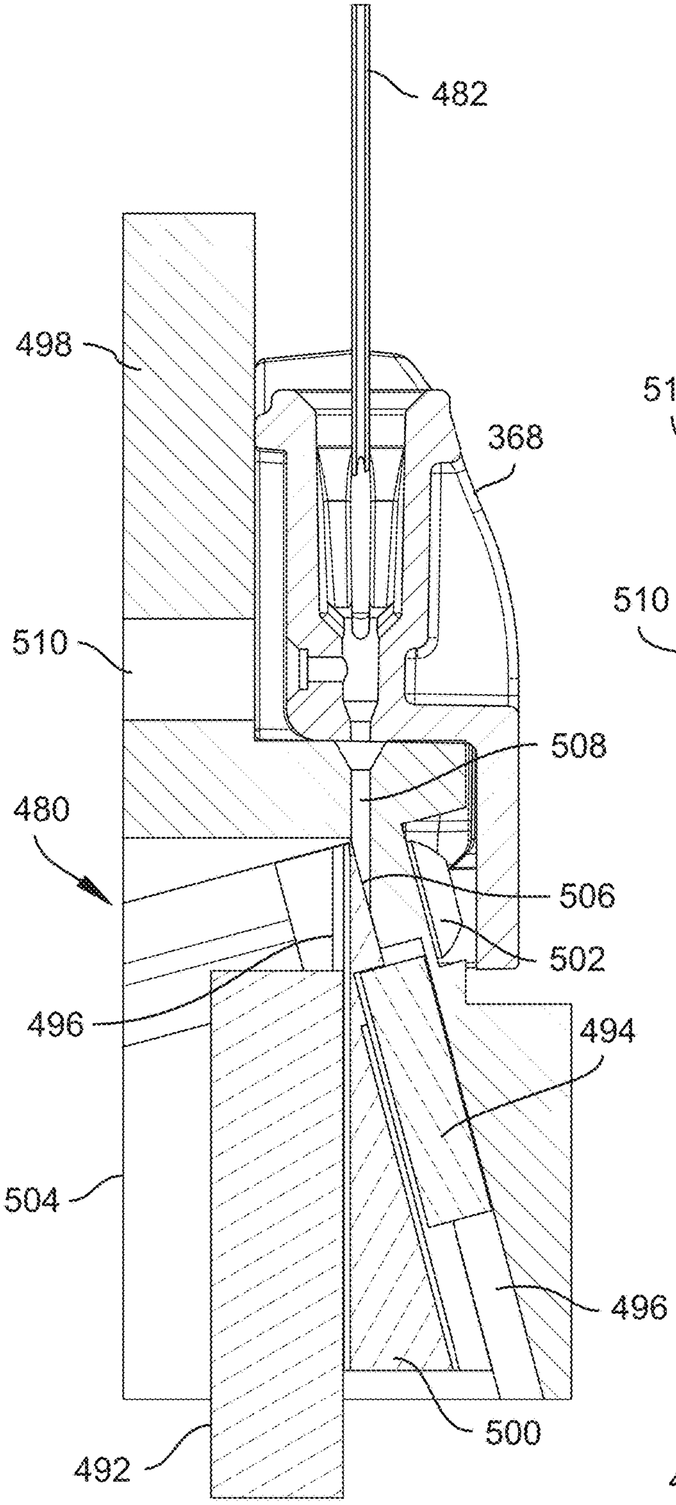
Figure 108:
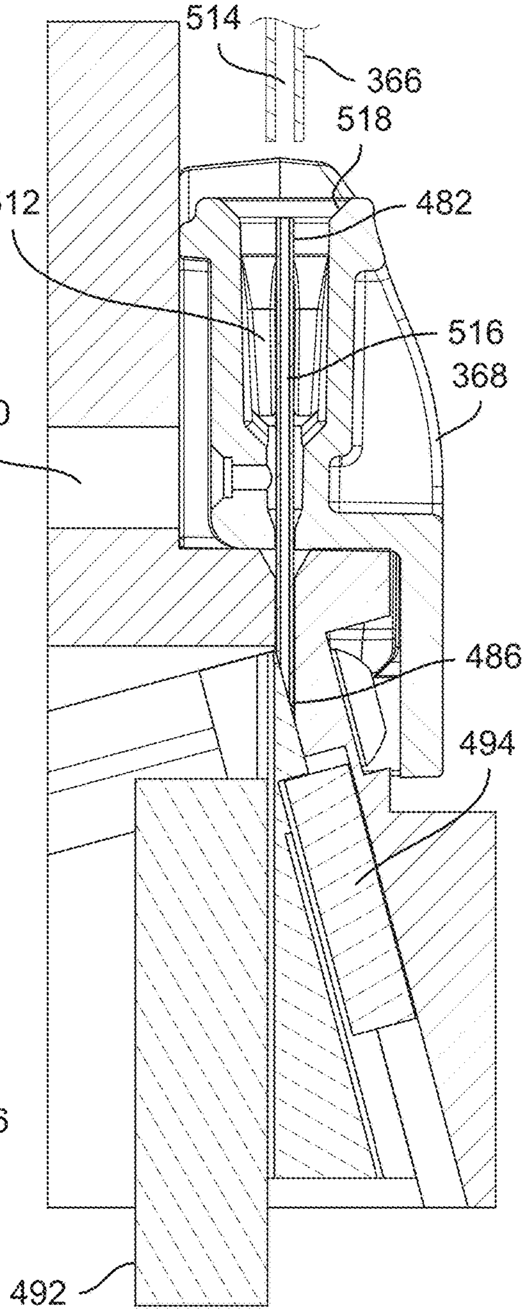
Figure 109:
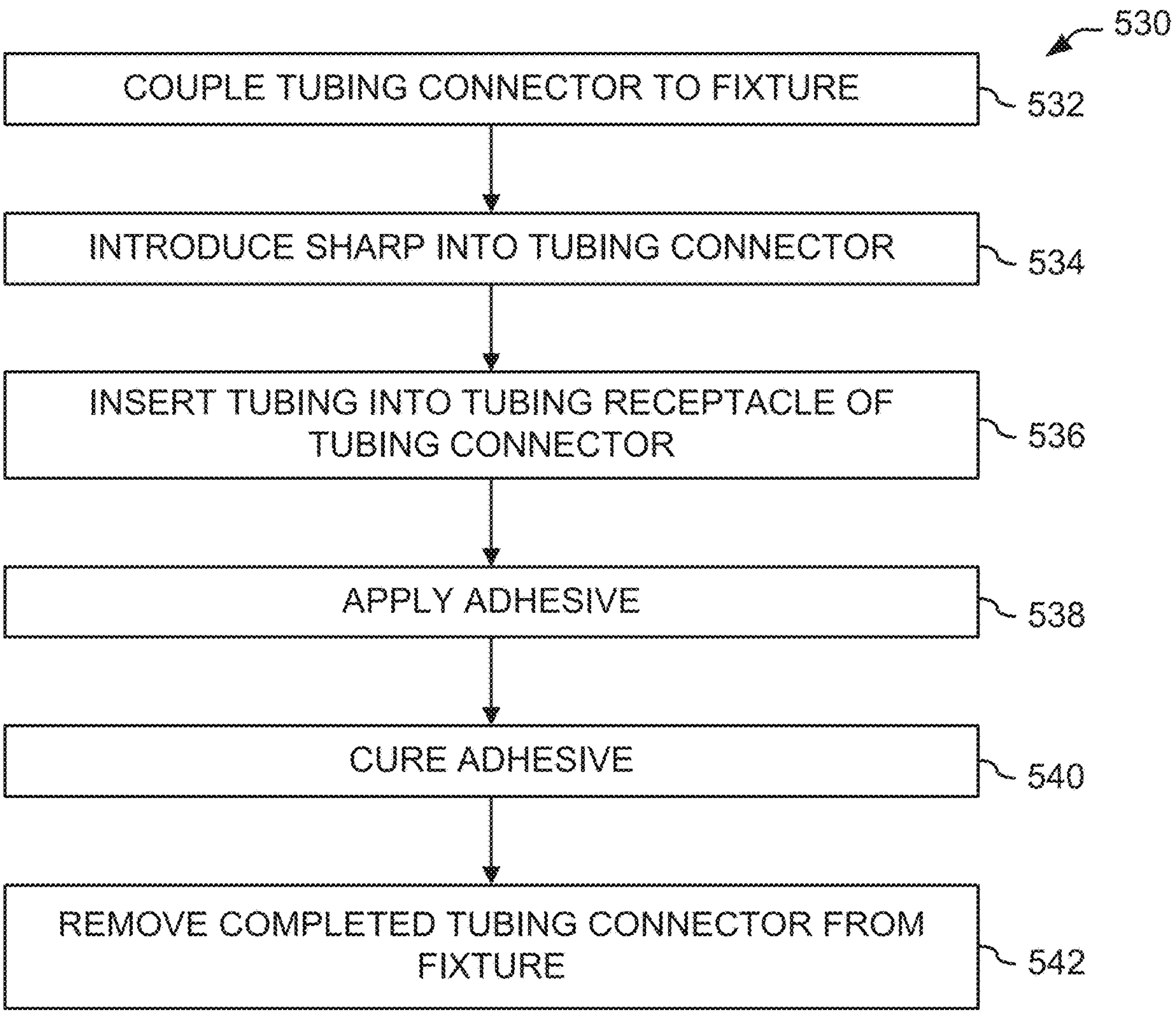

FIG. 99B depicts a cross sectional view of an example inserter assembly;

FIG. 100 depicts a cross sectional view of an example inserter assembly;

FIG. 101 depicts a perspective view of a cartridge coupled to an inserter assembly with an outer housing of the cartridge removed;

FIG. 102 depicts a perspective view of an example tubing connector;

FIG. 103A depicts a bottom up view of the tubing connector shown in FIG. 102;

FIG. 103B depicts a detailed view of a portion of FIG. 103A;

FIG. 104 depicts a perspective view of a tubing connector in place on a fixture;

FIG. 105 depicts a bottom up view of the fixture shown in FIG. 104;

FIG. 106 depicts a perspective view of a tubing connector aligned for installation into a fixture;

FIG. 107 depicts a cross-sectional view of a fixture with a tubing connector installed thereon and a sharp being introduced into the tubing connector;

FIG. 108 depicts a cross-sectional view of a fixture with a tubing connector installed thereon and a sharp in place and rotationally clocked to a prescribed position within the tubing connector; and FIG. 109 depicts a flowchart detailing a number of example actions which may be used to assembly of tubing connector.

DETAILED DESCRIPTION

In various embodiments, an infusion set may be used in conjunction with an infusion device, system, and related method as well as used in conjunction with an inserter assembly. In various embodiments, example infusion sets may be configured to be inserted into the subcutaneous layer of a user's skin and be fluidly connected to a fluid source. In various embodiments, example infusion sets may be fluidly connected to a length of tubing and/or to an infusion device. Infusion devices include any infusion pump and may include, but are not limited to, the various infusion devices described in U.S. patent application Ser. No. 13/788,260, filed Mar. 7, 2013 and entitled Infusion Pump Assembly, now U.S. Publication No. US-2014-0107579, published Apr. 17, 2014; U.S. Pat. No. 8,491,570, issued Jul. 23, 2013 and entitled Infusion Pump Assembly; U.S. Pat. No. 8,414,522, issued Apr. 9, 2013 and entitled Fluid Delivery Systems and Methods; U.S. Pat. No. 8,262,616, issued Sep. 11, 2012 and entitled Infusion Pump Assembly; and U.S. Pat. No. 7,306,578, issued Dec. 11, 2007 and entitled Loading Mechanism for Infusion Pump; all of which are hereby incorporated herein by reference in their entireties.

Various embodiments are described and shown herein. Each embodiment of each element of each device may be used in any other device embodiment. Each embodiment of the inserter assembly may be used with any embodiment of an infusion set.

Figure 1A:
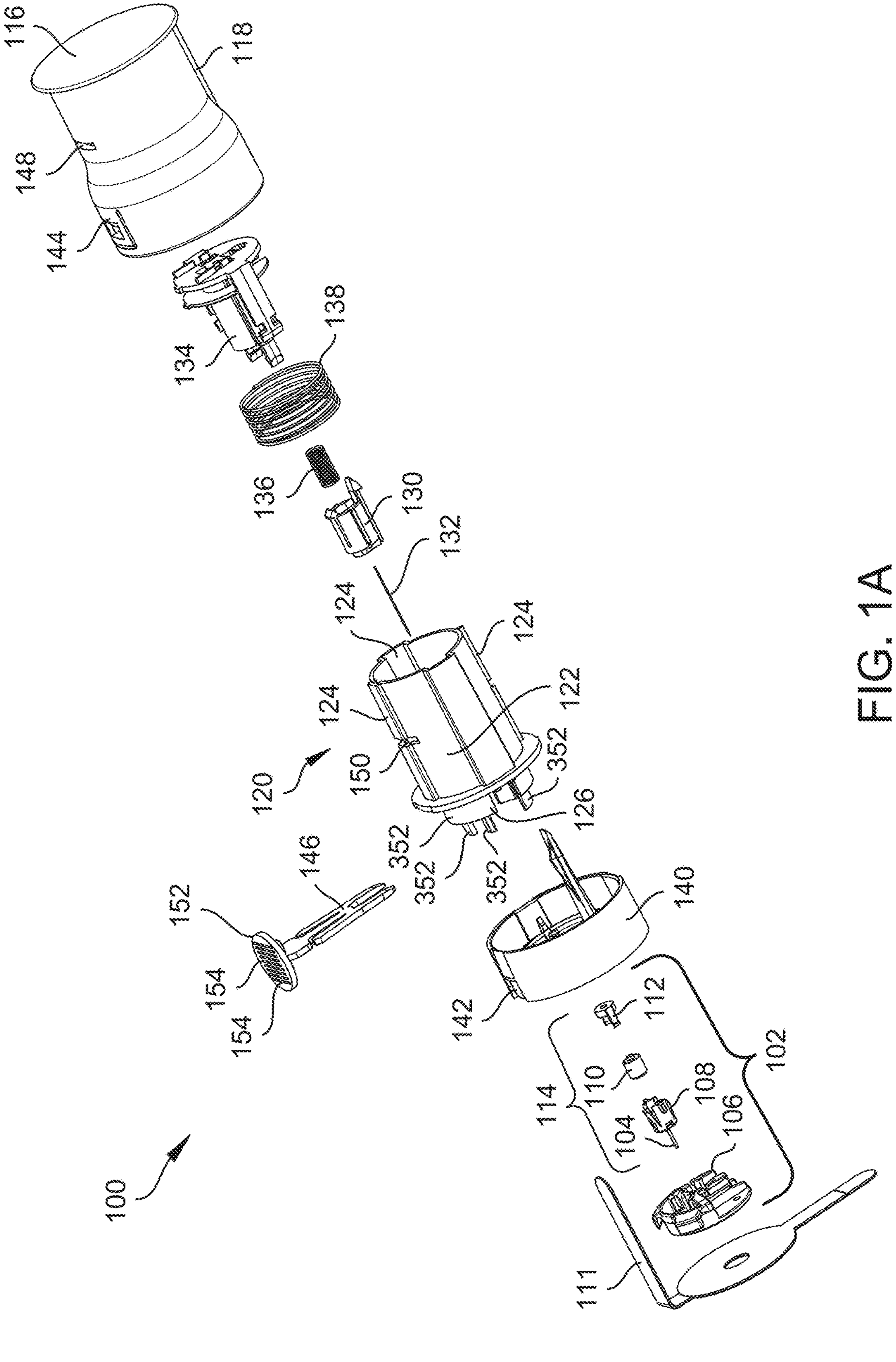
FIG. 1A depicts an exploded view of an exemplary inserter assembly.

FIG. 1A depicts an exploded view of an embodiment of an example inserter assembly 100. Inserter assemblies such as inserter assembly 100 may be used to place an infusion set 102 onto an infusion site of a patient and introduce a cannula 104 of an infusion set 102 into the patient's body. In some embodiments, inserter assemblies 100 may be used to place other patient care assemblies onto the body of a patient. For example, certain inserter assemblies 100 may be operated to place physiological monitors into working relationship with a patient's body. In certain examples, an analyte sensor may be placed onto a patient with an inserter assembly 100. Infusion sets 102 may be used to supply a drug from an infusion pump to a particular location (e.g. subcutaneously) within a patient's body.

Drugs supplied may include drugs which are generally supplied as a continuous or substantially continuous infusion though other drugs may also be used. This may include small molecules, biologicals, recombinantly produced pharmaceuticals, and analogs thereof. Hormones such as insulin or glucagon may be administered through an infusion set 102. Other drugs such as peptides (e.g. amylin) may be provided. Drugs affecting the cardiovascular system may also be provided via an infusion set 102. As another example, vasodilators such as treprostinil may be delivered to a patient with an infusion set 102. Chemotherapy drugs may additionally be used. Exemplary physiological monitors may include blood glucose monitors such as continuous glucose monitors. Any other type of body analyte monitor such as interstitial fluid analyte monitors may also be used.

In some embodiments, inserter assemblies 100 may place an infusion set 102 on a site as well as at least partially assemble the infusion set 102. For example, the infusion set 102 may be provided as a number of portions (e.g. separate components, subassemblies, or combinations thereof) within an inserter assembly 100. Actuation of the inserter assembly 100 may cause each portion of the infusion set 102 to be coupled together to complete the assembly of an infusion set 102. For example, assemblage of an infusion set 102 may occur as an initial stage of the actuation of the inserter assembly 100 or may occur as part of an insertion stage of inserter assembly 100 actuation which results in the cannula 104 being introduced into the patient.

As shown in the exploded view in FIG. 1A, the inserter assembly 100 contains components of an infusion set 102. The inserter assembly 100 may not be provided with an assembled infusion set 102 installed therein. The infusion set 102 may include a first portion and a second portion which are separate from one another, but coupled together during actuation of the inserter assembly 100 to form the infusion set 102. The first portion may include a base 106 which may be applied to the skin of a patient and may couple to a fluid pathway (e.g. via a terminal connector on the pathway) which is part of or extends from an infusion pump. Example infusion pumps may include any one or more disclosed in the various references incorporated by reference above, though in various embodiments, any infusion pump may be used. The base 106 may be provided with an adhesive (e.g. adhesive pad) which retains the infusion set 102 in place on the patient. The adhesive may be covered by an adhesive backing 111, liner, or film which is removed to expose the adhesive before use.

The second portion of the infusion set 102 may be a subassembly 114 of two or more components of the infusion set 102. The second portion may include a cannula 104, septum housing 108, septum 110, and septum retainer 112 for example. In some embodiments, though not all, one or more components of the second portion may be provided integrated to one another such that the components are manufactured as a single, monolithic part during, for example, a single molding operation. Any attachment, fastening, bonding, fitting together, or other assembly of these parts after manufacture may thus be avoided. The cannula 104 and the septum housing 108 are shown as such a single continuous unitary part in the example embodiment. This cannulated housing may be a molded part which is constructed of a single material such as, PTFE, Teflon, polypropylene, etc. for example. Certain components may also be joined to one another during manufacture. For example, the septum retainer 112 may be over molded onto the septum 110 or vice versa.

As shown in FIG. 1A, an insertion assembly 100 may include a number of additional components. For example, the insertion assembly 100 may include an exterior housing 116. The exterior housing 116 may enclose various components of the inserter assembly 100 and serve as the portion of the inserter assembly 100 which the user grips during operation. The exterior housing 116 in the example embodiment has a cross sectional shape which is round, though other embodiments may have different shapes such as any type of polygonal shape. In certain examples described elsewhere in the specification, a rectangular cross-sectional shape which easily fits within a pocket may be used. The cross sectional area in the example embodiment also varies with the bottom section (that most proximal the skin when in use) of the exterior housing 116 being wider than the top. The exterior housing 116 may include various ergonomic features which facilitate grasping of the inserter assembly 100 in which it is included. For example, texturing or a finger or thumb depression may be included on the outer surface of the exterior housing 116. Alternatively or additionally, a region of the external housing 116 may be thinner in width than the remaining portion of the external housing 116. This may make firm grasping of the inserter assembly 100 easier.

The exterior housing 116 may include a marking, tab, embossed section, recessed section, textured section, protuberance, color coding, appliqué, or other indicia which serves to indicate position and/or orientation of the infusion set 102 within the inserter assembly 100. For example, the exterior housing 116 in FIG. 1A includes a raised rib 118 on the outer surface of the exterior housing 116. The raised rib 118 in the example extends substantially parallel to a direction of elongation of the exterior housing 116, but may be disposed on any or partially on any exterior face(s) of the exterior housing 116 in alternative embodiments. The rib 118 is disposed to indicate the orientation of a portion of the infusion set 102 to which a fluid conduit from the infusion device may be connected. This may allow a user to position the inserter assembly 100 in a desired orientation so as to allow for a run of infusion tubing to be routed in a planned manner once the infusion set 102 is attached to the user.

An inserter assembly 100 may also include an interior housing 120. The interior housing 120 may be disposed inside of the external housing 116 when the inserter assembly 100 is assembled. Various interior housings 120 may have at least one segment which is asymmetrically designed. In the exemplary embodiment shown in FIG. 1A, the interior housing 120 includes a railed segment 122 which includes a number of rails 124. The rails 124 extend substantially parallel to one another and may be of at least two different widths. The interior face of the exterior housing 116 may include tracks or slots which cooperate with the rails 124. Due to the differing rail 124 widths, a keyed arrangement may be provided such that the interior housing 120 may only be nested within the exterior housing 116 in a prescribed orientation. The interaction of the rails 124 within the tracks may also inhibit rotation of the interior housing 120 and exterior housing 116 relative to the other. Though rails 124 are shown on the interior housing 120 in the example, the rails 124 may instead be present on the interior face of the exterior housing 116 in some embodiments. In such examples, the tracks may be located on the interior housing 120. Additionally, as shown, at least some of the rails 124 may also form channels or tracks in the interior face of the interior housing 120.

In other embodiments, a rail and track type arrangement may not be used. One of the interior housing 120 or exterior housing 116 may include at least one projection such as a tab which interfaces with a recess or guide in the other. This may similarly provide a keyed engagement and prevent relative rotation. In other embodiments, the cross sectional shape of the interior housing 120 and external housing 116 may only allow for the parts to be placed together in one orientation and may inhibit any relative rotation. For example, the cross section may be tear drop shaped or various asymmetric polygonal shapes.

The interior housing 120 may also include an infusion set base interfacing segment 126. This base interfacing segment 126 may include a number of projections 352 which may ensure that the base 106 may only be inserted into the inserter assembly 100 in a desired orientation. The projections 352 may also optionally aid in retention of the base 106 within the inserter assembly 100 and some friction between the projections 352 and surfaces of the base 106 may be present when the base 106 is installed in the inserter assembly 100. For example, the base 106 may be press fit into the projections 352. The tightness of the fit may be minimal so as to allow removal of the base 106 from the base interfacing segment 126 with little force. The projections 352 may also aid in maintaining the base 106 in a level orientation within the base interfacing segment 126.

An inserter assembly 100 may further include a sharp holder 130. The sharp holder 130 may retain an insertion sharp 132 thereon. The insertion sharp 132 may be glued or otherwise bonded into the sharp holder 130 so as to be fixedly located relative to the sharp holder 130. Any suitable type of sharp 132 may be used. For example, the sharp 132 may be a hollow or solid needle, stylet, or other pointed member which may be made of a metal material such as steel. A sharp retractor 134 and a number of springs 136, 138 may also be included in an inserter assembly 100. A retainer base 140 may serve to couple to a bottom portion of the inserter assembly 100 to hold the various components in place within the inserter assembly 100. In the example, the retainer base 140 includes retaining interfaces 142 which may snap into cantilevered retainer arms 144 included on the exterior housing 116. Other couplings are also possible such as a bayonet mount, interference fit, snap fit, adhesive, glue, threads, solvent bonding, welding, etc. When coupled together, the exterior housing 116 and retainer base 140 may form a casing of the inserter assembly 100.

As will be further described later in the specification, a latch arrangement may be included in the inserter assembly 100 and may hold the sharp holder 130 and sharp retractor 134 in place prior to and during portions of the inserter assembly 100 actuation. The latch arrangement may include a number of catches. When free to move, the springs 136, 138, may displace the sharp holder 130 and sharp retractor 134 as well as components retained thereon to complete the insertion of the cannula 104 into the patient and attach the infusion set 102 onto an infusion site. Retraction of the sharp 132 into the inserter assembly 100 may also occur as part of the actuation so as to displace the sharp 132 to a point where it is pulled out of the infusion set 102 and protected from contact with a user.

When unpacked by a user, an insertion assembly 100 may be provided with a lock member 146. The lock member 146 may be inserted through fenestrations 148, 150 in the exterior housing 116 and interior housing 120 respectively so as to span the width of at least a portion the interior housing 120. While present in the inserter assembly 100, the lock member 146 may prevent actuation of the inserter assembly 100. Example lock members 146 may mechanically prevent displacement of one or more component of the inserter assembly 100 which initiates the actuation action of the inserter assembly 100. In the example embodiment, the lock member 146 includes a flange 152 which may be grasped by a user during removal of the lock member 146.

As shown, a lock member 146 may include a number of raised sections 154 (e.g. ridges or bumps) thereon. These raised sections 154 may provide material which may help to bond to a portion of the adhesive backing 111 during a welding operation. As a result, the lock member 146 may be attached to the adhesive backing 111 such that a user would have a visual cue in the event that one of the lock member 146 or adhesive backing 111 is removed while the other is still in place. This may help to encourage removal of both components prior to an attempt to actuate the inserter assembly 100 making the device more intuitive.

Figure 1B:
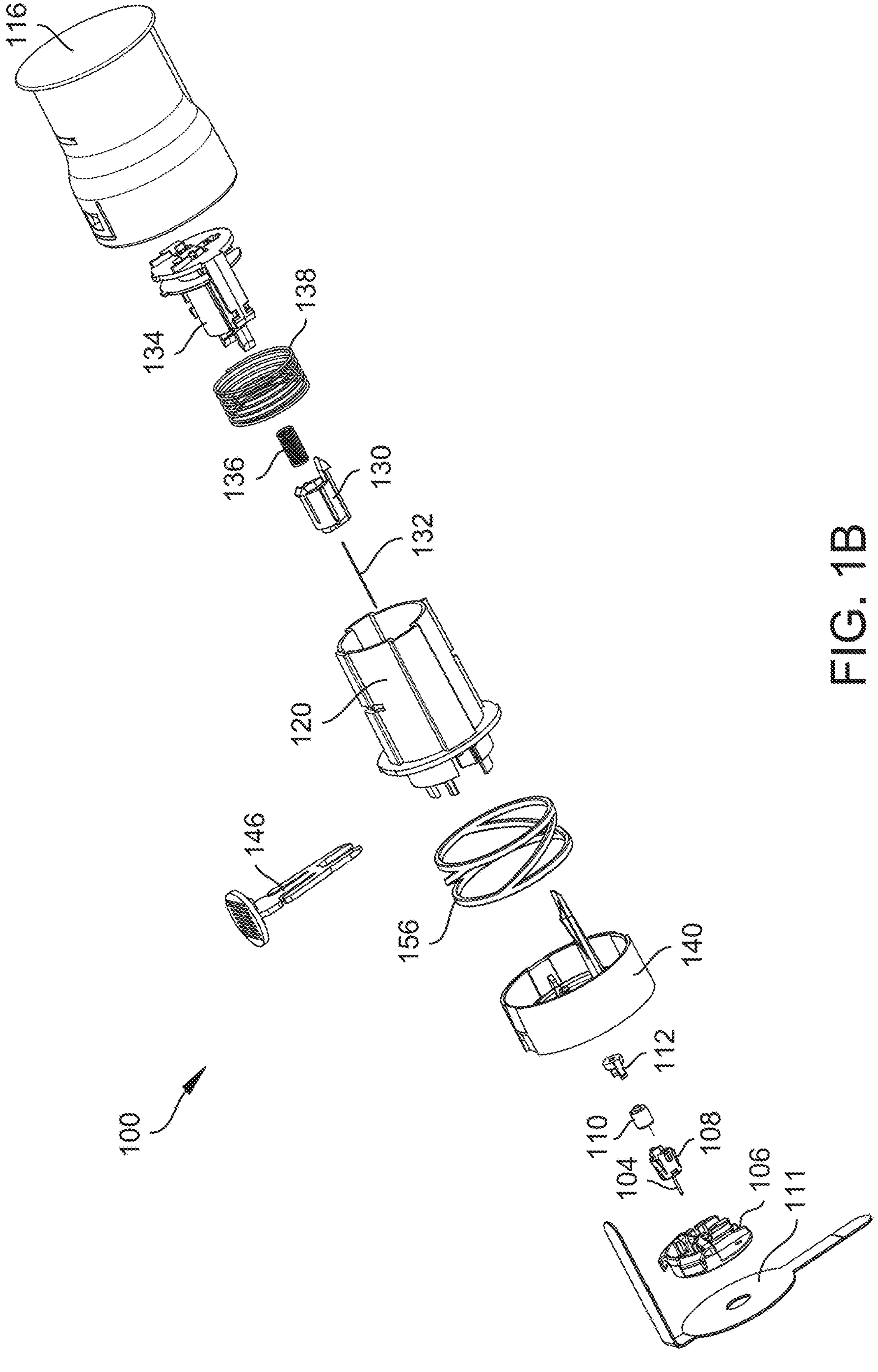
FIG. 1B depicts an exploded view of another exemplary inserter assembly.
Figure 1C:
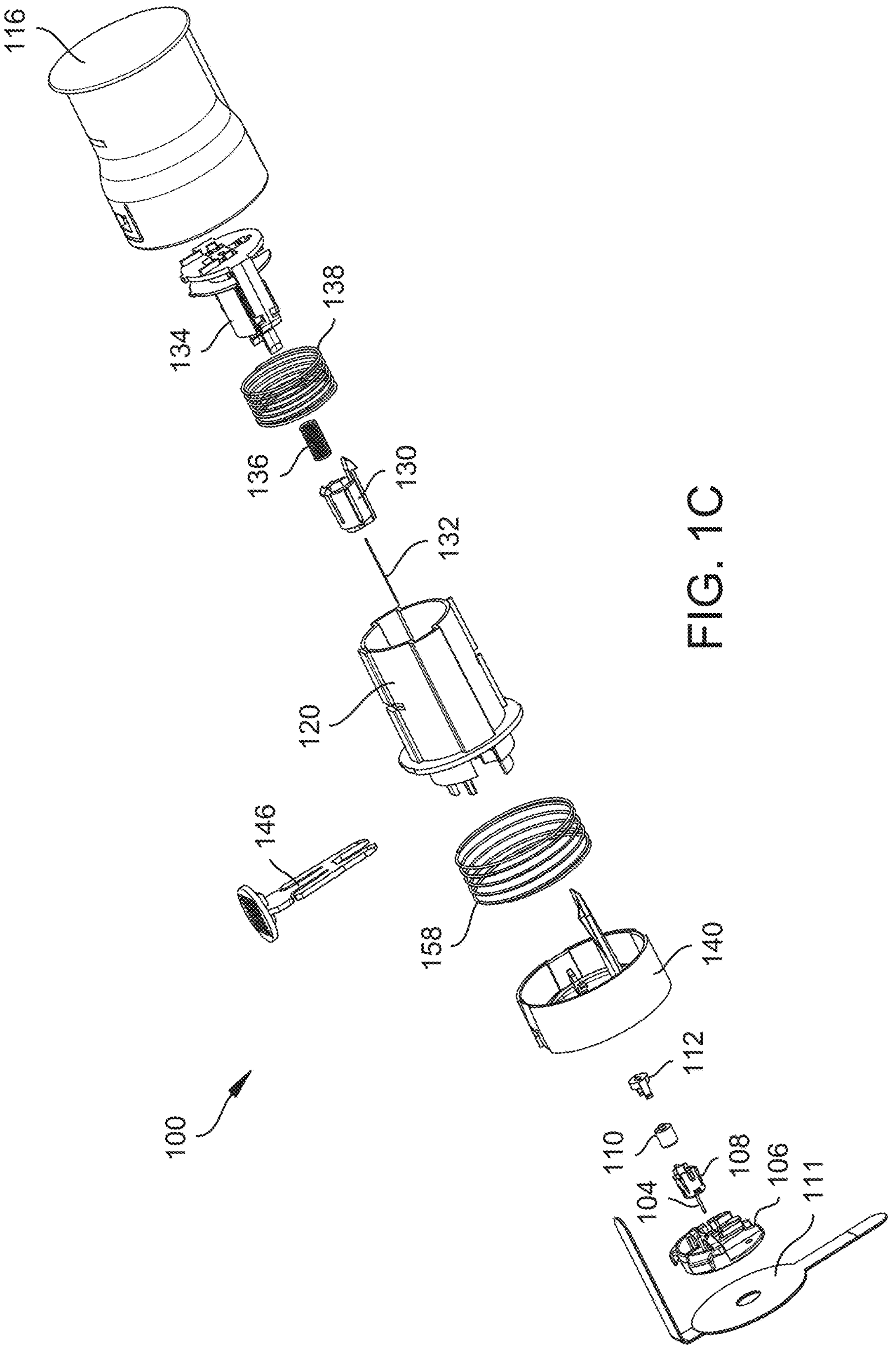
FIG. 1C depicts an exploded view of another exemplary inserter assembly.

Referring now also to FIGS. 1B and 1C, in some examples, an inserter assembly 100 may include one or more additional springs 156, 158. As shown in FIG. 1C, the additional spring 158 may be a conventional metallic spring. Alternatively, and as depicted in FIG. 1B, a plastic spring 156 may be used. In certain embodiments, the plastic spring 156 may be injection molded, cut out of a tube of material (e.g. via laser cut), made via a material additive process, or any other suitable method. Such springs 156, 158 will be further described later in the specification.

Figure 2:
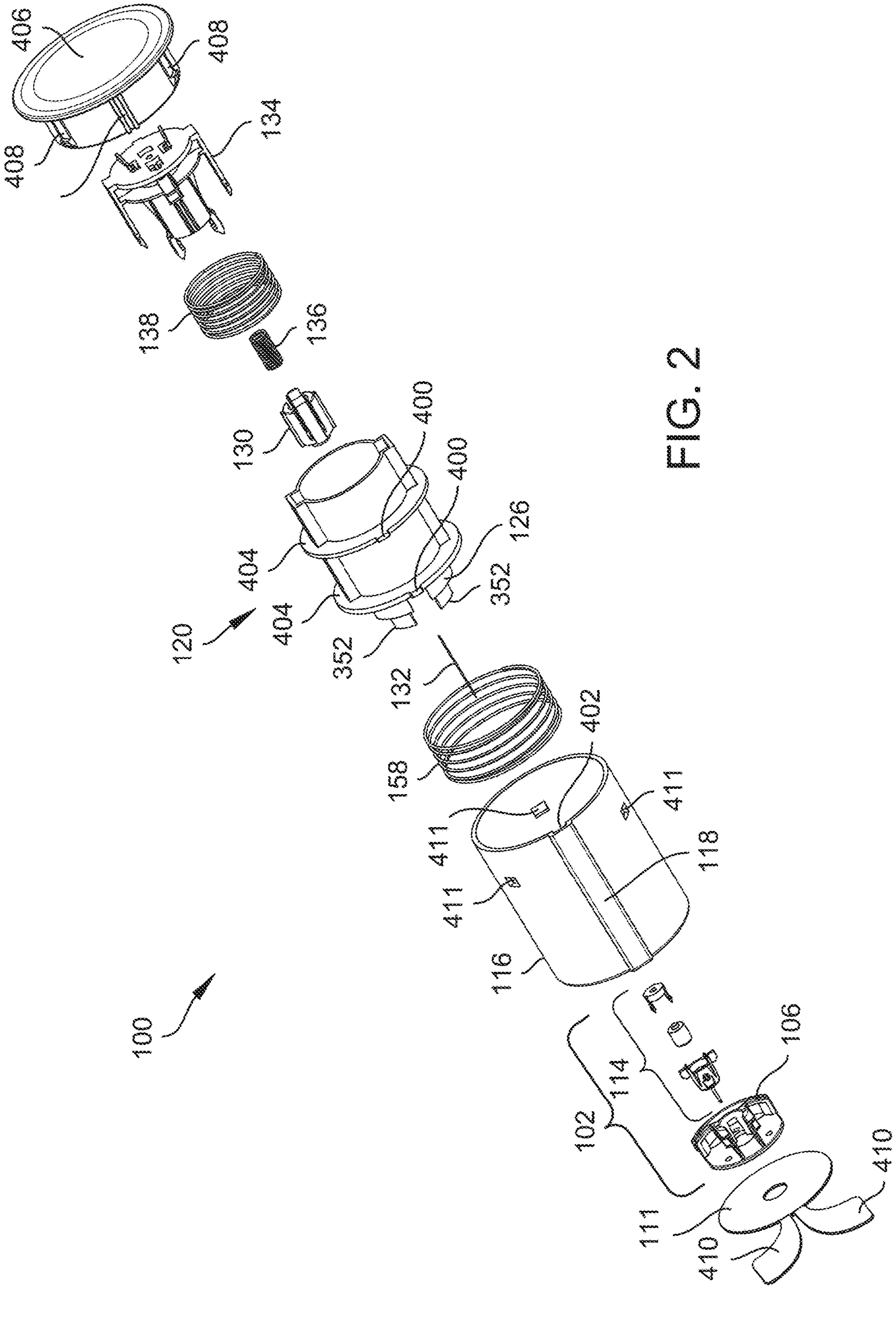
FIG. 2 depicts an exploded view of another exemplary inserter assembly.

Referring now also to FIG. 2, another inserter assembly 100 is depicted. The insertion assembly 100 in FIG. 2 includes an exterior housing 116 which may enclose various components of the inserter assembly 100 and serve as the portion of the inserter assembly 100 which the user grips during operation. Though depicted as round, the exterior housing 116 may have other cross-sectional shapes or various ergonomic features as described above. The exterior housing 116 includes a position indicium in the form of a raised rib 118 extending off the outer surface of the exterior housing 116. The rib 118 may be disposed to indicate the orientation a portion of an infusion set 102 contained within the inserter assembly 100.

An interior housing 120 is also included in FIG. 2 and may be keyed so as to ensure it is assembled into the inserter assembly 100 in a prescribed orientation and prevent relative rotation. As in FIG. 2, the interior housing 120 may be made asymmetric by the inclusion of at least one projection 400 such as a tab which interfaces with a recess or guide 402 in the exterior housing 116. In the example, the guide 402 is provided by a channel formed by the raised rib 118 on the interior face of the exterior housing 116. The projections 400 on the inserter assembly 100 in FIG. 2 are included on spacing plates 404 which ensure that the interior housing 120 fits snuggly within the exterior housing 116. An infusion set base interfacing segment 126 is also included on the example interior housing shown in FIG. 2.

A sharp holder 130 which may be affixed to an insertion sharp 132 is shown in the example embodiment. Additionally, a sharp retractor 134 and a number of springs 136, 138 may also be included. A retainer cap 406 may serve to couple to a top portion of the inserter assembly 100 to hold the various components in place within the inserter assembly 100. In the example, the retainer cap 406 includes cantilevered retainer arms 408 which may snap into retaining interfaces 411 included on the exterior housing 116. Other couplings are also possible such as a bayonet mount, interference fit, snap fit, adhesive, glue, threads, solvent bonding, welding, etc. When coupled together, the exterior housing 116 and retainer cap 406 may form a casing of the inserter assembly 100.

As described in detail elsewhere herein, a latch arrangement may be included in the inserter assembly 100 and may hold the sharp holder 130 and sharp retractor 134 in place prior to and during portions of the inserter assembly 100 actuation. The latch arrangement may include a number of catches. When free to move, the springs 136, 138, may displace the sharp holder 130 and sharp retractor 134 as well as components retained thereon to complete the insertion of the cannula 104 into the patient and attach the infusion set 102 onto an infusion site. Retraction of the sharp 132 into the inserter assembly 100 may also occur as part of the actuation.

In the example embodiment depicted in FIG. 2, the inserter assembly 100 does not include a lock member 146. In various embodiments, however, fenestrations similar to fenestrations 148, 150 in FIGS. 1A-1C in the exterior housing 116 and interior housing 120 may be included to accommodate a lock member 146. In these embodiments, the adhesive backing 111 could be bonded onto the lock member 146. In the example embodiment, however, the adhesive backing 111 includes two pull tabs 410 (though any suitable number may be included). These pull tabs 410 may be grasped by a user to facilitate removal of the adhesive backing 111. The additional spring 158 depicted in FIG. 1C is also included in FIG. 2.

Figure 3:
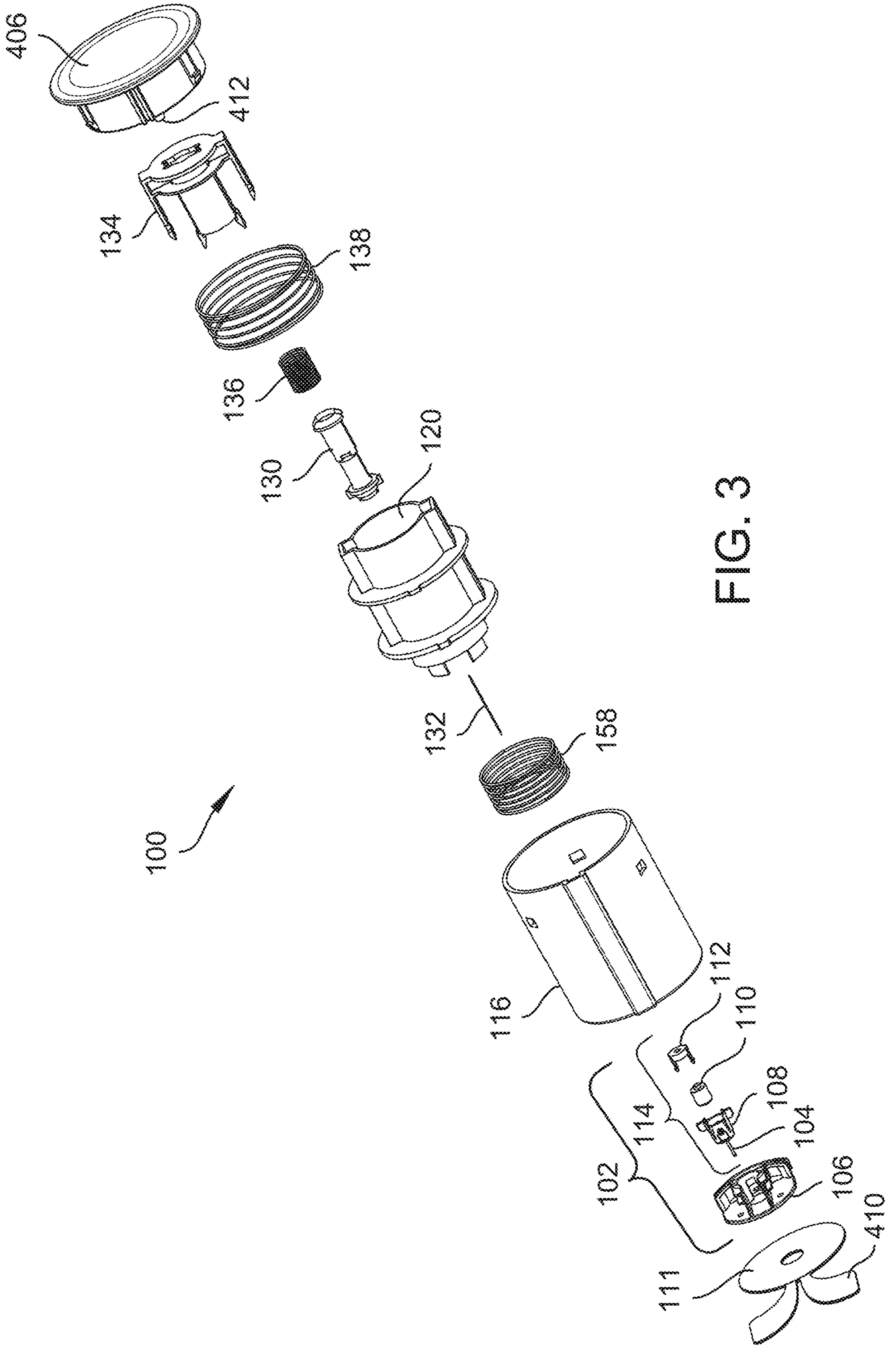
FIG. 3 depicts an exploded view of another exemplary inserter assembly.

Referring now to FIG. 3, another example embodiment of an inserter assembly 100 is depicted. As shown, the inserter assembly 100 in FIG. 3 includes an exterior housing 116 and interior housing 120 similar to those shown in the example depicted in FIG. 2. The sharp holder 130 and sharp retractor 134 differ from those depicted in FIGS. 1A-2. A retainer cap 406 may serve to couple to a top portion of the inserter assembly 100 to hold the various components in place within the inserter assembly 100 and form a casing of the inserter assembly 100. The retainer cap 406 couples to the exterior housing 116 in a similar manner to the embodiment described in relation to FIG. 2, however, any other type of coupling may be used in alternative embodiments. The retainer cap 406 also includes a projection 412 which may fit within a portion of the sharp holder 130 when the inserter assembly 100 is fully assembled and ready for actuation.

As described in detail elsewhere herein, a latch arrangement may be included in the inserter assembly 100 may hold the sharp holder 130 and sharp retractor 134 in place prior to and during portions of the inserter assembly 100 actuation. The latch arrangement may include a number of catches. When free to move, the springs 136, 138, may displace the sharp holder 130 and sharp retractor 134 as well as components retained thereon to complete the insertion of the cannula 104 into the patient and attach the infusion set 102 onto an infusion site. Retraction of the sharp 132 into the inserter assembly 100 may also occur as part of the actuation.

In the example embodiment depicted in FIG. 3, the inserter assembly 100 does not include a lock member 146. However, in various embodiments, fenestrations similar to fenestrations 148, 150 in FIGS. 1A-1C may be included in the exterior housing 116 and interior housing 120 to accommodate a lock member 146. In these various embodiments, the adhesive backing 111 may be bonded onto the lock member 146. In the example embodiment, however, the adhesive backing 111 includes two pull tabs 410. These pull tabs 410 may be grasped by a user to facilitate removal of the adhesive backing 111. The additional spring 158 depicted in FIG. 1C is also included in FIG. 3

Figure 4A:
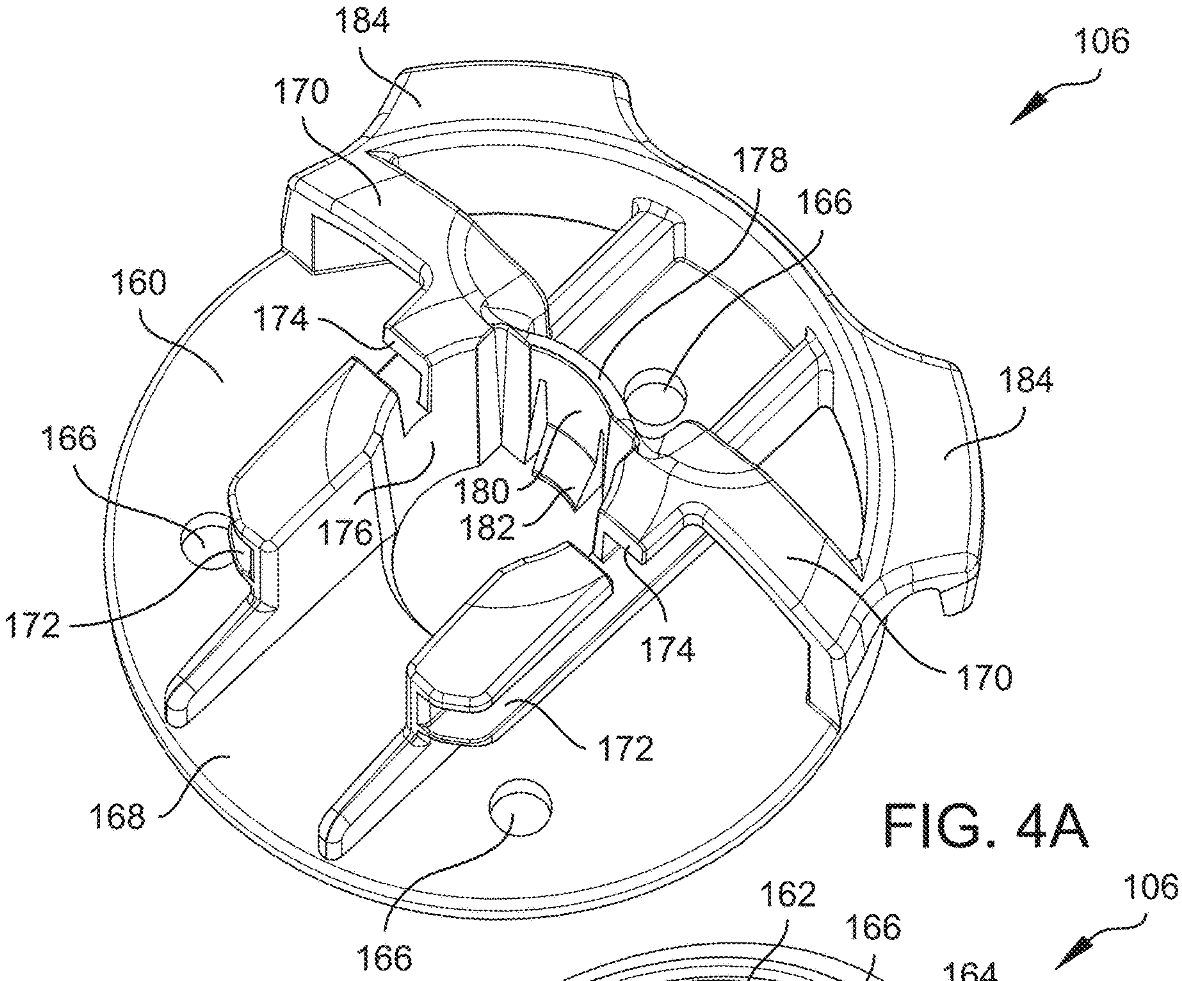
FIG. 4A depicts a perspective view of an exemplary infusion set base.
Figure 4B:
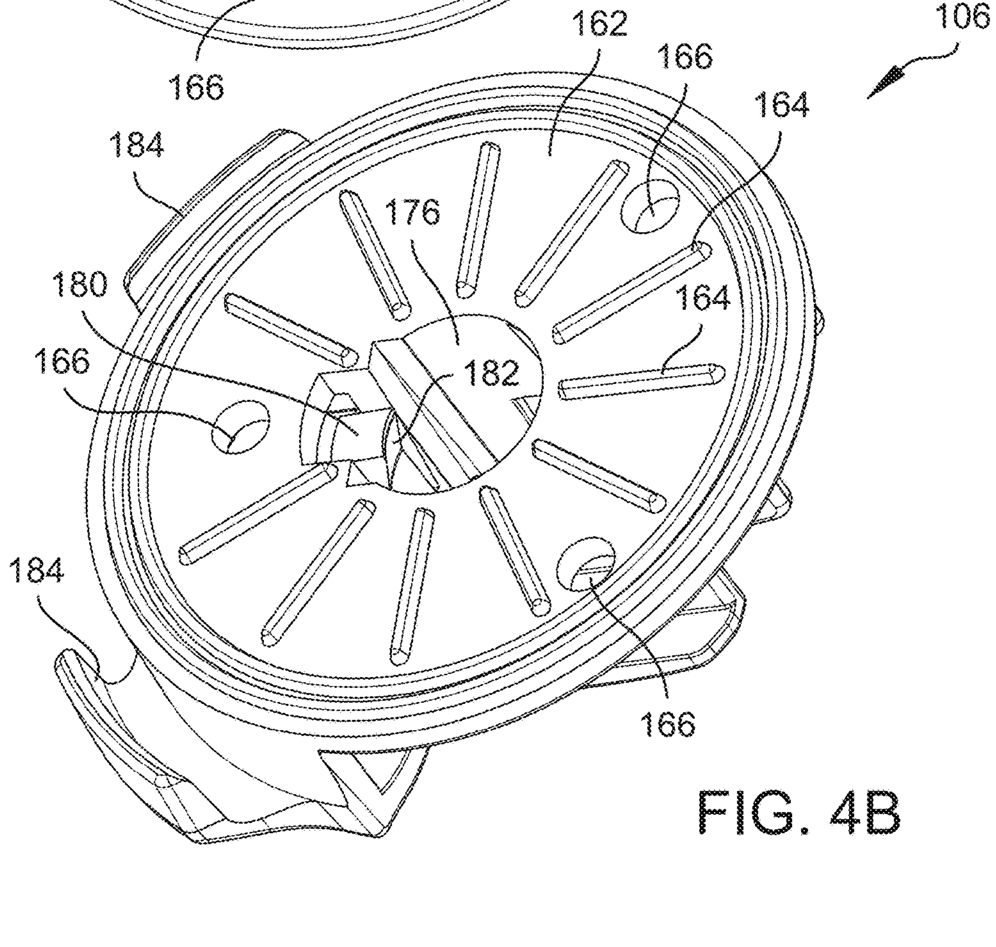
FIG. 4B depicts another perspective view of the example infusion set base of FIG. 4A.

Referring now to FIG. 4A-B top and bottom perspective views of an infusion set base 106 are respectively shown. As shown, the base 106 may have a platform portion 160. The platform portion 160 may be positioned against the skin of a patient while the infusion set 102 is in place on an infusion site. In the example embodiment, the platform portion 160 has a substantially round, and in this case generally circular, disc-like foot print. The platform portion 160 is also substantially flat. This, however, need not be the case in all embodiments.

In various embodiments, adhesive may be applied to the bottom face 162 of a platform portion 160. An adhesive backing 111 (see, e.g. FIG. 1A) may overlay the adhesive. In the example embodiment, the bottom face 162 of the platform portion 160 includes a number of raised segments 164. The exemplary raised segments 164 are depicted as radially arrayed ridges which are spaced at substantially regular angular intervals over a portion of the bottom face 162. Two concentric raised rings are also present around the periphery of the bottom face 162. In other embodiments, raised segments other than ridges may be included and/or the raised features may not be radially arrayed or regularly spaced. The raised segments 164 may allow for the adhesive to be bonded (e.g. ultrasonically or High frequency welded) onto the bottom face 162. For example, the adhesive may be included on a substrate which may be a plastic such as polypropylene or any other plastic which would be amenable to a welding operation. The raised segments 164 and substrate may melt together during the welding operation creating a bond which keeps the adhesive on the bottom face 162 of the infusion set base 106.

In various embodiments, a platform portion 160 may include a number of pass throughs 166. Three circular pass throughs 166 are shown in FIGS. 4A-B though any number may be included in other examples and their shape may differ. Pass throughs 166 may be provided for ease of manufacturing as they may allow for projections on a portion of an assembly line to interface therewith. This interface may aid in orienting or centering of the base 106 or any infusion set 102 subassemblies including the base 106 during manufacturing operations. Where the pass throughs 166 aid in orientation, it may be desirable that the pass throughs 166 be disposed in an asymmetric manner (though symmetric pass through 166 arrangements are also possible). In the example, the pass throughs 166 are disposed in a triangle type layout such that the base 106 would only mate into a set of corresponding projections in one orientation. Additionally, in some embodiments, any adhesive and adhesive liner 111 may include holes which align with the locations of pass throughs 166. Thus, even when the inserter assembly 100 is fully assembled and ready for triggering, the pass throughs 166 may be used to aid in the manufacturing process. The pass throughs 166 may also be engaged by a portion of any packaging that the inserter assembly 100 is provided in to help hold the inserter assembly 100 in place.

Though the pass throughs 166 may be helpful during manufacturing, the pass throughs 166 may also provide other benefits. For example, the pass throughs 166 may provide a window to view skin around the infusion site. As a result, a user may be able to assess the skin for signs of irritation or inflammation (e.g. rubor or redness). Additionally, the pass throughs 166 may provide a pathway through which ambient air may be in communication with space between any raised segments 164 on the bottom face 162 of the infusion set base 106. This may help to allow the area under an infusion set 102 to breathe while the infusion set 102 is adhered against the skin.

Extending from the periphery of the platform portion 160 may be a number of tubing retainers 184. The tubing retainers 184 may allow for infusion tubing 366 to be wrapped around a portion of the infusion set 102 and held in place. This may aid in inhibiting kinking of the tubing 366 and help a user to conveniently route infusion tubing 366 as needed.

Figure 6:
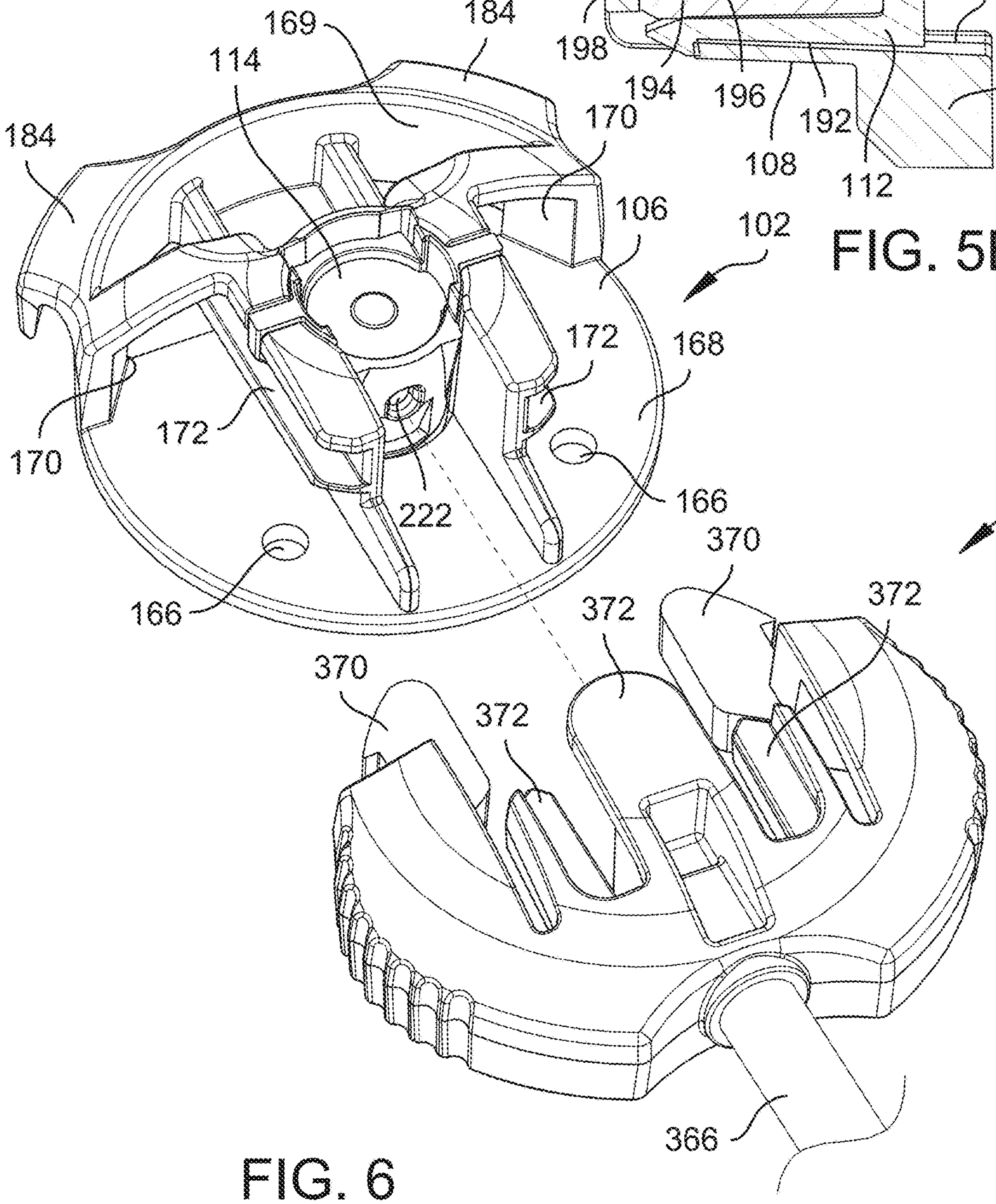
FIG. 6 depicts a perspective view of an example infusion set and tubing connector.
Figure 7A:
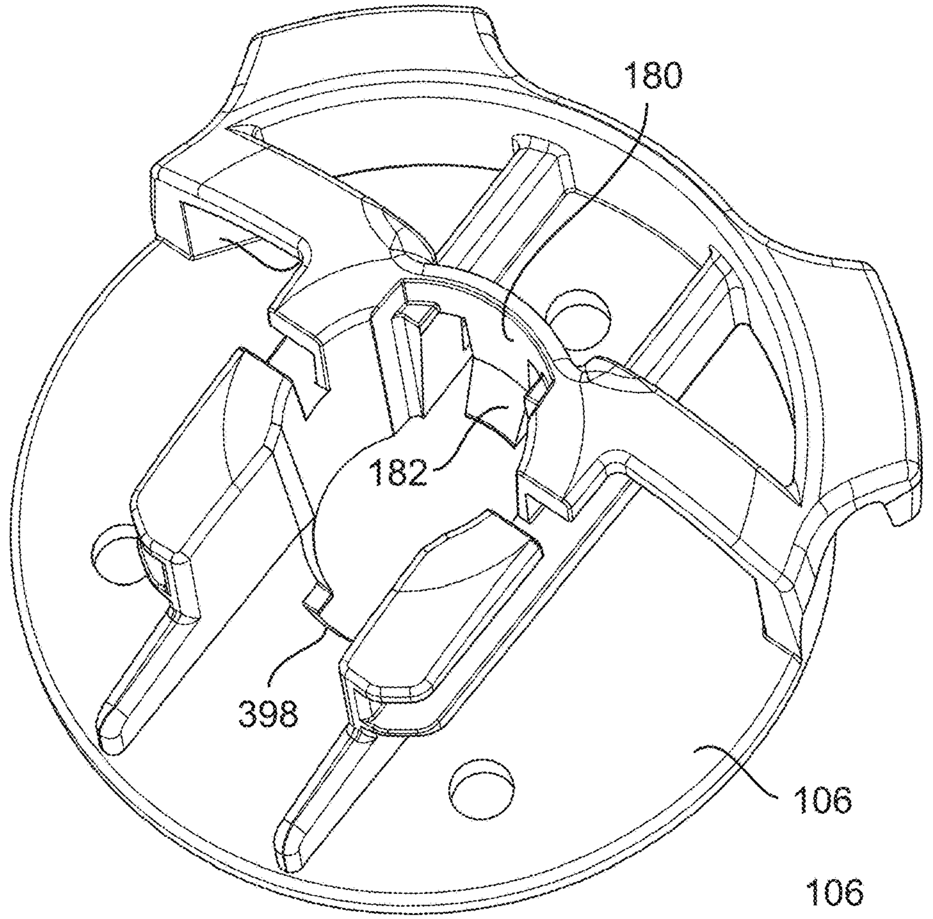
FIG. 7A depicts a perspective view of another exemplary infusion set base.
Figure 7B:
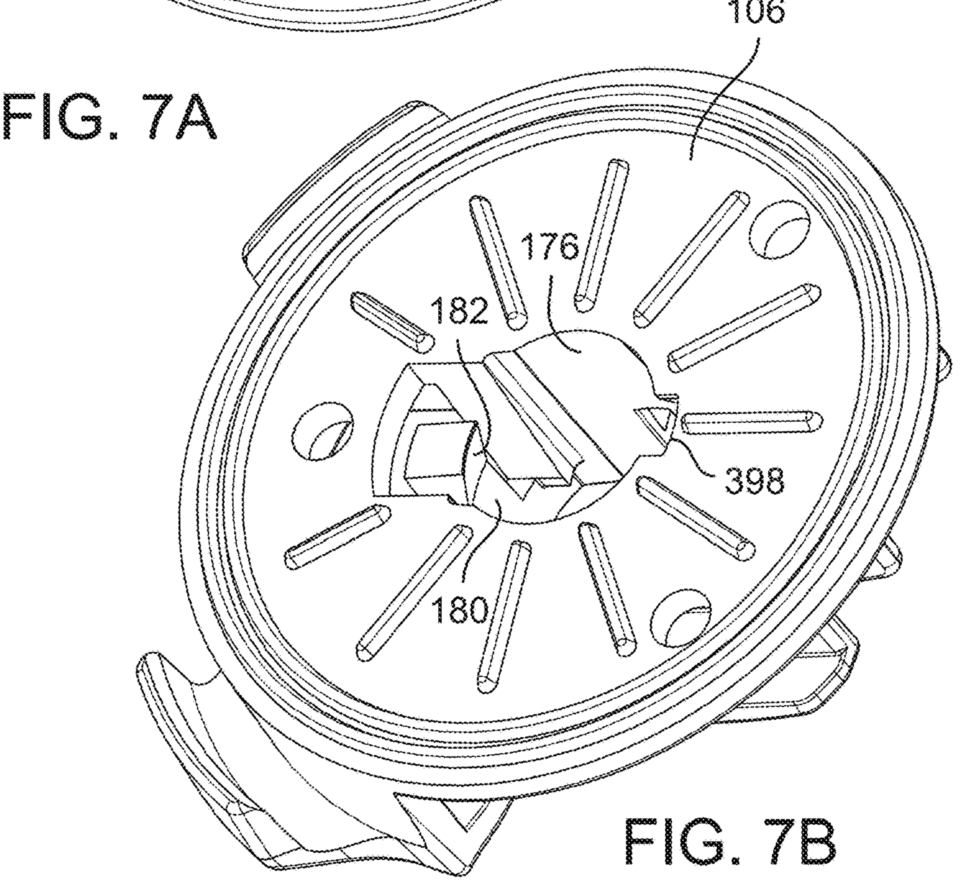
FIG. 7B depicts another perspective view of the example infusion set base of FIG. 7A.
Figure 8A:
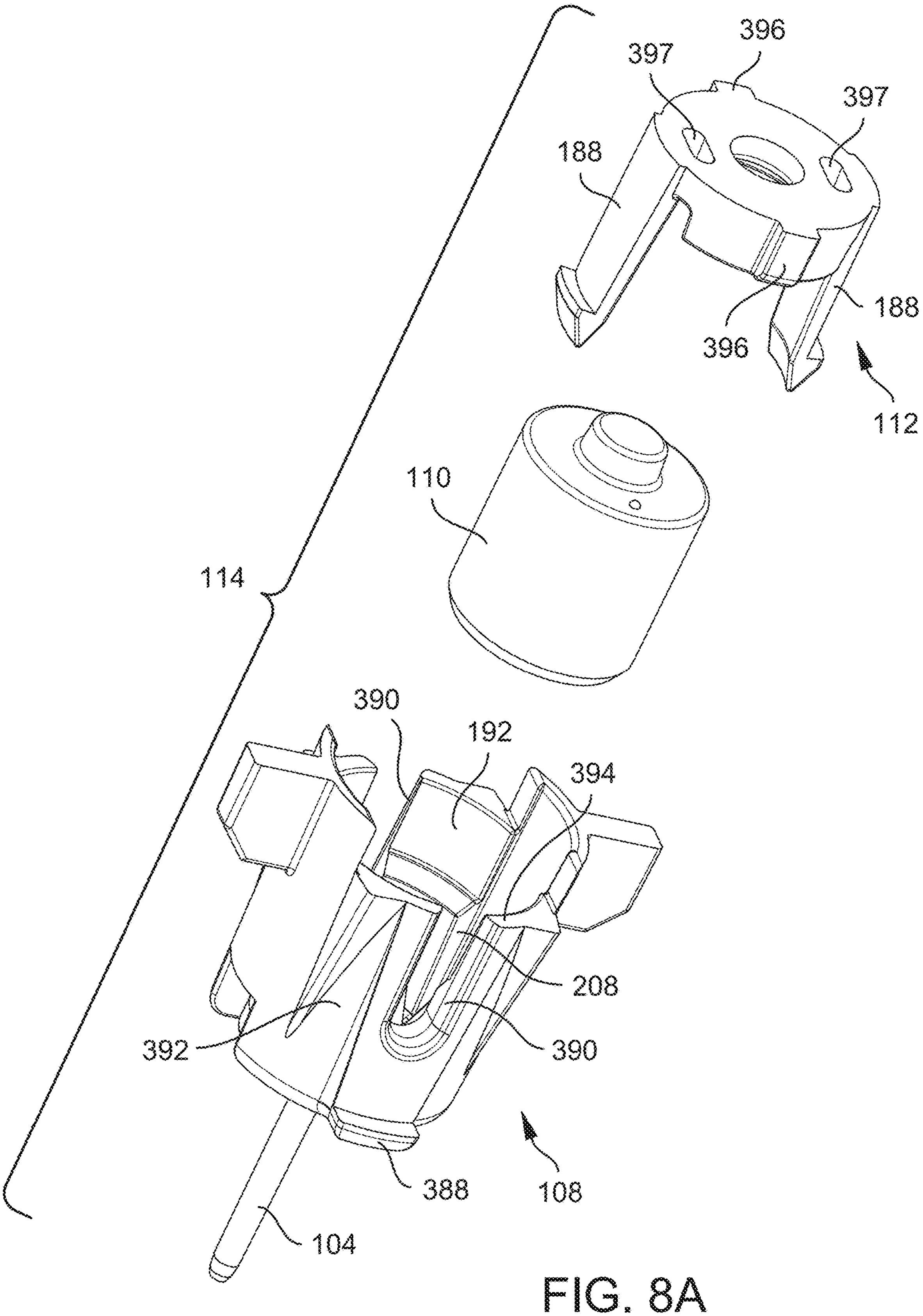
FIG. 8A depicts an exploded view of an exemplary cannula sub assembly.
Figure 8B:
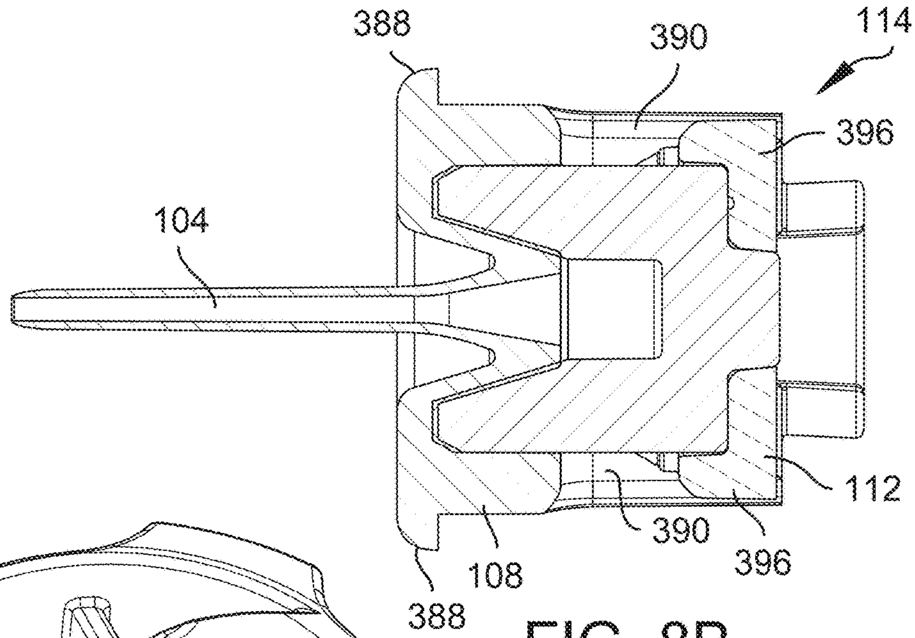
FIG. 8B depicts a cross-sectional view of the example cannula sub assembly shown in FIG. 8A.
Figure 9:
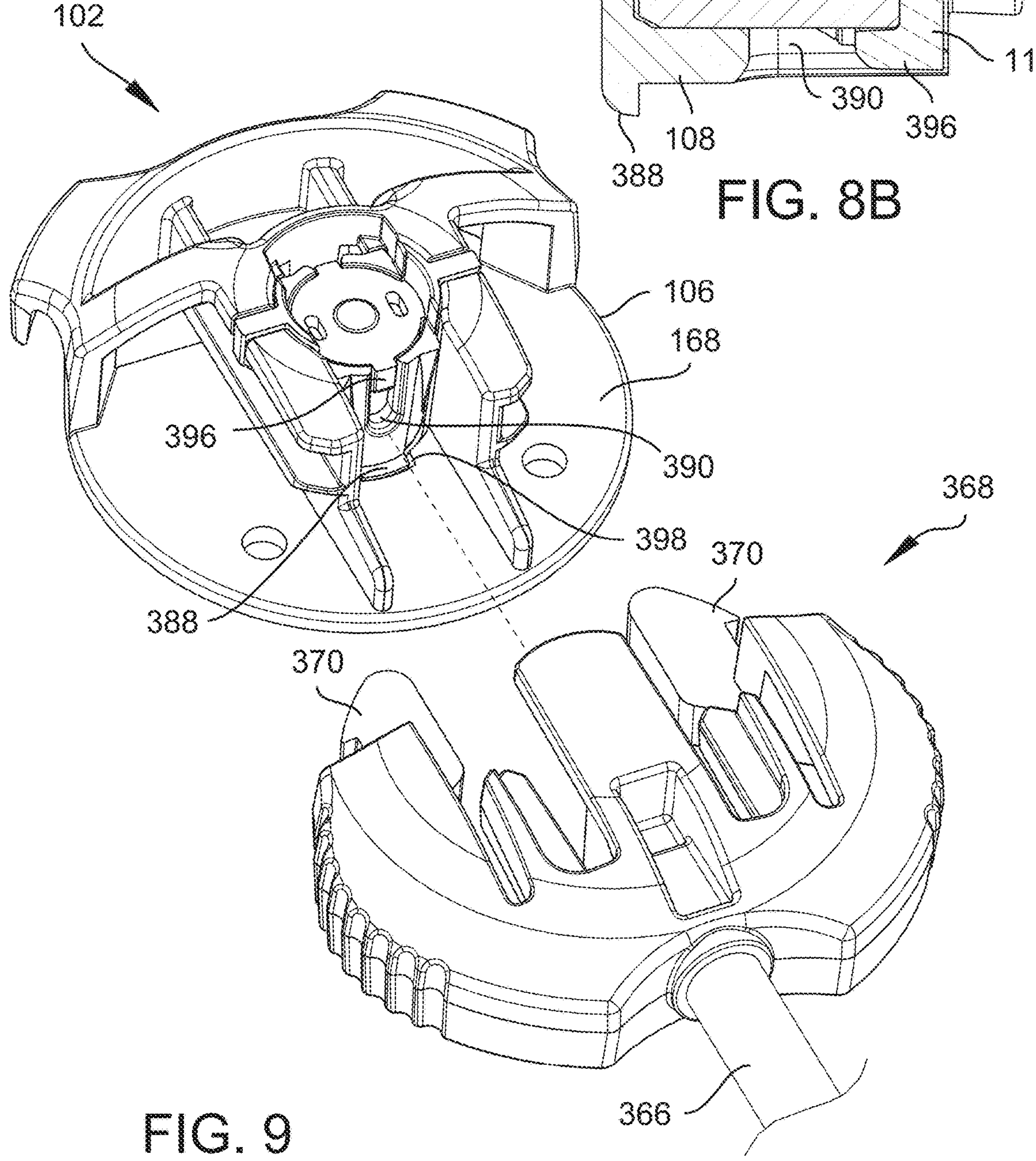
FIG. 9 depicts a perspective view of another example infusion set and tubing connector.

Referring now also to FIG. 6, the top face 168 of the platform portion 160 may include various receiving features extending therefrom which may mate or interface with a connector 368 included at a terminal end of infusion tubing 366 extending from an infusion pump. The infusion tubing 366 may be coupled to an infusion pump reservoir such as a syringe or an infusion pump outlet in various embodiments. Infusion tubing 366 may be coupled to an infusion pump via luer lock, or other mechanical coupling, adhesive, solvent boding, or in any other suitable fashion. The base 106 may include connector receivers 170 which cantilevered fingers 370 on the tubing set connector 368 may deflect around as the connector 368 is slid onto the base 106. Once past the connector receivers 170, the cantilevered fingers 370 may restore to their undeflected position and a bump or catch projection on the cantilevered fingers 370 may displace into latching engagement with a cooperating feature of the connector receivers 170. Sharp flanking projections 372 may also be present on the connector 368. These flanking projections 372 may extend substantially parallel to a sharp 482 included on the connector 368 and may present an obstacle which helps block accidental contact between the sharp 482 and the user. A shielding wall 169 may be provided on the base 106 and may help to block fingers or objects from inadvertently dislodging the cantilevered fingers 370 out of engagement with the connector receivers 170. The shielding wall 169 may be continuous with the connector receivers 170.

Guides 172 for each of the connector fingers 370 and the flanking projections 372 may also be included and in the example embodiment define a number of slots along which the connector fingers 370 and flanking projections 372 may be slid as the connector 368 is displaced into engagement with the infusion set 102. The guides 172 may make it easier for a user to couple the infusion set 102 and connector 368 together. Additionally, the guides 172 may help to ensure that a sharp 482 on the connector 368 is introduced into the infusion set 102 along or close to a desired insertion axis. In the example, the guides 172 include a notch 174. Each notch 174 may be sized to accept a projection on a component of the inserter assembly 100. Notches 174 may also be sized to accept at least a portion of a projection included on a cannula subassembly 114 (see, e.g. FIG. 5A). The flanking projections 372 may be sized so as to extend from the connector 368 a distance shorter than the location of the notches 174 when the connector 368 is attached to the infusion set 102. As described in further detail later in the specification, the notches 174 may aid in facilitating release of the base 106 from the inserter assembly 100 during actuation.

In various embodiments, the base 106 may also include a receptacle 176 for mating with a cannula subassembly 114 (see, e.g. FIG. 5A) of an infusion set 102. In the example, the receptacle 176 is generally centrally disposed on the base 106 and the receptacle 176 is flanked on each side by the guides 172. The receptacle 176 may be surrounded, at least partially, by a receptacle wall 178 which projects upwardly from the top face 168 of the platform portion 160. Thus the receptacle wall 178 and portions of the guides 172 including the notches 174 may define the receptacle 176. Part of the receptacle wall 178 may include a cantilevered section 180. The cantilevered section 180 may include a protuberance (e.g. barb or ramp) 182. In some embodiments, a portion of a receptacle wall 178 and/or guides 172 may include a tapered section (see, e.g. the embodiment depicted in FIGS. 10A-10B). The tapered section may be included at the portion of the receptacle wall 178 and/or guides 172 most distal to the platform 160. Such a tapered section may aid in guiding a cannula subassembly 114 into place as the infusion set 102 is assembled by funneling the cannula subassembly 114 into the receptacle 176.

Figure 5A:
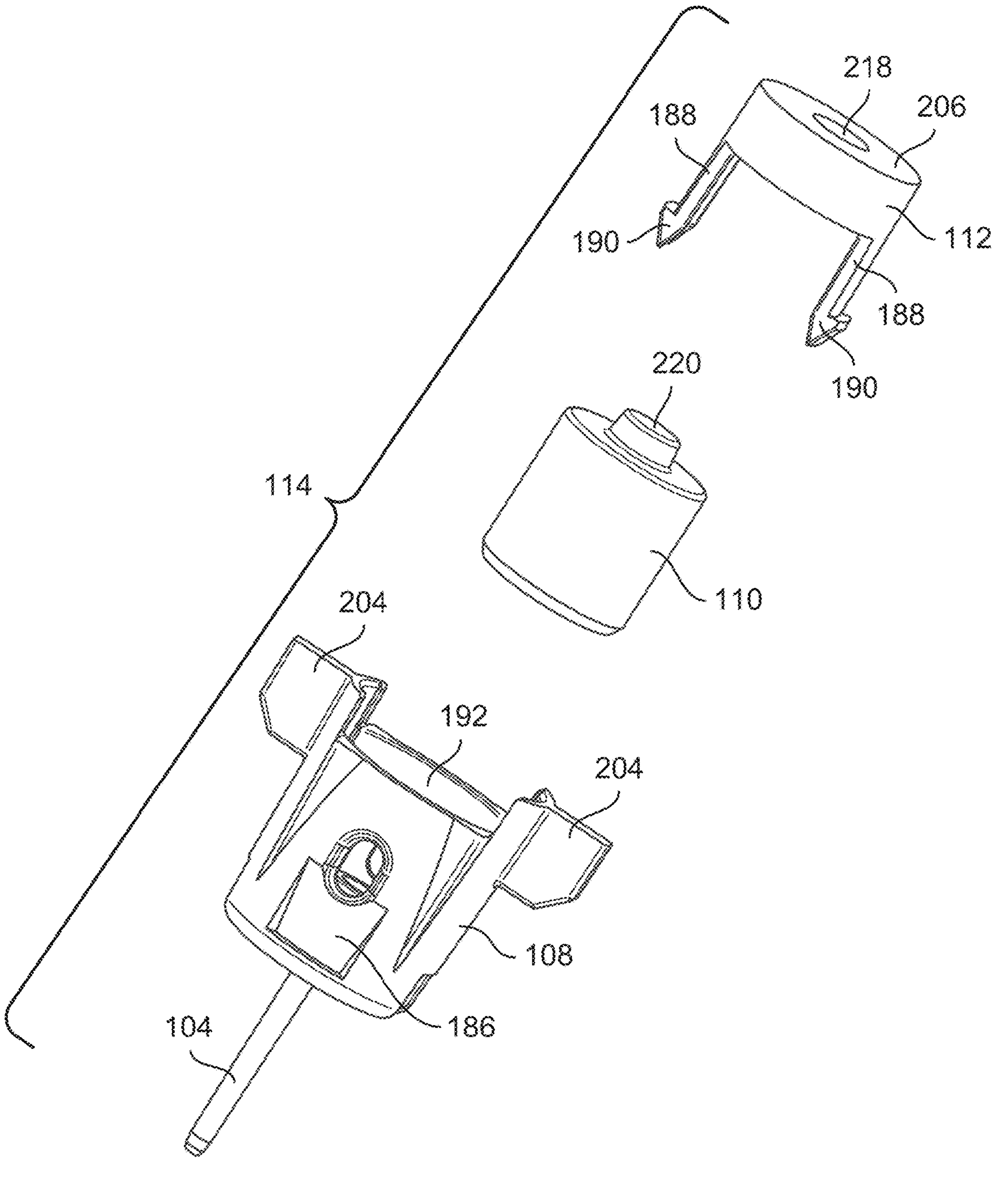
FIG. 5A depicts an exploded view of an exemplary cannula sub assembly.

Referring now also to FIG. 5A, an example cannula subassembly 114 is depicted. As shown, the septum housing 108 may include a notch 186. The notch 186 may be recessed into an exterior face of the septum housing 108. During displacement of the cannula subassembly 114 into the receptacle 176 of the base 106, the cantilevered section 180 of the base 106 may deflect around the septum housing 108 until the protuberance 182 is free to spring into the notch 186. Once the cantilevered projection 180 has restored into its undeflected state and the protuberance 182 is disposed within the notch 186, the cannula subassembly 114 may be retained within the base 106. In the retained state, ears or nubs 204 of the septum housing 108 may at least partially reside within the notches 174 of the base 106 (shown in FIG. 6).

Figure 5B:
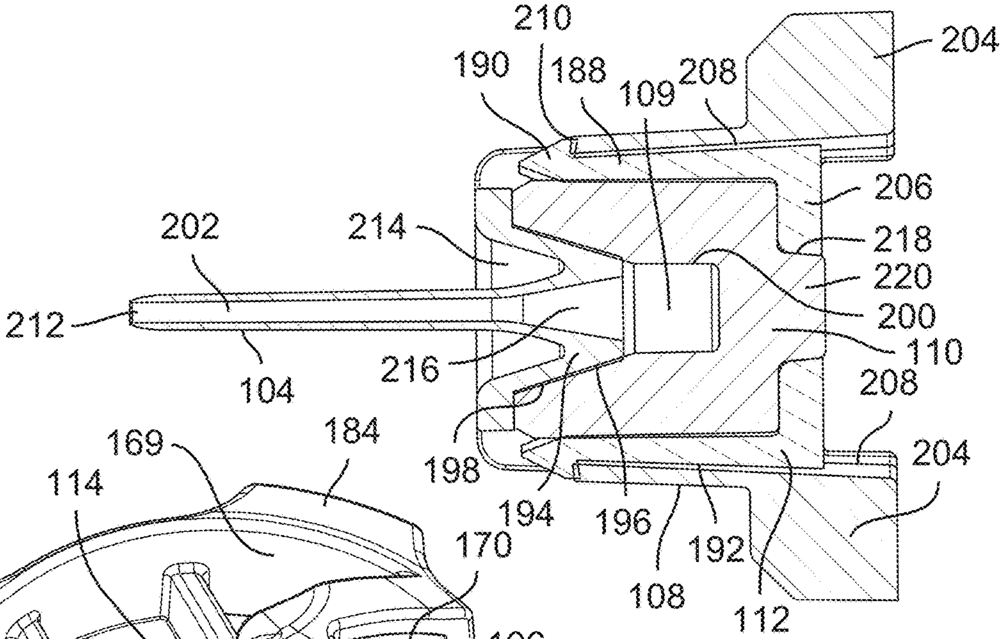
FIG. 5B depicts a cross-sectional view of the example cannula sub assembly shown in FIG. 5A.

Referring now additionally to FIG. 5B, which depicts a cross sectional view of an assembled cannula subassembly 114, the cannula subassembly 114 may further include a septum 110 and a septum retainer 112 in certain embodiments. The septum housing 108 may include a cup like receiving section or receptacle 192 into which the septum 110 may be introduced. The receiving section 192 may include a raised region 194 in a center thereof. In the example, the raised region 194 may have a conic frustum type shape though other shapes are also possible. The septum 110 may also have a cup like septum recess 196 included in the bottom face thereof. The septum recess 196 may include an enlarged or flared out section 198 which is formed as a negative version of the raised region 194 in the receiving section 192 of the septum housing 108. Thus the enlarged section of the septum recess 196 may self-center the septum 110 as the septum 110 is introduced into the receiving section 192 and may be referred to herein as a centering wall of the septum recess 196. A second section 200 of the septum recess 196 most distal to the bottom face of the septum 110 may define, at least partially, a fluid introduction volume into which a needle or sharp 482 included on the tubing connector 368 may penetrate to deliver fluid into the infusion set 102. Fluid may pass from the fluid introduction volume to the lumen 202 of the cannula 104 and into the patient. The second section 200 of the septum recess 196 may have any suitable cross section though in the example has a round, roughly circular cross section. The septum housing 108 may include a connector needle passage 222 in a sidewall thereof (as shown in FIG. 6) which may allow a needle or sharp 482 of the connector 368 access to the fluid introduction volume. In the example embodiment, the connector needle passage 222 is depicted as a fenestration extending though the septum housing 108. A connector needle passage 222 and notch 186 may (though need not be) be present on opposing sides of the septum housing 108 so as to allow the cannula subassembly 114 to be capable of being installed into the base 106 in two orientations. This may make assembly of the inserter assembly 100 simpler.

The receiving section 192 of the septum housing 108 may also receive a portion of a septum retainer 112. The septum retainer 112 may be constructed with a body 206 from which extends at least one cantilevered projection 188 including a terminal protuberance or latch member 190. In the example, the body 206 is substantially planar. Additionally, two cantilevered projections 188 which are disposed opposite one another and extend generally perpendicular to the body 206 are present. These cantilevered projections 188 may fit within guides 208 included on the interior surface of the receiving section 192 of the septum housing 108. The guides 208 shown are recessed into the interior surface of the receiving section 192 and are substantially in the same plane as the ears 204. The guides 208 are ramped such that distance between the two guides 208 decreases as distance from the cannula 104 decreases. This may deflect the cantilevered projections 188 of the septum retainer 112 toward the axis of extension of the cannula 104 as the septum retainer 112 is advanced into the receiving section 192. Once the septum retainer 112 has been advanced into the septum housing 108 a certain distance, the cantilevered projections 188 may spring outward such that the protuberance 190 on each cantilevered projection 188 enters into latching engagement with a catch 210 on the septum housing 108 as shown in FIG. 5B. In some embodiments, a portion of the cantilevered projections 188 may extend into or through an aperture included in the bottom of the septum housing 108 and enter into latching engagement with a catch adjacent to the aperture or formed by a wall of that aperture. With the septum retainer 112 latched into place within the cannula subassembly 114, the septum 110 may be placed into sealing relationship with the septum housing 108. Fluid contained in the fluid introduction volume of the septum 110 may thus be provided a sealed fluid flow path to the outlet 212 of the cannula 104.

As shown, the septum retainer 112 includes a channel 218 which extends therethrough. The example channel 218 is disposed in substantially the center of the body 206. When the septum retainer 112 is locked in place within the cannula subassembly 114, a nub or projection 220 of the septum 110 may extend into the channel 218. Thus the channel 218 may provide an access pathway for an insertion sharp 132 of the inserter assembly 100 to extend though the infusion set 102 and out of the outlet 212 of the cannula 212.

The cannula 104 may include an insertion sharp guide section 216 which may aid in directing the insertion sharp 132 into the lumen 202 of the cannula 104. The insertion sharp guide section 216 may have a funnel like shape though other shapes are also possible. In the example embodiment, the insertion sharp guide section 216 includes relatively steep sides and is encompassed by a flat (or perhaps chamfered or rounded) peripheral edge which forms a wall of the fluid introduction volume within the infusion set 102. This peripheral edge may be the uppermost face of the raised section 192 in some embodiments. The insertion sharp guide section 216 may be continuous with the walls of the lumen 202 of the cannula 104 and may be wetted by any fluid delivered through the infusion set 102. The insertion sharp guide section 216 may also be continuous with the raised region 194 in the receiving section 192 of the septum housing 108.

Referring primarily to FIG. 5B, a recess 214 may be included in the septum housing 108 which surrounds, or at least partially surrounds, the cannula 104. This recess 214 may not be covered by adhesive when the adhesive is placed onto the infusion set base 106. The recess 214 may provide room for the cannula 104 to move relative to the base 106 if the infusion set 102 or a portion of the patient's body causes a force to be applied to the cannula 104. This may minimize shearing action on the cannula 104. Additionally, the recess 214 may serve as a volume into which an agent may be placed. For instance, an antiseptic, disinfectant, anti-inflammatory, anesthetic, or other topical agent such as an ointment may be contained in the recess 214. This agent may be medicinal, nutritional, or some other type of agent. Thus upon application of the infusion set 102, the agent may be introduced to the skin of the patient and may be held in contact with therewith. In some examples, the agent may be kept in contact with the recess 214. This may be desirable or beneficial for a number of reasons including that it may aid in preventing infection, inflammation, or pain and may provide a way to apply the agent in a convenient manner. In the example embodiment, the recess 214 is shaped in the form of a conic section (e.g. hyperbola or parabola) revolved around the center axis of the cannula 104.

In various embodiments, the cannula 104 may be tapered or non-tapered. In some embodiments, the cannula 104 may include one or more tapered section and one or more untapered or straight section. Any tapered sections may extend at an angle to the long axis of the cannula 104. In some embodiments, instead of being at some constant angle to this axis, a curvature may be present. The angle or the degree of curvature over a tapered section may also vary over the extent of a tapered section.

In some embodiments, a first portion of the cannula 104 proximal the outlet 212 is tapered. The taper present at this section results in a reduced wall thickness as proximity toward the outlet 212 of the cannula 104 increases. Additionally, a second portion of the cannula 104 adjacent the point on the septum housing 108 from which it extends is also tapered. The angle of the taper of the second portion may be substantially equal to the angle of the insertion sharp guide section 216 in certain embodiments. The taper at the second portion decreases the width of the cannula 104 at this section without substantially decreasing the thickness of the wall of the cannula 104 surrounding the lumen 202. A straight section may be disposed intermediate the first and second portions of the cannula 104 in the example embodiment. Alternatively, a slightly tapered section may be used as the intermediate segment. This section may be tapered to a lesser degree than the first and second portion of the cannula and may or may not be tapered in a manner which maintains a constant wall thickness along the length of the intermediate segment.

Referring now to FIGS. 7A-9 another example infusion set 102 is depicted. As shown, the cannula sub assembly 114 of the example infusion set 102 is designed to allow production via straight pull molding. Features which may require molds with side actions or other special characteristics are not present on the example cannula sub assembly 114. For example, in some embodiments, undercut features may not be present. This may allow the cannula sub assembly 114 or components thereof to be constructed of a wider array of different materials.

As shown, the cannula sub assembly 114 includes a septum 110 similar to that shown in FIGS. 5A-5B. The septum housing 108 does not include notches 186. In place of the notches 186, the septum housing 108 includes salients 388 which extend outward from the outer surface of the septum housing 108. During joining of the cannula assembly 104 to the infusion set base 106, one of the salients 388 may deflect the cantilevered section 180 of the base 106 until the protuberance 182 is free to spring back into a position overhanging the salient 388. Once the cantilevered projection 180 has restored into its undeflected state and the protuberance 182 is over the salient 388, the cannula subassembly 114 may be retained within the base 106. In the retained state (see, e.g. FIG. 9), ears or nubs 204 of the septum housing 108 may at least partially reside within the notches 174 of the base 106. The receptacle 176 portion of the infusion set base 106 is widened with respect to that shown in FIG. 4A-B so as to accommodate the greater footprint of the cannula sub assembly 114. Additionally, the receptacle 176 includes a salient receiving region 398 opposite the cantilevered projection 180 so as to accept the salient 388 not engaged by the protuberance 182. This may allow the cannula sub assembly 114 to be made symmetrically and allow for it to be installed into the infusion set base 106 in two orientations. This may aid in simplifying manufacturing and assembly. In other embodiments, a salient 388 may only be included on one side of the cannula subassembly 114 and the salient receiving region 398 of the base 106 may be omitted.

Additionally, in the exemplary embodiment, the septum housing 108 does not include fenestrations which form a connector needle passage 222 (see, e.g. FIG. 6) in a sidewall thereof. The septum housing 108 in FIGS. 8A-9 includes slots 390 in the side wall 392 of the septum housing 108 recessed into the top face 394 of the side wall 392. The septum retainer 112 may include projections 396 which align with the slots 390 when the cantilevered projections 188 are fitted within guides 208 included on the interior surface of the receiving section 192 of the septum housing 108. When the cannula sub assembly 114 is coupled together (see, e.g. FIG. 8B), the projections 396 may occupy a portion of the slots 390. Thus an access hole for a sharp 482 or needle included on a tubing connector 368 may be provided in the cannula sub assembly 114. The septum retainer 112 also includes a number of pass throughs 397. The pass throughs 397 may aid in manufacture and assembly similar to pass throughs 166 in the infusion set base 106.

In some embodiments, the slots 390 in the side wall 392 of the septum housing 108 may be used in place of the salient 388 as a retention arrangement which cooperates with a protuberance included as part of the base 106. The protuberance may catch against or engage with a wall of one of the slots 390 inhibiting removal of the cannula subassembly 114. In such embodiments, the salients 388 may not be included on the septum housing 108. This may help to further simplify production of the cannula subassembly 114.

Figure 10A:
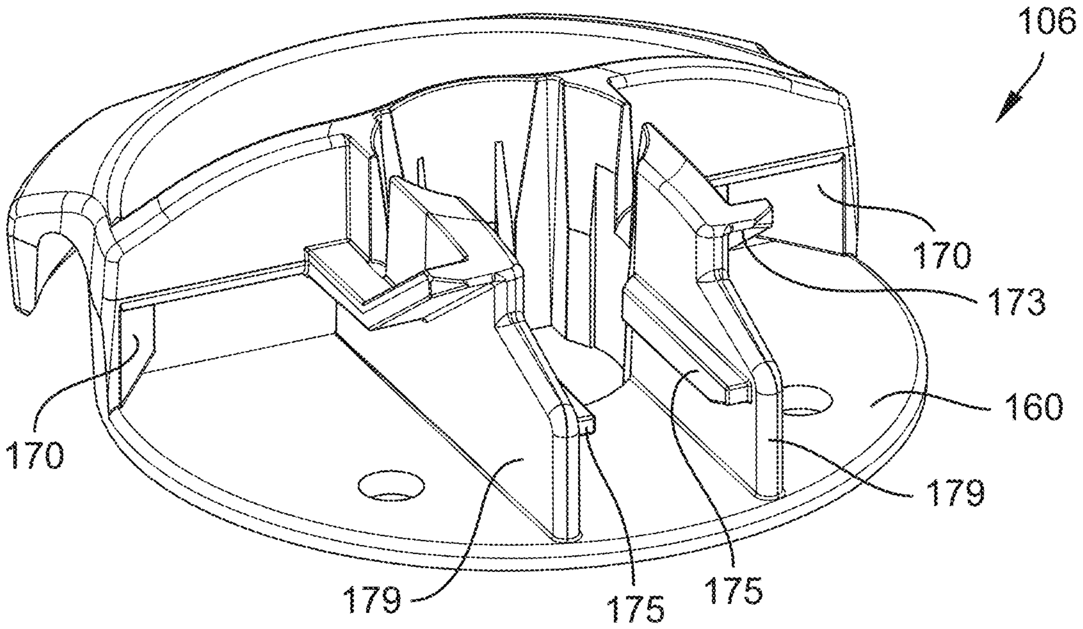
FIG. 10A depicts a perspective view of an example infusion set base.
Figure 10B:
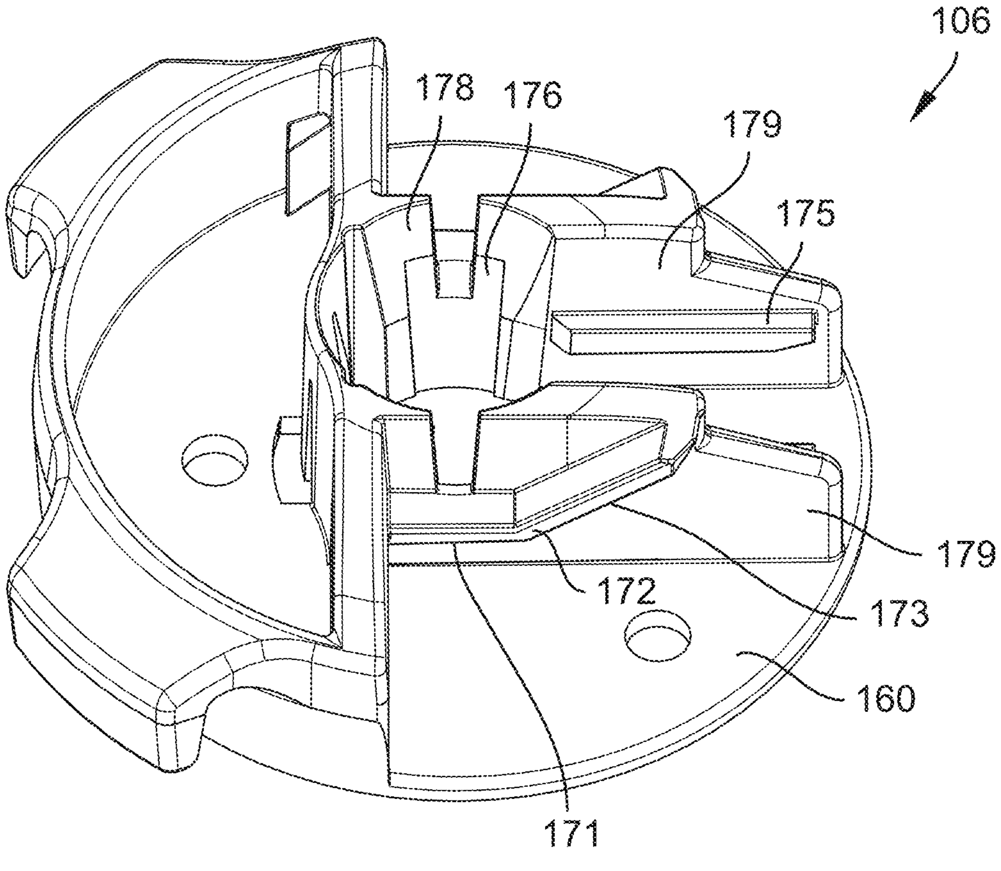
FIG. 10B depicts another perspective view of the infusion set base of FIG. 10A.

Referring now to FIGS. 10A and 10B, another example base 106 is depicted. As in FIG. 6, the top face 168 of the platform portion 160 may include various receiving features extending therefrom which may mate or interface with a connector 368. The base 106 may include connector receivers 170 which may allow for coupling of the base 106 with cantilevered fingers 370 on the tubing set connector 368 as described above (see, e.g. description of FIG. 6). Guides 172 for each of the connector fingers 370 may also be included in the example embodiment. As shown, the exemplary guides 172 include a first section 171 and a second section 173. The first section 171 of each guide 172 may be disposed so as to have a portion which extends in a substantially parallel fashion to the plane of the platform 160 of the base 106. The second section 173 of each guide 172 may include a portion disposed at an angle with respect to the first section 171. In the example, each of the first and second portion 171, 173 include a ledge which projects from a main portion of that guide 172. The distance between the platform 160 and the proximal surface of the ledge of the second section 173 of the guide 172 may increase as the second section 173 extends distally from the ledge of the first portion 171 of the guide 172. This may allow the tubing set connector 368 to initially be introduced at a substantial angle to the plane of the platform 160 of the base 106. Further introduction may cause the connector fingers 370 to contact the platform 160 and be redirected to an appropriate displacement pathway for coupling of the tubing set connector 368 to the base 106. Thus, the guides 172 may aid in allowing a user to blindly insert the connector fingers 370 into the connector receivers 170 as coupling of a base 106 and tubing set connector 368 is performed. As shown, a second set of additional guide ledges 175 may be included on receptacle wall extensions 179. These additional guide ledges 175 may extend to the periphery of the base 106. In the example embodiments, the second set of guide ledges 175 extend substantially perpendicularly from the medial faces of the receptacle wall extensions 179 and toward the axis along which the sharp 482 (see, e.g., FIGS. 102-106) of the tubing set connector 368 is inserted into the cannula subassembly 114. A face of each of the second set of guide ledges 175 which is disposed near an end of each receptacle wall extension 179 most proximal to the periphery of the base 106 may include a ramped region.

Figure 11A:
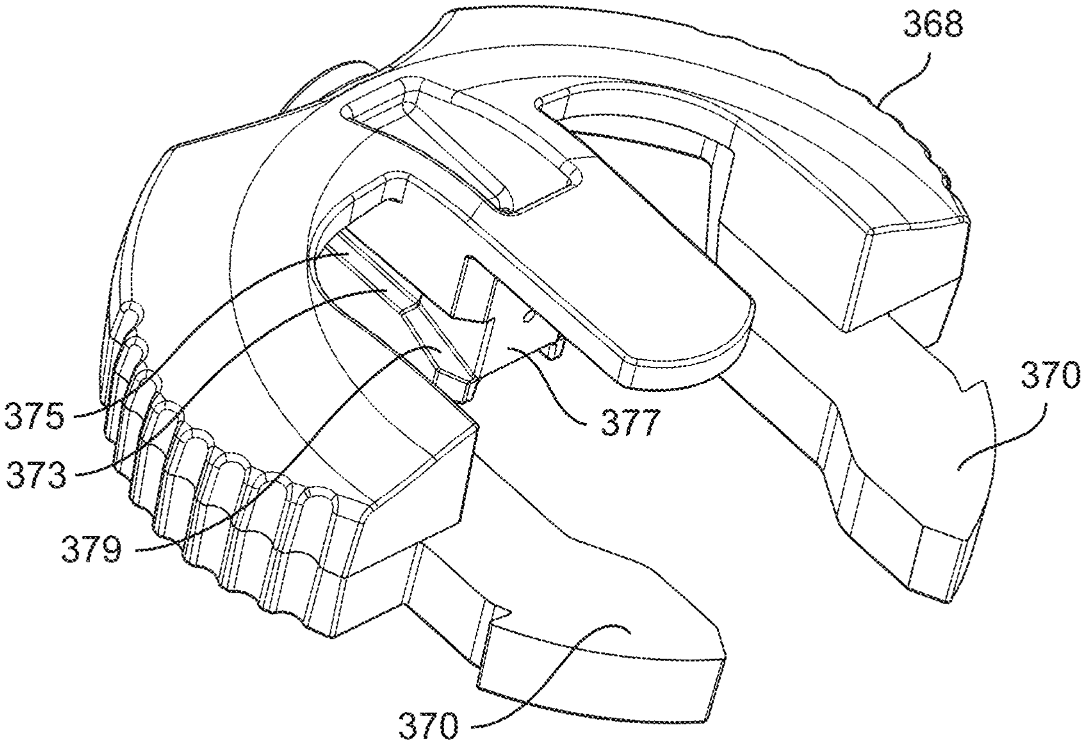
FIG. 11A depicts a perspective view of an example infusion set base.
Figure 11B:
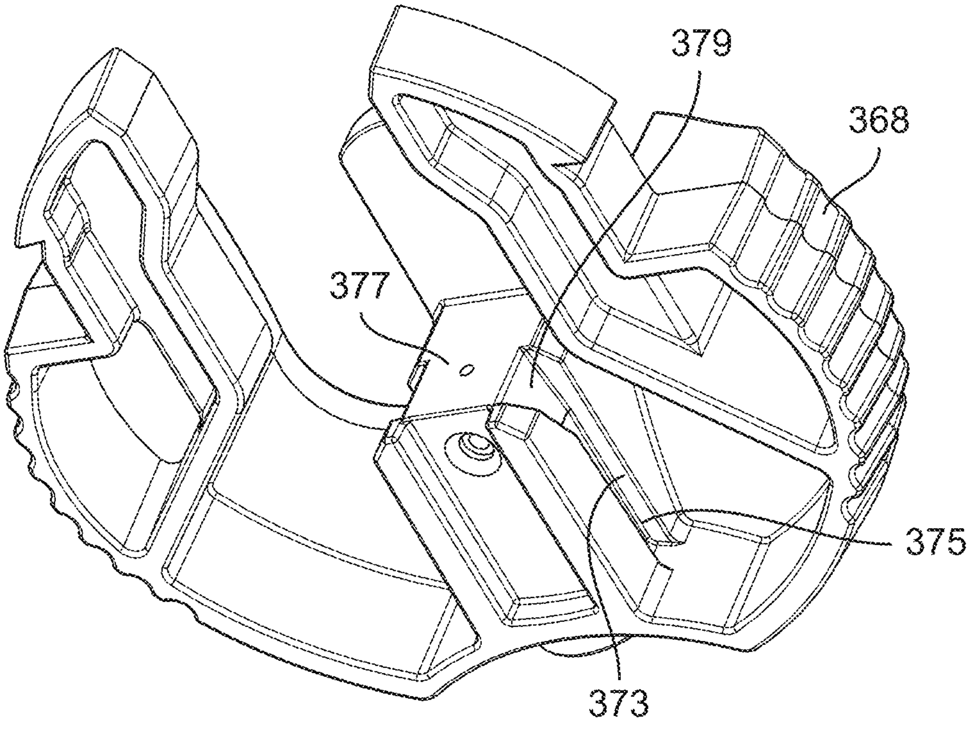
FIG. 11B depicts another perspective view of the infusion set base of FIG. 11A.
Figure 12A:
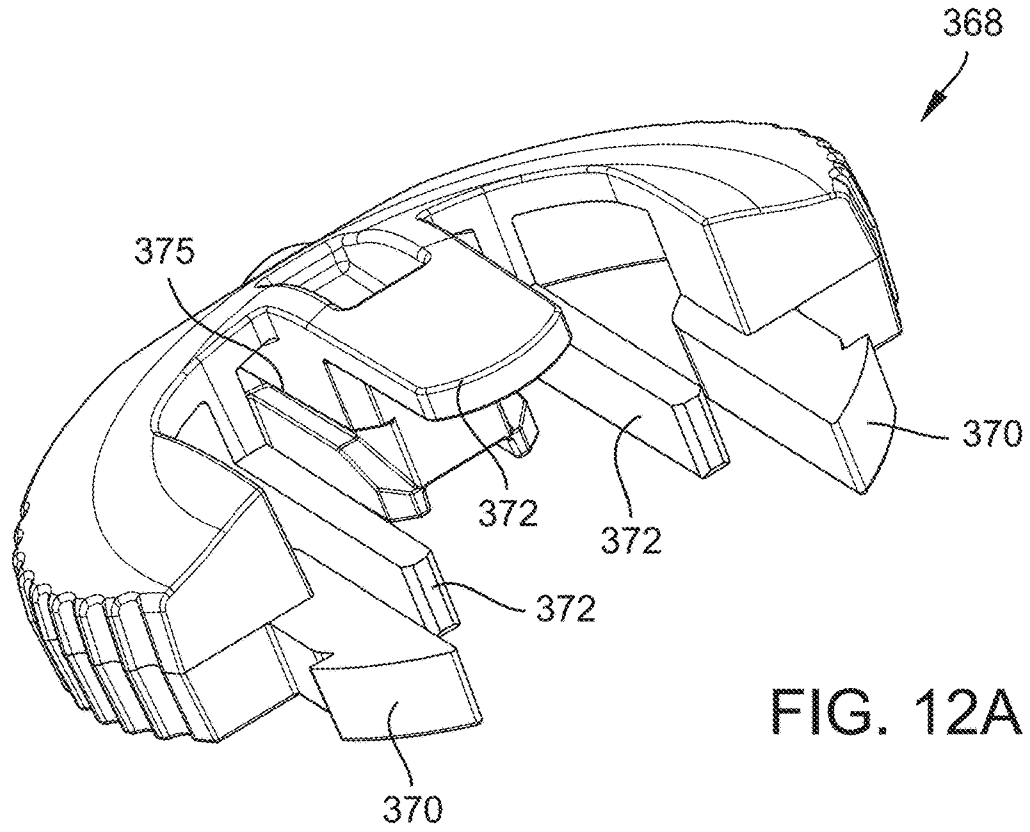
FIG. 12A depicts a perspective view of an example infusion set base.
Figure 12B:
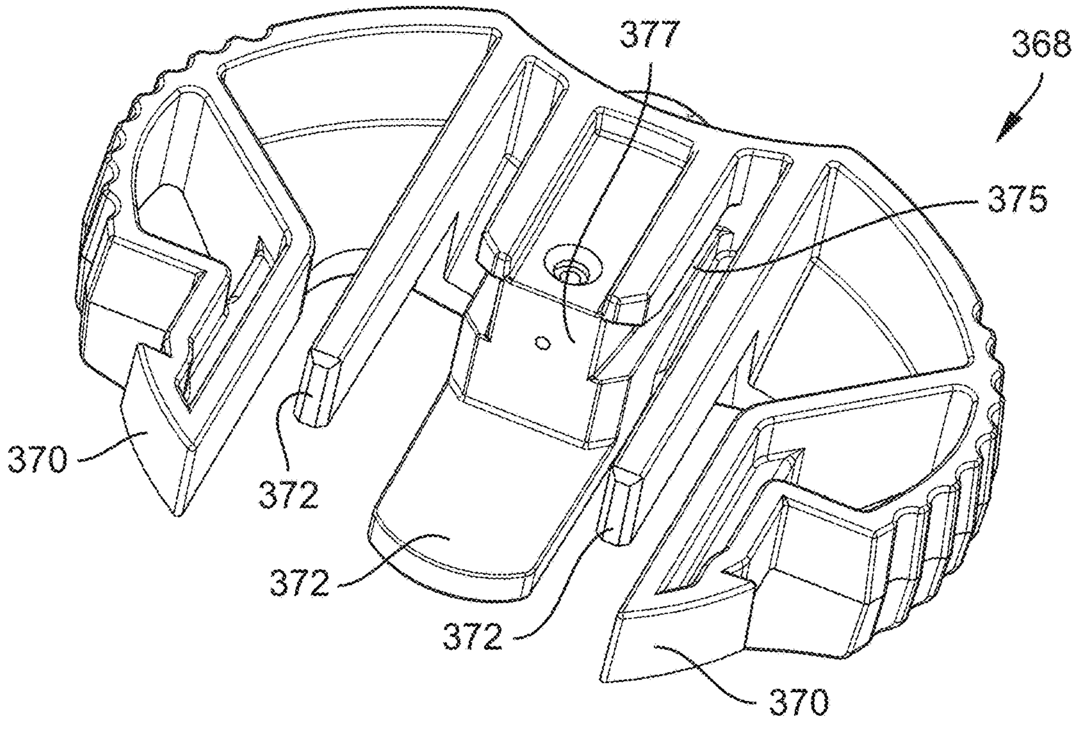
FIG. 12B depicts another perspective view of the infusion set base of FIG. 12A.

Referring now to also to FIGS. 11A-11B, the tubing set connector 368 may include a flow hub 377 to which tubing 366 and a sharp 482 (see, e.g., FIGS. 102-106) may be coupled. Fluid flowing through the connector 368 may pass through lumens 514 and 516 (see, e.g., FIGS. 102-106) of the tubing 366 and sharp 482 respectively within the flow hub 377. As shown in FIGS. 11A-11B, the flow hub 377 may include alignment channels 375 recessed therein. As shown, the alignment channels 375 include a constant width segment 373 and a variable width segment 379. Upon coupling of a tubing set connector 368 and infusion set 102, the alignment channels 375 may interact with the second set of guide ledges 175 of the base 106. The ramped section of each of the second set of guide ledges 175 and the variable width section 379 of the alignment channels 375 may allow the tubing sharp connector 368 to initially be introduced at a substantial angle to the plane of the platform 160 of the base 106. Further introduction may cause the second set of guide ledges 175 to contact the wall of their respective alignment channels 375 and redirect the tubing set connector 368 toward an appropriate displacement pathway for coupling of the tubing set connector 368 to the base 106. The second set of guide ledges 175 in conjunction with the alignment channels 375 may thus aid in allowing a user to blindly couple the base 106 and tubing set connector 368.

Referring now to FIGS. 12A-12B and FIGS. 13A-13B, in some embodiments, sharp flanking projections 372 may be included as part of the tubing set connector 368. As shown, the sharp flanking projections 372 may extend parallel to the axis of a sharp 482 (see, e.g., FIGS. 102-106) which may be included in the tubing set connector 368. The sharp flanking projections 372 may aid in preventing any user contact with the sharp 482 by providing an obstruction which inhibits a finger from reaching the sharp 482. The sharp flanking projections 372 may include a centrally disposed projection 372 which extends over the sharp 482 from a top face of the tubing set connector 368. The sharp flanking projections 372 may also include a set of projections which are in the same plane as the connector fingers 370 of the tubing set connector 368, but disposed more medially than the connector fingers 370. In the example embodiments, the connector fingers 370 and this set of projections 372 are in line with the bottom face of the tubing set connector 368. Each projection 372 of this set of projections 372 may be disposed so as to extend from a point on the body of the tubing set connector 368 which is intermediate the flow hub 377 and the connector fingers 370. These projections 372 may be disposed so as to interact with guides 172 of a base 106 during coupling of the tubing set connector 368 to a corresponding base 106. In such embodiments, the connector fingers 370 may not interact with guides 172 on the base 106.

Figure 13A:
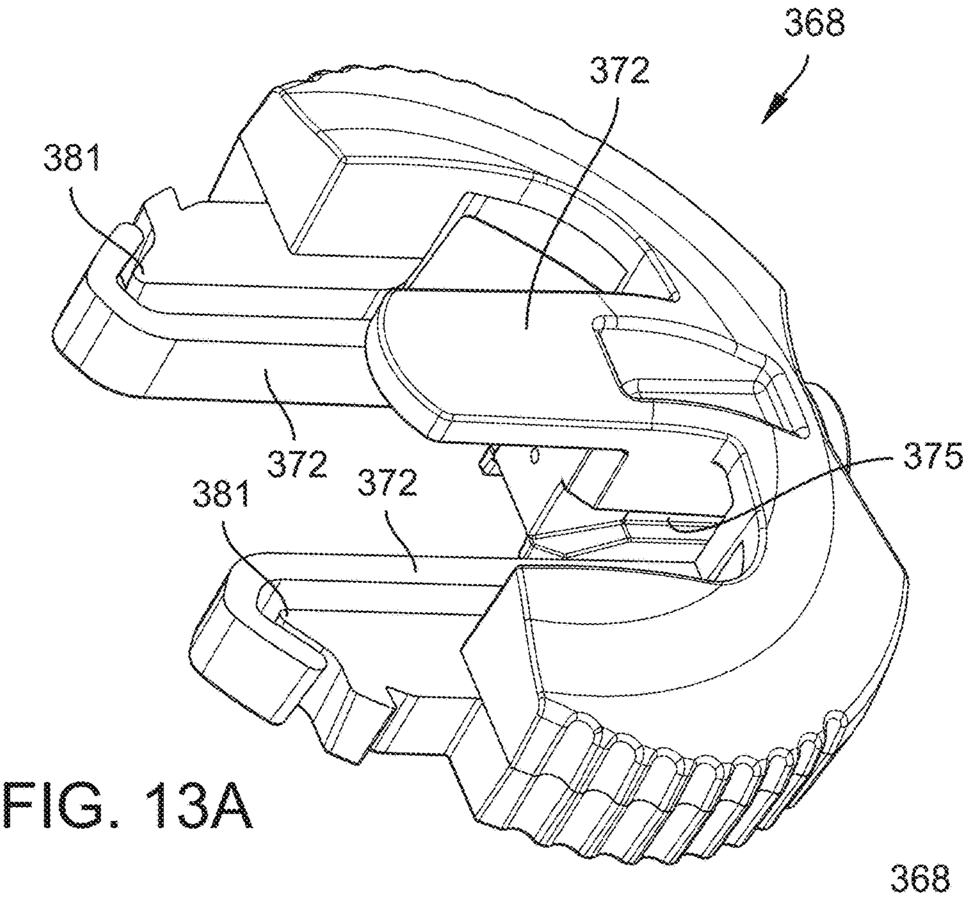
FIG. 13A depicts a perspective view of an example infusion set base.
Figure 13B:
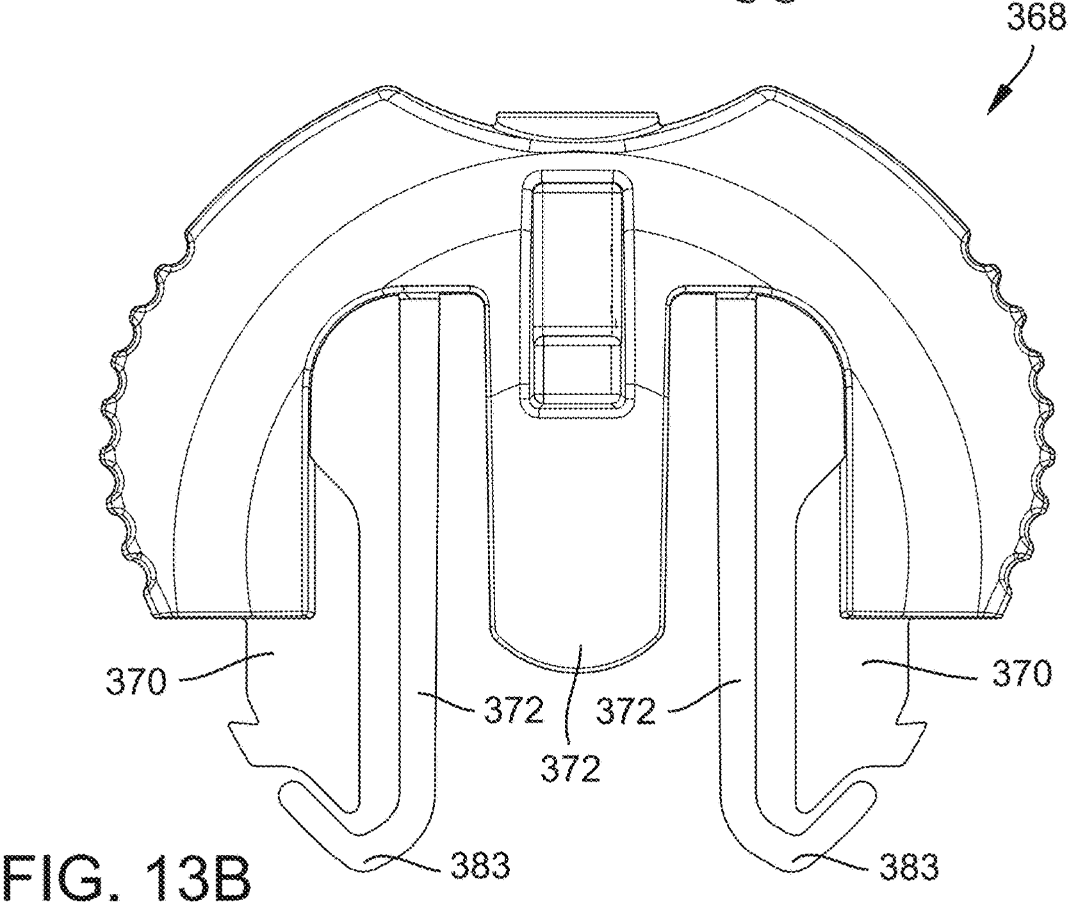
FIG. 13B depicts a bottom plan view of the infusion set base of FIG. 13A.

In some embodiments, and as shown in FIGS. 13A-13B, the pair of sharp flanking projections 372 which are in the plane of the connector fingers 370 may extend beyond the tips 381 of the connector fingers 370. These projections 372 may include a curved end region 383 at an end of the projections 372 opposite that attached to the body of the tubing set connector 368. The curved end regions 383 may curve in a direction lateral to the axis of the sharp 482 (see, e.g., FIGS. 102-106) of the tubing set connector 368. In the example, the curved end regions 383 may have a curvature which swings an arc greater than 90°. In the example, the curved end regions 383 have a curvature such that the curved end regions 383 begin to extend back toward the body of the tubing set connector 368. The radius of the curved end regions 383 may or may not be constant. Additionally, the curved end regions 383 may include one or more straight expanse. As shown best in FIG. 13B, the portion of the curved end region 383 leading to the terminus of the projection may be substantially straight. In the example, the curved end regions 383 curve around and in front of a portion of the respective connector fingers 370. The distance between the projections 372 may be slightly smaller than the spacing between the guides 172 of a corresponding base 106. The distance between the projections 372 at the curved end regions 383, however, may be slightly greater facilitating maneuvering of the projections 372 into their respective guides 172. Once the projections 372 are located within the guides 172, advancement of the tubing set connector 368 may cause the projections 372 to be resiliently splayed apart. Due to the resiliency of the projections 372, the projections 372 press against a surface of the guides 172 ensuring a tight and substantially wiggle free fit. This may help to further confine displacement of the tubing set connector 368 along a desired path as coupling of a tubing set connector 368 to a base 106 is completed.

Figure 14A:
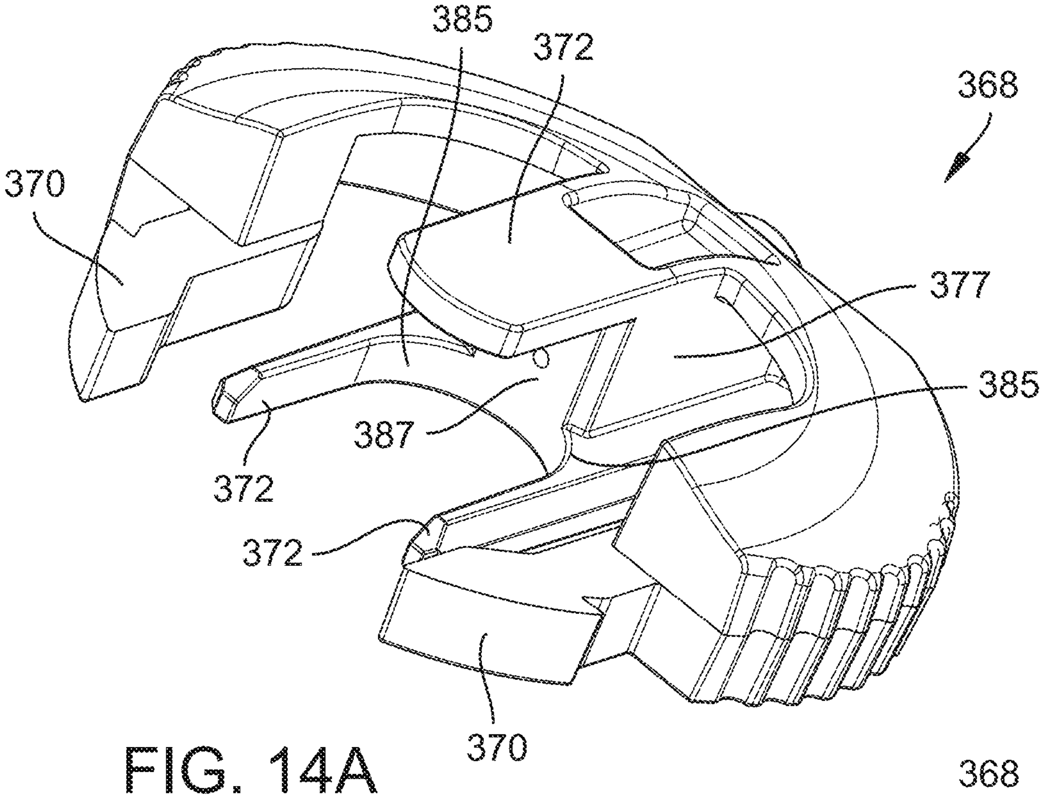
FIG. 14A depicts a perspective view of an example infusion set base.
Figure 14B:
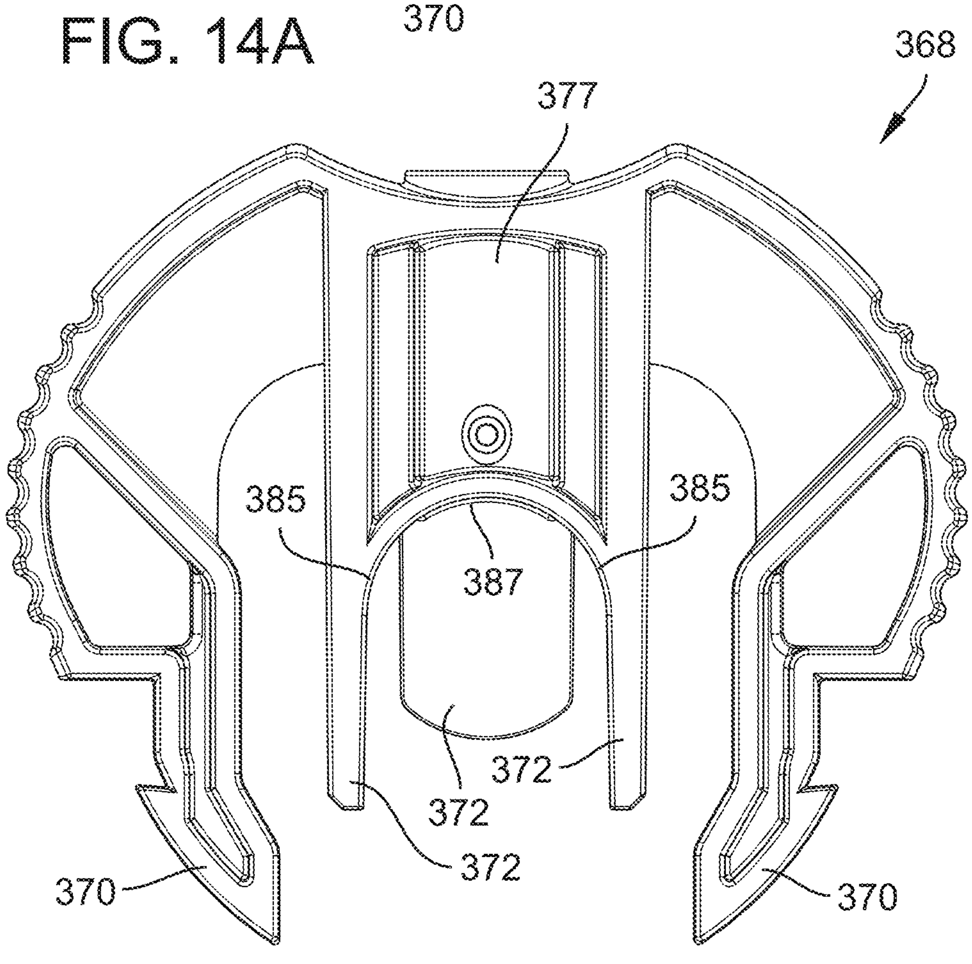
FIG. 14B depicts a bottom plan view of the infusion set base of FIG. 14A.

In certain examples, and referring now to FIGS. 14A-14B, a set of sharp flanking projections 372 in line with the connector fingers 370 may extend from the flow hub 377. This may decrease the gap between the sharp flanking projections 372 of the tubing set connector 368 and may help to further minimize the ability of the user to access space in the vicinity of the sharp 482 (see, e.g., FIGS. 102-106) with a finger. In the example embodiment depicted in FIGS. 14A-14B, a set of sharp flanking projections 372 which extend along and from opposing faces of the flow hub 377 lateral to the axis of the sharp 482 are included. These projections 372 may each include a support segment 385.

These support segments 385 may be located in the region of the sharp flanking projections 372 which extends beyond the face 387 of the flow hub 377 from which the sharp 482 extends. As shown, the support segments 385 are disposed in the portion of this region most proximal to the flow hub 377. The support segments 385 in the example embodiment include an arched face which may lend additional robustness to the set of sharp flanking projections 372. The face 387 of the flow hub 377 from which the sharp 482 extends may also be arched which may further add robustness to the projections 372.

Figure 15A:
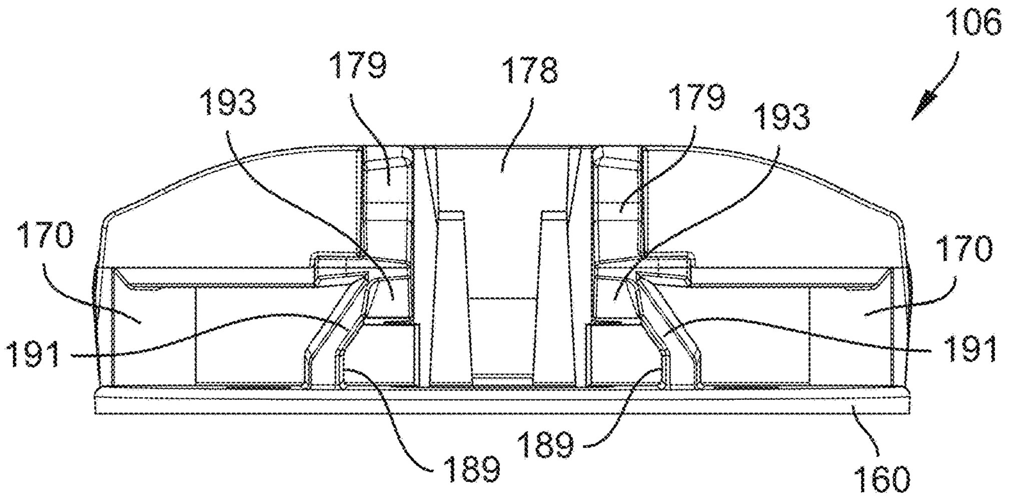
FIG. 15A depicts a side view of an example infusion set base.
Figure 15B:
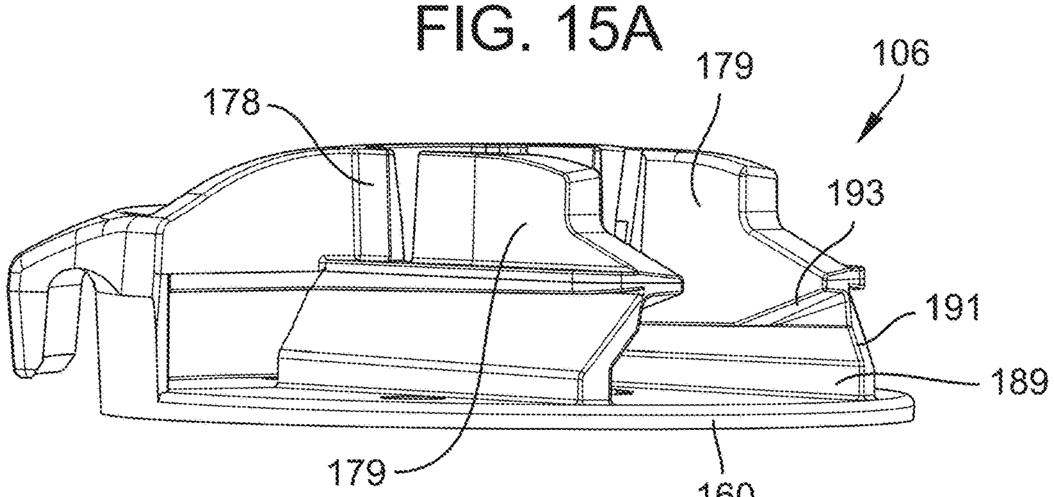
FIG. 15B depicts another side view of the example infusion set base of FIG. 15A.
Figure 15C:
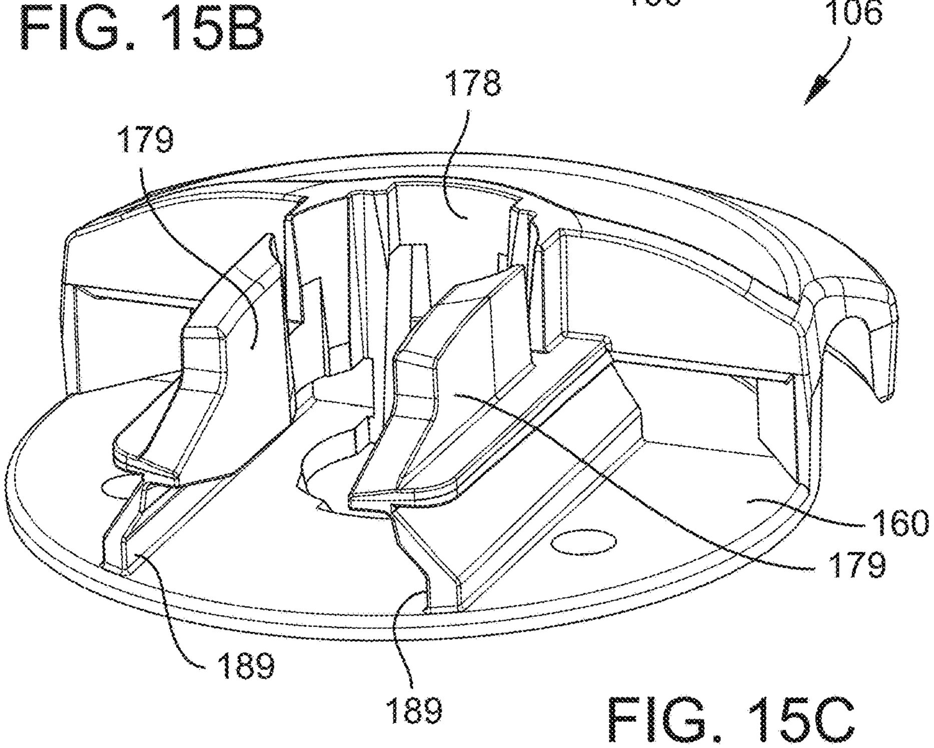
FIG. 15C depicts a perspective view of the example infusion set base of FIG. 15A.

Referring now also to FIGS. 15A-15C, another example base 106 is depicted. The example base 106 may couple to a tubing set connector 368 such as that shown in FIGS. 14A and 14B. The base 106 may include connector receivers 170 which may allow for coupling of the base 106 with cantilevered fingers 370 on the tubing set connector 368 as described elsewhere herein. Though not shown in the example embodiment, guides 172 for each of the connector fingers 370 such as those shown in FIG. 6 and FIG. 10A may be included. As shown, the base 106 may define receiver tracks 189 which may accept a set of sharp flanking projections 372 which are in the plane of the connector fingers 370. As shown, the receptacle wall extensions 179 and the portions of the receptacle wall 178 which extend parallel to one another may be separated from one another by a channel. The receiver tracks 189 are recessed into the receptacle wall extensions 179 and the portions of the receptacle wall 178 which extend parallel to one another adjacent the platform 160. Thus, the width of the channel between the receptacle wall extension 179 and portions of the receptacle wall 178 may be greatest adjacent the platform 160. The width of the channel may decrease as distance from the platform 160 increases. As shown, the receiver tracks 189 may each include a sloped wall 191. The sloped wall 191 may aid in locating of the sharp flanking projections 372 of a tubing set connector 368 in the receiver tracks 189. Additionally, the base 106 may include ramped sections 193 which are located at the open end of the receiver tracks 189. The ramped section 193 may, similarly to the second section 173 of the guides 172 in FIGS. 10A-10B, allow the tubing set connector 368 to initially be introduced at a substantial angle to the plane of the platform 160. Further introduction may cause the flanking projections 372 to be redirected into the receiver tracks 189. Thus, the sloped walls 191 and ramped section 193 may facilitate blind insertion of the tubing set connector 368 into coupled relationship with the base 106.

Figure 16A:
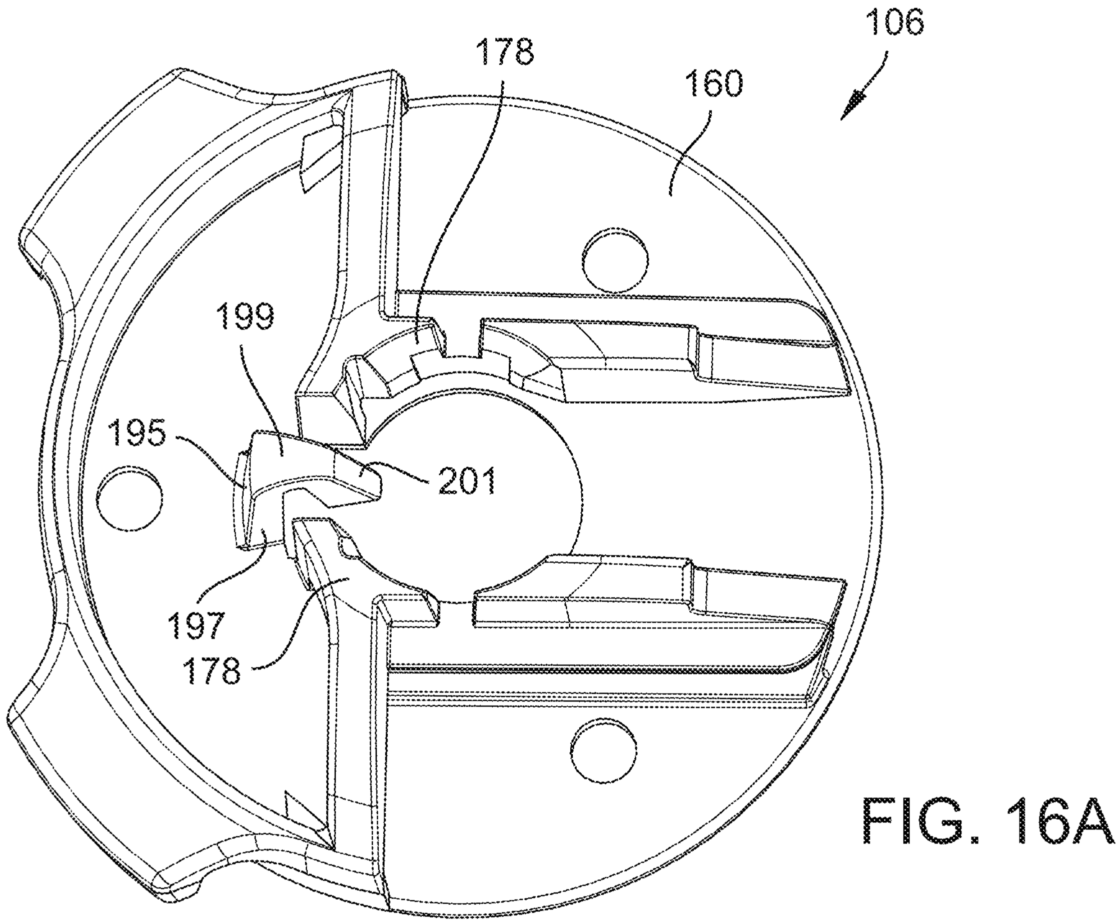
FIG. 16A depicts a perspective view of an example infusion set.
Figure 16B:
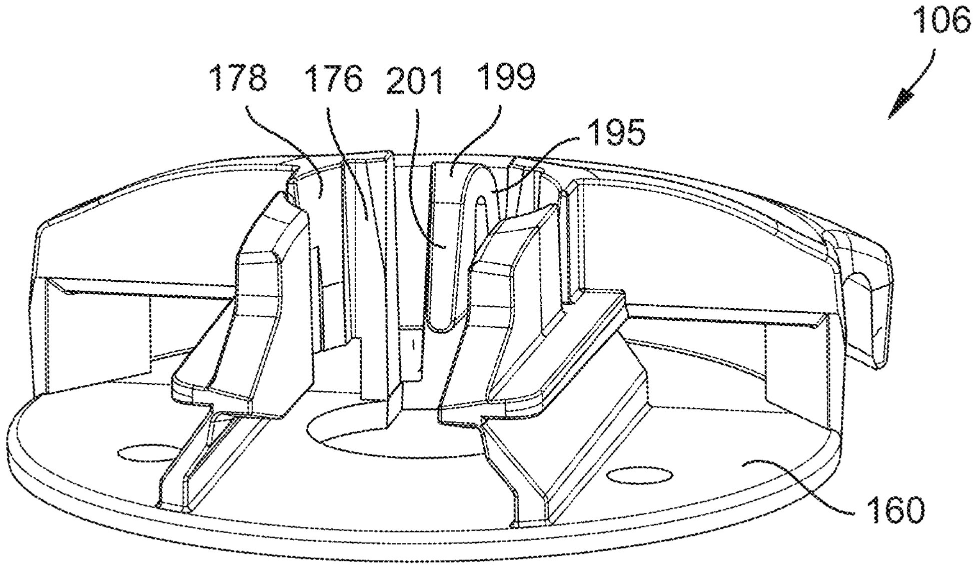
FIG. 16B depicts another perspective view of the example infusion set of FIG. 16A.

Referring now to FIGS. 16A and 16B, in certain embodiments, a base 106 may not include a receptacle wall 178 which has a cantilevered projection 180 (see, e.g., FIG. 4A) defined therein. As shown in FIGS. 16A and 16B, in some examples, a base 106 may include a retainer member 195 which extends from the platform 160. The retainer member 195 may be freestanding and not supported by or continuous with the receptacle wall 178. In FIGS. 16A and 16B, the retainer member 195 is depicted as a hooked body which extends from the platform and is located in an opening between the two sections of the receptacle wall 178. In other examples, a hooked body may not be used. Instead, a cantilevered member including a protuberance 182 such as a barb or ramp which engages a portion of a cannula subassembly 114 may be used. The hooked body may include a shank region 197 which is attached to and continuous with the platform 160. The shank region 197 may extend from the platform 160 to a bend region 199. The shank region 197 may be perpendicular to the platform 160 or may be angled so as to extend toward the receptacle 176. The hooked body may also include a catch segment 201 which extends from the bend region 199. The catch segment 201 may be disposed orthogonally to the shank region 197. In the example, the catch segment 201 extends at an acute angle with respect to the shank 197. For example, the catch segment 201 may be disposed at an angle of 35-40° with respect to the shank 197.

Upon introduction of a cannula subassembly 114 into the base 106, the septum housing 108 (see, e.g., FIG. 8A) may contact the catch segment 201 and resiliently deform the retainer member 195 such that the catch segment 201 is bent out of the way. After advancement of the cannula subassembly 114 into the receptacle 176 beyond a certain point, an engagement surface of the septum housing 108 may pass the end of the catch segment 201. At this point, the catch segment 201 may be free to spring back from its deflected position. The catch segment 201 may include a least a portion which overhangs the engagement surface of the septum housing 108 once sprung back to its unstressed state. Thus, the catch segment 201 may inhibit removal of the cannula subassembly 114 from the base 106. The engagement surface of the septum housing 108 may be any suitable engagement surface on any portion of the cannula subassembly 118. For example, the engagement surface may be a notch 186 (see, e.g. FIG. 5A) in the septum housing 108, a wall of a fenestration in the septum housing 108 (see, e.g. connector needle passage 222 of FIG. 6), a wall of a slot 390 included in the septum housing 108, or a salient 388 included as part of the septum housing 108.

Figure 17A:
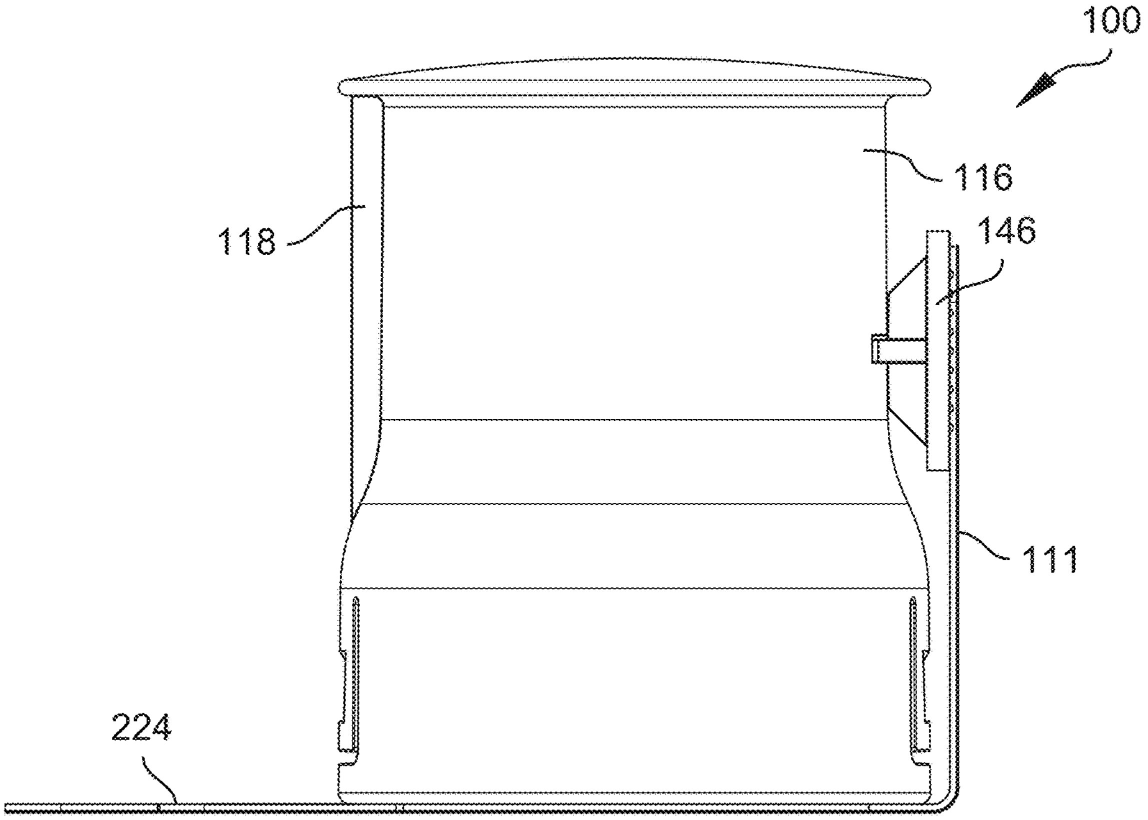
FIG. 17A depicts a side view of an example inserter assembly having an exemplary lock member installed therein.
Figure 17B:
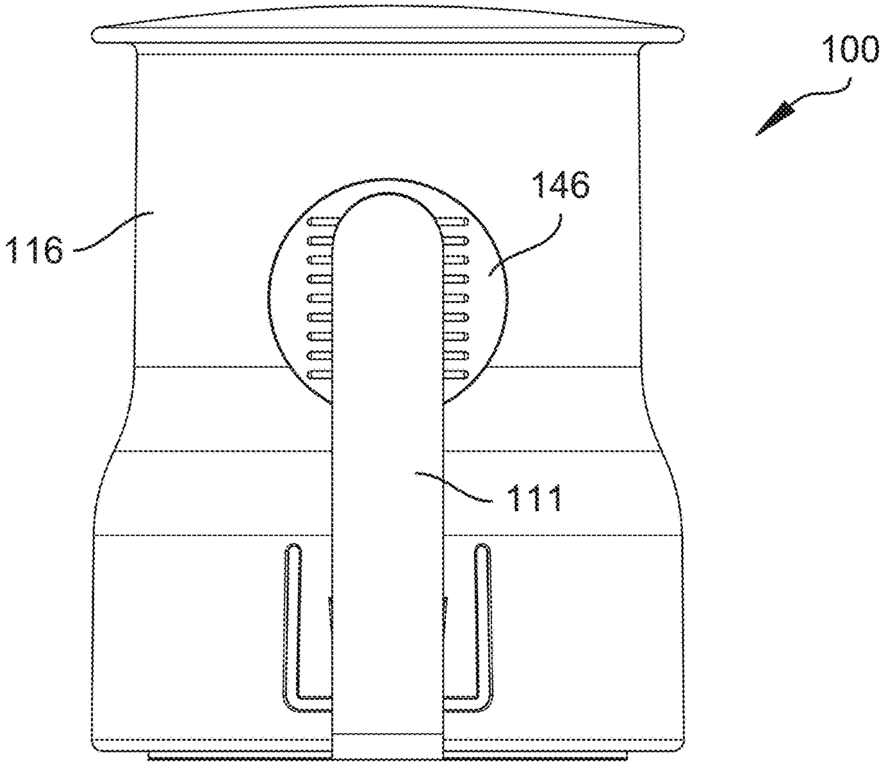
FIG. 17B depicts another side view of an example inserter assembly having an example lock member installed therein.

Referring now to FIG. 17A and FIG. 17B, two side views of an inserter assembly 100 are depicted. The inserter assembly 100 in FIG. 17B has been rotated clockwise 90° from its orientation in FIG. 17A. The example inserter assembly 100 is an assembled version of the exploded view depicted in FIG. 1A. The two views may be representative of the appearance of the inserter assembly 100 before use and after the inserter assembly 100 has been removed from its shipping/storage packaging. As shown, the exterior housing 116 of the inserter assembly 100 is visible and the lock member 146 is in place. Additionally, the adhesive backing 111 is present and covers an adhesive layer present on the bottom face 162 of the infusion set base 106. The adhesive backing 111 may include a gripping region 224 which may be in the form of a flange, tab, or other projection of backing material which extends beyond the footprint of the inserter assembly 100. This gripping region 224 may be grasped by a user and used to peel the adhesive backing 111 off of the infusion set 106. Once the backing 111 has been removed, the inserter assembly 100 may be placed against the desired infusion site using the raised rib 118 to aid in alignment. The lock member 146 may then be pulled out of the inserter assembly 100 to allow for the inserter assembly 100 to be actuated. As the example adhesive backing 111 is attached to the lock member 146, extraction of the lock member 146 may complete disassociation of the adhesive backing 111 from the inserter assembly 100. In the event that the user is unsatisfied with the location the inserter assembly 100 has been placed, the user may leave the lock member 146 in the inserter assembly 100 and pull the inserter assembly 100 off of the body. The presence of the lock member 146 may prevent actuation as this occurs and may allow the user to choose another infusion site.

Figure 18A:
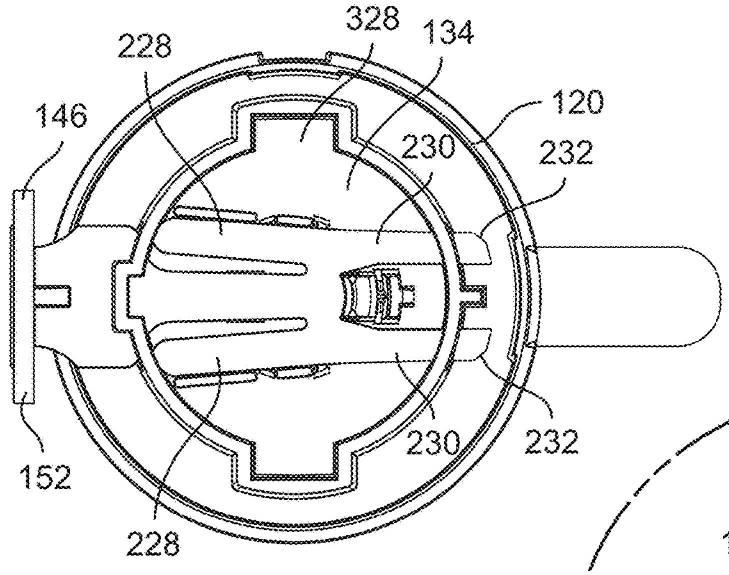
FIG. 18A depicts a top down view of an example inserter assembly with its exterior housing removed.
Figure 18C:
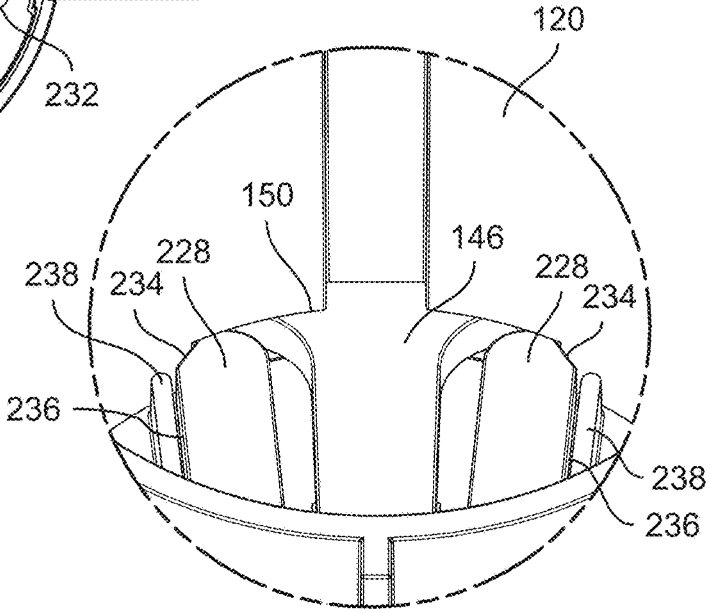
FIG. 18C depicts a detailed view of a portion of the FIG. 18B.
Figure 18B:
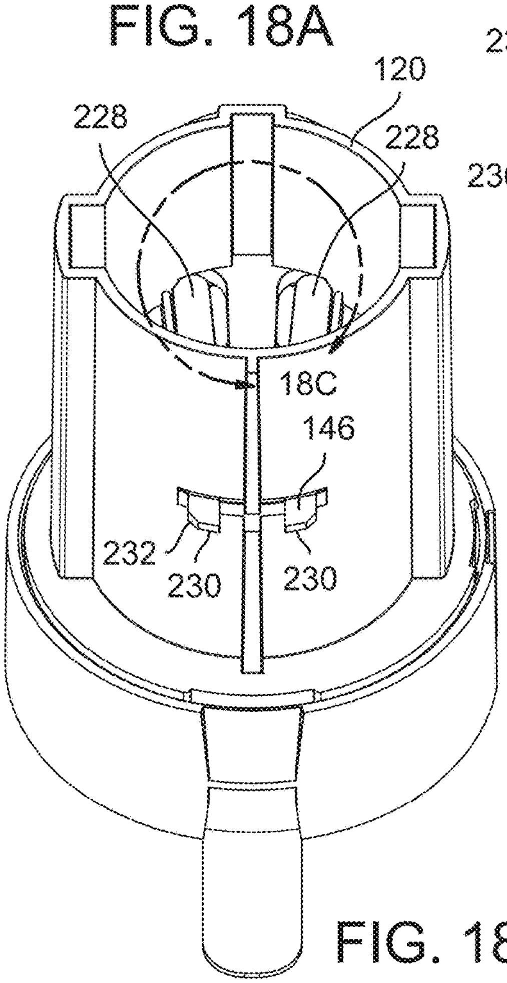
FIG. 18B depicts a perspective view of an example inserter assembly with its exterior housing removed.
Figure 19:
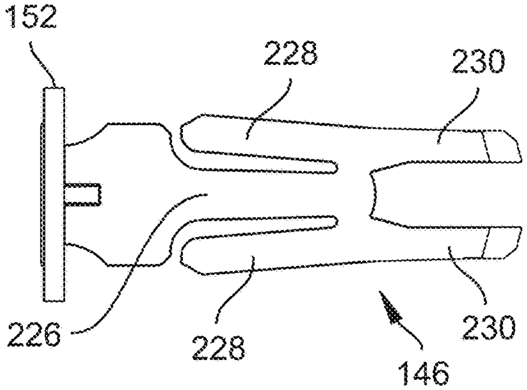
FIG. 19 depicts a top down view of an example lock member.

Referring now also to FIG. 18A-19, various views of the inserter assembly 100 with the exterior housing 116 removed and a view of the lock member 146 in isolation (FIG. 19) are depicted. As shown, when in place within the inserter assembly 100, the lock member 146 may act as a safety. The inserter assembly 100 may be designed such that it cannot fire until the lock member 146 has been removed. The lock member 146 may extend across the entire width of the interior housing 120 and be above other components of the inserter assembly 100. The lock member 146 may be directly adjacent to at least one of the other components so as to prevent its movement.

The lock member 146 may include a flange 152 which may be grasped to aid in extraction. The lock member 146 may also include a stem portion 226 which projects away from the flange 152. The stem portion 226 may support a number of arms 228, 230. In the example embodiment, the arms 228, 230 are arranged in an "H" like pattern and the stem portion 226 is connected to the arms 228, 230 via the cross piece of the "H". Arms 230 may reside in the fenestration 150 of the interior housing 120 most distal to the flange 152. Arms 230 may also include a chamfer feature 232 which may aid in guiding the lock member 146 during its installation into the inserter assembly 100.

As shown, arms 228 may be cantilevered so as to be able to deflect inward toward the stem portion 226. The distance between the outer edges of the arms 228 may be greater than the width of the fenestration 150 through which they pass when the lock member 146 is installed into the inserter assembly 100. During installation, the arms 228 may deflect toward the stem portion 226 to allow the arms 228 to pass through the fenestration 150. Once through the fenestration 150, the arms 228 may spring back outward to their unstressed state. Thus, as best shown in FIG. 18C, the width between the outer edges of the arms 228 may be wider than the width of the fenestration 150 when the lock member 146 is in place. This may ensure that some force may be required to remove the lock member 146 from the inserter assembly 100 and may inhibit the lock member 146 from being inadvertently dislodged. As shown, the arms 228 may include a chamfer region 234. The chamfer region 234 may abut a wall of the fenestration 150 of the interior housing 120 most proximal to the flange 152. The chamfer region 234 may aid in deflection of the arms 228 toward the stem portion 226 during extraction of the lock member 146 from the inserter assembly 100. Though an angled chamfer is shown, a rounded or curved region may be included in alternative embodiments.

In various examples, at least one component of the inserter assembly 100 may include at least one lock member constraining member such as raised bumpers 238. In the example embodiment, the bumpers 238 are included on the needle retractor 134 and extend from a top plate 328 thereof. The raised bumpers 238 may flank or be positioned aside or adjacent at least a portion of the lock member 146. The bumpers 238 may thus prevent any wobbling or pivoting of the lock member 146 within the inserter assembly 100. The bumpers 238 may also aid in redirecting the lock member 146 during installation if the lock member 146 is introduced into the inserter assembly 100 crookedly. A bumper 238 may also be provided to limit the depth which the lock member 146 may be pressed into the inserter assembly 100.

Figure 20A:
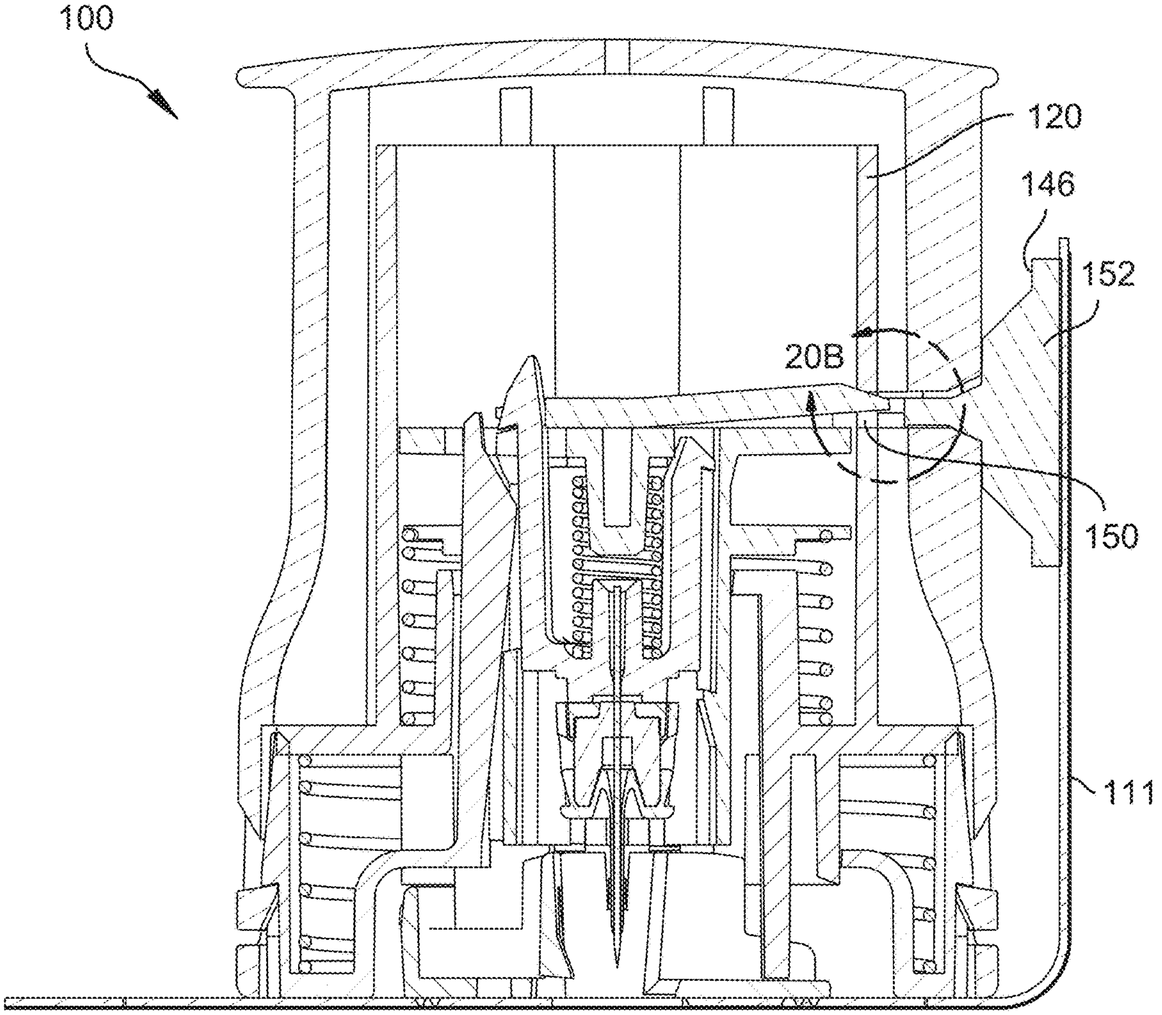
FIG. 20A depicts a cross sectional view of an example inserter assembly having an example lock member installed therein.
Figure 20B:
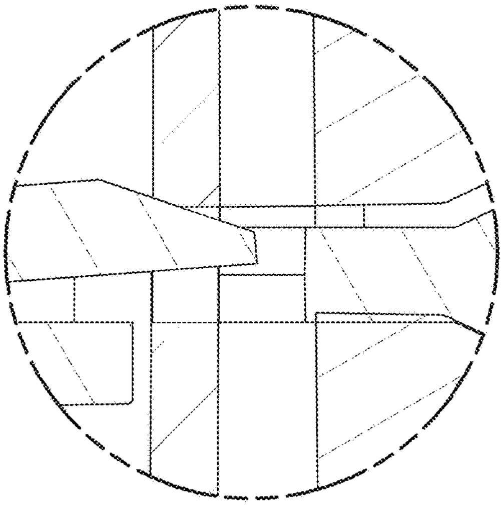
FIG. 20B depicts a detailed view of a portion of FIG. 20A.
Figure 21:
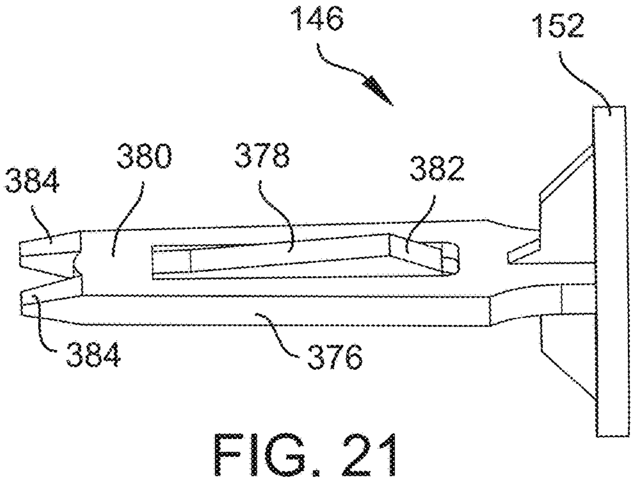
FIG. 21 depicts a perspective view of an example lock member.

Referring now also to FIG. 20A-21, various views of an inserter assembly 100 with an alternative lock member 146 and a view of the alternative lock member 146 in isolation (FIG. 21) are depicted. As above, when in place within the inserter assembly 100, the lock member 146 may act as a safety, preventing firing until the lock member 146 has been removed. The example lock member 146 extends across a portion, but not the entirety of the width of the interior housing 120 and is located above other components of the inserter assembly 100 to prevent movement. The interior housing 120 may only include one fenestration 150 instead of a set of opposing fenestrations 150.

The lock member 146 may include a flange 152 which may be grasped to aid in extraction. The lock member 146 may also include an appendage 376 which projects away from the flange 152. A tine 378 may be included within the appendage 376. The tine 378 is cantilevered to the appendage 376 at a portion of the tine 378 most distal to the flange. The tine 378 is also constructed to as to naturally project above a face 380 of the appendage 376 but be flexible when force is applied to the unsupported end of the tine 378. As shown, the unsupported end of the tine 378 includes a ramped region 382. The end of the appendage 376 most distal to the flange 152 may also include a chamfer feature 384 which may aid in guiding the lock member 146 during its installation into the inserter assembly 100. As the lock member 146 is installed into the inserter assembly 100, the top wall of the fenestration 150 may deflect the tine 378 toward the surface of the appendage 376 such that the tine 378 may pass through the fenestration 150. After completing introduction of the lock member 146, the tine 378 may spring back toward its initial unstressed state. Thus, as best shown in FIG. 20B, a portion of the tine 378 may be disposed above the top wall of the fenestration 150 when the lock member 146 is in place. This may ensure that some force may be required to remove the lock member 146 from the inserter assembly 100 and may inhibit the lock member 146 from being inadvertently dislodged. As shown, the ramped section 382 may abut the top wall of the fenestration 150. The ramped section 382 may aid in deflection of the tine 378 toward the surface 380 of the appendage 376 during extraction of the lock member 146 from the inserter assembly 100. Though an angled section 382 is shown, a rounded or curved region may be included in alternative embodiments. Lock member constraining features similar to the raised bumpers 238 shown in FIGS. 18A-19 may be included as well.

Figure 22:
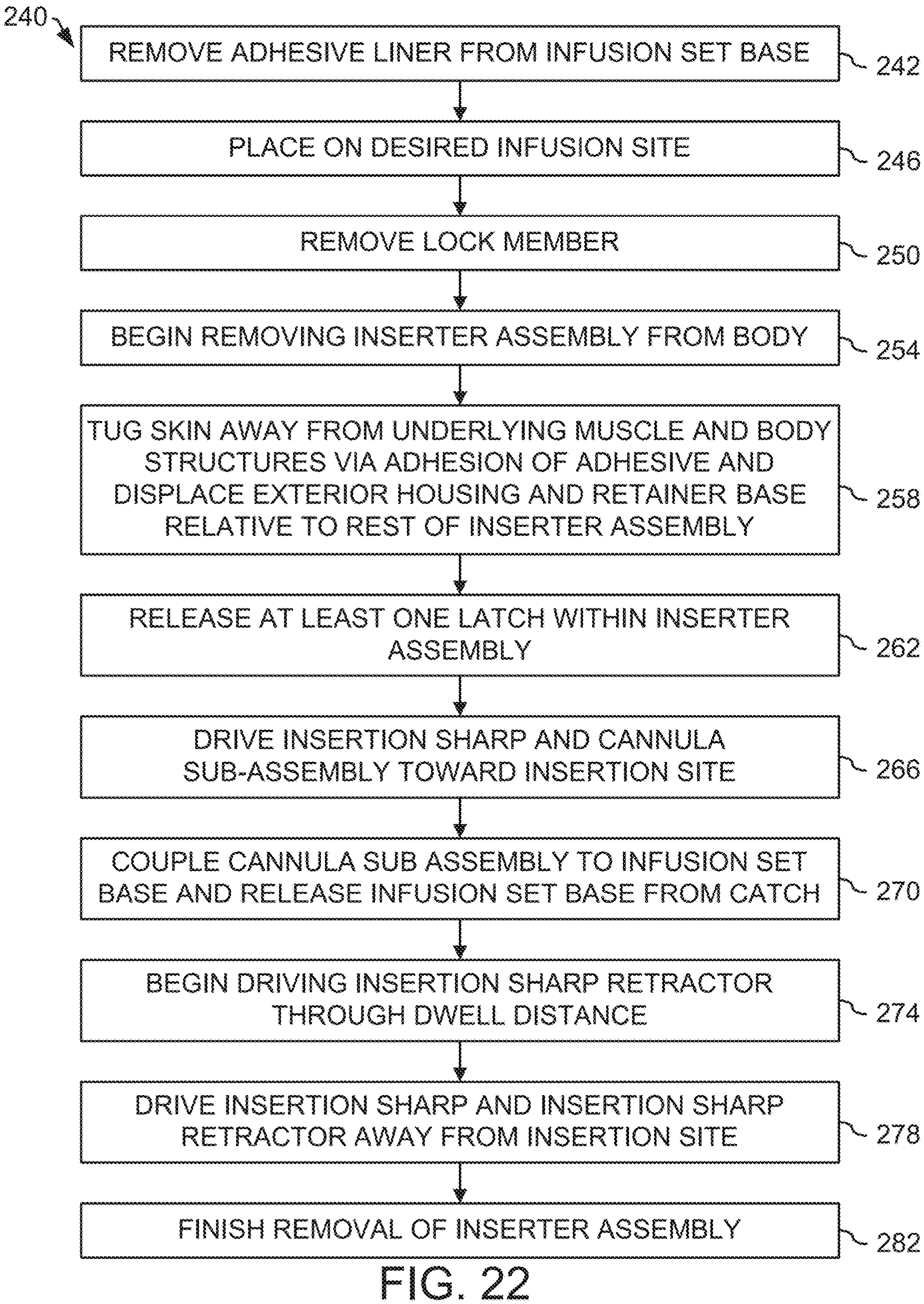
FIG. 22 depicts a flowchart detailing a number of actions which may be used to actuate an inserter assembly.

Referring now to FIG. 22, a flowchart 240 depicting a number of example actions which may be executed to place an infusion set 102 on a patient with an inserter assembly 100 is shown. Certain inserter assemblies 100, such as that shown in FIG. 1A, may be placed on the skin and be designed to prevent actuation until the skin has been displaced from its normal, resting position on the body. Actuation of an inserter assembly 100 may be precluded until some degree of displacement of the skin has occurred. Actuation of an inserter assembly 100 may be prohibited until a certain amount of relative displacement between components of an inserter assembly 100 has occurred. This relative displacement may be effected as the skin is lifted and the inserter assembly 100 is withdrawn away from the body. The adhesion of the base 106 of the infusion set 102 to the skin may cause certain components (e.g. at least one component coupled to the base 106) to be restricted in their displacement as the user withdraws the inserter assembly 100. As the inserter assembly 100 is withdrawn, the elasticity of the skin may exert a force on the base 106 (and any coupled component) pulling it toward or holding it closer to the body. At least one other component of the inserter assembly 100 may be free to displace or have greater freedom to displace as the inserter assembly 100 is removed. Relative movement may, in certain examples, be inhibited until a certain force is exerted against the base 106 by the skin. A trigger for the inserter assembly 100 may be kept from actuation until the skin has been tugged away from the rest of the body a distance sufficient to generate the force required to begin relative movement. Triggering may not be possible until a requisite amount of relative displacement has occurred.

In some embodiments, inserter assemblies 100 may be placed on the skin and trigger actuation as the inserter assembly 100 is lifted up so as to be removed. No other depression, twisting, squeezing, etc. of a trigger, button, housing sleeve or other portion of an inserter assembly 100 by a user may be needed to provoke the actuation, however, the actuation may still be under the control of the user. The relative movement of the free component(s) of the inserter assembly 100 with respect to the restricted component(s) may trigger actuation, by, for example, displacing or dislodging a latch and freeing one or more bias members to begin driving actuation. Thus, a trigger internal to the inserter assembly 100 may be actuated as a result of the removal action of the inserter assembly 100 from the body. From the perspective of a user, such an inserter assembly 100 may simply be placed on the skin and then withdrawn to execute placement of the infusion set 102.

In alternative embodiments, a discrete manual triggering action may be employed to trigger actuation of an inserter assembly 100. Any arrangement which would be apparent to one skilled in the art may be used to facilitate manual triggering. An inserter assembly 100 may include, for example, one or more button which when displaced may trigger actuation by dislodging a latch within the inserter assembly 100. Alternatively, a portion of the inserter assembly 100 may be deformable and squeezing the inserter assembly 100 may press a projection which displaces with the deformable section into a latch to dislodge the latch. The button or deformable section may, for instance, be included on exterior housing 116 in certain examples. A twisting action may be employed to trigger actuation of an inserter assembly 100. Such a twisting action of one portion of the inserter assembly 100 (e.g. the casing) relative to another (e.g. the remainder the inserter assembly 100) may sweep a projection of the inserter assembly 100 into a latch to dislodge the latch. In other embodiments, a pin or similar member may be pulled out of the inserter assembly 100 after the inserter assembly has been pulled away from the skin to trigger actuation. In embodiments including a lock member 146 (see, e.g., FIG. 19), the lock member 146 may be kept in place until the user has begun withdrawing the inserter assembly 100 from the skin. Actuation may be triggered when removal of the lock member 146 allows components of the inserter assembly 100 to displace relative to one another such that, for example, a latch may be released. Various combinations of manual triggering arrangements may also be used. A button press or squeeze followed by a twist or vice versa may trigger actuation for instance. The manual triggering action may not be possible until after the skin has been displaced from a resting position and/or until a certain degree of relative movement between the free and restricted components of the inserter assembly 100 has occurred. Any arrangement which would be apparent to one skilled in the art may be used to facilitate such a lockout. An interlock, for example, may prevent button displacement, twisting, squeezing, etc. until the skin has been displaced or until relative movement beyond a threshold magnitude has occurred. Alternatively, an interlock may block access to a latch within the inserter assembly 100 preventing it from being dislodged until the skin has been displaced or until relative movement beyond a threshold magnitude has occurred. In some embodiments, button displacement, twisting, squeezing, etc. may be possible but rendered impotent by the interlock until the skin has been displaced or until relative movement beyond a threshold magnitude has occurred. As one skilled in the art would appreciate, the inserter assembly 100 embodiments described herein could be otherwise modified to allow for various types of additional manual actuation schemes.

While such designs may make triggering actuation simple, intuitive, and more foolproof, other advantages may also be realized. For example, as the inserter assembly 100 is lifted, the inserter assembly 100 may be designed so as to tug the skin to which the base 106 of the infusion set 102 is attached away from the underlying muscle and other body structures. Thus, when inserted, the cannula 104 of the infusion set 102 may be more reliably placed within a subcutaneous layer of adipose tissue. This may reduce pain upon insertion, help minimize bruising, increase the potential body area over which infusion sites may be chosen, and may lead to more predictable absorption of agents such as insulin. The skin may also be pulled taut facilitating easy penetration of the insertion sharp 132 through the skin. As the skin is passively lifted along with the inserter assembly 100, no pneumatic vacuum is required to be generated. This may allow an inserter assembly 100 to be less complicated and made with fewer parts. Additionally, pneumatic seals either against the skin or within the inserter assembly 100 may be omitted. Lifting of the skin may be more reliably accomplished as the contour of the body at the infusion site (which could present a sealing challenge) may be largely irrelevant. Furthermore, no pinching of the skin may be needed to pull the skin away from the underlying structures. This may help to make the insertion more comfortable, may limit bruising, and may more reliably pull the skin away from underlying structures. The inserter assembly 100 may also ensure that insertion of the cannula 104 into the skin occurs at a prescribed orientation. The skin may be held in place so as to be parallel or perpendicular to a reference plane or axis (e.g. parallel to the bottom face 162 of the base 106 of the infusion set 102 or perpendicular to the axis of the insertion sharp 132 or insertion sharp displacement path) which moves with the inserter assembly 100. Thus, the angle of the inserter assembly 100 or path along which the inserter assembly 100 is pulled away with respect to the body may not alter insertion angle. Example embodiments shown herein depict an insertion angle which is substantially perpendicular to the skin, however, insertion at any angle (just over 0° to 90°, e.g. 30°, 45°, 60° etc.) may be similarly ensured by fixing the skin relative to a reference plane or axis which moves with the inserter assembly 100. Another potential benefit is that there may be less psychological concern associated with the triggering of the actuation. As depression, twisting, squeezing, etc. of some actuator by the user may not be necessary, there may be less anxiety built up in anticipation of triggering the actuation. The exact moment of actuation as the inserter assembly 100 is withdrawn may not be known to the user. This may help to limit psychological concerns and may lower perceived pain.

As shown in FIG. 22, in block 242, an adhesive liner or backing 111 may be removed from an infusion set base 102 retained within the inserter assembly 100. The inserter assembly 100 may then be placed on a desired infusion site in block 246. This may cause the adhesive on the infusion set base 102 to stick to the skin of the patient. It may be desirable to press the inserter assembly 100 against the skin to ensure a robust attachment of the adhesive to the skin. A lock member 146 may be removed from the inserter assembly 100 in block 250. The inserter assembly 100 may begin to be removed from the body in block 254. In block 258, the skin may be tugged away from underlying muscle and body structures via the adhesion of the adhesive. The exterior housing 116 and retainer base 140 may also be displaced relative to the rest of the inserter assembly 100 in block 258. In block 262, at least one latch within the inserter assembly 100 may be released. As discussed above, this may occur automatically, or as a result of some manual triggering action. An insertion sharp 132 and cannula sub assembly 114 may be driven towards the insertion site in block 266. The cannula sub assembly 114 may couple into the infusion set base 106 in block 270. Additionally, a catch may be released from the infusion set base 106 in block 270. The act of coupling the cannula sub assembly 114 into the set base 106 may cause release of the catch from the infusion set base 106. The insertion sharp retractor 134 may be driven through a dwell distance in block 274 (described in further detail later in the specification). The insertion sharp retractor 134 and insertion sharp 132 may be driven away from the infusion site in block 278. The removal of the inserter assembly 100 may be completed in block 282. With the removal of the inserter assembly 100 completed, the infusion set 102 may be fully assembled and in place on the infusion site. Additionally, the cannula 104 may be in place in the subcutaneous layer of skin.

Figure 23:
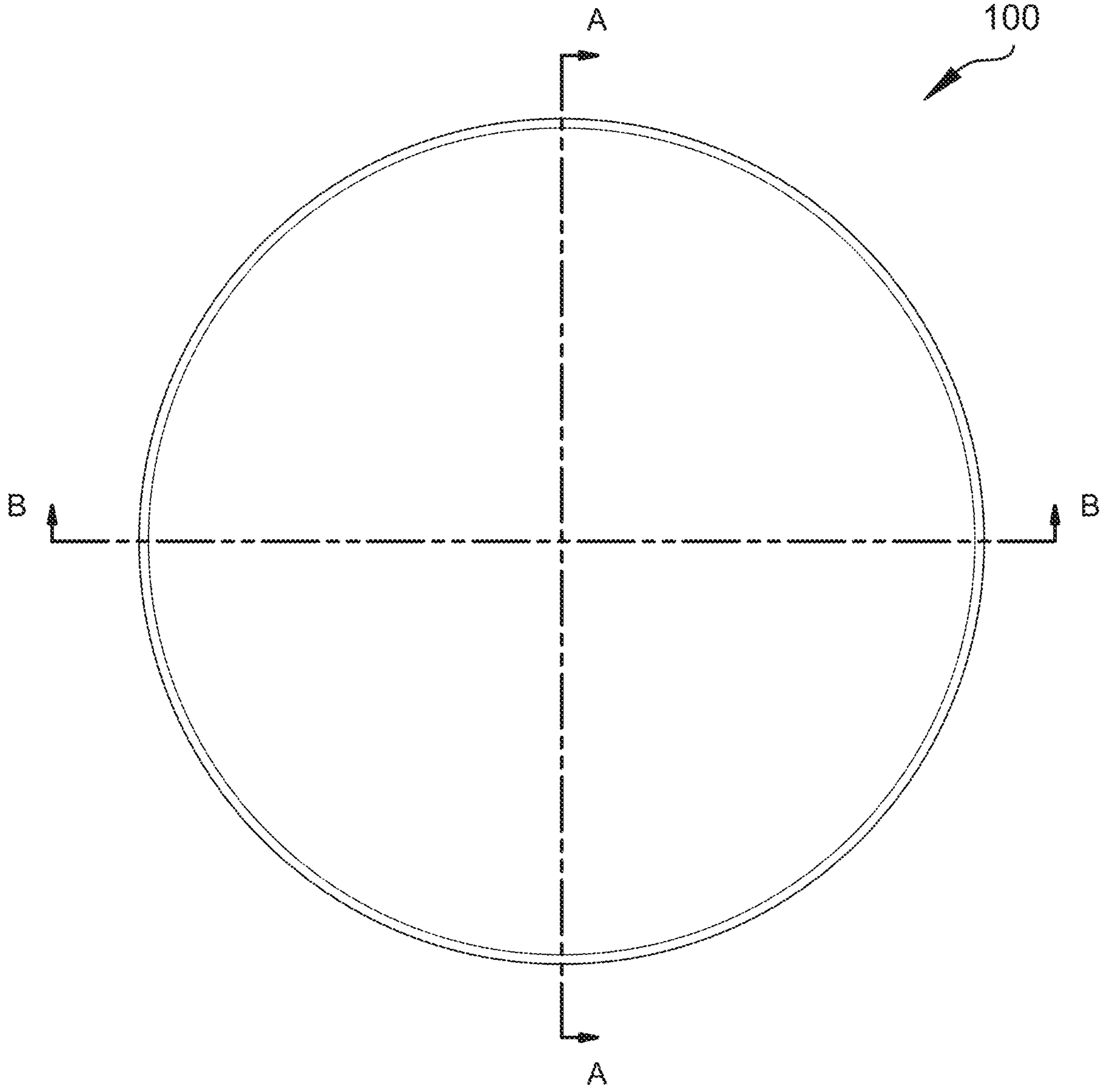
FIG. 23 depicts a top down view of an example inserter assembly.

Referring now to FIG. 23, a top down view of an inserter assembly 100 with a first and second cut plane superimposed thereon is depicted. The first cut plane is labeled A-A. The second cut plane is labeled B-B. This figure is provided for reference purposes in relation to a number of the forthcoming figures. Several of these figures are cross-sectional views of the inserter assembly 100 taken at the location of one or the other of these planes and depict the inserter assembly 100 in various stages of operation. Unless described otherwise, where one of the following inserter assembly 100 cross-sections is given with a figure numeral followed with the letter A, the figure is depicting a cross-section of the inserter assembly 100 at the location of plane A-A. Where one of the following inserter assembly 100 cross-sections is given with a figure numeral followed with the letter B, the figure is depicting a cross-section of the inserter assembly 100 at the location of plane B-B.

Figure 24A:
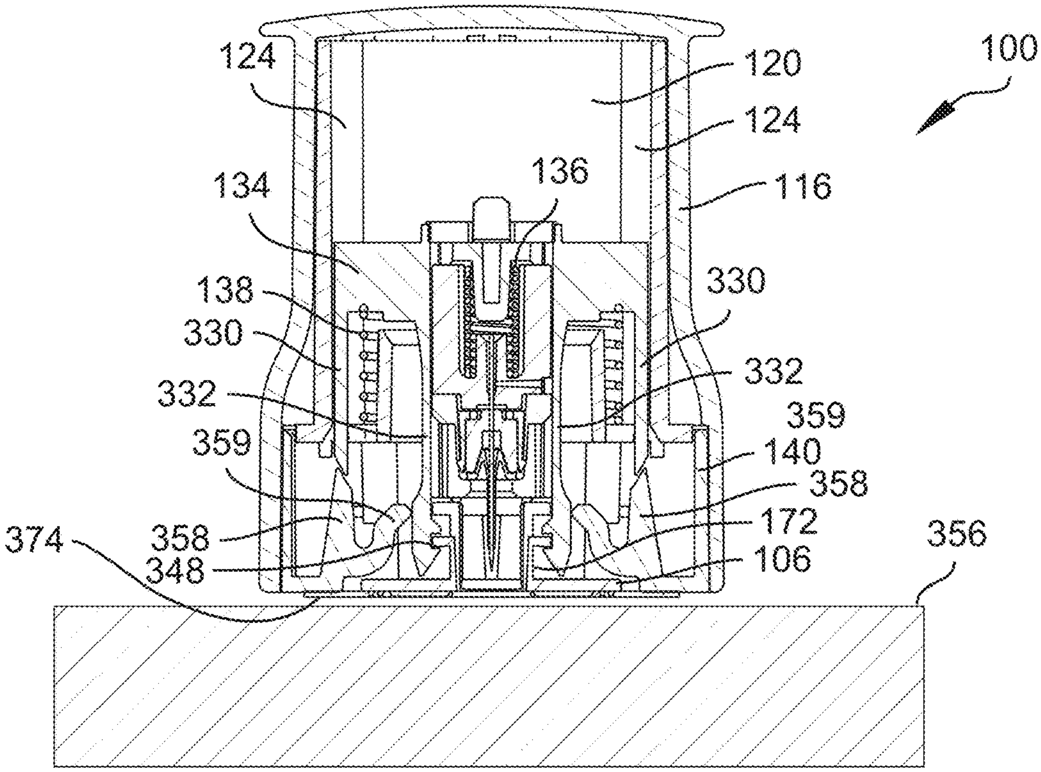
FIG. 24A-B depict cross-sectional views of an exemplary inserter assembly about to be applied to a user's skin.
Figure 24B:
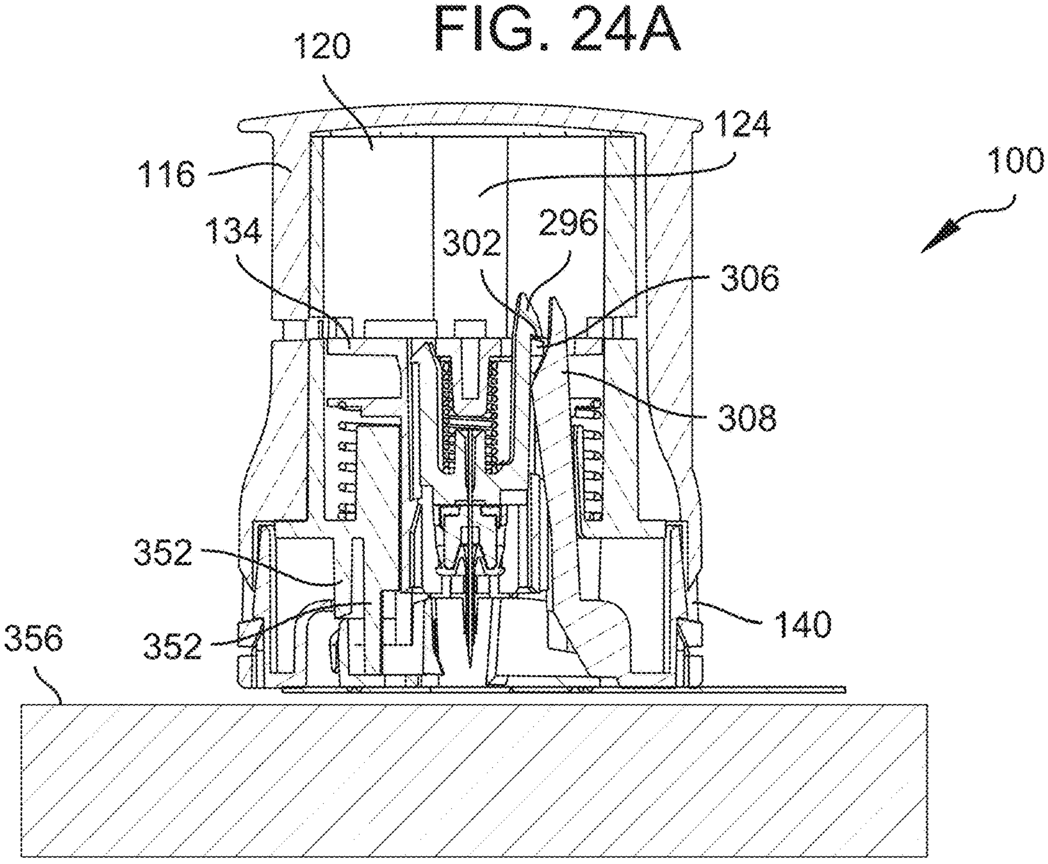
Figure 25:
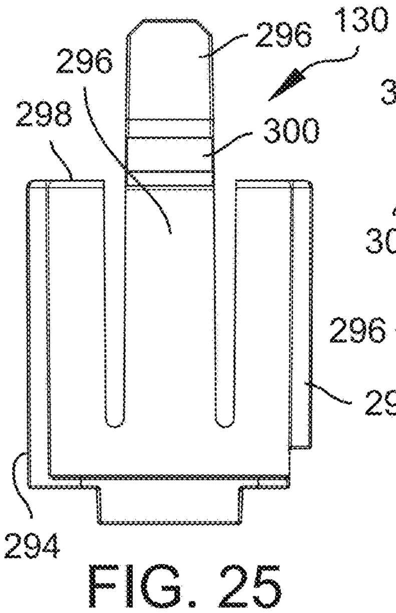
FIG. 25 depicts a side view of an exemplary sharp holder.
Figure 26:
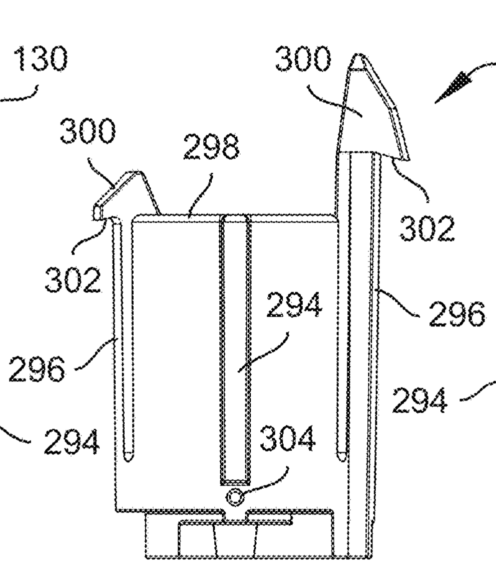
FIG. 26 depicts another side view of the exemplary sharp holder shown in FIG. 25.
Figure 27:
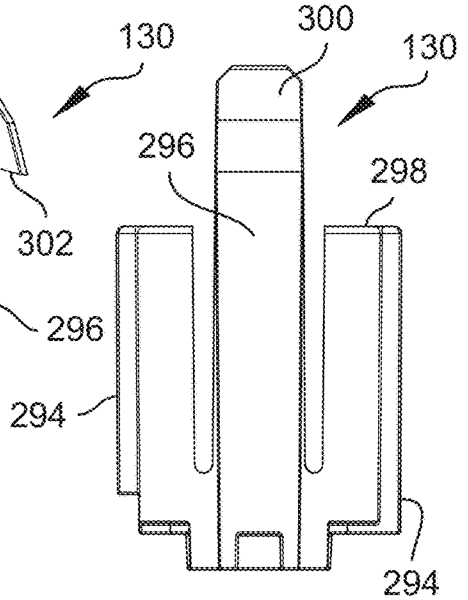
FIG. 27 depicts yet another side view of the example sharp holder shown in FIG. 25.
Figure 28:
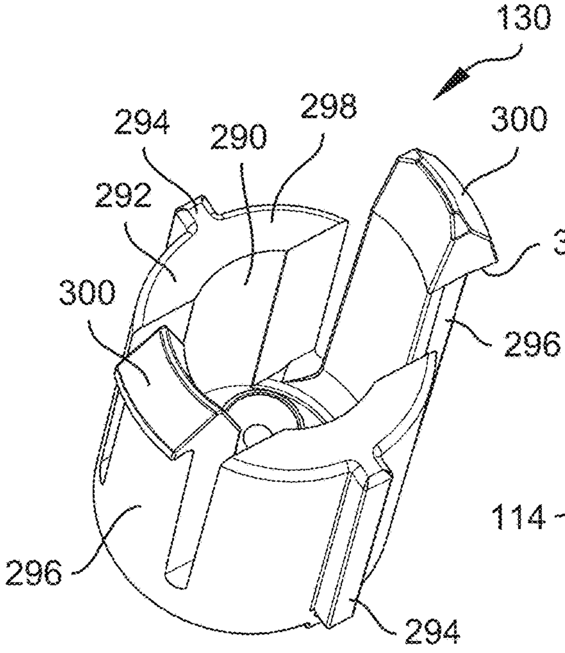
FIG. 28 depicts a perspective view of the example sharp holder shown in FIG. 25.
Figure 29:
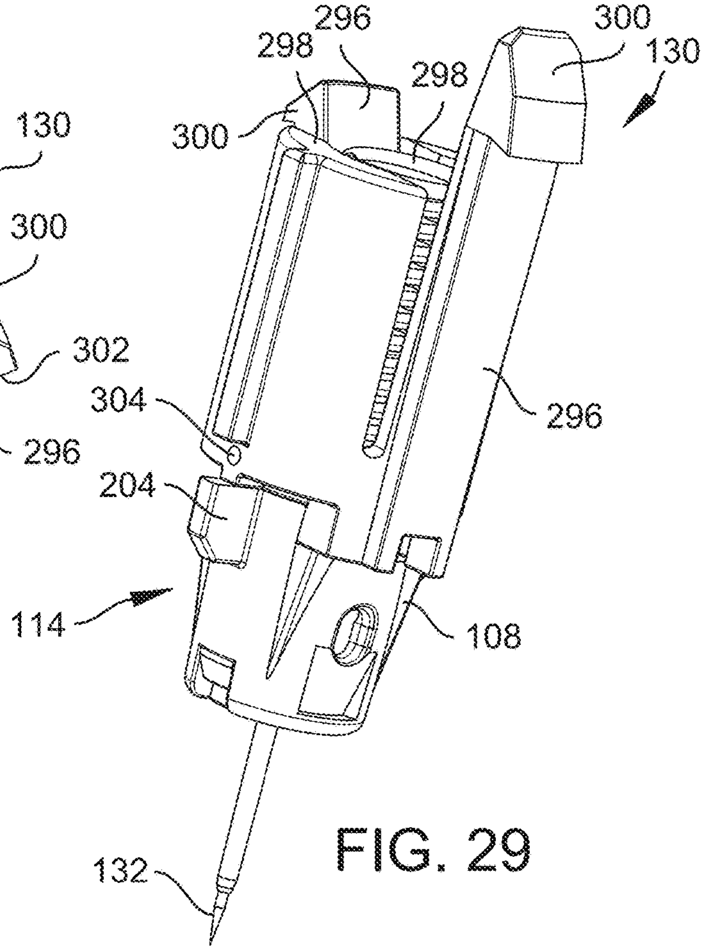
FIG. 29 depicts a perspective view of a sharp holder, sharp, and cannula assembly.
Figure 30:
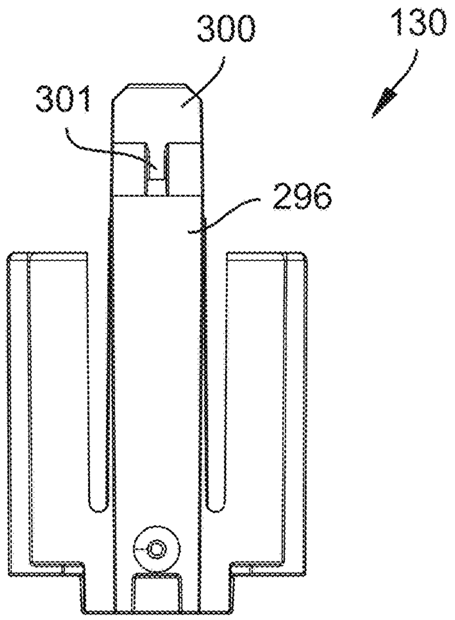
FIG. 30 depicts a side view of an example sharp holder.
Figure 31:
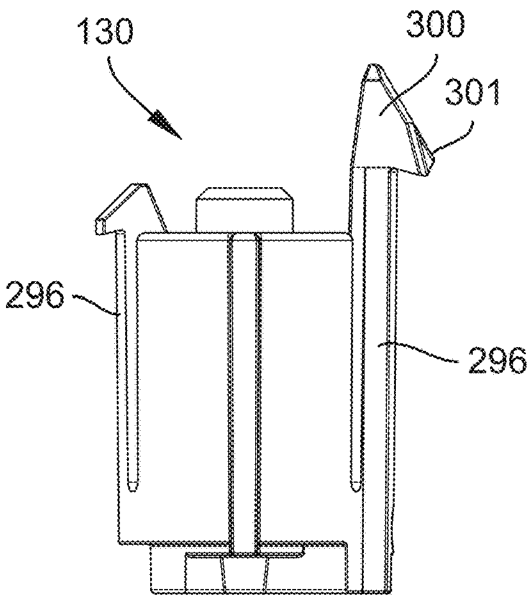
FIG. 31 depicts another side view of the example sharp holder of FIG. 30.
Figure 32:
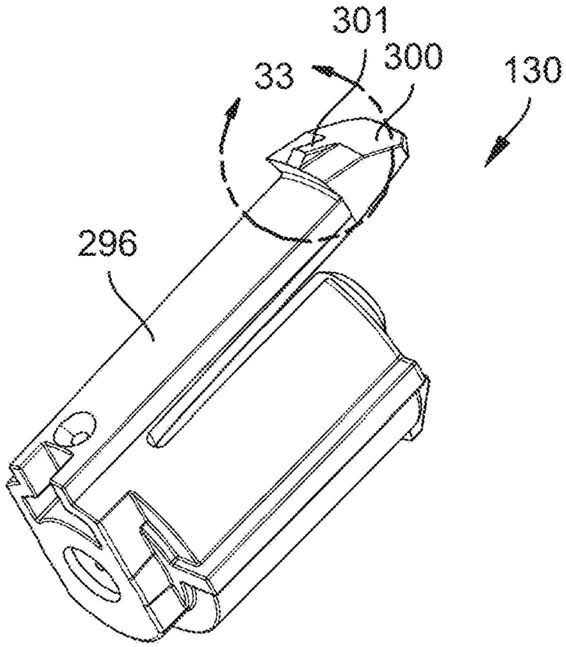
FIG. 32 depicts a perspective view of the example sharp holder of FIG. 30.
Figure 33:
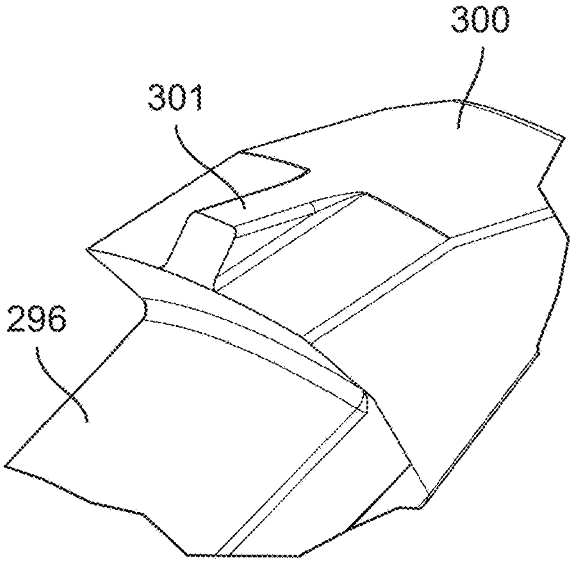
FIG. 33 depicts a detailed view of the indicated region of FIG. 32.

Referring now to FIG. 24A-B, two cross-sectional views of an inserter assembly 100 are depicted. The inserter assembly 100 is depicted just as it is about to be applied to the skin 356. The lock member 146 (see, e.g., FIG. 21) and adhesive backing 111 (see, e.g., FIG. 1A) have been removed in FIGS. 24A-B. The adhesive 374 is depicted on the bottom face 162 of the infusion set base 106. As shown, both springs 136, 138 may be in an energy storing state, which in this particular embodiment is a compressed state. In the example, spring 136 serves as an insertion driving bias member while spring 138 serves as an insertion sharp retraction driving bias member. Spring 136 is held in compression between the insertion sharp holder 130 and the insertion sharp retractor 134 and when released drives the sharp holder 130 and components carried there on from a raised state to a forward state. Spring 138 is held in compression between the interior housing 120 and the sharp retractor 134. Upon release, spring 138 drives the sharp retractor 134 and sharp holder 130 from a post insertion state to a retracted state.

Referring now also to FIGS. 25-29, a number of views of a sharp holder 130 are depicted. The sharp holder 130 may include a bias member receiving bay 290 in which the spring 136 may be disposed. The sharp holder 130 may also include a wall 292 which surrounds the bias member receiving bay 290. The wall 292 may include two projections 294 on an exterior face thereof. The two projections 294 in the example embodiment are rails which are disposed opposite one another on the sharp holder 130. These rails may ride along guides 354 (see, e.g., FIG. 35A, B) on a portion of the sharp retractor 134. The projections 294 may extend from the sharp holder 130 so as to match the width of the cannula sub assembly 114 at a plane of the cannula sub assembly 114 including the ears 204 of the septum housing 108.

In various embodiments, the wall 292 may also include interrupted regions which create one or more cantilevered arms 296. In the example embodiment, the cantilevered arms 296 are disposed opposite one another on the sharp holder 130. One of the cantilevered arms 296 may have a greater length than the other of the cantilevered arms 296. In other embodiments, both cantilevered arms 296 may be identical mirror images (see, e.g., FIG. 43C) to allow for easier assembly of the inserter assembly 100. Both of the cantilevered arms 296 may extend above a top face 298 of the remainder of the wall 292. Each of the cantilevered arms 296 may include a protuberance 300 disposed at an unsupported or terminal end thereof. A ledge section 302 may be defined by a portion of each of the protuberances 300. At least one of the ledges 302 may extend substantially perpendicular to the cantilevered arms 296. At least one of the ledges 302 may be angled with respect to the cantilevered arm 296 on which it is included such that the undercut region has a triangular cross section. In the example embodiment, the ledge 302 on the longer of the two cantilevered arms 296 is so undercut. A sharp holder 130 may also include a port 304. The port 304 may be used to supply glue or adhesive into the sharp holder 130 to fixedly retain the insertion sharp 132 into the sharp holder 130.

An alternate embodiment of a sharp holder 130 is shown in FIGS. 30-33. As shown, the longer of the two cantilevered arms 296 of the sharp holder 130 includes a protuberance 300 with a ridge 301. The ridge 301 may be medially located on the protuberance 300 though may be located. As shown, the protuberance 300 may be double beveled. The portion of the protuberance 300 adjacent the ledge section 302 may have a steeper bevel than the portion of the protuberance 300 distal to the ledge section 302. The ridge 301 may be formed on the portion of the protuberance adjacent the ledge section 302. In the example, the ridge 301 is formed as an extension of the bevel angle from the portion of the protuberance 300 distal to the ledge section 302 which extends to the portion of the protuberance 300 adjacent the ledge section 302. Such a ridge 301 may be included on any of the sharp holder 130 embodiments depicted herein.

As best shown in FIG. 24B, the ledge 302 on the longer of the cantilevered arms 296 may rest on a catch 306. The catch 306 in the example embodiment is included on the sharp retractor 134. This may inhibit the release of energy stored in spring 136 and hold the spring 136 under compression in the example embodiment. The catch 306 may have an angle which cooperates with any angle of the ledge 302 to firmly retain the ledge 302 on the catch 306. A finger 308 extending from the base retainer 140 of the insertion assembly 100 may extend through a void 322 (see, e.g., FIG. 35C) adjacent the catch 306. Displacement of the finger 308 relative to the catch 306 may cause disengagement of the ledge 302 with the catch 306. Though depicted as an upstanding finger 308, other types of actuation projections may be used. Additionally, in some embodiments, the finger 308 or other actuation projection may be included on another part of the inserter assembly 100. For example, a finger 308 may project from the interior surface of the top face of the exterior housing 116.

Figure 34:
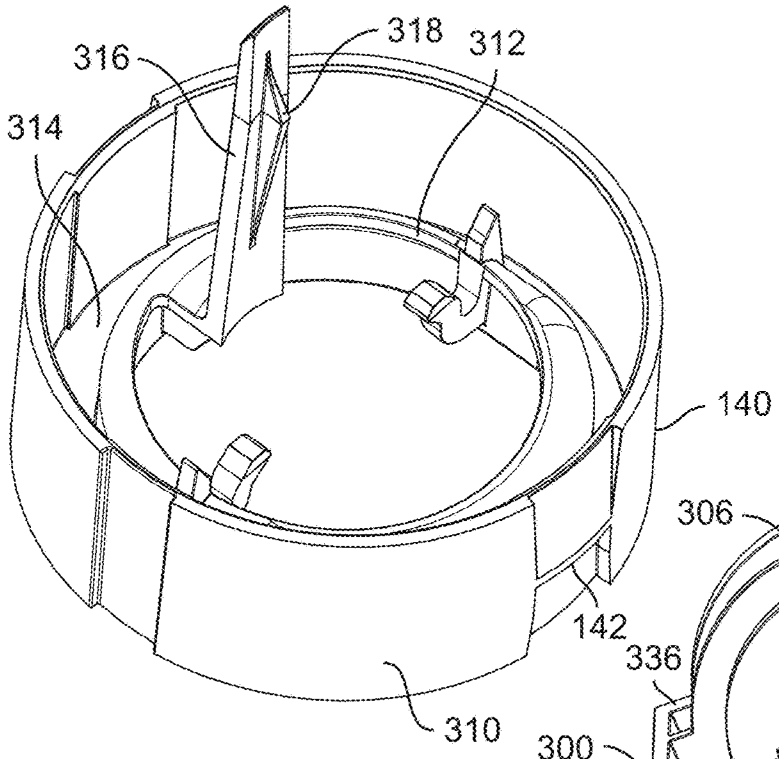
FIG. 34 depicts a perspective view of an example retainer base.
Figure 35B:
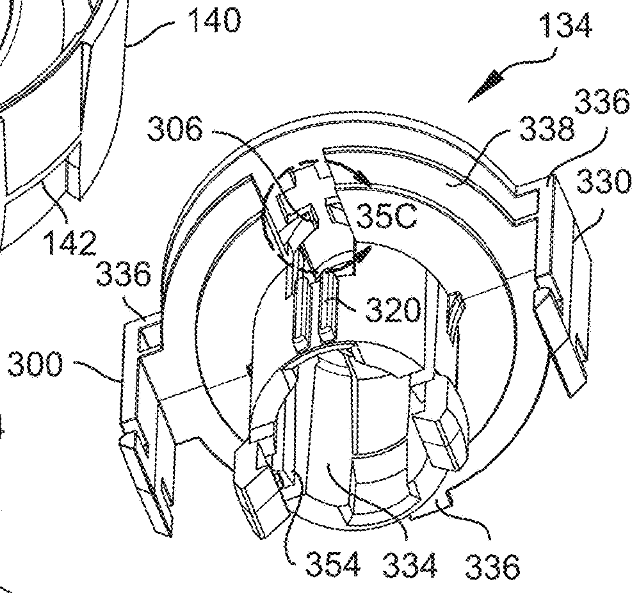
FIG. 35B depicts another perspective view of the exemplary sharp retractor shown in FIG. 35A.
Figure 35A:
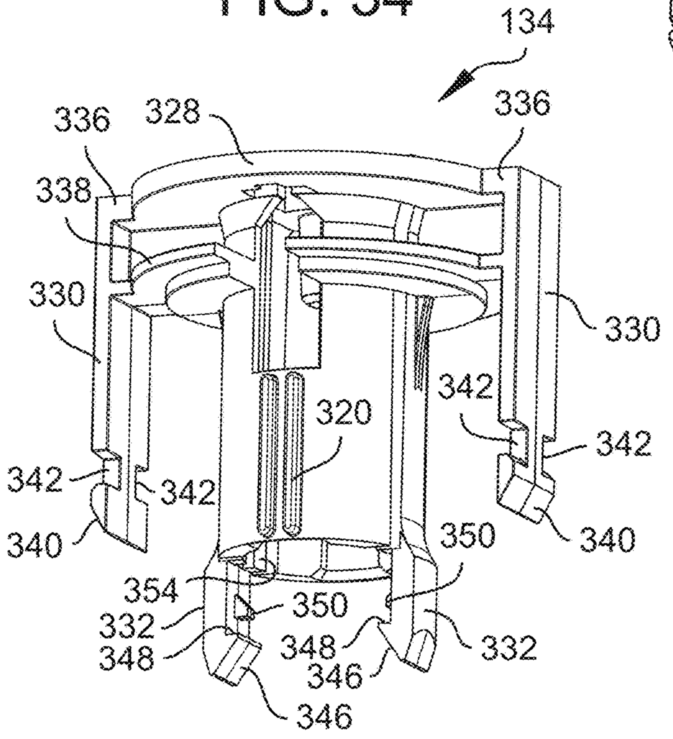
FIG. 35A depicts a perspective view of an example sharp retractor.
Figure 35C:
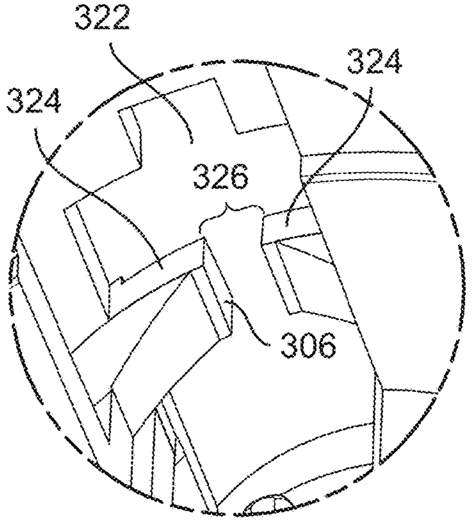
FIG. 35C depicts a detailed view of a portion of FIG. 35B.

Referring now also to FIGS. 34-35C, a number of views of a retainer base 140 and sharp retractor 134 are depicted. As shown, the finger 308 of the retainer base 140 (FIG. 34) is formed as a continuous part of the retainer base 140. The example retainer base 140 includes a first ring portion 310 and a second ring portion 312. The first ring portion 310 and second ring portion 312 are connected by an intermediary region 314 and may be concentric with one another. The intermediary region 314 may be generally flat and may serve as a skin contacting portion of the inserter assembly 100 which is substantially level with the bottom face 162 of the infusion set base 106. The finger 308 extends from the second ring portion 312. As shown, the finger 308 includes an upstanding segment 316 and a fin 318.

In various embodiments, the sharp retractor 134 may include a guide 320 along which the fin 318 may slide during assembly. The guide 320 may also, in certain embodiments, ride along the fin 318 during at least a portion of the retraction of the sharp retractor 134. The example guide 320 is formed as two raised parallel ribs. The catch 306 includes two supports 324 which the ledge 302 of the cantilevered arm 296 may engage with. The supports 324 may include a gap 326 therebetween. The gap 326 may have a width equal to or wider than the width of the fin 318. The fin 318 may be advanced through the gap 326 during lifting of the inserter assembly 100 from the skin 356. This may cause the fin 318 to come into abutment with the protuberance 300 on the cantilevered arm 296 and force the cantilevered arm 296 to bend inward. Once the fin 318 has progressed a certain distance, the cantilevered arm 296 may be deflected to the point that the ledge 302 no longer engages the catch 306 and the spring 136 may be released. The location of the fin 318 on the finger 308 and/or the height of the finger 308 may be adjusted to alter the displacement distance at which release of the ledge 302 from the catch 306 occurs. In embodiments where the protuberance 300 includes a ridge 301 (see, e.g., FIGS. 30-33), the ridge 301 may be sized so as to fit through the gap 326. Thus, the ridge 301 may increase the total amount that the cantilevered arm 296 may be deflected by the fin 318 and provide extra assurance that ledge 302 is fully displaced off of the catch 306. As a result, the range of acceptable tolerances on various features related to the catch 306 and sharp holder 130 may be greater.

Still referring to FIGS. 24A-B in conjunction with FIGS. 34-35B, spring 138 may be held in an energy storing state by at least one latching engagement as well. As shown, the sharp retractor 134 may include a first set of arms 330 and a second set of arms 332. The first set of arms 330 may extend from a top plate 328 of the sharp retractor 134. These arms 330 may extend substantially parallel to one another and may be disposed in opposing fashion on the sharp retractor 134. Additionally, the first set of arms 330 may extend laterally to a central cavity 334 of the sharp retractor 134. In some embodiments, the first set of arms 330 may be attached to the top plate 328 of the sharp retractor 134 at outcropped regions 336 of the top plate 328. The arms 330 may thus fit within channels formed by rails 124 of the interior housing 120 to prevent rotation and guide any displacement of the sharp retractor 134 during actuation. Additionally, outcropped regions 336 may be included in an asymmetric fashion on the sharp retractor 134 to ensure that the sharp retractor 134 is assembled into the inserter assembly 100 in a prescribed orientation. The first set of arms 330 may be cantilevered and attached to the sharp retractor 134 at the top plate and a second plate 338 which may extend parallel to the top plate 328 and below the top plate 328. Thus, the arms 330 may form resilient projections which may deflect if sufficient force is exerted against them. The unsupported end of the arms 330 may include a curved or ramped section 340. This section 340 may abut against a complimentarily contoured face of deflector members 358 to facilitate and or direct such deflection. A notch or pair of notches 342 may also be present on each of the first set of arms 330. In the example, each arm 330 includes a pair of notches 342 located near the unsupported ends of the arms 330.

Figure 36:
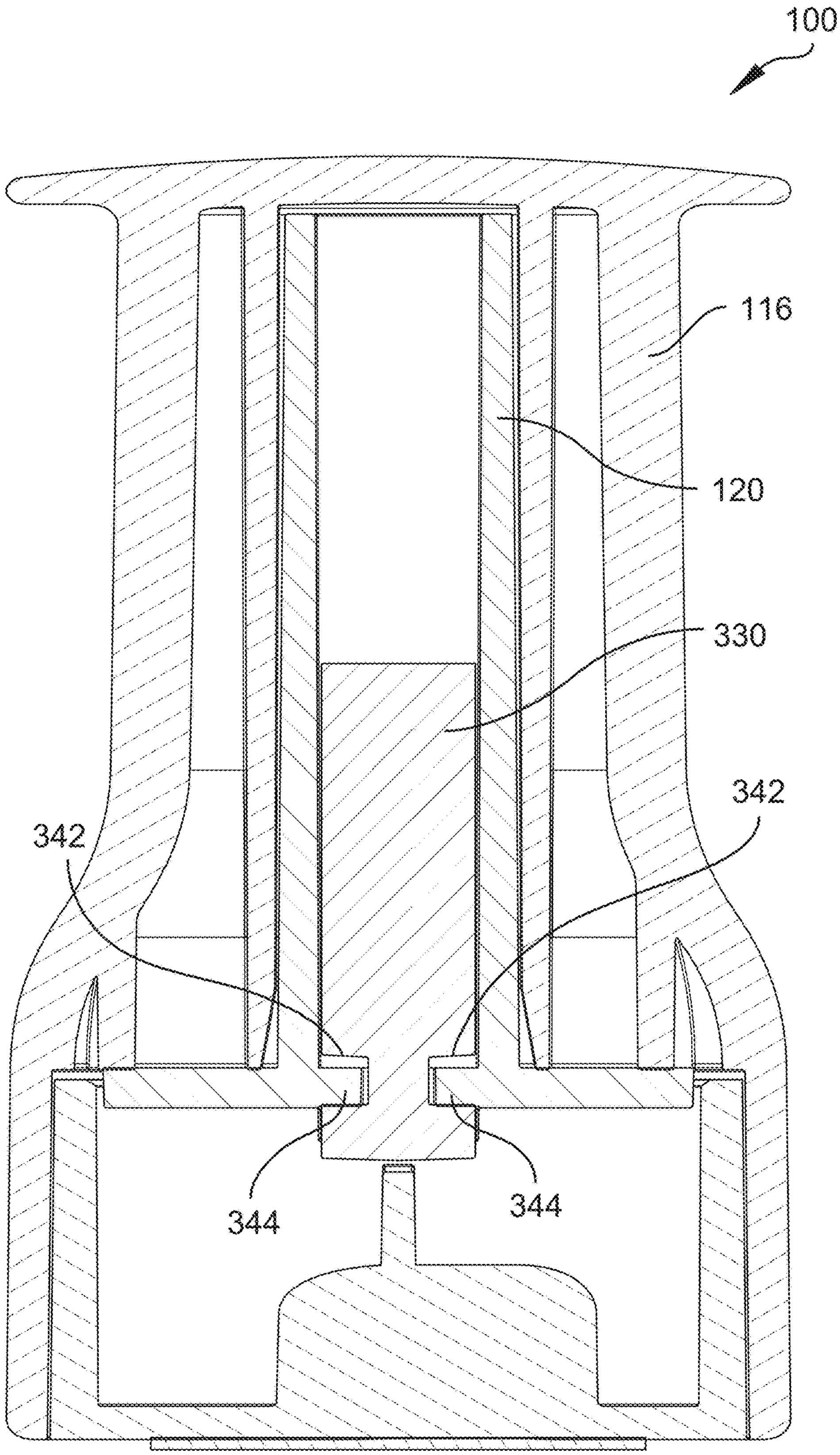
FIG. 36 depicts a cross-sectional view of an example inserter assembly taken through an arm included on a sharp retractor of the inserter assembly.

FIG. 36 depicts a cross-section of an inserter assembly 100 taken through a plane in one of the arms 330 which extends along the length of the arm 330. As shown, each of the one or more notches 342 may engage with a cooperating projection 344. The cooperating projection 344 may be included on the interior housing 120. Thus, the interaction of the notch(es) 342 and cooperating projection(s) 344 may maintain the spring 138 under compression and serve as a retraction prevention latch. This may be particularly helpful during assembly as the infusion set base 106 may not be in place and the spring 138 may otherwise be free to relax. Additionally, this engagement may ensure that the top plate 328 of the sharp retractor 134 is disposed slightly below the fenestrations 148, 150 to allow for introduction of a lock member 146. Though notches 342 are shown, the arms 330 and interior housing 120 may engage in other ways. For example, the arms 330 or interior housing 120 may include a projection which forms a ledge. The ledge may engage with a catching recess in the other of the arms 330 or interior housing 120.

Again referring now primarily to FIGS. 24A-B in conjunction with FIGS. 34-35B, in some embodiments additional latches may be included in an inserter assembly 100 which aid in maintaining one of the springs 136, 138 in an energy storing state. In the example embodiment, spring 138 is held in an energy storing state by an additional latch arrangement. As shown, the second set of arms 332 of the sharp retractor 134 extend from a bottom portion of the wall defining the central cavity 334. The second set of arms 332 may be disposed in opposing relationship to one another and may be cantilevered. Each of the second set of arms 332 may include a protuberance 346 disposed at an unsupported end thereof. Each protuberance 346 may form a ledge 348 on the arm 332 on which it is included. Additionally, the arms 332 may include a nub 350 or raised ramp which increases in thickness as distance from the cavity 334 increases. The nub 350 may be disposed intermediate the unsupported end of the arm 332 and its attachment point to the remainder of the sharp retractor 134.

As best shown in FIG. 24A the ledge 348 may capture a portion of the infusion set base 106. Specifically, the ledges 348 may catch on an outcropped portion of the infusion set base 106. The base 106 may include rails, step features, nubs or any other suitable protrusions to provide a complimentary catch surface for the ledges 348. In certain embodiments, the ledges 348 may catch on guides 172 (see, e.g., FIG. 4A) of the infusion set base 106. Thus the infusion set base 106 may be retained within the inserter assembly 100. Ledges 348 may be angled with respect to the cantilevered arm 332 on which it is included such that the undercut has a triangular cross section. The portion of, for example, the guides 172 (or any other catch feature) on which each ledge 348 catches may be angled in a cooperating manner to help ensure a robust engagement. The retainer base 140 (or the exterior housing 116 in embodiments like that shown in FIG. 38A-B) may include retaining projections 359 which may abut or nearly abut arms 332 and hold the arms 332 from displacement out of engagement with the infusion set base 106 prior to inserter assembly 100 actuation. This may help prevent any accidental firing of the inserter assembly 100.

In certain embodiments, only one arm 332 may be included. In some embodiments, the arms 332 on the sharp retractor 134 may not engage the infusion set base 106. The arms 332 may engage a portion of the interior housing 120 so as to prevent premature retraction of the sharp retractor 134. The interior housing 120 may also include latch which may interface with the guide 172 or another cooperative portion of the infusion set base 106 to retain the infusion set base 106 in place.

A number of standoffs or alignment projections 352 may be included in the inserter assembly 100 to aid in ensuring that the infusion set base 106 is assembled into the inserter assembly 100 in a desired orientation. The standoffs 352 may be disposed on an interior housing 120 of the inserter assembly 100 as shown. While retained by the arms 332 of the sharp retractor 134, the infusion set base 106 may be held such that surfaces of the infusion set base 106 are adjacent to the standoffs 352. This may prevent infusion set base 106 and the sharp retractor 134 on which it is retained from displacing into the inserter assembly 100 due to the presentation of a mechanical interference by the standoffs 352. As a consequence, the catching of the ledges 348 of the arms 332 on the infusion set base 106 may also aid in holding the spring 138 in an energy storing state. The standoffs 352 may also ensure that the infusion set base 106 is positioned within the inserter assembly 100 such that the adhesive 374 may be pressed against the skin 356. In the example, the standoffs 352 ensure that the infusion set base 106 is substantially even with the skin contact face on the retaining base 140.

With the infusion set base 106 so positioned, the infusion set base 106 may also act as a protective barrier. As the cannula sub assembly 114 and insertion sharp 132 may be internal to the inserter assembly 100, when the infusion set base 106 in the initial retained position, the user may be protected from accidental contact with the insertion sharp 132. This may additionally help to keep the cannula 104 or insertion sharp 132 from coming into contact with contaminants. Though a void for receipt of the cannula sub assembly 114 may extend through the entirety of the infusion set base 106, the void may be sized to prevent finger ingress (e.g. have a cross-section smaller than that of a finger). Thus the infusion set base 106 may present an obstacle which blocks unintentional access to the insertion sharp 132 and cannula 104. Additionally, as the cannula subassembly 114 is internal to the inserter assembly 100, any adhesive backing 111 provided on the infusion set base 106 need not include an interruption to allow for passage of the cannula 104 therethrough. Thus, the void in the infusion set base 106 for the cannula subassembly 114 may be blocked by the adhesive backing 111 until just prior to use. This may further prevent finger ingress and may mitigate potential for detritus to enter the inserter assembly 100. In some examples, the adhesive 374 may also extend over this opening and may be punctured through during insertion of the cannula 104 into the skin 356.

Figure 37:
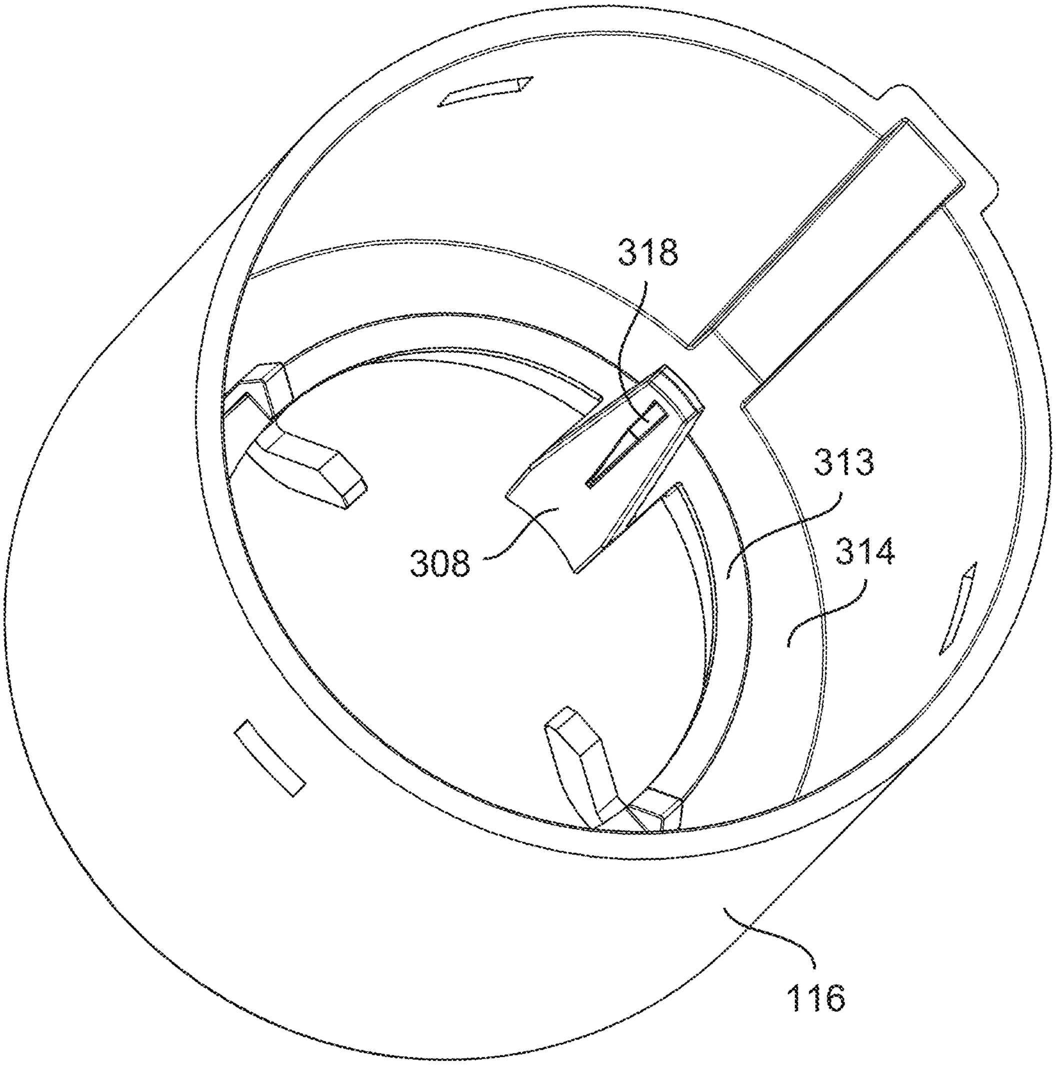
FIG. 37 depicts a perspective view of an example exterior housing.

Referring now to FIG. 37, an isolated view of the alternative exterior housing 116 depicted in the inserter assembly 100 embodiment of FIG. 2 is shown. As shown, instead of a retainer base 140, various features of the retainer base 140 may be included in the exterior housing 116. These features may all be formed unitarily and integral to one another as a single monolithic component during a molding operation for example. As shown, the finger 308 and fin 318 are included as part of the exterior housing 116. The finger 308 may extend from a central ring portion 313 connected by an intermediary region 314 to the rest of the exterior housing 116. The deflector members 358 are similarly included as part of the exterior housing 116.

Figure 38A:
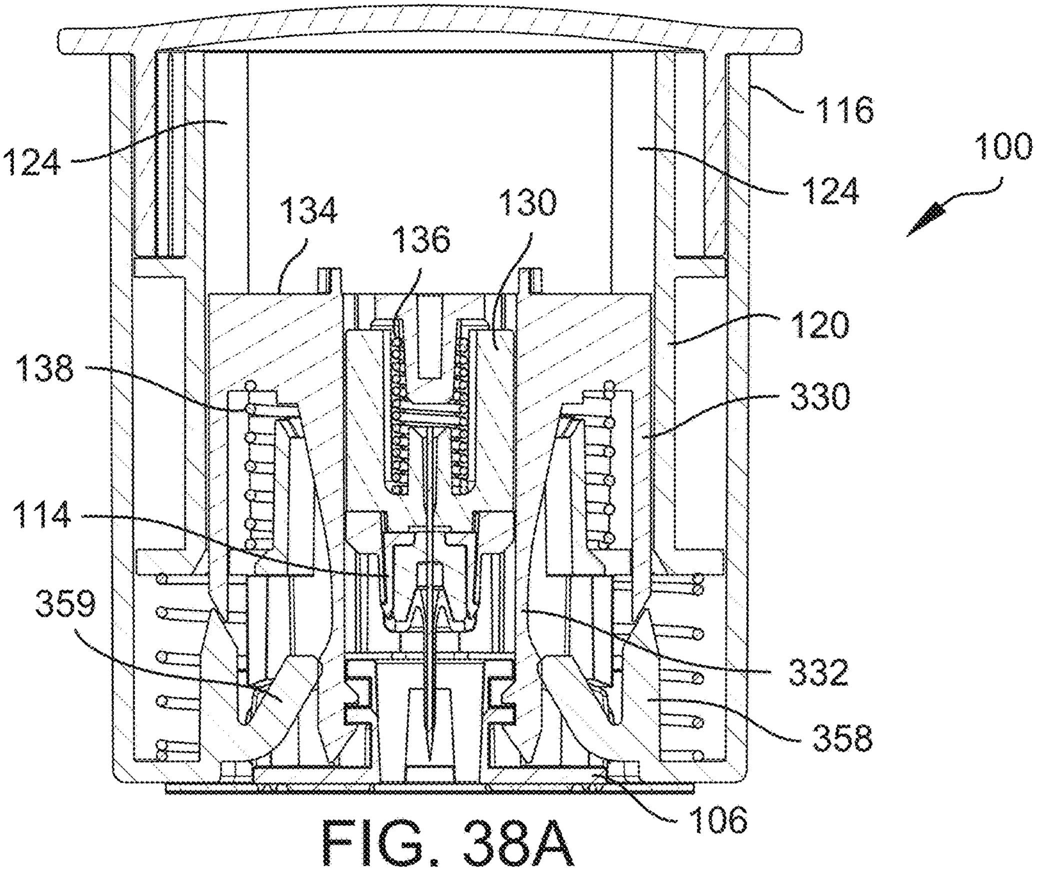
FIG. 38A-B depict cross-sectional views of an example inserter assembly including the exterior housing depicted in FIG. 37.
Figure 38B:
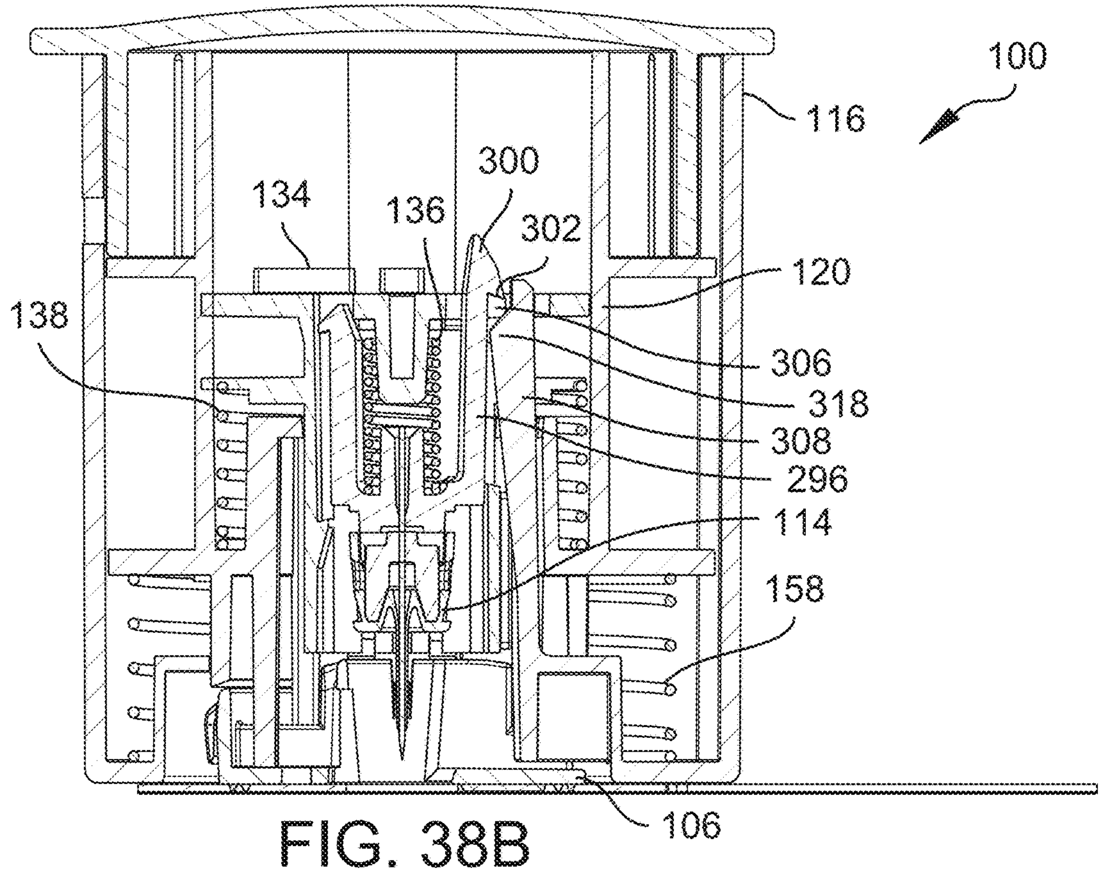

Cross sectional views of the example embodiment of the inserter assembly 100 in FIG. 2 are shown in FIGS. 38A-B. This inserter assembly 100 includes the exterior housing 116 depicted in FIG. 37. The views in FIGS. 38A-B show this alternate embodiment of the inserter assembly 100 in the same state as the inserter assembly 100 depicted in FIGS. 24A-B and FIG. 36. The inserter assembly 100 shown in FIGS. 38A-B may operate similarly to the inserter assembly 100 depicted in FIGS. 24A-B and FIG. 36. For sake of brevity, the following describes various operational states of the inserter assembly 100 shown in FIGS. 24A-B and FIG. 36.

Figure 39A:
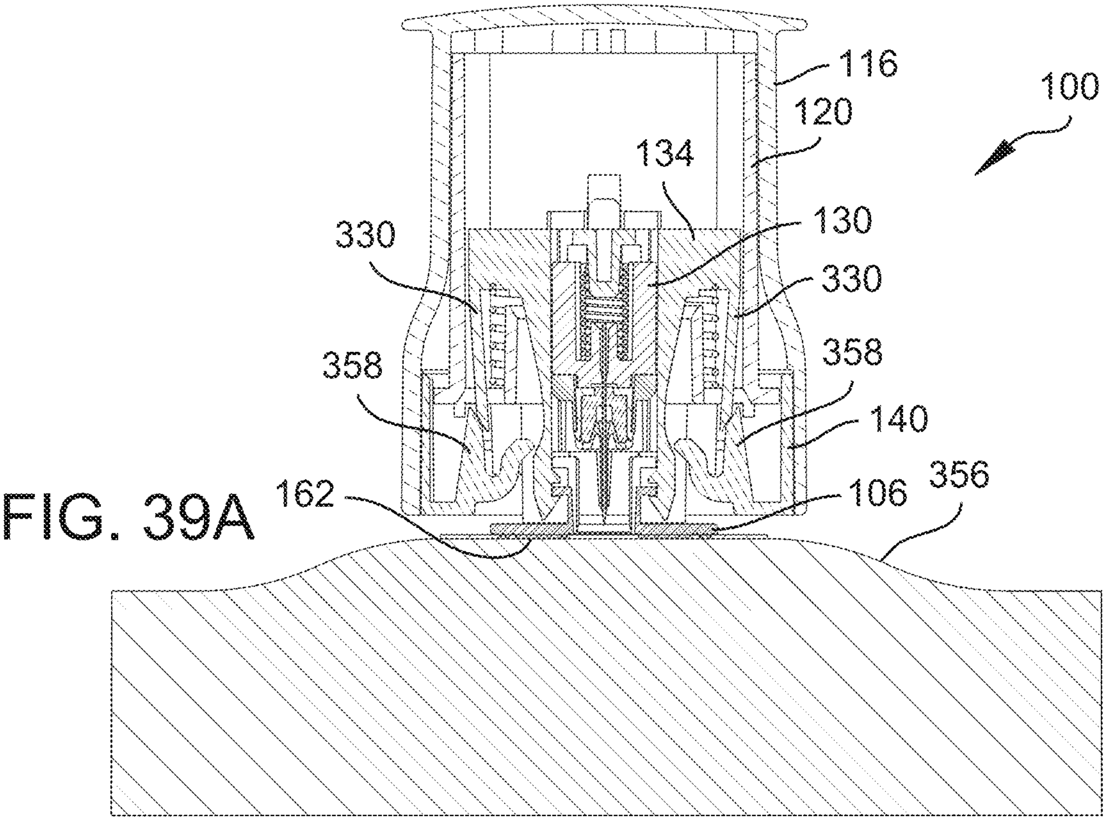
FIG. 39A-B depict cross-sectional views of an example inserter assembly being withdrawn away from a user after application to the skin.
Figure 39B:
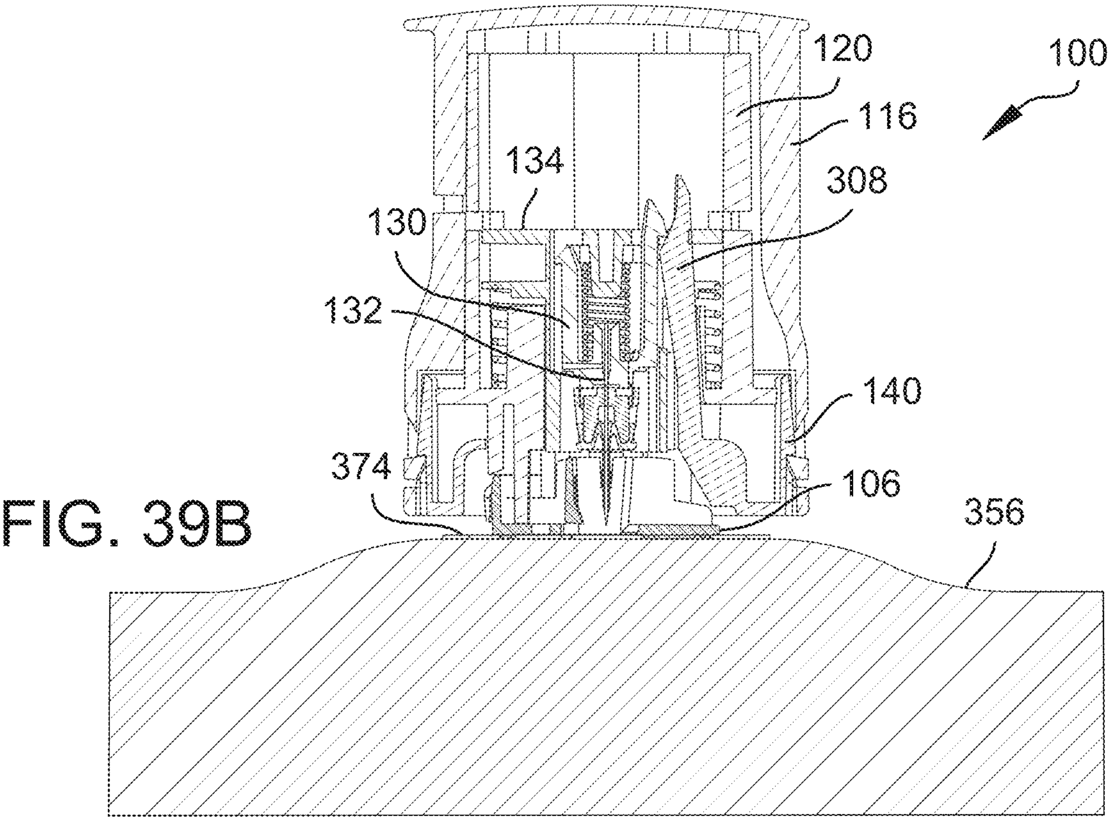

Referring now to FIGS. 39A-B, two cross sectional views of an inserter assembly 100 are shown. In FIGS. 39A-B, the example inserter assembly 100 has been placed against the skin 356 at a desired infusion site and is beginning to be withdrawn by a user. As shown, the adhesive 374 on the bottom face 162 of the infusion set base 106 may adhere to the skin 356 resulting in the skin 356 being tugged upward with the inserter assembly 100 as the inserter assembly 100 is pulled away from the body by the user. The exterior housing 116 and retainer base 140 may displace together with the hand of the user as the user removes the inserter assembly 100 from their body. The other components of the inserter assembly 100 may not be constrained to displace as a unit with the exterior housing 116 and retainer base 140. As the infusion set base 106 is in latching engagement with the sharp retractor 134 and the sharp retractor 134 is in latching engagement with the interior housing 120 and sharp holder 130, these components may be held behind. During removal, the exterior housing 116 and retainer base 140 may displace away from the skin 356 relative to these components substantially along the axis of the insertion sharp 132. This may cause deflector members 358 included on the retainer base 140 to bend arms 330 inward. It may also cause the finger 308 on the retainer base 140 to advance into the void 322 (see, e.g. FIG. 35C). The resiliency of arms 330 may cause the entire inserter assembly 100 to move as a unit for at least a portion of the inserter assembly 100 withdrawal motion from the body. Portions of the inserter assembly 100 may displace relative to one another once the force exerted by the elasticity of the skin exceeds a force threshold.

In various embodiments, the resiliency of the arms 330 may control, at least in part, a distance which a given user's skin 356 is tugged away from the body before actuation of the inserter assembly 100 occurs. As the skin 356 is tugged away from the body, the elasticity of the skin 356 may exert a pulling force which presses the arms 330 against the deflector members 358. The type, amount, and/or arrangement of adhesive 374 on the infusion set base 106 may be selected so as to withstand this force while maintaining adherence to the skin 356 and compatibility with the skin 356. Once this force overcomes the resiliency of the arms 330 and the components of the inserter assembly 100 described above begin to move relative to one another, the finger 308 may begin to advance into the void 322. Prior to this, triggering of actuation may be prohibited. The resiliency may be chosen such that an inserter assembly 100 may be used on a wide range of individuals having different skin 356 properties (e.g. elasticity) while still ensuring the skin 356 is tugged at least some minimum distance before actuation is triggered. In some embodiments, inserter assemblies 100 may be produced with differing arm 330 resiliencies which may be suitable for different user groups. For example, arms 330 with less resiliency (e.g. an elderly resiliency) may be available for use for older user groups whose skin 356 has a tendency to be less elastic.

The steepness of the ramped section 340 on each arm 330 may be modified to alter the amount of force applied before relative movement occurs. Shallower angles on the ramped section 340 may be employed where more force before relative movement occurs is desired. Sharper angles on the ramped section 340 may be used where a lower force may be desirable. There may be a high (e.g. juvenile), medium (e.g. adult), and low (e.g. elderly) skin elasticity ramp angle in certain implementations. Additionally, the thickness of the arms 330 may be altered to change their resiliency. Thinner arms may be used where less force is desired and thicker arms may be used where more force is desired. Various supporting features such as buttresses may also be included and may support the arms 330 against deflection at a point near the supported end of the arms 330. The location of the second plate 338 may also be modified in certain examples to alter the length of the deflectable portion of the arms 330 making them more or less resilient. The material used to form the arms may also be selected based on its resiliency properties.

The length of the finger 308 and location of the fin 318 on the finger 308 may play a role in controlling, at least in part, the distance a user's skin 356 is tugged away from the body. These parameters may be modified to alter this distance.

Figure 39C:
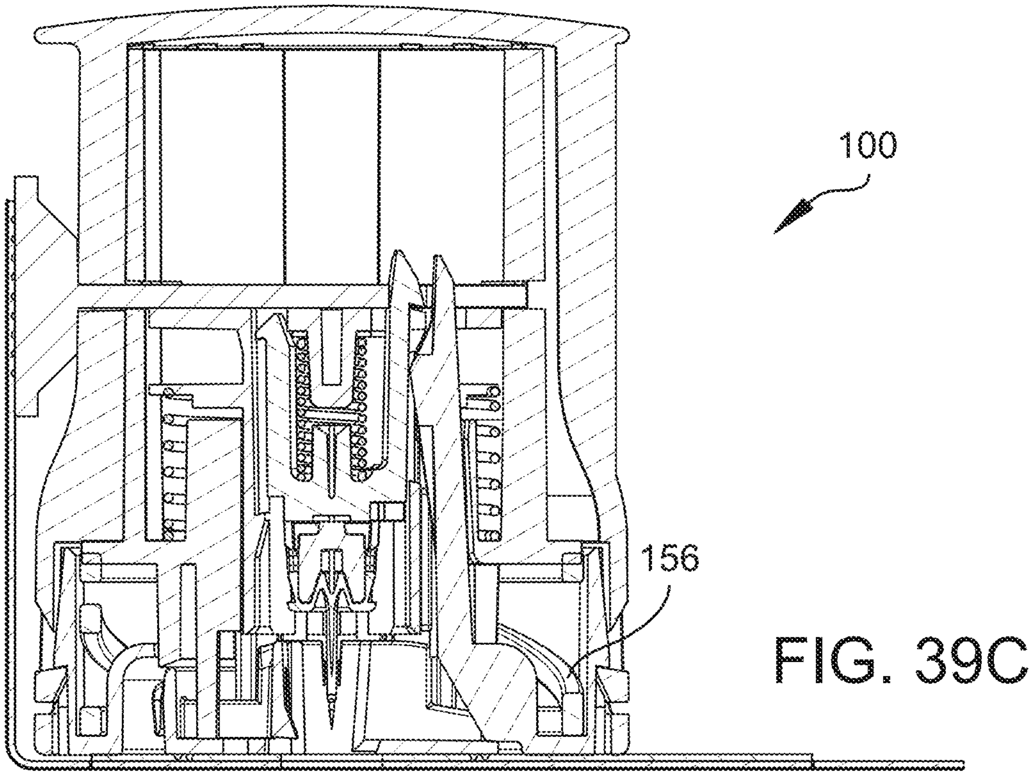
FIG. 39C-D depict cross-sectional views of exemplary inserter assemblies including additional springs.
Figure 39D:
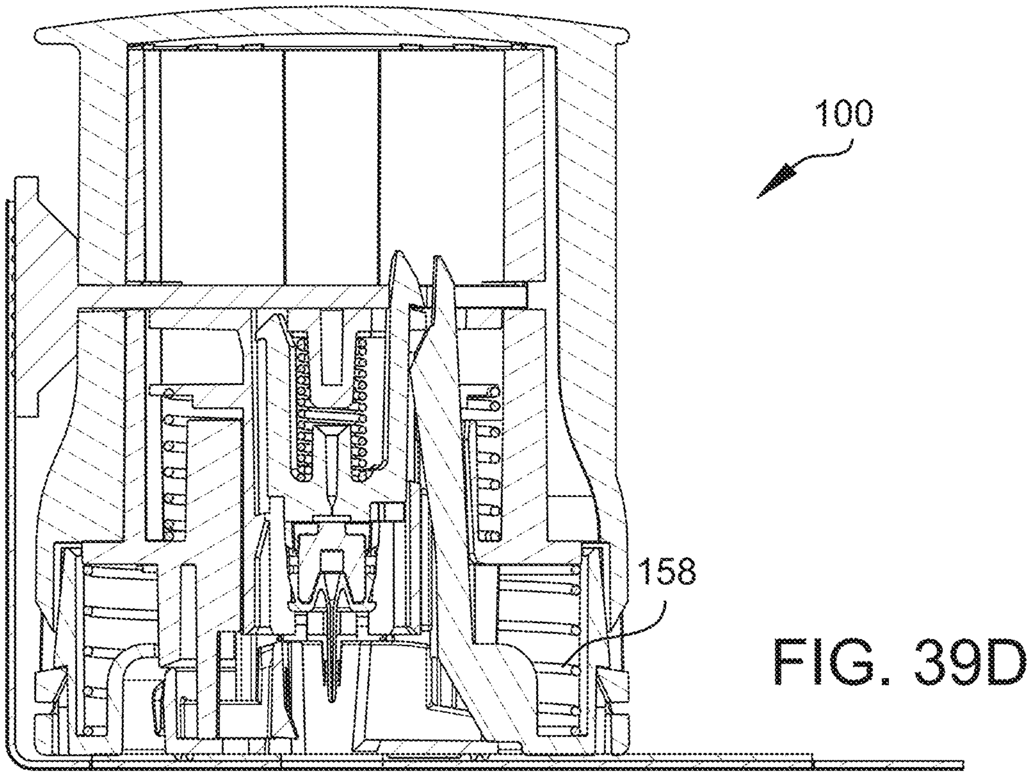

Referring now to FIGS. 39C-D two additional cross-sections of an example inserter assembly 100 are shown. Each of the example inserter assemblies 100 includes an additional spring 156, 158. These springs 156, 158, are described above in relation to FIGS. 1B-1C. An additional spring 156, 158 may be used to adjust the amount of force build up before the fin 318 triggers the beginning of inserter assembly 100 actuation. Springs 156, 158 may also help to remove any mechanical slop which may be present due to tolerancing of various components of the inserter assembly 100. Varying the characteristics described in the above paragraphs may allow one to empirically determine appropriate designs for various patient populations (e.g. juvenile, adult, elderly or high skin elasticity, medium skin elasticity, low skin elasticity). A skin turgor test, elastomer, or other testing may be used to match an appropriate inserter assembly 100 type to a particular patient.

Figure 40A:
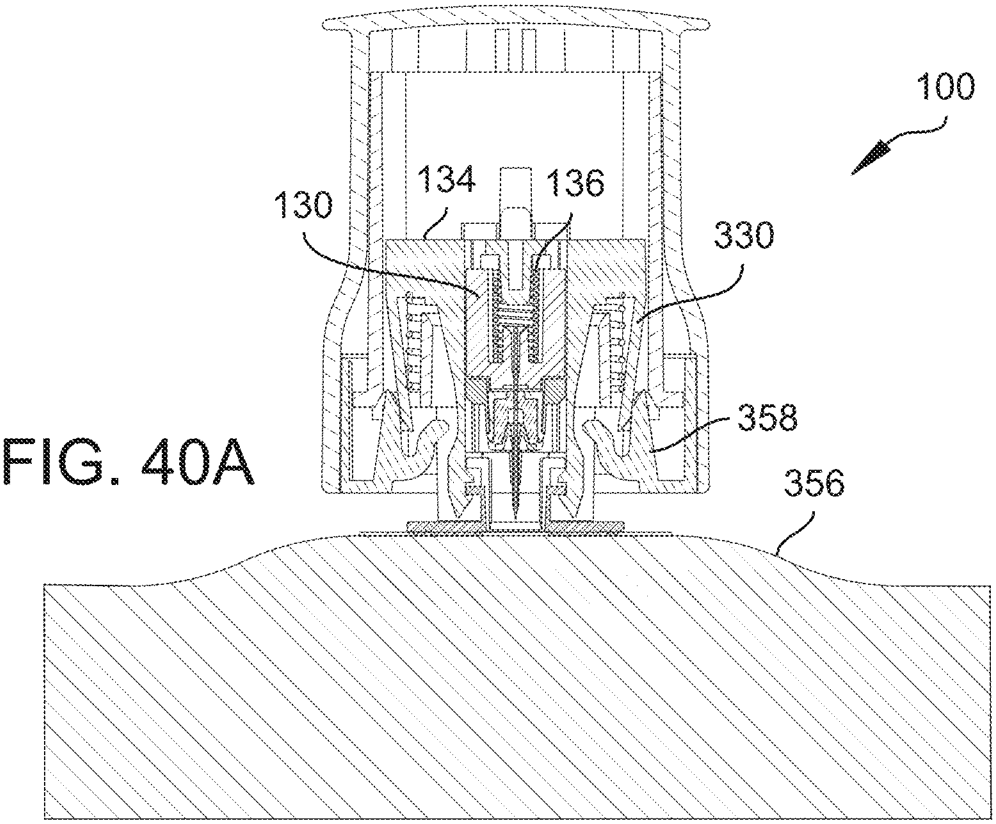
FIG. 40A-B depict cross-sectional views of an example inserter assembly being withdrawn away from a user after application to the skin.
Figure 40B:
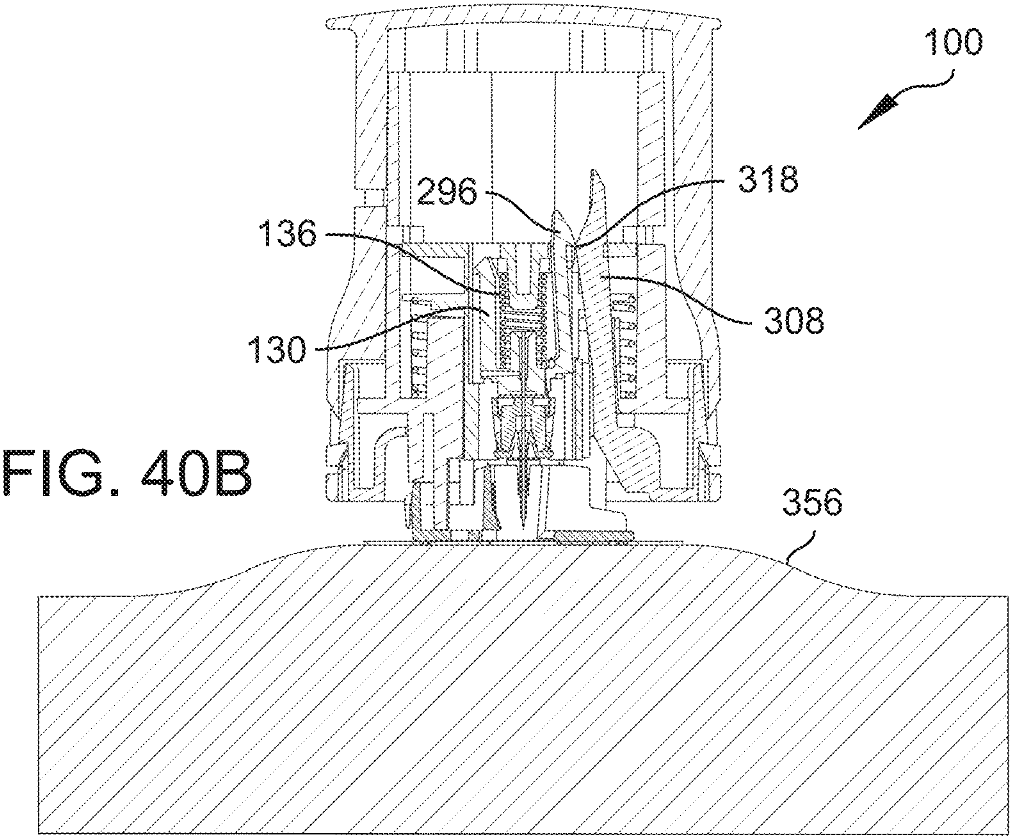

Referring now to FIG. 40A-B two cross sectional views of an inserter assembly 100 are shown. In FIGS. 40A-B, the example inserter assembly 100 has been further withdrawn from the skin 356. The exterior housing 116 and retainer base 140 have continued to displace away from the skin 356 relative to the rest of the inserter assembly 100. The deflector members 358 included on the retainer base 140 have continued to flex the arms 330 inward. The finger 308 on the retainer base 140 has advanced into the void 322 (see, e.g. FIG. 35C) such that the fin 318 of the finger 308 has dislodged the cantilevered arm 296 of the sharp holder 130 from the catch 306 (see, e.g., FIG. 35C). Thus the movement of the exterior housing 116 and retainer base 140 has advanced the inserter assembly 100 to an insertion release point in FIG. 40A-B. With disengagement of the cantilevered arm 296 from the catch 306, the spring 136 is free to release its stored energy and begin driving actuation of the inserter assembly 100.

Prior to the magnitude of relative displacement between the portions of the inserter assembly 100 increasing to this insertion release point threshold, the inserter assembly 100 may be precluded from triggering actuation. This may ensure that the skin is lifted some distance before actuation of the trigger arrangement for the inserter assembly 100 can occur.

Figure 41A:
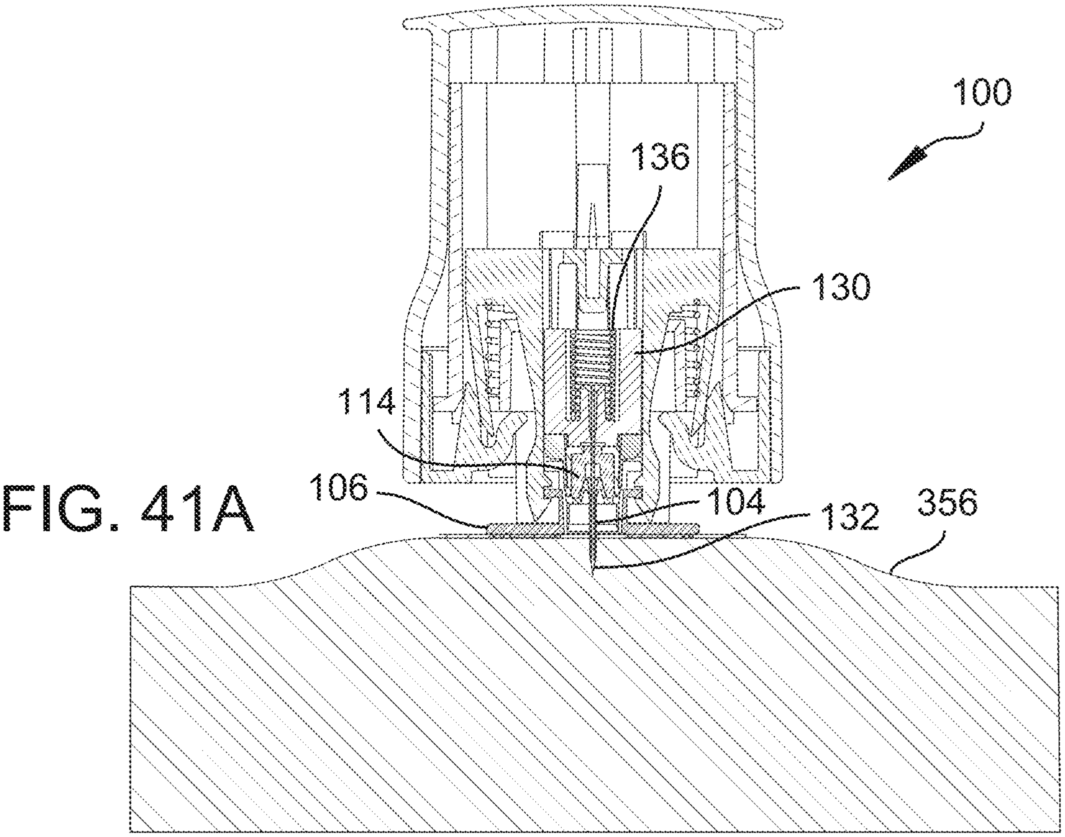
FIG. 41A-B depict cross-sectional views of an example inserter assembly after the sharp of the inserter assembly has pierced the skin of the user.
Figure 41B:
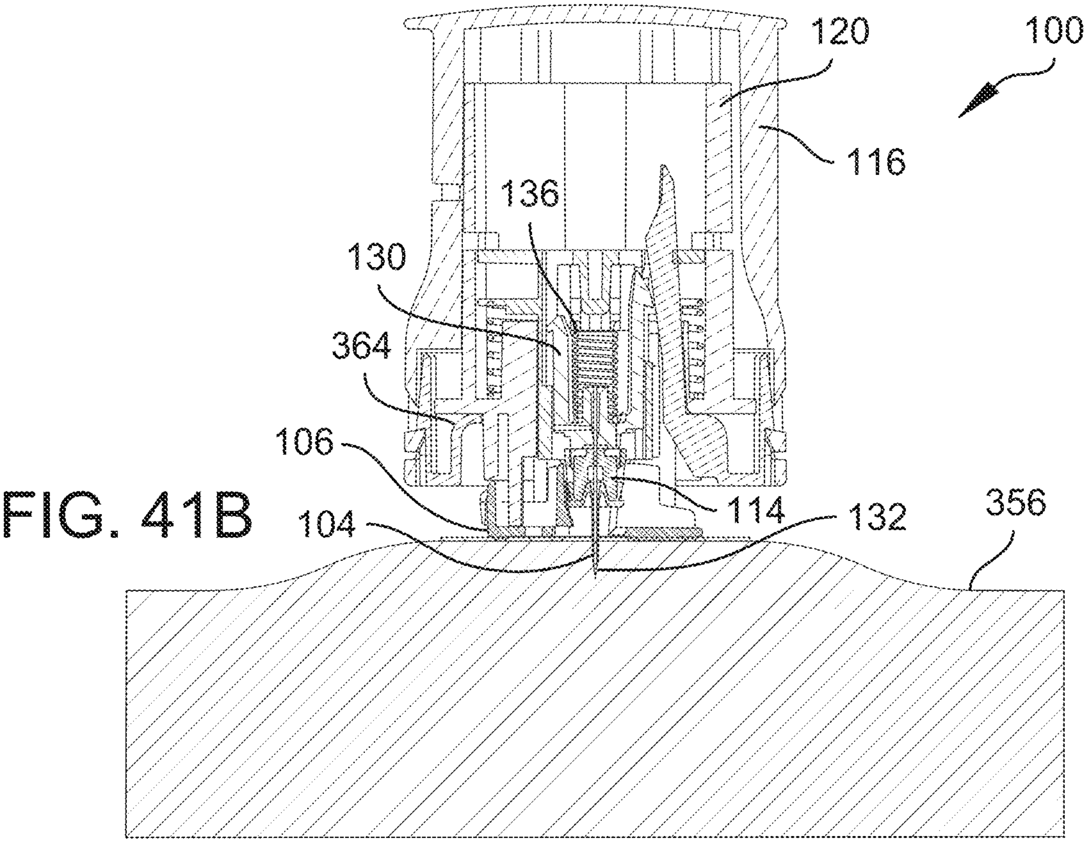

Referring now to FIG. 41A-B two cross sectional views of an inserter assembly 100 are shown. In FIGS. 41A-B, the example inserter assembly 100 has been further withdrawn from the skin 356. As shown, the restoring action of the spring 136 may drive the sharp holder 130, insertion sharp 132, and cannula subassembly 114 toward the skin 356 along an insertion path. In the example embodiment, the sharp holder 130 at least partially extends out of the cavity 334 of the sharp retractor 130. As shown, the insertion sharp 132 and cannula 104 have just punctured through the skin 356. During puncture, the skin 356 may still be in a state in which it is tugged up away from muscle and other underlying body structures. The cannula subassembly 114 has also begun to be advanced toward the infusion set base 106. It should be noted that the spring 136 is still depicted in a compressed state in the forthcoming figures. This is for ease of illustration. As would be understood by one of skill in the art, the example spring 136 would expand over the course of the insertion movement. Also as shown, the retainer base 140 of the inserter assembly 100 may include a stop 364 which prevents relative movement beyond a certain point between the interior housing 120 and the casing formed by the exterior housing 116 and retainer base 140 (which may be connected to one another). This stop 364 may be included as a portion of the second ring 312 of the retainer base 140.

Figure 42A:
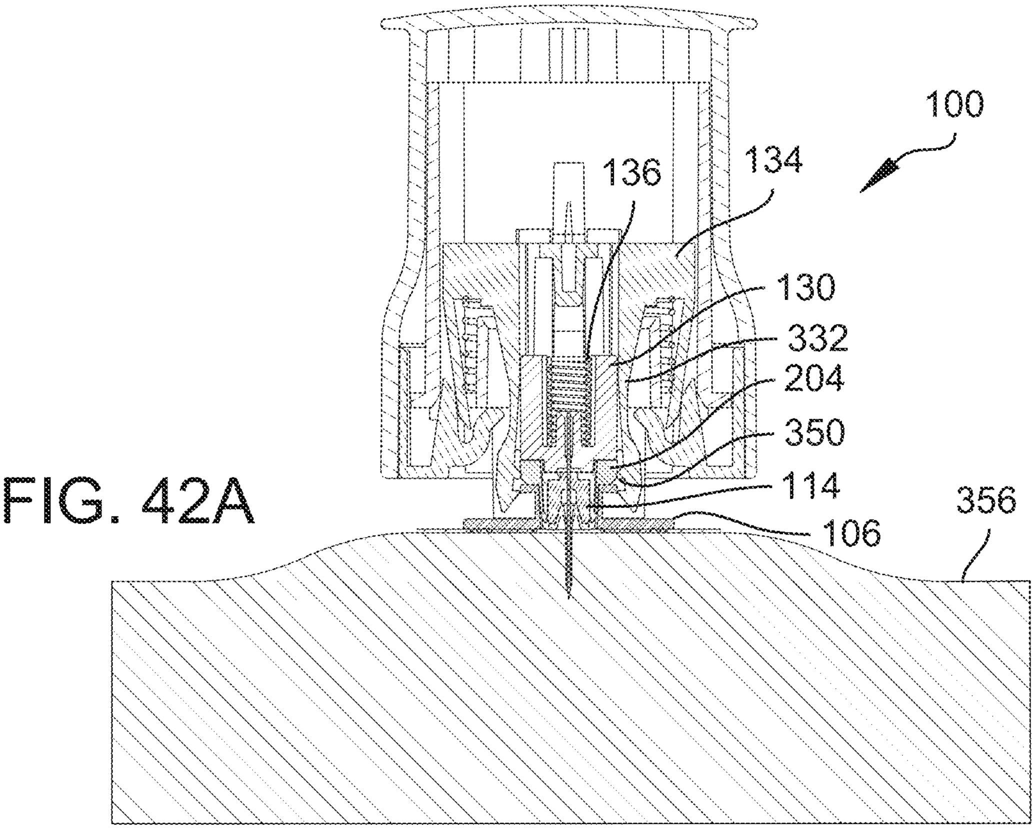
FIG. 42A-B depict cross-sectional views of an example inserter assembly after the sharp retractor has been freed to retract.
Figure 42B:
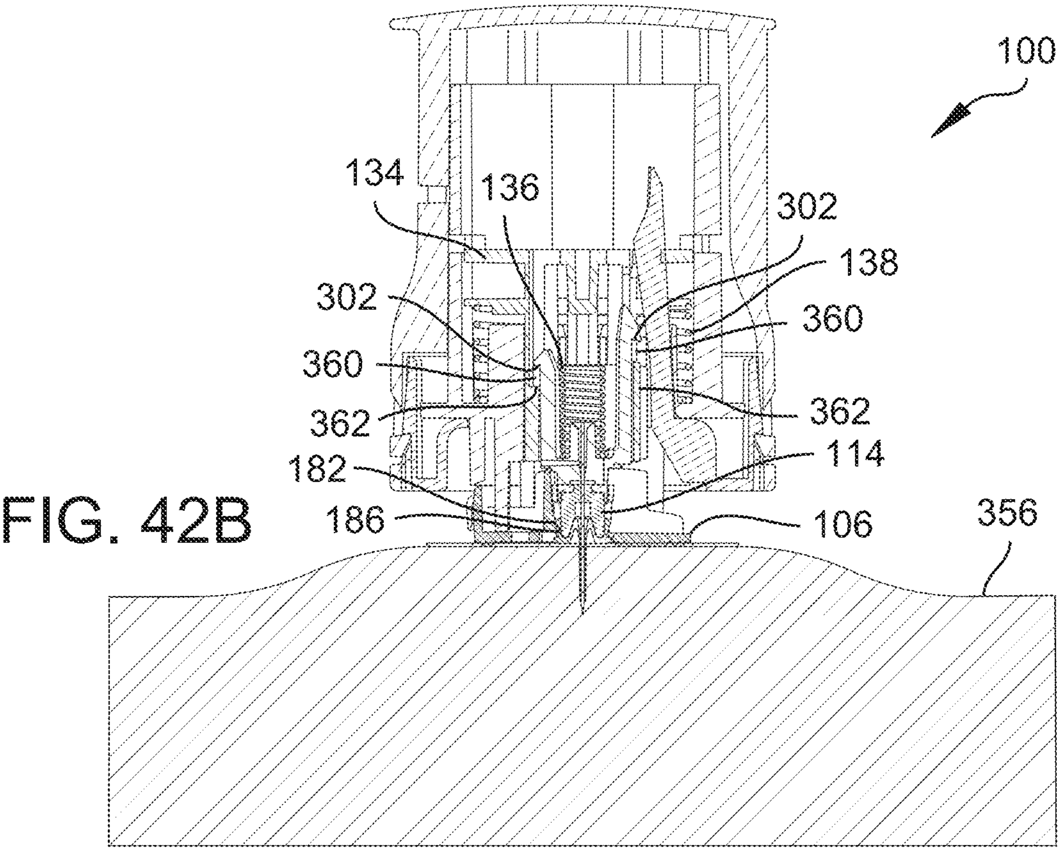

Referring now to FIGS. 42A-B, two cross sectional views of an inserter assembly 100 are shown. As shown, the spring 136 has restored to a relaxed state and completed the insertion movement of the sharp holder 130, insertion sharp 132, and cannula subassembly 114 toward the skin 356. The relaxed state may be a completely relaxed state or a comparatively relaxed state where the spring 136 is still exerting some pressure against the sharp holder 130 to prevent it from jostling about. The notch 186 of the cannula subassembly 114 is shown in engagement with the protuberance 182 of the infusion set base 106 locking the cannula subassembly 114 and completing assembly of the infusion set 102. As shown, when the cannula subassembly 114 latches into the base 106, the ears 204 on the cannula subassembly 114 may press against the nubs 350 included on the arms 332. This may cause the arms 332 to be splayed apart resulting in disengagement of the arms 332 from the infusion set base 106. In turn, this may free spring 138 to begin releasing stored energy. Thus, FIGS. 42A-B depict the insertion assembly 100 at a retraction release state and the arms 332 may serve as a retraction prevention latch.

In certain embodiments, retraction may not be automatic and/or may not be spring biased. For example, the insertion sharp 132 may remain in the advanced position and the removal action of the user may manually pull the insertion sharp 132 out of the cannula 104. In such embodiments, spring 138 may be omitted. In some embodiments, disengagement of the arms 332 from the infusion set base 106 may not be automatic. Any arrangement which would be apparent to one skilled in the art may be used to facilitate manual decoupling of the arms 332 from the infusion set base 106. A twisting action may be employed to free the arms 332 from the infusion set base 106 allowing the insertion sharp 132 to then automatically retract or be manually pulled out. One or more button may be included in alternative embodiments. Displacement of the one or more button may uncouple the arms 332 from the infusion set base 106 allowing the insertion sharp 132 to then be manually or automatically retracted out of the cannula 104. Squeezing of a deformable portion of the inserter assembly 100 may similarly cause uncoupling of the arms 332 from the infusion set base 106. As would be appreciated by one skilled in the art, the inserter assembly 100 embodiments described herein could be otherwise modified to allow for various types of other manual arm 332 release schemes.

In alternative embodiments where the infusion set base 106 is retained by a portion of the interior housing 120 and the arms 332 engage a portion of the interior housing 120, displacement of the sharp holder 130 may similarly cause release of the infusion set 102 and trigger retraction. For example, the ears 204 may collide with and cause displacement of catch features (e.g. spread them away from the infusion set 102) on the interior housing 120 resulting in them decoupling from the infusion set 102. Additional ears 204 or other projections on the cannula sub assembly 114 may be included to cause disengagement of the arms 332 (e.g. via spreading of the arms 332) from the interior housing 120 to permit retraction.

In certain embodiments, there may be a dwell period during inserter assembly 100 actuation where retraction of the insertion sharp 132 has been triggered and the sharp retractor 134 is displacing, however, the insertion sharp 132 remains substantially static. During this dwell period, spring 136 may continue to exert pressure on the cannula subassembly 114 through the sharp holder 130. This may block any possible tendency of the cannula subassembly 114 to bounce or rebound as it is propelled into the infusion set base 106 and ensure it is firmly retained in the base 106. As shown, once the insertion movement is complete, a dwell gap 360 may be present between a stop 362 on the sharp retractor 134 and the ledge 302 on each cantilevered arm 296 of the sharp holder 130. Spring 136 may still have energy stored therein and continue to press against the sharp holder 130. The dwell gap 360 on each side may be equal in size.

Figure 43A:
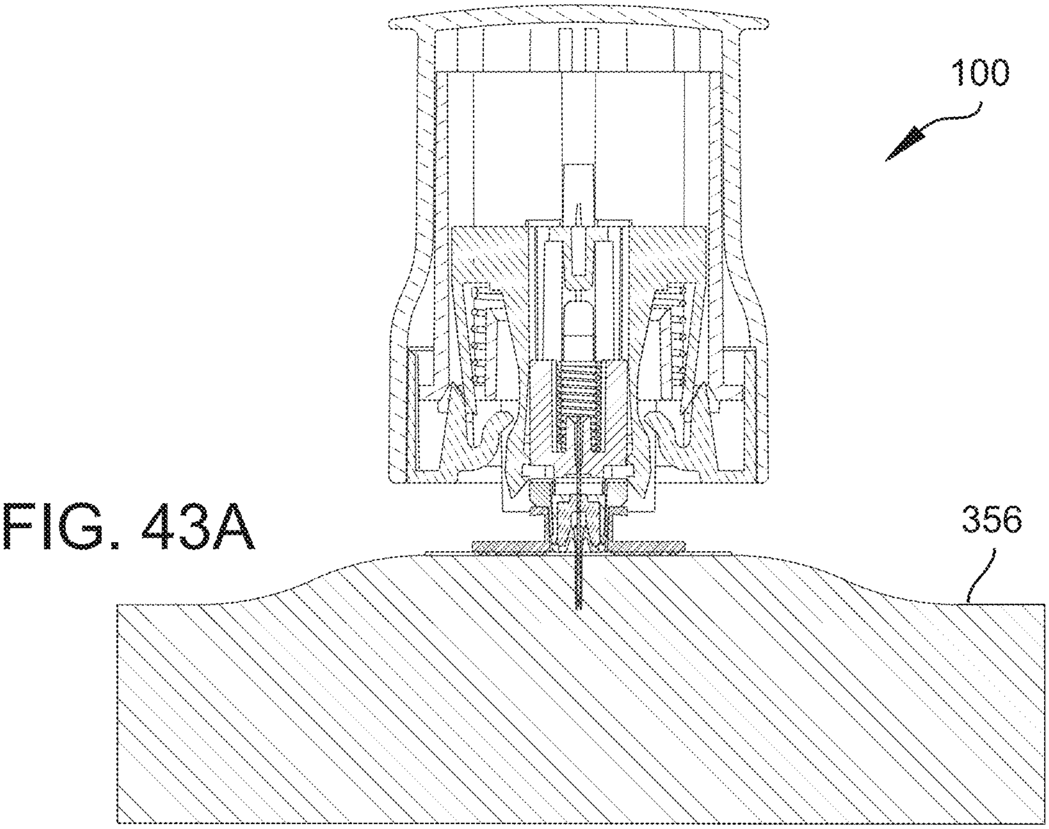
FIG. 43A-B depict cross-section views of an example inserter assembly during retraction of the sharp retractor.
Figure 43B:
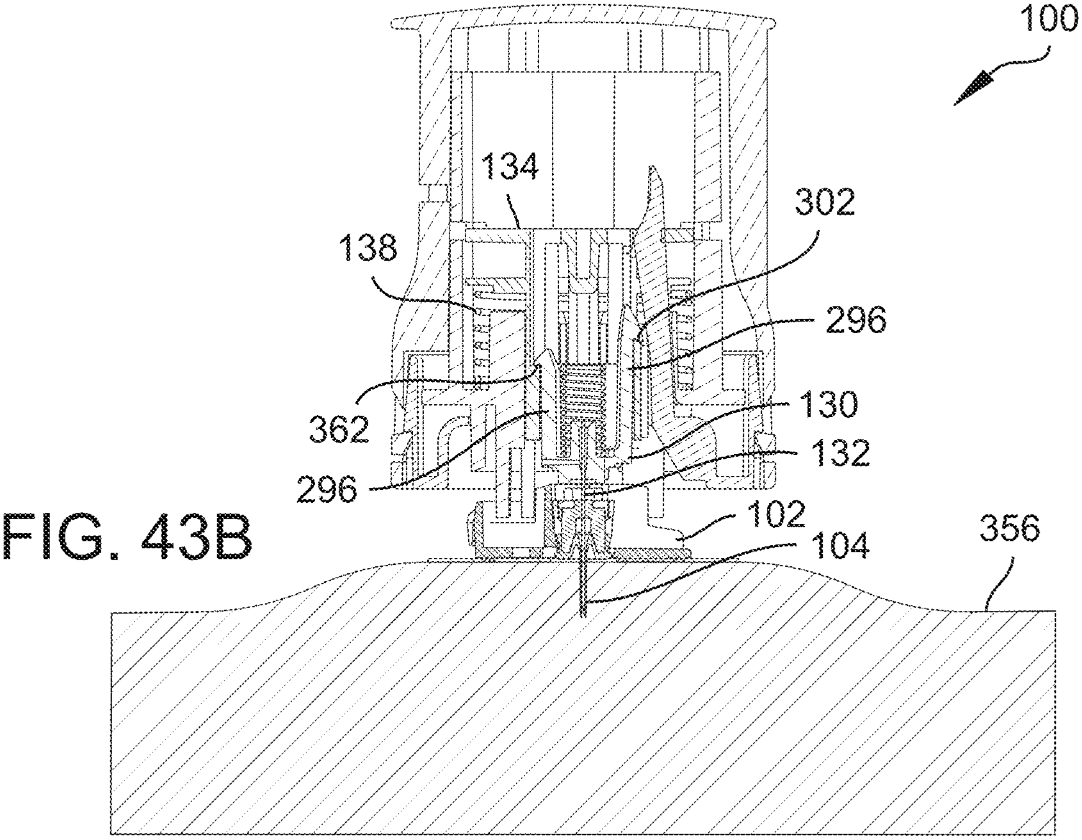
Figure 43C:
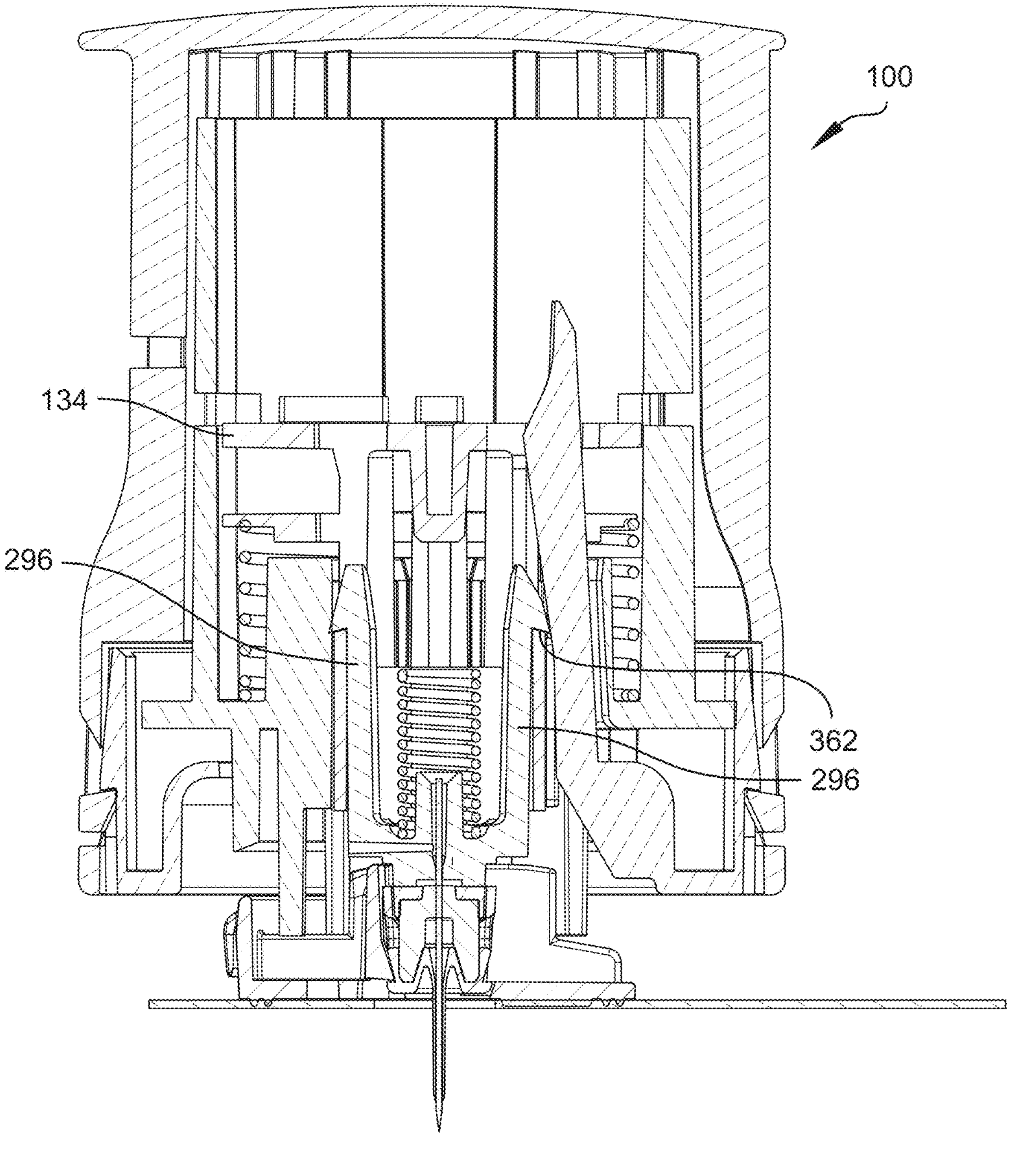
FIG. 43C depicts a cross sectional view of an alternative embodiment of an inserter assembly.

Referring now additionally to FIGS. 43A-B, which depict two cross sectional views of an inserter assembly 100, the dwell gap 360 may decrease until the stops 362 on the sharp retractor 134 contact the ledges 302 of the cantilevered arms 296 on the sharp holder 130. Once this occurs, the restoring action of spring 138 may begin to displace the sharp holder 130 and insertion sharp 132 affixed thereon along with the sharp retractor 134. This displacement may retract the insertion sharp 132 out of the cannula 104 and the infusion set 102. An alternative embodiment of an inserter assembly 100 at this stage of actuation is shown in FIG. 43C. In FIG. 43C the cantilevered arms 296 are equal length mirror images of one another. The stops 362 on the sharp retractor 134 may be at even height with one another in such embodiments.

Figure 44A:
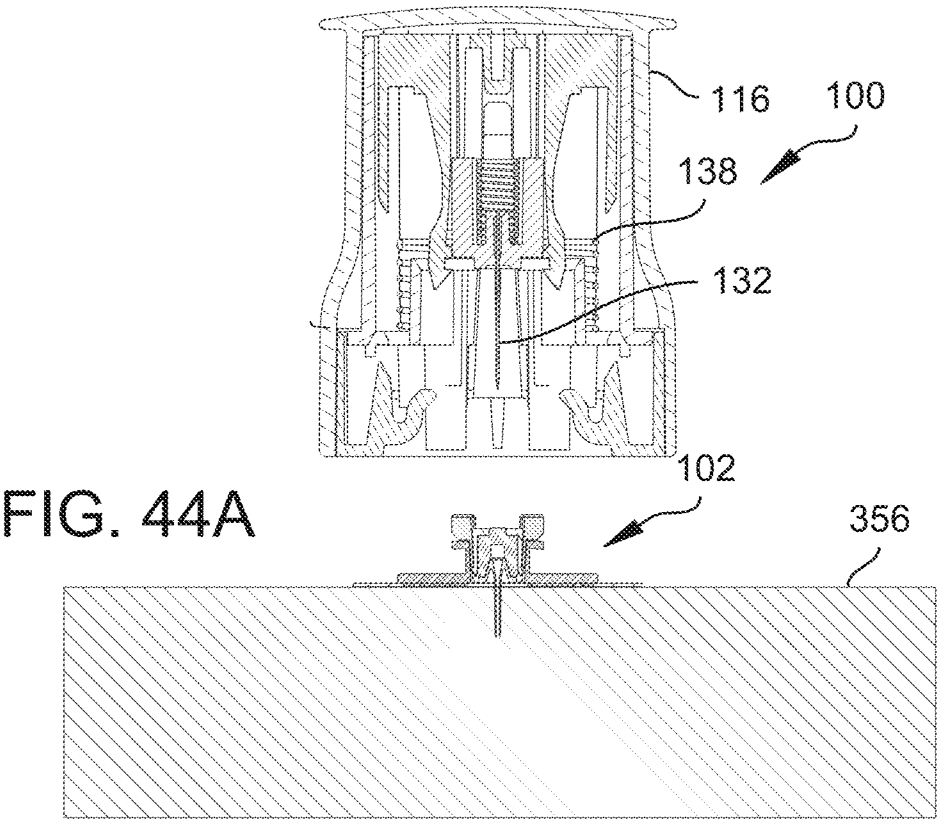
FIG. 44A-B depict cross-sectional views of an inserter assembly after inserter assembly actuation has completed.
Figure 44B:
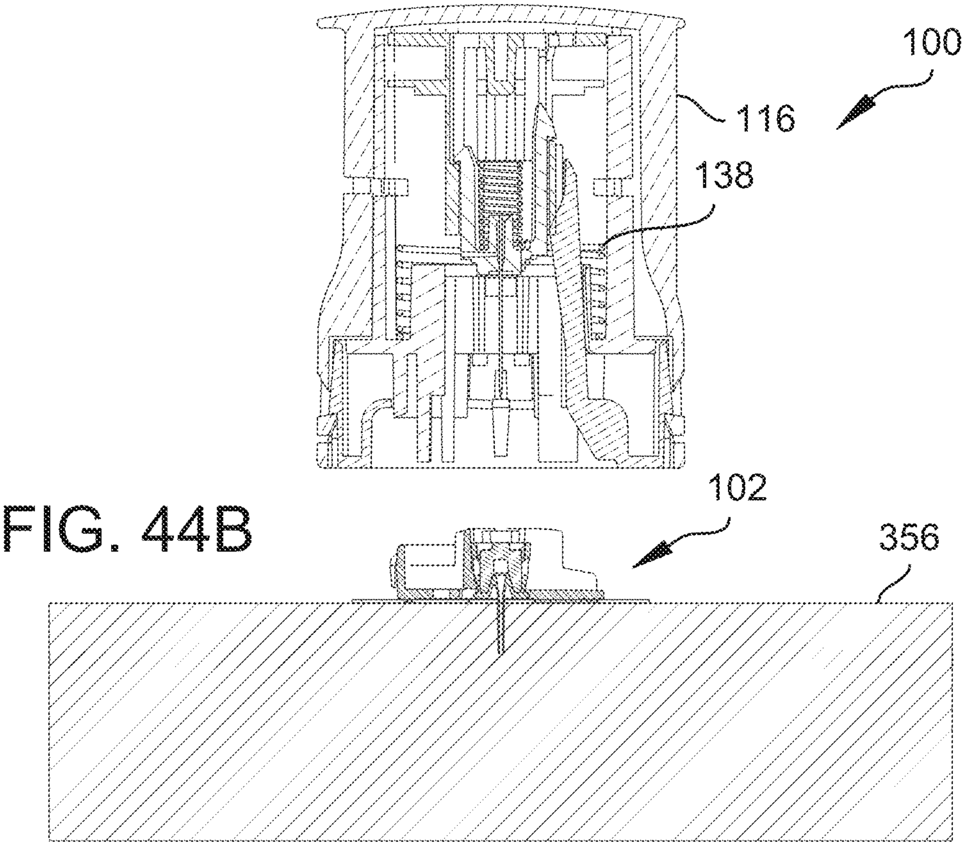

As shown in FIGS. 44A-B, once retraction has completed the sharp retractor 134 may be pressed against the exterior housing 116 by spring 138. For ease of illustration the spring 138 is still depicted in the compressed state, but would uncompress to a relaxed state over the progression of the retraction as would be understood by one skilled in the art. As with spring 136, the relaxed state may be a completely relaxed state or a comparatively relaxed state where the spring 138 is still exerting some pressure against the sharp retractor 134 to prevent it from jostling about. After retraction, the insertion sharp 132 may be housed within the inserter assembly 100 to aid in protecting against unintentional finger sticks or the like. In the example embodiment, the insertion sharp 132 is housed further within the inserter assembly 100 after retraction when compared to its starting position. In other embodiments, the retracted location of the insertion sharp 132 may differ but may be at least housed as deep within the inserter assembly 100 as its initial starting location. The infusion set 102 may be held in place on the skin 356 with the cannula 104 indwelling in the patient.

Figure 45:
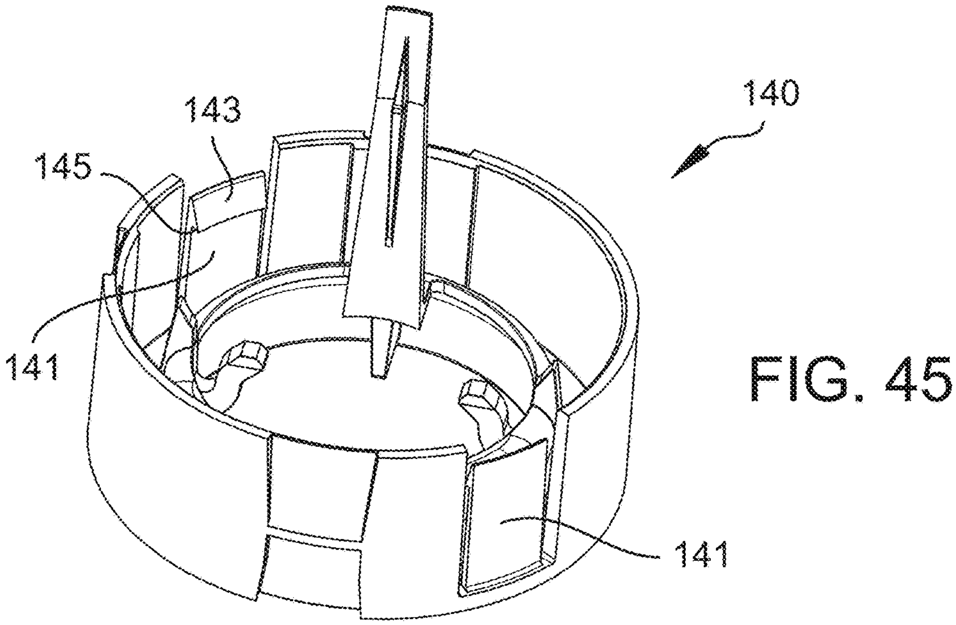
FIG. 45 depicts a perspective view of an example retainer base.
Figure 46:
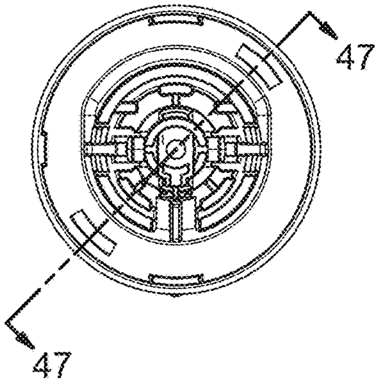
FIG. 46 depicts a bottom view of an example inserter assembly.
Figure 47:
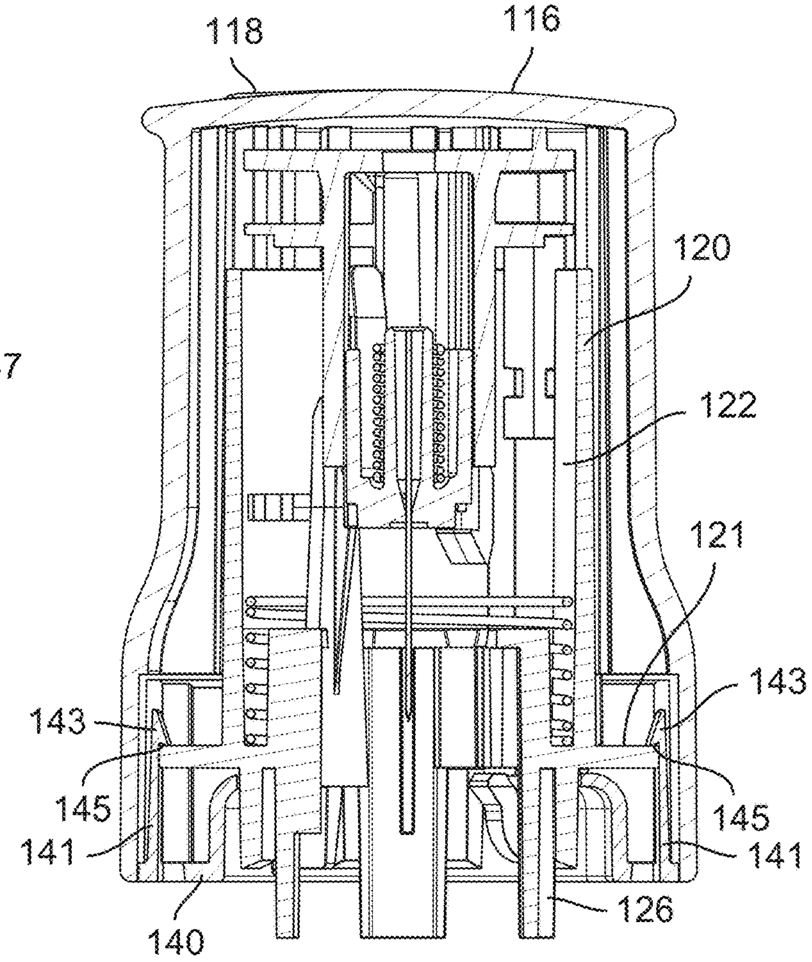
FIG. 47 depicts a cross-sectional view taken at the indicated cut plane of FIG. 46.

Referring now to FIGS. 45-47, in certain embodiments, after actuation certain components of the inserter assembly 100 may be locked in place. Alternatively, certain components may be prevented from displacement in particular directions or prevented from displacement beyond a predefined distance in particular directions. This may inhibit reuse of the inserter assembly 100 and may aid in protecting a user from unintended finger sticks. Some embodiments of retainer bases 140 may include one or more lock members 141. As shown, two lock members 141 are included though other embodiments, may include a greater or lesser number (e.g. three or four). The lock members 141 in the example embodiment are disposed opposite one another on the retainer base 140.

The exemplary lock members 141 in the example embodiment are depicted as cantilevered lock tabs. Each cantilevered tab includes a protuberance 143 which is disposed on a portion of that lock member 141 most distal to the skin contacting intermediary region 314 of the retainer base 140. The protuberance 143 be ramped and may define a ledge region 145. As the exterior housing 116 and the retainer base 140 displace relative to the interior housing 120 during withdrawal of the inserter assembly 100 from the skin 356, a portion of the interior housing 120 may contact ramped portion of the protuberance 143. As shown, the interior housing 120 includes a radial flange 121 which separates the infusion set base interfacing segment 126 of the interior housing 120 from the railed segment 122 (see FIG. 1A) of the interior housing 120. This radial flange 121 may be the portion of the interior housing 120 which contacts the protuberances 143 of the lock members 141. Further relative displacement may cause deflection of the lock members 141 to allow for passage of radial flange 121 of the interior housing 120 passed the protuberance. As shown, in FIG. 47, once the radial flange 121 has displaced beyond the protuberances 143, the lock members 141 may resiliently restore back to their unstressed state. In the event that a user presses against the interior housing 120 after actuation, the radial flange 121 may abut against the ledges 145 of the lock members 141 may be unable to further displace into the exterior housing 116. Thus, the interior housing 120 may be constrained after actuation such a portion of the interior housing 120 is held a predefined distance from the tip of the insertion sharp 132. This portion may present an obstruction which may aid in blocking inadvertent contact of the insertion sharp 132 with a user after actuation.

Figure 48A:
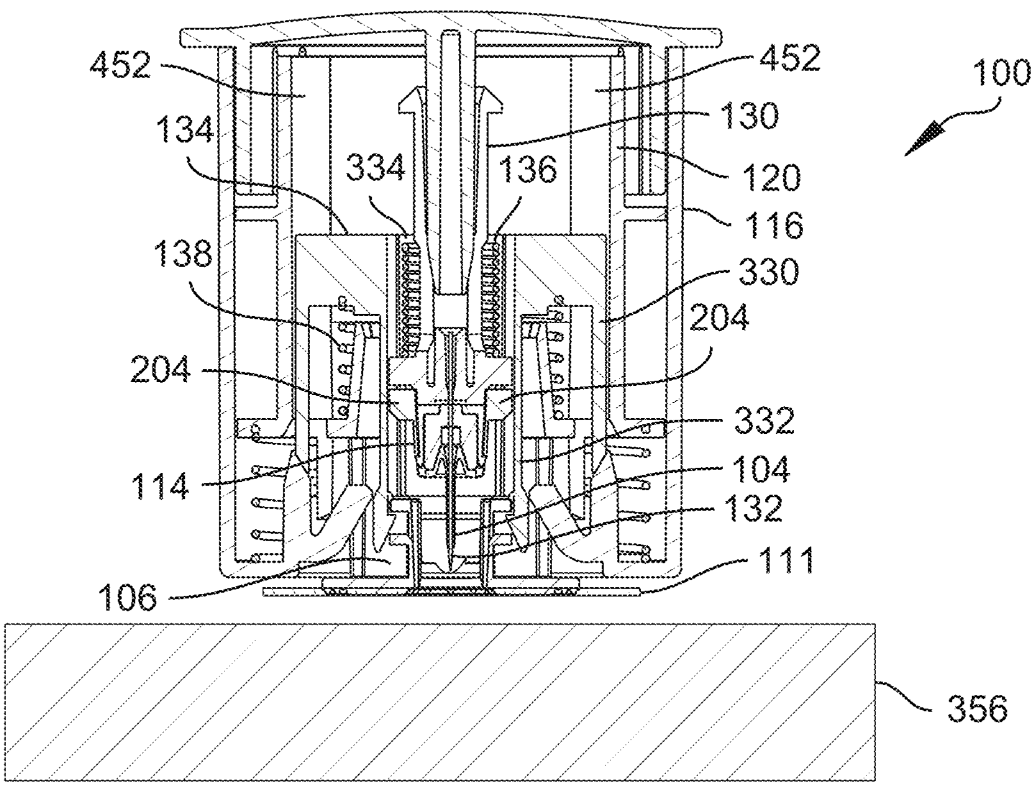
FIG. 48A-B depict cross-sectional views of another exemplary inserter assembly about to be applied to a user's skin.
Figure 48B:
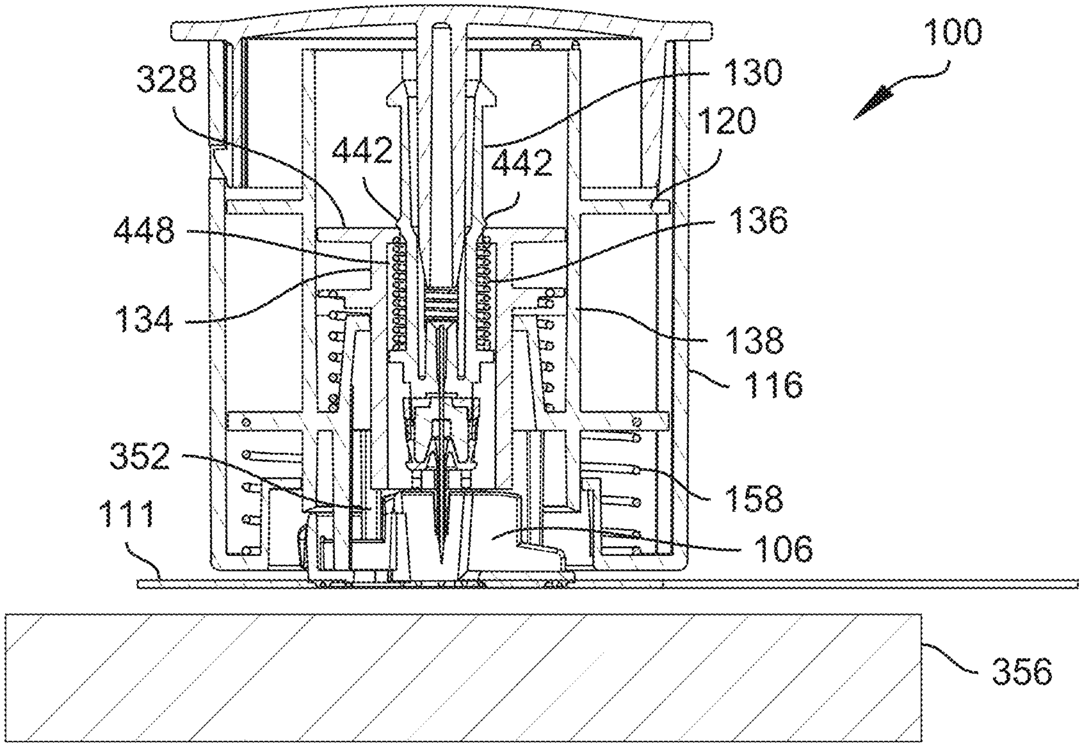
Figure 49A:
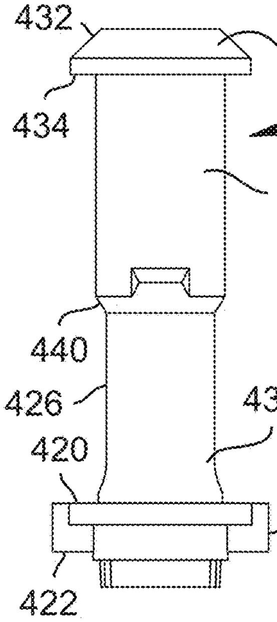
FIG. 49A depicts a side view of an alternative embodiment of a sharp holder.
Figure 49B:
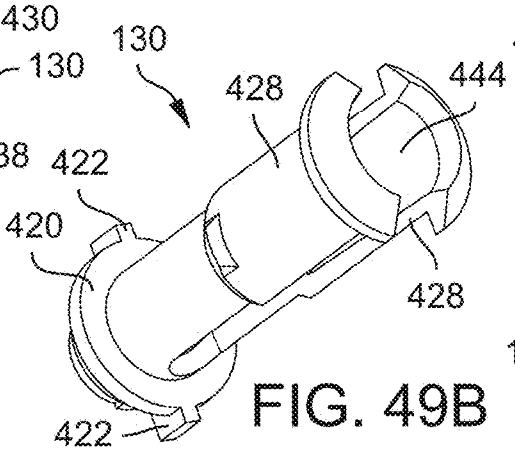
FIG. 49B depicts a perspective view of the sharp holder shown in FIG. 49A.
Figure 49C:
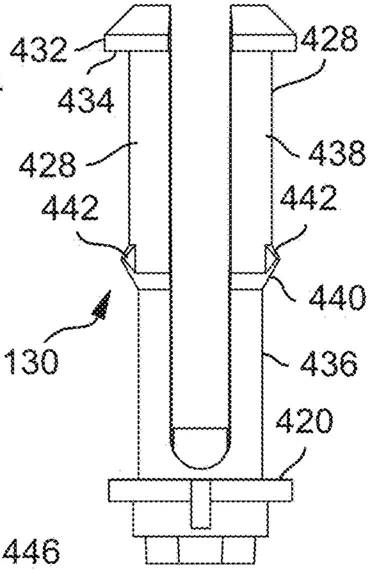
FIG. 49C depicts another side view of the sharp holder illustrated in FIG. 49A.

Referring now to FIG. 48A-B, two cross-sectional views of the example inserter assembly 100 depicted in FIG. 3 are shown. The inserter assembly 100 is depicted just as it is about to be applied to the skin 356. The adhesive backing 111 may be removed to expose the adhesive on the infusion set base 106. As shown, both springs 136, 138 may be in an energy storing state, which in this particular embodiment is a compressed state. In the example, spring 136 serves as an insertion driving bias member while spring 138 serves as an insertion sharp 132 retraction driving bias member. Spring 136 is held in compression between the insertion sharp holder 130 and the insertion sharp retractor 134 and, when released, drives the sharp holder 130 and components carried there on from a raised state to a forward state. Spring 138 is held in compression between the interior housing 120 and the sharp retractor 134. Upon release, spring 138 drives the sharp retractor 134 and sharp holder 130 from a post insertion state to a retracted state. An additional spring 158 is included in the example embodiment, though is optional. The additional spring 158 may alter the amount of force build up before actuation of the inserter assembly 100 is triggered and may help to remove any mechanical slop which may be present due to tolerancing of various components of the inserter assembly 100.

Referring now also to FIGS. 49A-52, a number of views of a sharp holder 130 and a retainer cap 406 are depicted. The sharp holder 130 may include a bias member receiving shelf 420 against which the spring 136 is held. The shelf 420 may include two projections 422 on a side thereof. The two projections 422 in the example embodiment are rails which are disposed opposite one another on the sharp holder 130. These rails may ride along guides 354 (see, e.g., FIGS. 53A-B) on a portion of the sharp retractor 134. The projections 422 may extend from the sharp holder 130 so as to match the width of the cannula sub assembly 114 at a plane of the cannula sub assembly 114 including the ears 204 of the septum housing 108.

A wall 426 may extend upward from the shelf 420. The exemplary wall 426 shown in FIGS. 49A-C includes interrupted regions which create one or more wall sections 428. The wall sections 428 may be crescent shaped as shown and are separated by an interrupt region formed by a U-shape recess which extends from the top face 430 of the sharp holder 130 nearly to the shelf 420. The recess may extend at least 90-95% or more of a distance extending from the top face 430 to the shelf 420. The recesses may allow deflection of the wall sections 428. The wall sections 428 may be disposed opposite one another on the sharp holder 130 and may be of equal length. In other embodiments, both wall sections 428 may not be identical mirror images. Each of the wall sections 428 may include a protuberance 432 at the end of the wall section 428 opposite the shelf 420. The protuberance 432 has a pileus type shape which generally widens as distance from the shelf 420 decreases. During assembly, this may facilitate installation of the sharp holder 130 into the insertion assembly 100 through the side of the sharp retractor 134 from which the arms 330, 332 (see, e.g. FIG. 48A) extend. A ledge section 434 may be defined by a portion of each of the protuberances 432. At least one of the ledges 434 may extend substantially perpendicular to the wall sections 428. At least one of the ledges 434 may be angled with respect to the wall section 428 on which it is included such that the undercut region has a triangular cross section.

Additionally, each wall section 428 may include a first section 436 and a second section 438. The first section 436 may have a smaller width than the second section 438 and may be the more proximal of the regions to the shelf 420. The first section 436 and second section 438 may be connected by an intermediary region 440. The intermediary region 440 may be angled or curved so as to transition between the differing widths of the first section 436 and second section 438. A nub 442 may be included projecting from the intermediary section 440 or a portion one of the first section 436 and second section 438 adjacent to the intermediary section 440. Though not shown a glue or adhesive supply port similar to port 304 of FIG. 26 may be included.

Figure 50:
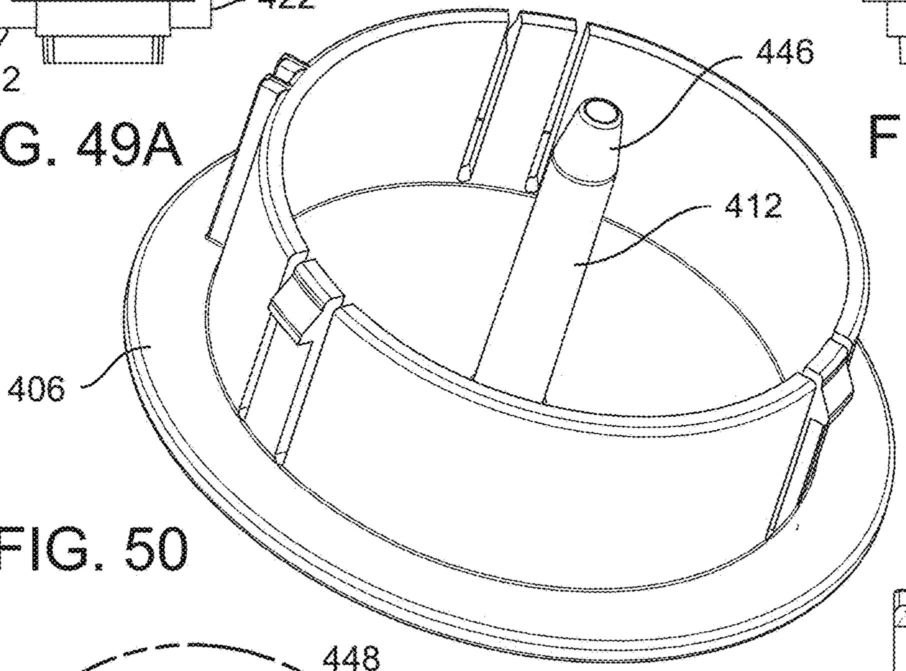
FIG. 50 depicts a perspective view of an exemplary retainer cap.
Figure 52:
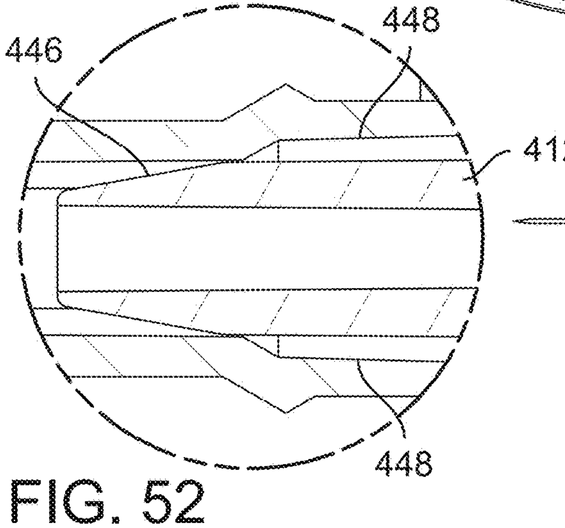
FIG. 52 depicts a detailed view of a portion of FIG. 51.
Figure 51:
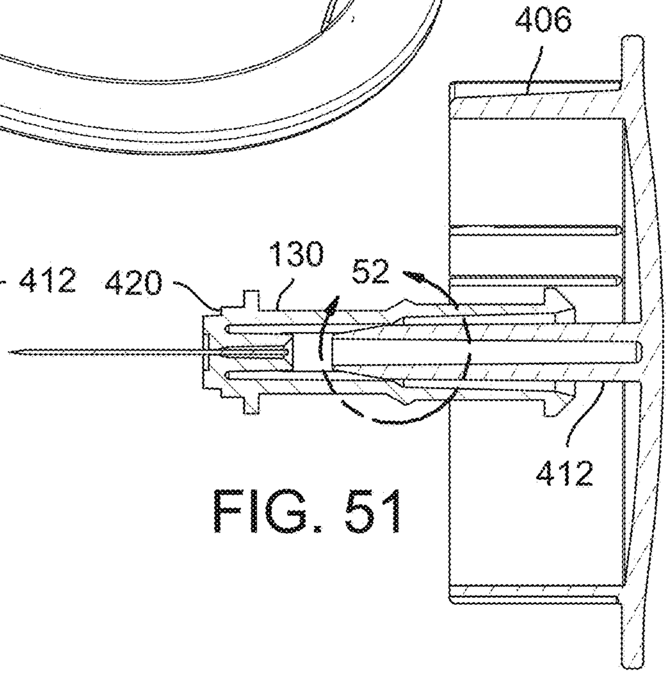
FIG. 51 depicts a cross-sectional view of an example retainer cap and sharp holder.

Referring now primarily to FIGS. 50-52, a projection 412, which may be referred to herein as a spreader pin 412, extending from the cap retainer 406 of the insertion assembly 100 may project into a receiving void 444 between the wall sections 428. The spreader pin 412 may include a tapered region 446 on an end thereof and may or may not be hollow. The tapered region 446 may abut into the interior faces 448 of the wall sections 428 as the spreader pin 412 is advanced into the sharp holder 130 beyond a certain distance and may help guide the spreader pin 412 as it is displaced into the sharp holder 130. Further displacement of the spreader pin 412 into the sharp holder 130 may cause the wall sections 428 to be resiliently deflected apart or spread apart from one another thus widening the sharp holder 130 in order to accommodate the spreader pin 412 therein. This may also cause the distance between outward facing surfaces of the nubs 442 to increase when the spreader pin 412 is present.

Figure 53A:
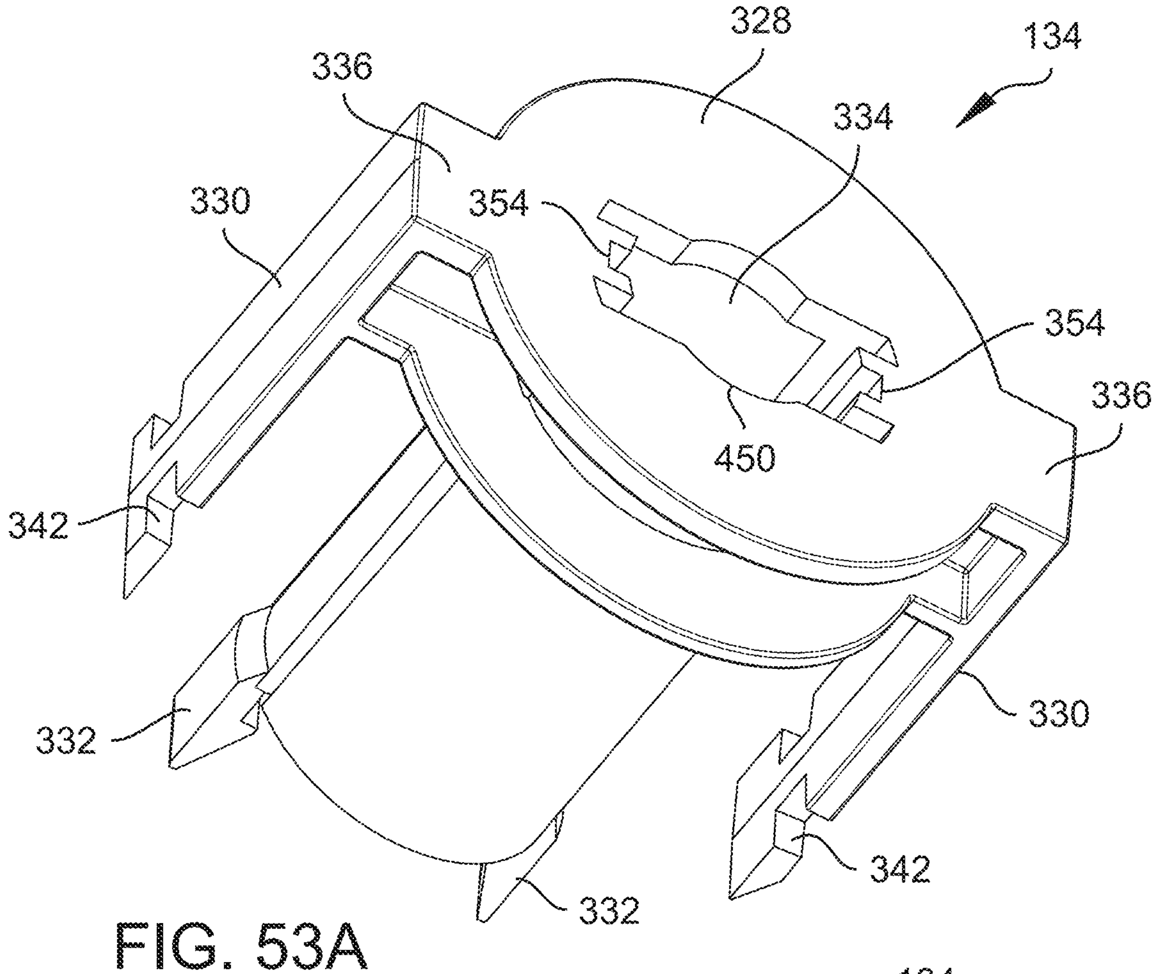
FIG. 53A depicts a perspective view of an exemplary sharp retractor.
Figure 53B:
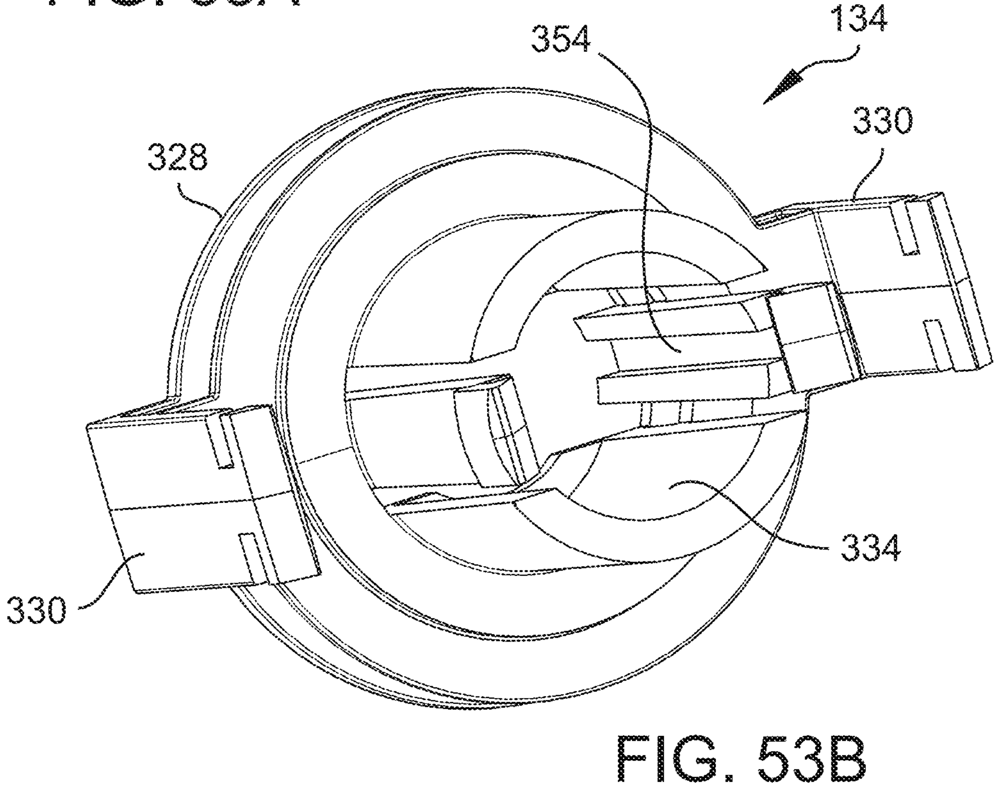
FIG. 53B depicts another perspective view of the sharp retractor shown in FIG. 53A.

Referring now primarily to FIG. 48B and FIGS. 53A-B, the nubs 442 may interact with another component of the inserter assembly 100 and prevent the force exerted by spring 136 against the shelf 420 from displacing the sharp holder 130 to a forward position. In the example shown, the nubs 442 are sized such that they may not fit into a cavity 334 included in the sharp retractor 134 when the spreader pin 412 is in place within the sharp holder 130. As spring 136 is captured between the shelf 420 of the sharp holder 130 and an interior face of the top plate 328 of the sharp retractor 134, the nubs 442 may inhibit release of energy stored in spring 136.

Still referring to FIGS. 48A-B in conjunction with FIGS. 53A-B, spring 138 may be held in an energy storing state by at least one latching engagement as well. As shown, the sharp retractor 134 may include a first set of arms 330 and a second set of arms 332. These arms 330, 332 may be substantially as described above in relation to FIGS. 35A-B. The sharp retractor 134 in this embodiment is depicted as having a symmetric design so as to allow the sharp retractor 134 to be assembled into an inserter assembly 100 in multiple orientations. This may help to simplify assembly. The sharp retractor 134 of FIGS. 35A-B may also be constructed symmetrically by including voids 322 (see, e.g., FIG. 35C) on opposing sides of the cavity 334.

Each of the one or more notches 342 or the arms 330 may engage with a cooperating projection 344 (see, e.g. FIG. 36) on the interior housing 120. Thus, the interaction of the notch(es) 342 and cooperating projection(s) 344 may maintain the spring 138 under compression and serve as a retraction prevention latch. This may be particularly helpful during assembly. Though notches 342 are shown, the arms 330 and interior housing 120 may engage in other ways as described elsewhere herein.

Again referring now primarily to FIGS. 48A-B in conjunction with FIGS. 53A-B, in some embodiments additional latches may be included in an inserter assembly 100 which aid in maintaining one or more of the springs 136, 138 in an energy storing state. In the example embodiment, spring 138 is held in an energy storing state by an additional latch engagement provided by features of the arms 332 interacting with features of the infusion set base 106. This latch arrangement may be similar to as described above in relation to FIGS. 24A-B. While retained by the arms 332 of the sharp retractor 134, the infusion set base 106 may be held such that surfaces of the infusion set base 106 are adjacent to the standoffs 352. This may prevent the infusion set base 106 and the needle retractor 134 on which it is retained from displacing into the inserter assembly 100 due to the presentation of a mechanical interference by the standoffs 352. As a consequence, the engagement of the arms 332 with the infusion set base 106 may also aid in holding the spring 138 in an energy storing state. The standoffs 352 may also ensure that the infusion set base 106 is positioned within the inserter assembly 100 such that the adhesive 374 may be pressed against the skin 356. In the example, the standoffs 352 ensure that the infusion set base 106 is substantially even with the skin contact face on the retaining base 140. As described elsewhere herein, with the infusion set base 106 so positioned, the infusion set base 106 and/or adhesive liner 111 may also act as a protective barrier.

Still referring primarily to FIGS. 48A-B, as the retainer pin 412 is withdrawn from the sharp holder 130, the wall sections 428 may restore back to a non-deflected state. This may decrease the distance between the nubs 442 so as to allow passage of the nubs 442 into the cavity 334 in the sharp retractor 134. In turn, this may allow the spring 136 to begin releasing energy and displace the sharp holder 130 toward a forward position. As shown, in FIGS. 48A-B, the example inserter assembly 100 is configured such that the entire inserter assembly 100 may move as a unit for at least a portion of the inserter assembly 100 withdrawal motion from the body. This may cause the skin 356 to be lifted a certain distance before the retainer pin 412 begins to be withdrawn and actuation is triggered. The amount the skin 356 is lifted or the force applied before portions of the inserter assembly 100 displace relative to one another may be modified as described in relation to the discussion of FIGS. 39A-B.

In various embodiments, the ledge section 434 of the sharp holder 130 may prevent displacement of the sharp holder 130 beyond a certain amount. Alternatively, the ledge section 434 may be disposed on the sharp holder 130 such that a dwell gap 360 (see, e.g., FIG. 42B) is present after the sharp holder 130 is propelled to the forward position. As described elsewhere herein, a dwell gap 360 may help to ensure the cannula sub assembly 114 is firmly retained in the base 106.

In various embodiments, as the sharp holder 130 displaces, the cannula sub assembly 114 may be coupled into the infusion set 106 as described elsewhere herein. Additionally, ears 204 of the cannula sub assembly 114 may cause the arms 332 to spread apart as the sharp holder 130 is displaced leading to release of the infusion set base 106 from the arms 332. This may release spring 138 and begin retraction of the insertion sharp 132. During retraction, the dwell gap 360 may decrease (if present) until top plate 328 of the sharp retractor 134 contacts the ledges 434 on the sharp holder 130. Once this occurs, the restoring action of spring 138 may begin to displace the sharp holder 130 and insertion sharp 132 affixed thereon along with the sharp retractor 134. This displacement may retract the insertion sharp 132 out of the cannula 104 and the infusion set 102. Once retraction has completed the sharp retractor 134 may be pressed against the exterior housing 116 by spring 138 and the insertion sharp 132 may be housed within the inserter assembly 100 to aid in protecting against unintentional finger sticks or the like. The infusion set 102 may be held in place on the skin 356 with the cannula 104 indwelling in the patient.

Figure 54:
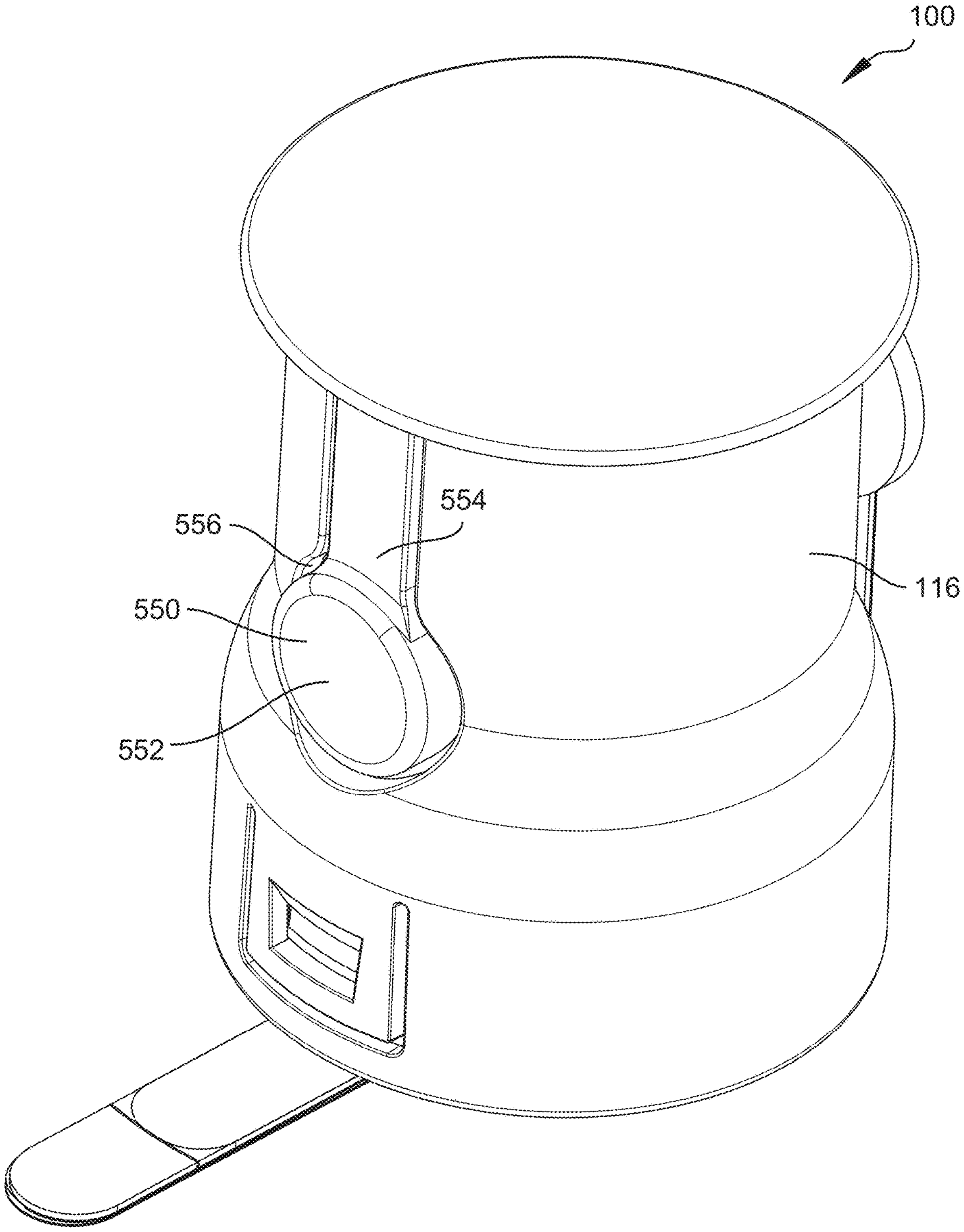
FIG. 54 depicts a perspective view of an example inserter assembly including a button.

Referring now to FIG. 54, another embodiment of an inserter assembly 100 including a manual trigger is depicted. The example inserter assembly 100 includes a button 550 which when displaced may trigger actuation. The button 550 may be included as a separate part which is assembled into the inserter assembly 100. Alternatively, and as shown, the button 550 may be formed monolithically with another portion of the inserter assembly 100. In the example embodiment, the button 550 is formed as a continuous part of the exterior housing 116. In the example embodiment, the button 550 includes an enlarged region that may include a depression 552 which may be substantially centrally located therein. The depression 552 may facilitate interaction with a user's finger. The button 550 may also include a cantilevered beam portion 554 which connects the button 550 to the rest of the exterior housing 116. In the example embodiment, the enlarged portion of the button 550 is disposed at a terminal unsupported end of the cantilevered beam portion 554, though may be located anywhere along the length of the cantilevered beam portion 554 in other embodiments. The cantilevered beam 554 extends in a direction substantially parallel to the longitudinal axis of the inserter assembly 100 and toward the top of the inserter assembly 100 in the example embodiment. In other embodiments, the cantilevered beam section 554 may extend in any direction. The cantilevered beam portion 554 may include a curvature which matches that of the exterior housing 116. A gap 556 surrounding the button 550 may be included to provide clearance for displacement or deflection of the button 550 during use. During actuation, the button 550 may be displaced at least partially into the inserter assembly 100 to trigger the insertion.

In some embodiments, the button 550 may not include a cantilevered beam section 554 and may instead be formed as a strip of material defined by cutouts flanking both sides of the strip. The enlarged section may be placed at or near the center of the strip. The strip may be deflected inward toward the inside of the inserter assembly 100 with application of pressure to trigger the insertion.

Figure 55C:
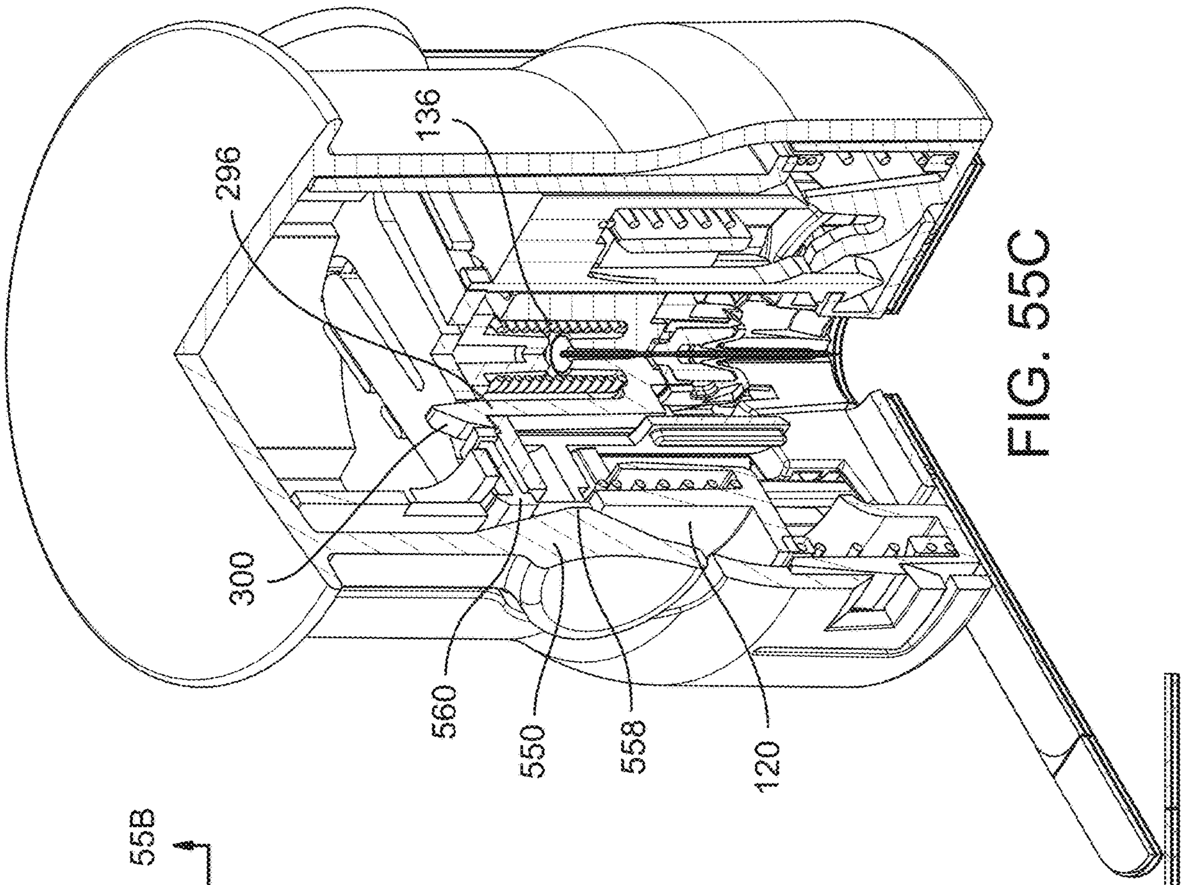
FIG. 55C depicts a perspective three-quarter section view taken along 55C-55C of FIG. 55A.
Figure 55A:
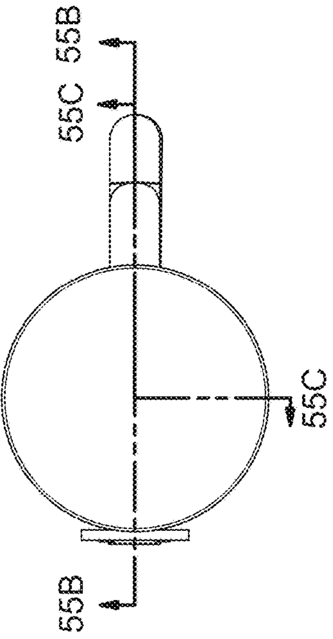
FIG. 55A depicts a top down view of the inserter assembly shown in FIG. 54.
Figure 55B:
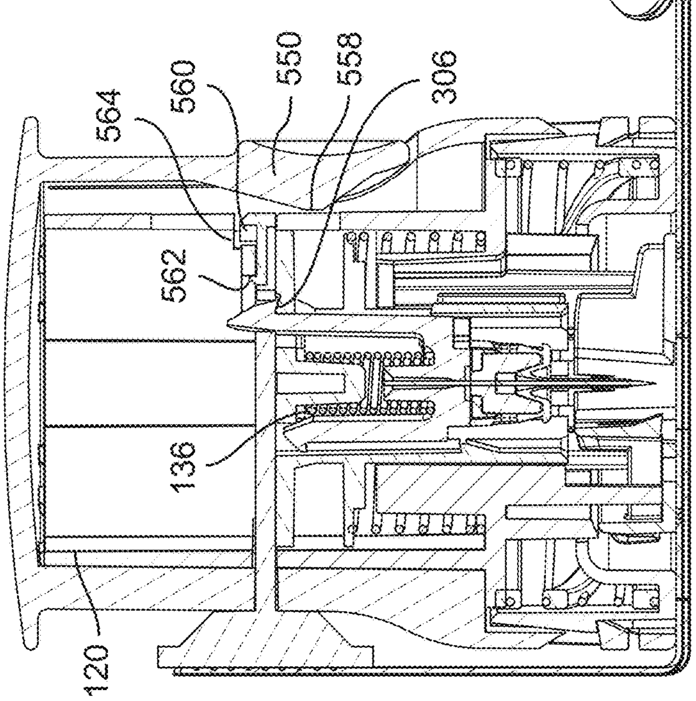
FIG. 55B depicts a cross-sectional view taken at cut plane 55B-55B of FIG. 55A.
Figure 56:
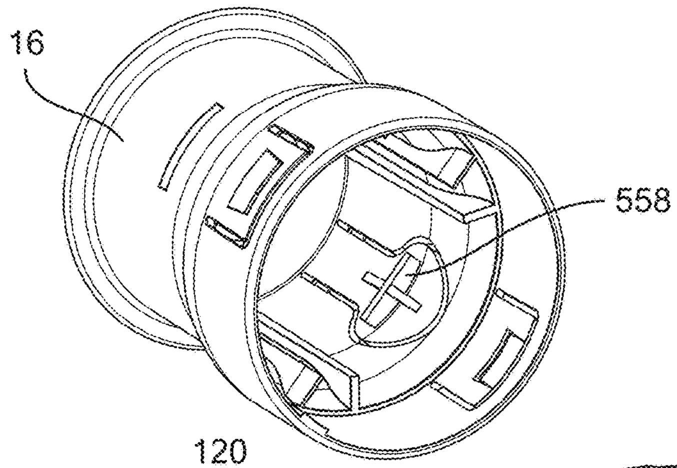
FIG. 56 depicts a perspective view of an example exterior housing of an inserter assembly including a button.
Figure 58:
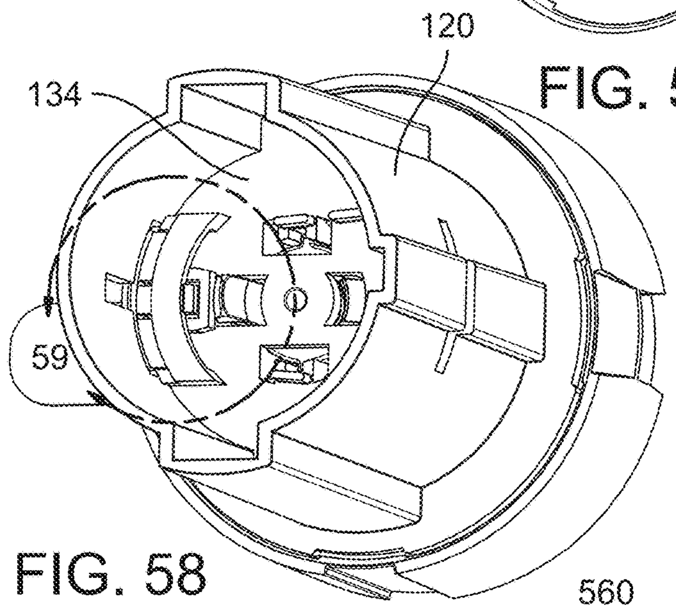
FIG. 58 depicts a perspective view of an example inserter assembly with an exterior housing of the inserter assembly removed.
Figure 57:
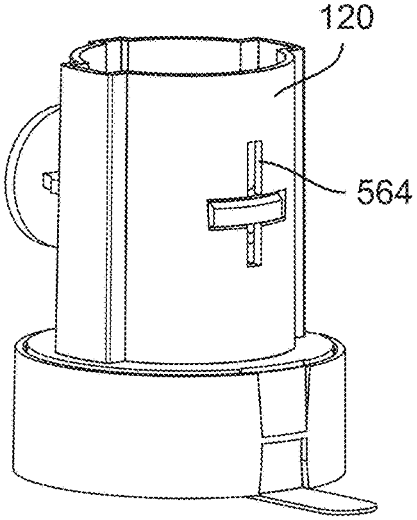
FIG. 57 depicts a perspective view of an example inserter assembly with an exterior housing of the inserter assembly removed.

Referring now also to FIGS. 55A-C and FIG. 56, an interlock may be included which prevents the button 550 from actuating the inserter assembly 100 until the skin has been displaced or until relative movement beyond a threshold magnitude has occurred. As shown, the button 550 may include a protuberance 558 (best shown in FIG. 56) on an inward face thereof. The protuberance 558 may be disposed opposite the depression 552 of the enlarged region of the button 550 as shown. In an initial state, the protuberance 558 may be out of alignment with a sled member 560 as shown in FIG. 55B for example. As the inserter assembly 100 is withdrawn from the body, the skin is lifted, and relative displacement of portions of the inserter assembly 100 occurs, the protuberance 558 may be brought into alignment with the sled 560. At this point, portions of the inserter assembly 100 may be disposed similarly to as shown in FIG. 40B. Once in the aligned state, the button 550 may be displaced so as to come into contact with the sled 560. Button 550 displacement may then drive the sled 560 into the protuberance 300 disposed at the terminal end of a cantilevered arm 296 on the sharp holder 130. As the sled 560 continues to advance, the protuberance 300 may be displaced off the catch 306 freeing bias member 136.

Referring primarily to FIGS. 56-59, in the initial state, the sled 560 may be may be disposed within a receiving void 564 included in the interior housing 120. The sled 560 may have a curved wall 566 which is substantially flush with the exterior face of the interior housing 120 in the initial state. As shown, the receiving void 564 is shaped so as to receive the protuberance 558 of the button 550. In the example embodiment, the protuberance 558 is cruciform in shape and the receiving void 564 mimics this shape. Until the inserter assembly 100 is in the aligned state, the wall of the interior housing 120 presents a mechanical interference which prevents the button 550 from being depressed. Once in the aligned state, the protuberance 558 may pass into the receiving void 564 and into the sled 560. Though a cruciform shape is used, any other type of shape may be used. For example, a star or asterisk type shape may be used in alternative embodiments. As shown best in FIG. 56, the shape chosen may include a ramped portion or portions which extend substantially parallel to the longitudinal axis of the inserter assembly 100. This may allow for increased tolerancing on the sled 560 and protuberance 558 and aid in ensuring smooth operation as the inserter assembly 100 is withdrawn from the body.

Figure 60:
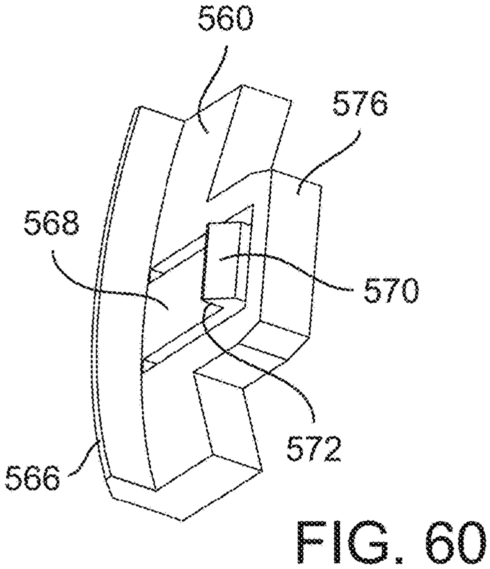
FIG. 60 depicts a perspective view of an exemplary sled which may be included in an inserter assembly.
Figure 59:
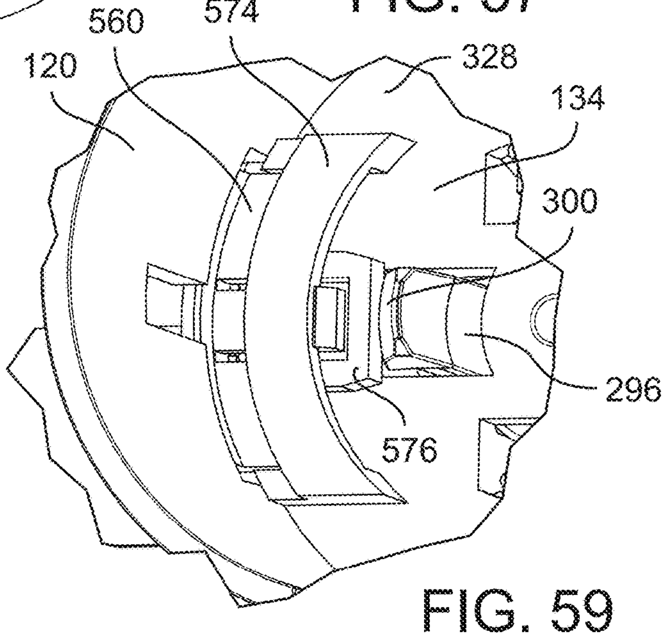
FIG. 59 depicts a detailed view of the indicated region of FIG. 58.

Referring primarily to FIGS. 59-60, the sled 560 may include a cantilevered member 568 including a sled protuberance 570 at a terminal unsupported end thereof. The cantilevered member 568 may be included within an actuation projection 576 of the sled 560. The sled protuberance 570 may form a ledge 572 which may catch on a component of the inserter assembly 100 to retain the sled 560 within the inserter assembly 100. As shown, the top plate 328 of the sharp retractor 134 includes a bridge 574. The bridge 574 forms an underpass which is in line with the receiving void 564 of the interior housing 120 when the inserter assembly 100 is assembled. During assembly, the sled 560 may be passed through the receiving void 564 and an actuating projection 576 of may travel through the underpass formed by the bridge 574. The ledge 572 of the cantilevered member 568 may catch on a surface of the bridge 574 retaining the sled 560 within the inserter assembly 100. The sled protuberance 570 on the cantilevered member 568 may be ramped so as to facilitate deflection of the cantilevered member 568 around the bridge 574 during installation of the sled 560. The bridge 574 may also act as a guide providing a displacement channel for the sled 560 as the sled 560 is driven into the protuberance 300 of the cantilevered arm 296.

Figure 61:
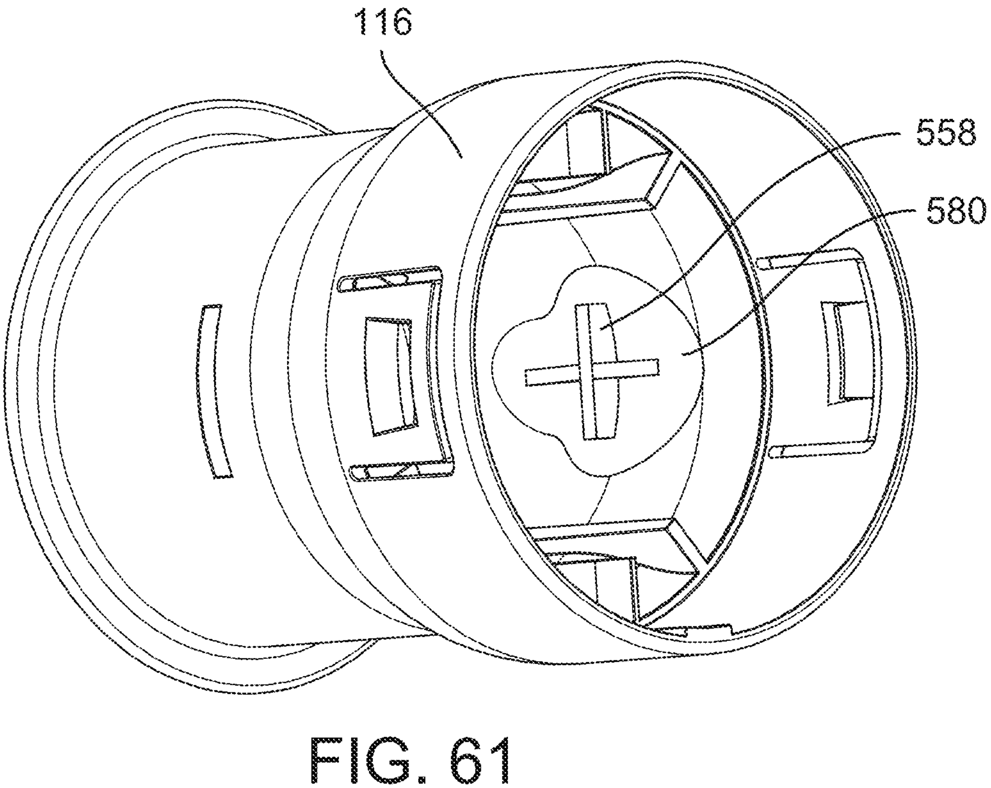
FIG. 61 depicts a perspective view of an example exterior housing for an inserter assembly including a deformable region.

Referring now also to FIG. 61, in some embodiments, a button 550 may not be included, however, a section of the exterior housing 116 may be deformable. In the example shown in FIG. 61, the exterior housing 116 includes a deformable region 580 including a protuberance 558 thereon. The deformable region 580 may be coupled to (e.g. over molded onto or otherwise adhered) the exterior housing 116 in certain examples. In embodiments including a deformable region, once the inserter assembly 100 is in an aligned state, a user may squeeze the exterior housing 116 at the deformable region 580 to drive the protuberance 558 into the sled 560 (see, e.g., FIG. 59) to trigger actuation.

Figure 62:
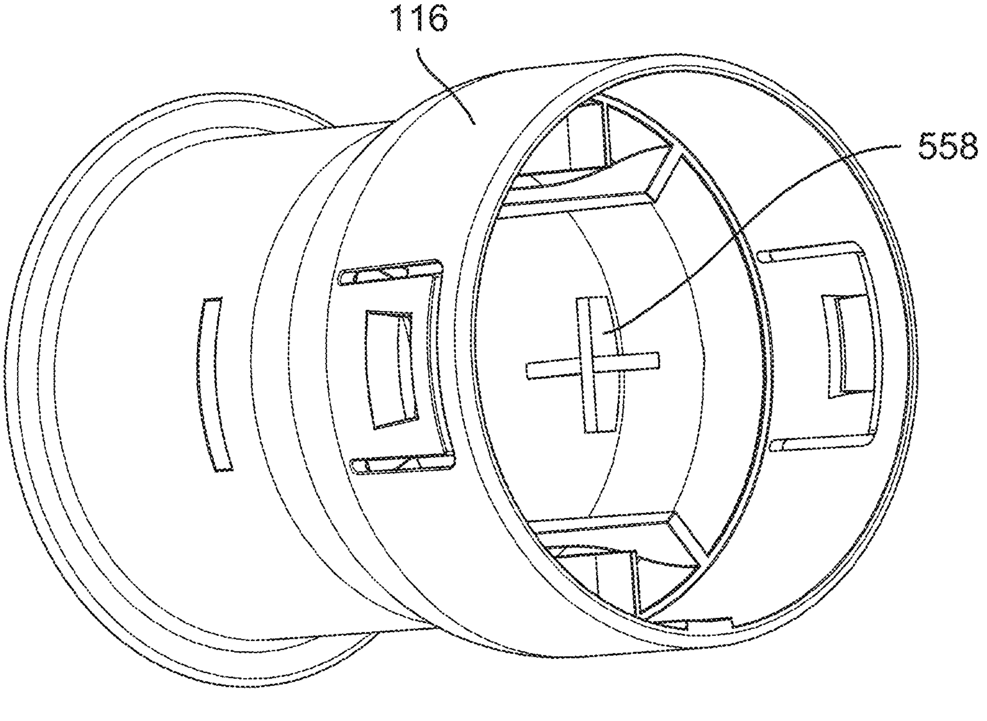
FIG. 62 depicts a perspective view of another example exterior housing for an inserter assembly including a protuberance on an interior face thereof.

In some embodiments, and referring now to FIG. 62, the interior face of the exterior housing 116 may include a protuberance 558. No button 550 or deformable region 580 may be included. During the withdrawal action of the inserter assembly 100 from the body, relative displacement of components of the inserter assembly 100 may automatically trigger the inserter assembly 100. The relative displacement may bring the protuberance 558 into contact with the sled 560 (see, e.g., FIG. 59) and drive the sled into 560 the protuberance 300 (see, e.g. FIG. 55B) on the cantilevered arm 296 (see, e.g. FIG. 55B) which may then be displaced off the catch 306 (see, e.g. FIG. 55B) freeing bias member 136 (see, e.g. FIG. 55B). The interior housing 120 may include an appropriately sized channel which accommodates the protuberance 558.

Figure 63:
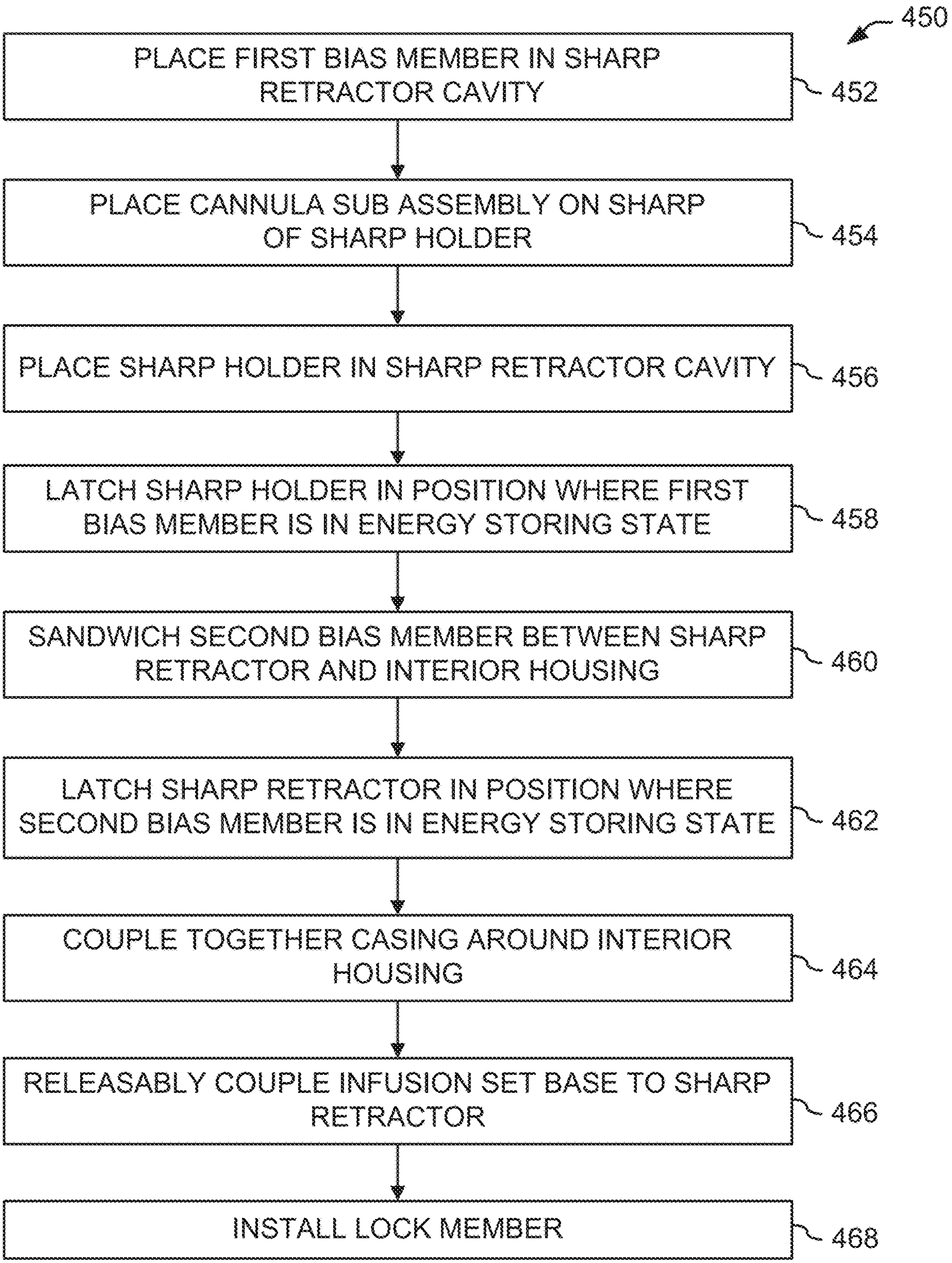
FIG. 63 depicts a flowchart detailing a number of actions which may be used to assemble an inserter assembly.

Referring now to FIG. 63, a flowchart 450 depicting a number of exemplary actions which may be executed to assemble an inserter assembly 100 such as that depicted in FIG. 24A-B is shown. In block 452, a first bias member such as spring 136 may be placed into a cavity 334 in a sharp retractor 134. A cannula sub assembly 114 may be placed on a sharp 132 attached to a sharp holder 130 in block 454. The sharp holder 130 may be placed into a sharp retractor 134 cavity 334 in block 456. In block 458, the sharp holder 130 may be latched into a position where the first bias member is in an energy storing state. This may be a compressed state in various examples. A second bias member such as spring 138 may be sandwiched between the sharp retractor 134 and an interior housing 120 in block 460. The sharp retractor 134 may be latched in a position in which the second bias member is in an energy storing state in block 462. This may be a compressed state in various embodiments. In block 464, a casing (which may be formed of an exterior housing 116 and retainer base 140) may be coupled together around the interior housing 120. An infusion set base 106 may be releasably coupled to the sharp retractor 134 in block 466. A lock member 146 may be installed into the inserter assembly 100 in block 468. As mentioned elsewhere herein the lock member 146 may be welded to the adhesive liner 111 coving adhesive on the infusion set base 106 in certain embodiments. During assembly of the components, any rails, guides, keyed features, fingers etc. included on a component may be aligned with cooperating features of the components in which they are being placed. Latching together of the various components of the inserter assembly 100 may simplify assembly of the inserter assembly 100 as the components may hold themselves in the proper orientation or position against any spring bias. Thus an assembler (human or robotic) may simply bring components into latching engagement with one another and be able to release the components thereafter. This may allow partially assembled portions of inserter assemblies 100 to be moved about a production facility or shipped to other facilities and may simplify any fixturing used during assembly.

Figure 64:
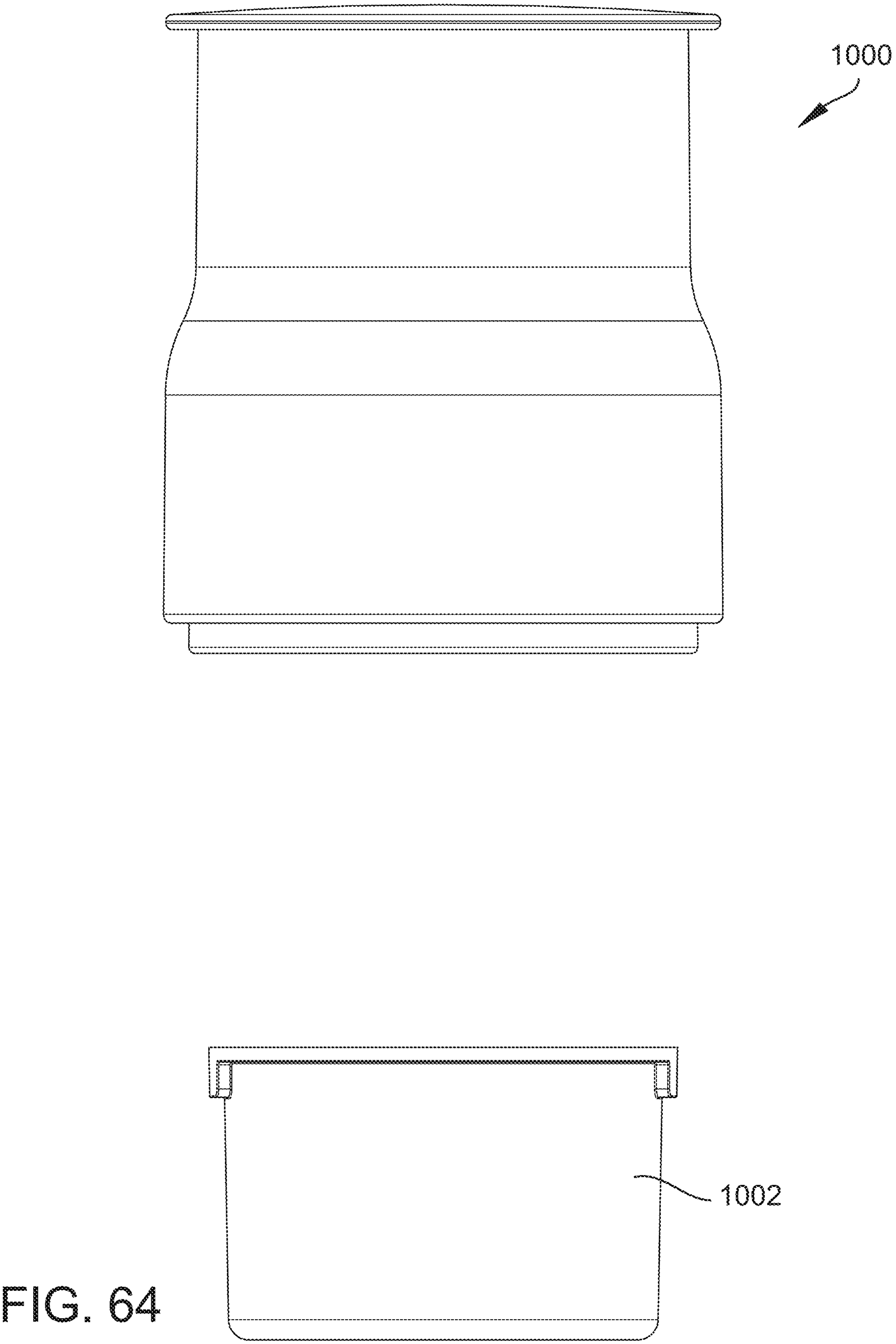
FIG. 64 depicts a side view of an example inserter assembly and an example cartridge which may be coupled to the inserter assembly.

Referring now to FIG. 64, in some examples, an inserter assembly 1000 may be reusable. After actuation, certain inserter assembly 1000 embodiments, may be reset and used to install a next infusion set 102 (or analyte sensor in certain examples). Thus, the same inserter assembly 1000 may be used to install a plurality of different infusion sets 102. For example, a container of infusion sets 102 may include a single inserter assembly 1000 (or a number of inserter assemblies 1000 which is less than the number of infusion sets 102). The single inserter assembly 1000 may be intended to be used to install each of the infusion sets 102 in the container onto the patient. Thus, the waste and cost associated with site changes may be reduced. In embodiments where the inserter assembly 1000 is a multi-use device, infusion sets 102 may be provided in separate set cartridges 1002. Similarly, where the inserter assembly 100 is configured to apply a sensor to the patient, sensors may be provided in sensor cartridges which are separate from the inserter assembly 1000. As in other embodiments described herein, the infusion set 102 may be provided partially assembled within the set cartridges 1002. A set cartridge 1002 is depicted separate from the inserter assembly 1000 in FIG. 64. The set cartridge 1002 may be coupled to the inserter assembly 1000. Once coupled, the inserter assembly 1000 may be actuated to install the infusion set 102 at a desired infusion site. After actuation, the spent cartridge 1002 may be separated from the inserter assembly 1000 and disposed of. The inserter assembly 1000 may be reset when another set cartridge 1002 is coupled thereto and used to install another infusion set 102.

Depending on the embodiment, actuation of the inserter assembly 1000 may also cause assembly of the infusion set 102 to be completed. The infusion set 102 may be provided as a number of portions (e.g. separate components, subassemblies, or combinations thereof) within a set cartridge 1002. Actuation of the inserter assembly 1000 may cause each portion of the infusion set 102 to be coupled together to complete the assembly of an infusion set 102. For example, assemblage of an infusion set 102 may occur as an initial stage of the actuation of the inserter assembly 1000 or may occur as part of an insertion stage of inserter assembly 1000 actuation which results in the cannula 104 being introduced into the patient.

Figure 65A:
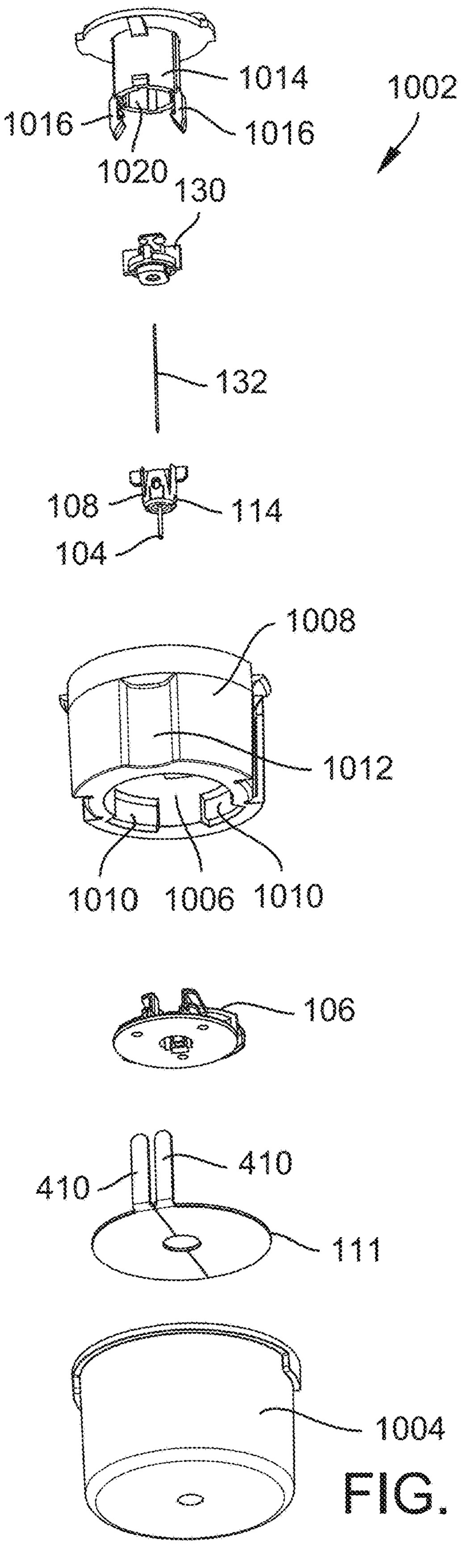
FIG. 65A depicts an exploded view of an example cartridge.
Figure 65B:
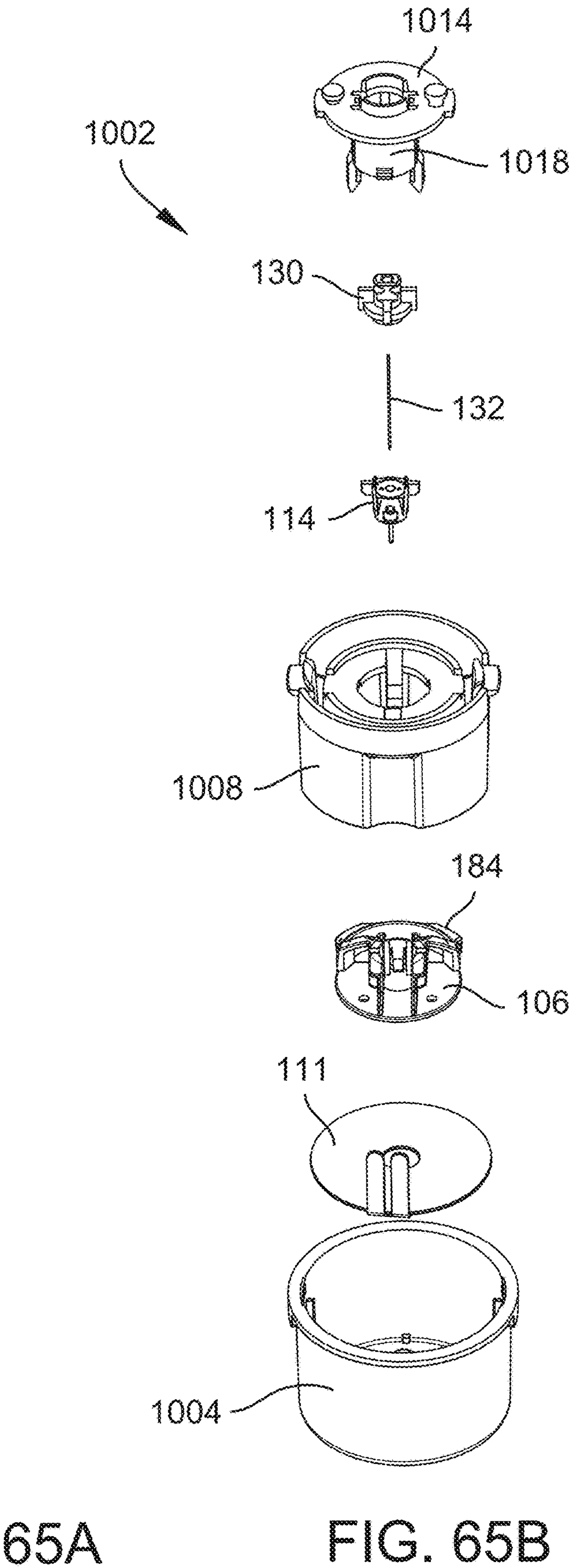
FIG. 65B depicts another exploded view of the example cartridge shown in FIG. 65A.

Referring now to FIGS. 65A-65B, exploded views of an exemplary set cartridge 1002 are depicted. As shown, the set cartridge 1002 may include an exterior housing 1004. When the set cartridge 1002 is assembled, the exterior housing 1004 may contain the other components of the set cartridge 1002. The exterior housing 1004 may thus also be referred to herein as a container. In the example, the exterior housing 1004 is shown as a cup and includes an open top. Depending on the embodiment, when fully assembled, the open top of the exterior housing 1004 may be covered by a barrier member so as to completely enclose the components of the set cartridge 1002. This barrier member may be permeable to a sterilizing agent to allow for sterilization of the set cartridge 1002 after assembly. A barrier member may also help minimize contact of components in the exterior housing 1004 with the surrounding environment or a user.

As shown, an infusion set 102 may be contained within the set cartridge 1002 as a first portion and a second portion which are separate from one another, but coupled together during actuation of the inserter assembly 1000 to form the infusion set 102. The first portion may include a base 106 which may be applied to the skin of a patient and may couple to a fluid pathway (e.g. via a terminal connector on the pathway) which is part of or extends from an infusion pump. An adhesive backing, film, or liner 111 may be included and may be applied over adhesive 374 included on the infusion set base 106. The infusion set base 106 may seat within a receiving bay 1006 of an interior housing 1008 of the set cartridge 1002. The receiving bay 1006 may include notches 1010 which may accept tube retainers 184 included on the infusion set base 106. In the example embodiment, the notches 1010 may also serve to ensure that the base 106 may only be installed within the receiving bay 1006 in a desired orientation. As shown, the interior housing 1008 may include an indention 1012. The indention 1012 may be sized so as to accept pull tabs 410 included on the adhesive liner 111. As the indention 1012 may be visible to the user, the indention 1012 may be used as an orientation indicator. This may help the user install the infusion set 102 in a manner which accommodates their planned routing pathway for infusion tubing which is to be coupled to the infusion set 102. Indicators which show the orientation of the infusion set 102 may be included on portions of the inserter assembly 1000 as well. This may be particularly true in embodiments where the set cartridge 1002 may only be coupled to the inserter assembly 1000 in a single orientation.

The second portion of the infusion set 102 may be a subassembly 114 of two or more components of the infusion set 102. The second portion may include a cannula 104, septum housing 108, septum 110, and septum retainer 112 for example (an exemplary cannula subassembly 114 is shown exploded apart in FIG. 1A). Any cannula sub assembly 114 described herein may be used. The cannula 104 and the septum housing 108 are shown a single continuous unitary part in the example embodiment. This cannulated housing may be a molded part which is constructed of a single material such as, PTFE, Teflon, polypropylene, etc. for example. When the set cartridge 1002 is assembled, the insertion sharp 132 may extend through the cannula sub assembly 114 and the cannula sub assembly 114 may be disposed against the sharp holder 130. In sensor cartridge embodiments, the cannula sub assembly 114 and infusion set base 106 may be replaced by a sensor assembly.

A set cartridge 1002 may further include a sharp holder 130. The sharp holder 130 may retain an insertion sharp 132 thereon. The insertion sharp 132 may be glued or otherwise bonded into the sharp holder 130 so as to be fixedly located relative to the sharp holder 130. The insertion sharp 132 may alternatively be press fit into the sharp holder 130 or the sharp holder 130 and insertion sharp 132 may be joined in an overmolding process. Any suitable type of sharp 132 may be used. For example, the sharp 132 may be a hollow or solid needle, stylet, or other pointed member which may be made of a metal material such as steel.

Figure 66:
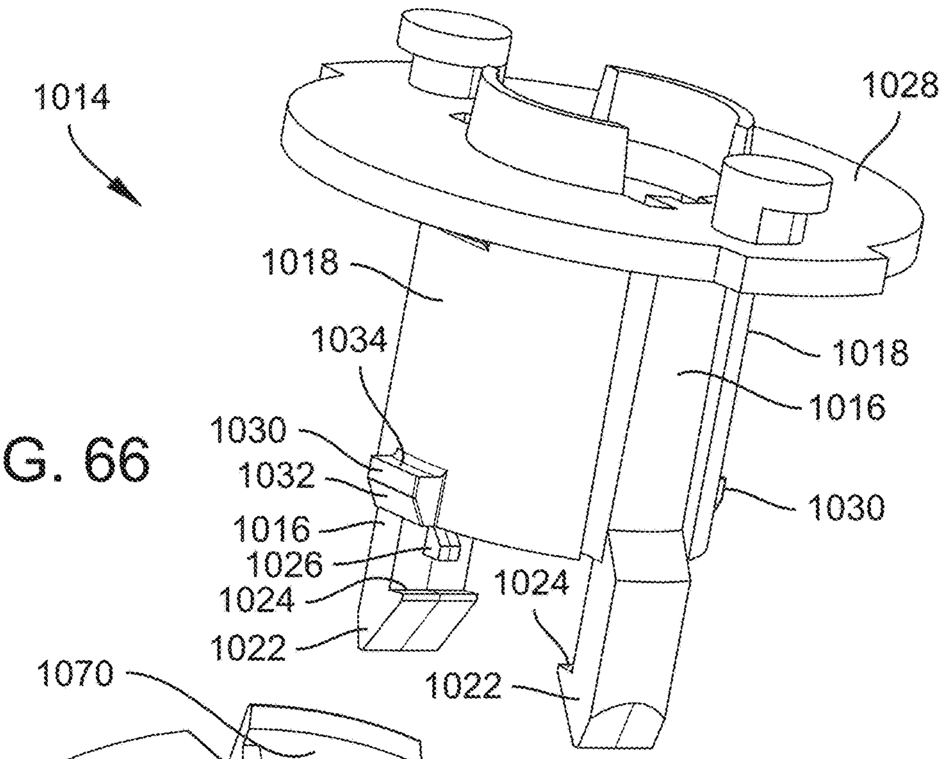
FIG. 66 depicts a perspective view of an exemplary infusion set base retainer.

Referring now primarily to FIG. 66, an infusion base retainer 1014 may also be included in a set cartridge 1002. The infusion base retainer 1014 may include a set of retainer arms 1016. The retainer arms 1016 may extend from an end plate 1028 of the infusion base retainer 1014. The arms 1016 may be separated from a wall 1018 defining the central cavity 1020 of the infusion base retainer 1014 by interrupt regions included in the wall 1018. The wall 1018 may also include a set of protuberances 1030. The protuberances 1030 may be disposed opposite one another on the wall 1018 and may be roughly spaced 90° from the arms 1016. The protuberances 1030 may include a ramped face 1032 on a portion of each protuberance 1032 most distal to the end plate 1028. The protuberances 1030 may also define a catch face 1034 on a portion of the protuberances 1030 most proximal to the end plate 1028.

Figure 67:
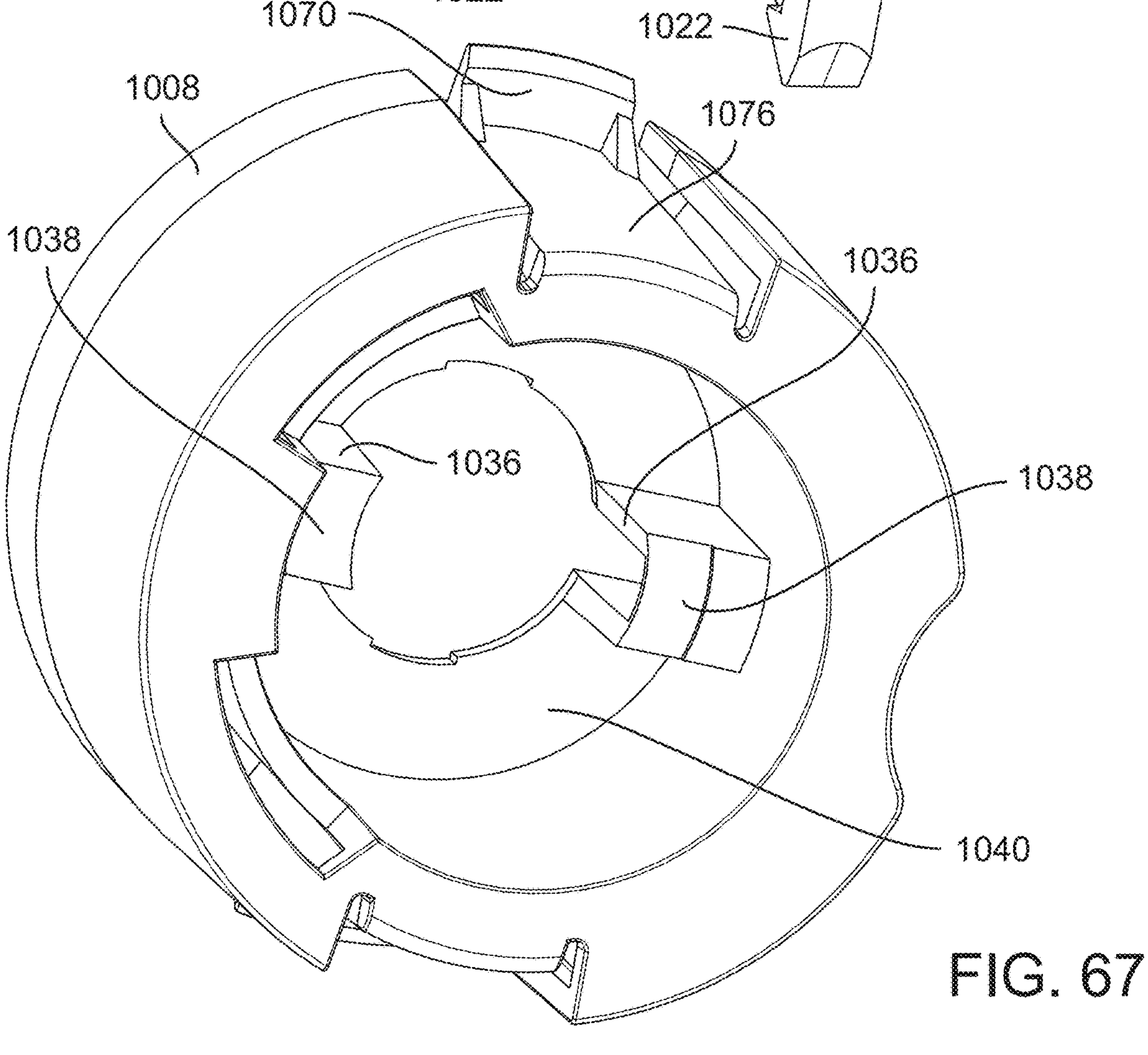
FIG. 67 depicts a perspective view of an example interior housing of an example cartridge.

Referring now also to FIG. 67, during assembly of the infusion base retainer 1014 into the interior housing 1008, the protuberances 1030 may travel along respective channels 1036 defined in the interior housing 1008. As shown, a terminus of the channels 1036 may be closed by a stop wall 1038. As the protuberances 1030 are driven into the stop wall 1038 the portions of the wall 1018 on which the protuberances 1030 are included may resiliently deflect inward so as to allow passage of the protuberances 1030 beyond the stop wall 1038. The ramped face 1032 may facilitate this deflection. Once the protuberances 1030 have passed the stop wall 1038, the portions of the wall 1018 may restore back to an unstressed state. When the portions of the wall 1018 are in the unstressed state, the catch faces 1034 of the protuberances 1030 may be latched against the stop walls 1038 of the channels 1036 preventing the infusion base retainer 1014 from being pushed out of the interior housing 1008. The end plate 1028 of the infusion base retainer 1014 may abut a rim 1040 which prevents further displacement of the infusion base retainer 1014 into the interior housing 1008. Thus the infusion base retainer 1014 may be fixed in place within the interior housing 1008.

Referring again primarily to FIG. 66, the set of arms 1016 of the infusion base retainer 1014 may be disposed in opposing relationship to one another and may be cantilevered from the end plate 1028. Each of the arms 1016 may include a protuberance 1022 disposed at an unsupported end thereof. Each protuberance 1022 may form a ledge 1024 on the arm 1016 on which it is included. Additionally, the arms 1016 may include a nub 1026 or raised ramp which increases in thickness as distance from the cavity 1020 (see, e.g., FIG. 65A) increases. The nub 1026 may be disposed intermediate the unsupported end of the arm 1016 and its attachment point to the remainder of the infusion base retainer 1014.

Figure 68:
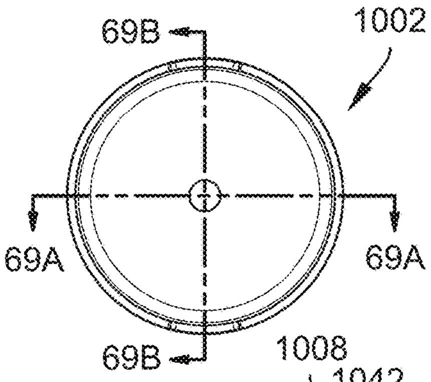
FIG. 68 depicts a bottom plan view of an example cartridge.
Figure 69A:
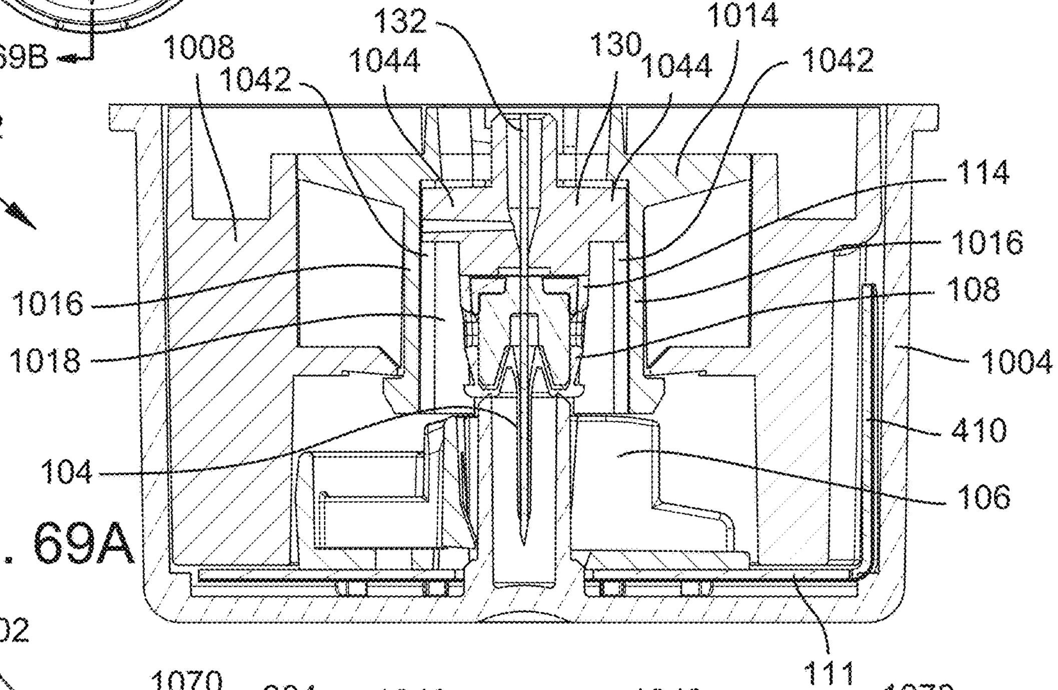
FIG. 69A depicts a cross sectional view taken at cut plane 69A-69A of FIG. 68.
Figure 69B:
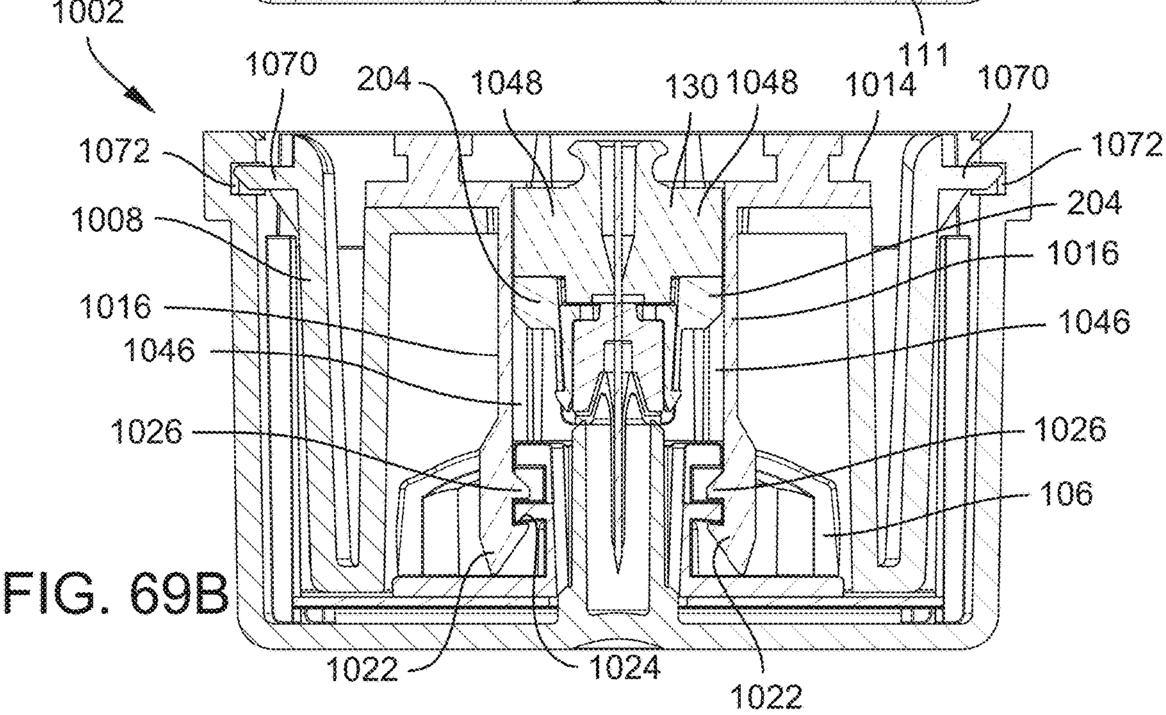
FIG. 69B depicts another cross sectional view taken at cut plane 69B-69B of FIG. 68.

Referring now to FIGS. 68-69B and as best shown in FIG. 69B, each ledge 1024 may capture a portion of the infusion set base 106. Specifically, the ledges 1024 may catch on an outcropped portion of the infusion set base 106. The base 106 may include rails, step features, nubs or any other suitable protrusions to provide a complimentary catch surface for the ledges 1024. In certain embodiments, the ledges 1024 may catch on guides 172 of the infusion set base 106. Thus the infusion set base 106 may be retained within the set cartridge 1002. Ledges 1024 may be angled with respect to the cantilevered arm 1016 on which they are included such that the undercut has a triangular cross section. The portion of, for example, the guides 172 (or any other catch feature) on which each ledge 1024 catches may be angled in a cooperating manner to help ensure a robust engagement.

In certain embodiments, only one arm 1016 may be included. In some embodiments, the interior housing 1008 may also or instead include latch which may interface with the guide 172 or another cooperative portion of the infusion set base 106 to retain the infusion set base 106 in place.

With the infusion set base 106 retained by the arms 1016, the infusion set base 106 may also act as a protective barrier. As the cannula sub assembly 114 and insertion sharp 132 may be internal to the set cartridge 1002, when the infusion set base 106 is in the initial retained position, the user may be protected from accidental contact with the insertion sharp 132. This may additionally help to keep the cannula 104 or insertion sharp 132 from coming into contact with contaminants. Though a void for receipt of the cannula sub assembly 114 may extend through the entirety of the infusion set base 106, the void may be sized to prevent finger ingress (e.g. have a cross-section smaller than that of a finger). Thus the infusion set base 106 may present an obstacle which blocks unintentional access to the insertion sharp 132 and cannula 104. Additionally, as the cannula subassembly 114 is internal to the set cartridge 1002, any adhesive backing 111 provided on the infusion set base 106 need not include an interruption to allow for passage of the cannula 104 therethrough. Thus, the void in the infusion set base 106 for the cannula subassembly 114 may be blocked by the adhesive backing 111 until just prior to use. This may further prevent finger ingress and may mitigate potential for detritus to enter the set cartridge 1002. The exterior housing 1004 may also present a barrier which inhibits a user from interacting with the insertion sharp 132 and/or cannula 104.

As shown in FIGS. 69A-69B, the infusion base retainer 1014 may include at least one guide in various embodiments. In the example embodiment, the infusion base retainer 1014 includes a set of sharp holder guides 1042 (see, FIG. 69A). The sharp holder guides 1042 may be recessed into a cavity facing side of the wall 1018 of the infusion base retainer 1014. The sharp holder 130 may include fins 1044 which may ride within the sharp holder guides 1042 during displacement of the sharp holder 130 within the set cartridge 1002. In alternative embodiments, the sharp holder 130 may include recesses and the wall may include rails projecting from the cavity facing side of the wall 1018. The rails may be received within the recesses of the sharp holder 130 and guide displacement of the sharp holder 130 as it displaces within the set cartridge 1002.

The infusion base retainer 1014 may also include a set of septum housing guides 1046. The septum housing guides 1046 (see, FIG. 69B) may be recessed into the cavity facing sides of the arms 1016. Ears 204 of the septum housing 108 may ride within the septum housing guides 1046 during displacement of the cannula sub assembly 114 within the set cartridge 1002. As shown, the sharp holder 130 may also include fins 1048 which are in line with the ears 204 and which may also ride within the septum housing guides 1046. When the cannula subassembly 114 latches into the base 106, the ears 204 on the cannula subassembly 114 may press against the nubs 1026 included on the arms 1016. This may cause the arms 1016 to be splayed apart resulting in disengagement of the arms 1016 from the infusion set base 106. In turn, this may free the now assembled infusion set 102 from the set cartridge 1002.

Referring now to FIGS. 70A-70B and FIGS. 71A-71B, exploded views of two example embodiments of an inserter assembly 1000 are depicted. Inserter assemblies such as inserter assembly 1000 may be coupled to set cartridges 1002 and subsequently used to place an infusion set 102 onto an infusion site of a patient and introduce a cannula 104 of an infusion set 102 into the patient's body. As mentioned elsewhere, some inserter assemblies 1000 may be used to place other patient care assemblies onto the body of a patient. For example, certain inserter assemblies 1000 may be operated to place physiological monitors or analyte sensors into working relationship with a patient's body. Blood sugar monitors such as continuous glucose sensors may be placed using an inserter assembly 1000. In certain embodiments, the same inserter assembly 1000 may be mated with a set cartridge 1002 or sensor cartridge depending on the type of device a patient intends to place on their body. In some embodiments, inserter assemblies 1000 may also be coupled to lancet cartridges (e.g. a set cartridge 1002 without a cannula subassembly and infusion set base 106) to create a skin puncture for collection of a body sample with an analyte testing strip.

As shown in the exploded views in FIGS. 70A-71B, an insertion assembly 1000 may include an exterior housing 116. The exterior housing 116 may enclose various components of the inserter assembly 1000 and serve as the portion of the inserter assembly 1000 which the user grips during operation. The exterior housing 116 in the example embodiment of FIGS. 70A-70B has a cross sectional shape which is round, though other embodiments may have different shapes such as any type of polygonal shape. In certain examples, a rectangular or obround cross-sectional shape such as that shown in FIGS. 71A-71B may be used. Such a shape may more easily fit within a pocket or may more easily fit into smaller pockets which may, for example, be more typical of woman's clothing. The cross sectional area in the example embodiments also vary with the bottom section (that most proximal the skin when in use) of the exterior housing 116 being wider or having a greater cross-sectional area than the top. An exterior housing 116 may include various ergonomic features which facilitate grasping of the inserter assembly 1000 in which it is included. For example, texturing or a finger or thumb depression may be included on the outer surface of the exterior housing 116. Alternatively or additionally, a region of the external housing 116 may be thinner in width than the remaining portion of the external housing 116. This may make firm grasping of the inserter assembly 1000 easier.

Example exterior housings 116 may include a marking, tab, embossed section, recess section, textured section, protuberance, color coding, appliqué, or other indicia which serves to indicate position and/or orientation of the infusion set 102 within the insertion assembly 1000. A raised rib 118 such as that shown in FIG. 1A for example, may be included. This may allow a user to position the inserter assembly 1000 in a desired orientation so as to allow for a run of infusion tubing 366 (see, e.g. FIG. 6) to be routed in a planned manner once the infusion set 102 is attached to the user.

A retainer cap 406 may serve to couple to a top portion of the inserter assembly 1000 to hold the various components in place within the inserter assembly 1000. In the examples shown in FIGS. 70A-71B, the retainer caps 406 include cantilevered retainer bodies 408 which may snap into retaining interfaces 411 (see, e.g. FIG. 70A) included on the exterior housing 116. Other couplings are also possible such as a bayonet mount, interference fit, snap fit, adhesive, glue, threads, solvent bonding, welding, etc. When coupled together, the exterior housing 116 and retainer cap 406 may form a casing of the inserter assembly 1000. The exterior housing 116 and the retainer cap 406 together may form a first unit of the inserter assembly 1000. The remaining components of the inserter assembly 1000 may be referred to as a second unit of the inserter assembly 1000.

Still referring to FIGS. 70A-71B, an inserter assembly 1000 may also include an interior housing 120. The interior housing 120 may be disposed inside of the external housing 116 when the inserter assembly 1000 is assembled. The first unit of the inserter assembly 1000 may be displaceable relative to the interior housing 120 and other components of the second unit of the inserter assembly 1000 contained therein. Various exterior housings 116 may have at least one keying feature which constrains the interior housing 120 such that it may only be installed in a limited number of orientations within the exterior housing 116. The cross-sectional shape may be chosen so as to dictate such a constraint (see, e.g., FIGS. 71A-71B). Alternatively, the exterior housing 116 may include at least one rail 1090 (see, e.g., FIGS. 70A-70B). In the exemplary embodiment shown in FIGS. 70A-70B, two rails 1090 are included directly opposite one another (only one is visible) on the interior facing surfaces of the exterior housing 116. The rails 1090 extend substantially parallel to one another. If it is desired to limit the interior housing 116 to a single installation orientation, the rails 1090 may be of different widths. The exterior face of the interior housing 120 may include tracks 1092 which cooperate with the rails 1090. The interior housing 120 may be inhibited from displacing into the exterior housing 116 until the rails 1090 are aligned with the tracks 1092. The interaction of the rails 1090 within the tracks 1092 may also inhibit rotation of the interior housing 120 and exterior housing 116 relative to the other. Though rails 1090 are shown on the exterior housing 116 in the example, the rails 1090 may instead be present on the exterior face of the interior housing 120 in some embodiments. In such examples, the tracks 1092 may be located on the exterior housing 116.

Figure 70A:
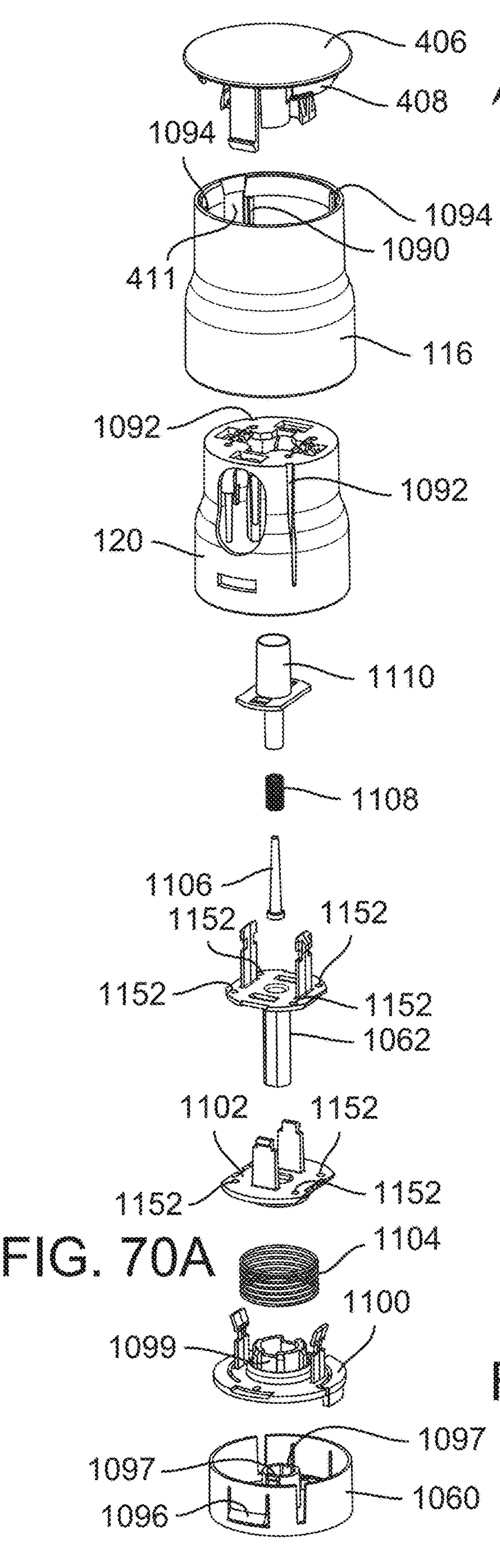
FIG. 70A depicts an exploded view of an example inserter assembly which may be reusable.
Figure 70B:
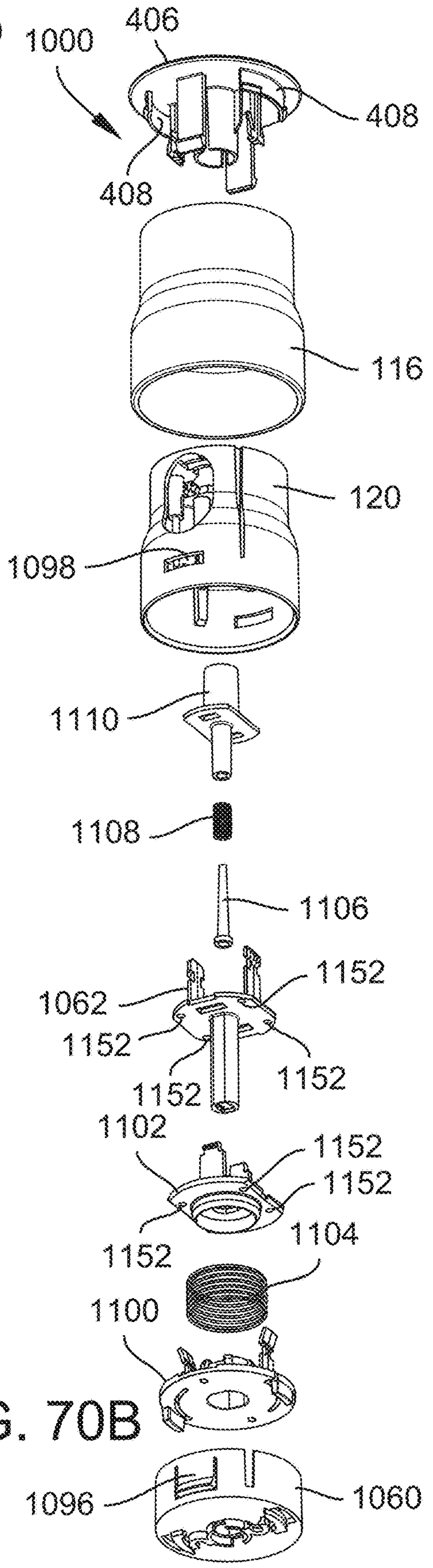
FIG. 70B depicts another exploded view of the example inserter assembly in FIG. 70A.

As shown in FIGS. 70A-70B, the exterior housing 116 may also include stop protrusions 1094 on the interior face of the exterior housing 116. The stop protrusions 1094 may be nubs, pins, rails or any suitable feature. The stop protrusions 1094 may limit the travel of the interior housing 120 along the axis of the exterior housing 116. In the example embodiment, the stop protrusions 1094 extend from an end of the exterior housing 116 in a direction parallel to the rails 1090. In certain examples, the retainer arms 408 of the retainer cap 406 may also act as stops which limit travel of the interior housing 120 relative to the exterior housing 116.

A receptacle body 1060 (described in greater detail in relation to FIGS. 73-75, and FIG. 77) may serve to couple to a bottom portion of the inserter assembly 1000 to hold the various components in place within the inserter assembly 1000. In the examples shown in FIGS. 70A-71B, the receptacle bodies 1060 include cantilevered retention arms 1096 which may snap into retainer interfaces 1098 included on the interior housing 120. Other couplings are also possible such as a bayonet mount, interference fit, snap fit, adhesive, glue, threads, solvent bonding, welding, etc. Lock members 1112A, B which may be part of another component (e.g. the retraction latch body 1100 in FIG. 70A-70B) or as individual separate components (see, e.g., FIG. 71A-71B) may be included and may project through the receptacle body 1060.

A retraction latch body 1100 and a retracting spring retainer 1102 may also be included. As will be further described later in the specification, the retraction latch body 1100 and retraction spring retainer 1102 may engage with one another to hold a bias member such as spring 1104 (or springs 1104A, B of FIGS. 71A-71B) and spring 1108 in an energy storing state during portions of the inserter assembly 1000 actuation. The retraction latch body 1100 may be coupled in place on the receptacle body 1060 via interaction of latch fingers 1097 of the receptacle body 1060 with catch bodies 1099 on the retraction latch body 1100.

An insertion driver 1062 may also be included in an inserter assembly 1000. As will be further described later in the specification, the insertion driver 1062 may have a plunger 1106 and a spring 1108 housed in a portion of the insertion driver 1062. An assembly resetting body 1110 may be included. As further described later in the specification, the resetting body 1110 may act on various components of the inserter assembly 1000 to place the components in a ready state in preparation for an actuation. When freed to transition from an energy storing state to a relaxed state, the spring 1108, may displace the insertion driver 1062 to cause insertion of a cannula 104 from an attached set cartridge 1002 and complete assembly of the infusion set 102 of the set cartridge 1002. Retraction of the sharp 132 into the set cartridge 1002 may also occur as spring 1104 (or springs 1104A, B of FIGS. 71A-71B) is freed to transition from an energy storing state to a relaxed state. During this transition, the spring 1104 may in some embodiments, drive the retraction spring retainer 1102 towards a retracted state within the inserter assembly 1000. This may cause the insertion driver 1062 (which may be attached to the sharp holder 130, see e.g. discussion of FIG. 73) to be driven to a retracted state.

Figure 71A:
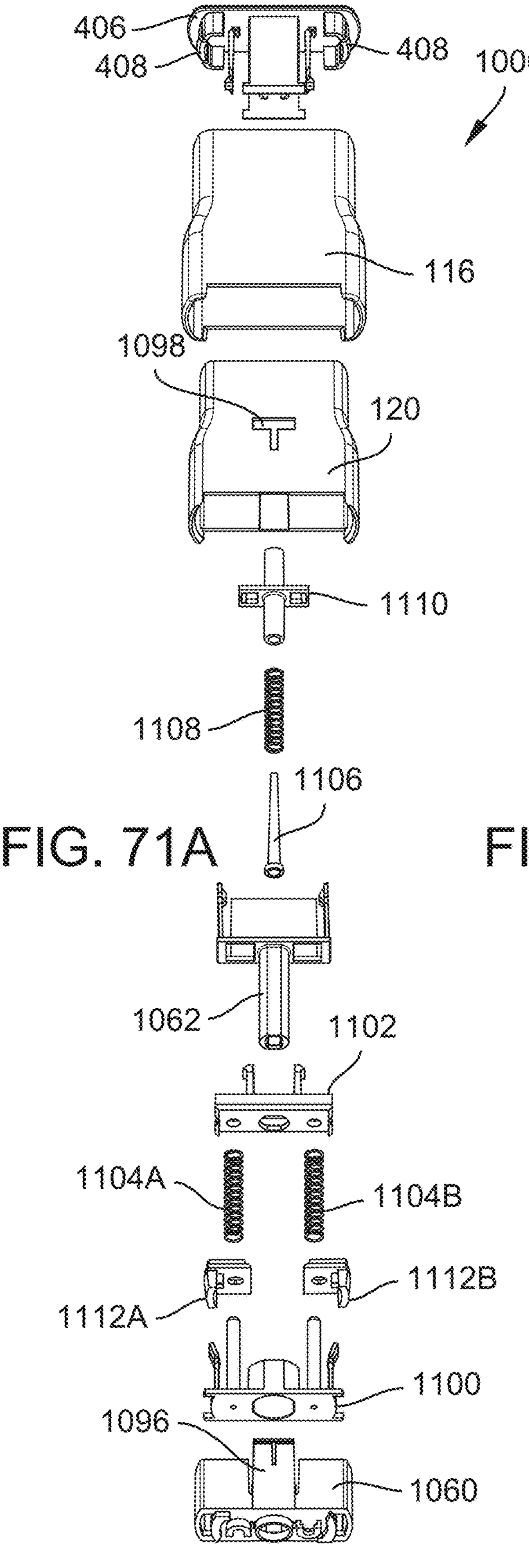
FIG. 71A depicts an exploded view of another example inserter assembly which may be reusable.
Figure 71B:
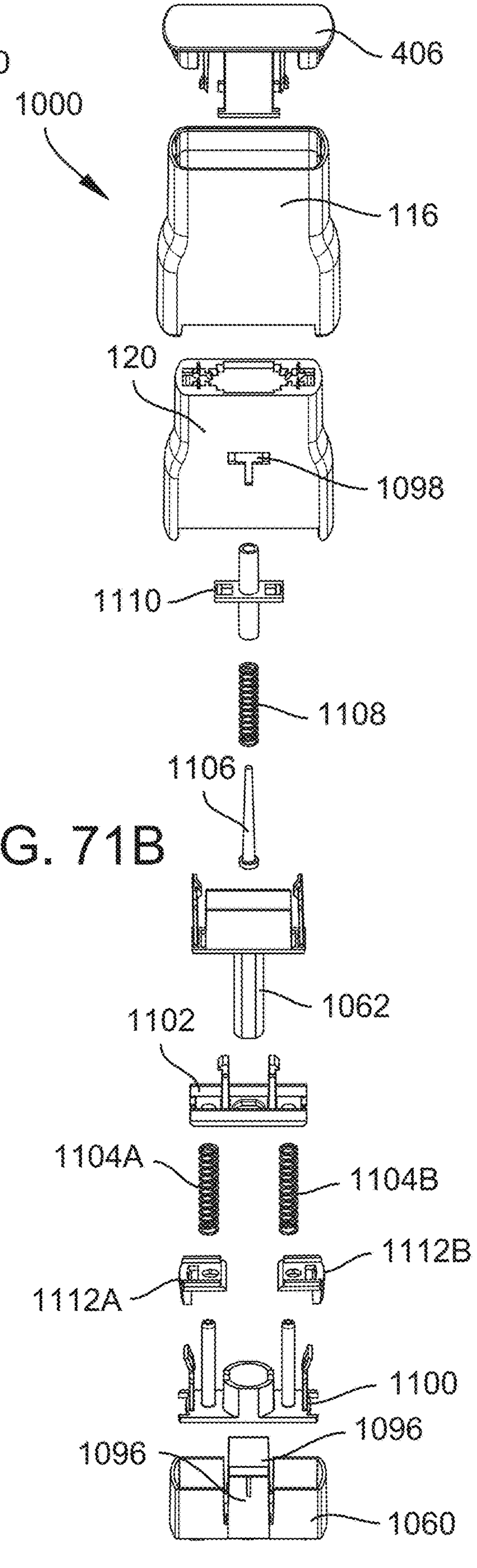
FIG. 71B depicts another exploded view of the example inserter assembly in FIG. 71A.
Figure 72:
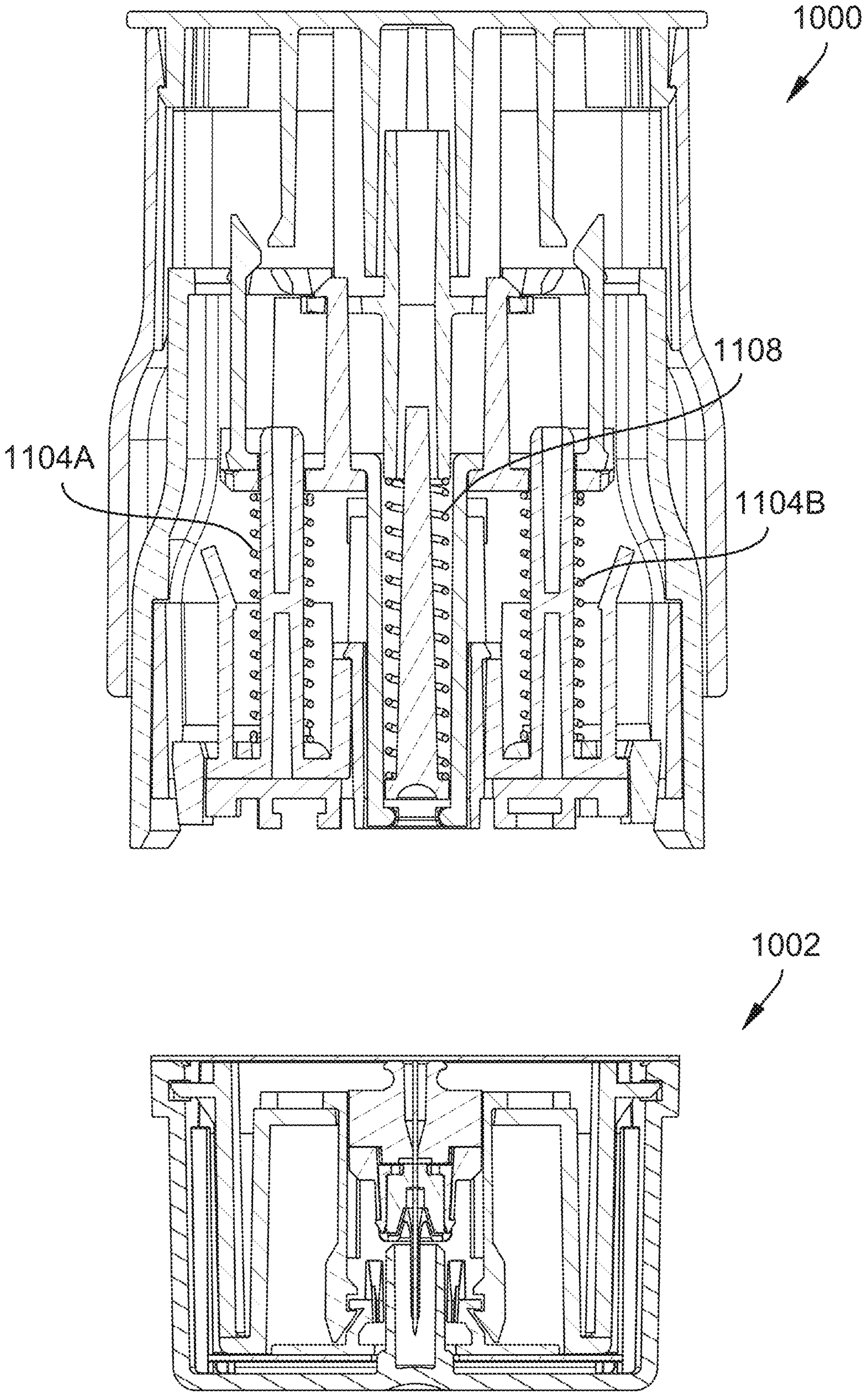
FIG. 72 depicts a cross sectional view of an example inserter assembly.
Figure 74:
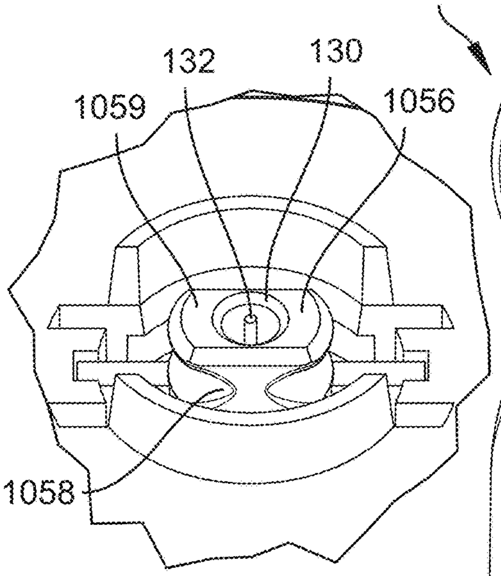
FIG. 74 depicts a detailed view of the indicated region of FIG. 73.

Referring FIG. 72, a cross-sectional view of the inserter assembly 1000 of FIGS. 71A-71B is depicted. The inserter assembly 1000 is depicted in a relaxed or storage state. As shown, no set cartridge 1002 is attached to the inserter assembly 1000. In some embodiments, an end cover may be included for storage and may be placed over the end of the inserter assembly 1000 to which a cartridge 1002 may be coupled. Additionally, in FIG. 72, all of the bias members 1108, 1104A, B are shown in a relaxed or unstressed state. The inserter assembly 1000 may be in the relaxed state between usages of the inserter assembly 1000. As the inserter assembly 1000 may typically only be used during site changes (e.g. every three days), the inserter assembly 1000 may be in the relaxed state for the vast majority of its usage life. Thus, the bias members 1108, 1104A, B may only be required to be in an energy storing state or stressed state (a compressed state in the example embodiment) for short periods of time. Bias members 1108 and 1104 of the inserter assembly 1000 of FIGS. 70A-70B may similarly be in a substantially unstressed state when the inserter assembly 1000 is in its storage state.

A storage state in which bias members 1108, 1104A, B are in an unstressed state may facilitate use of a wide variety different of bias members 1108, 1104A, B or bias member 1108, 1104A, B materials. For example, spring relaxation and/or creep may be less of a concern allowing materials such as various polymers to more easily be utilized in construction of the bias members 1108, 1104A, B. Additionally, other components of an inserter assembly 1000 may not be subjected to sustained stress exerted by bias members of the inserter assembly 1000 being in a stressed state when the inserter assembly 1000 is being stored (e.g. during shipping or when sitting in stock). Consequentially, any creep engendered by this sustained stress may be removed.

This in turn may allow for greater design flexibility in other components of the inserter assembly 1000. For example, a greater variety of materials may be used or certain components may be made smaller. It should be noted that in certain examples, the set cartridge 1002 (or sensor cartridge or lancet cartridge) may not include any bias members. Instead, all bias members may be included in the inserter assembly 1000. As a result, the components of the set cartridge 1002 may also be stored in a state where they are not subjected to sustained stress. This may similarly assist in providing greater design flexibility for components of cartridges 1002.

Figure 73:
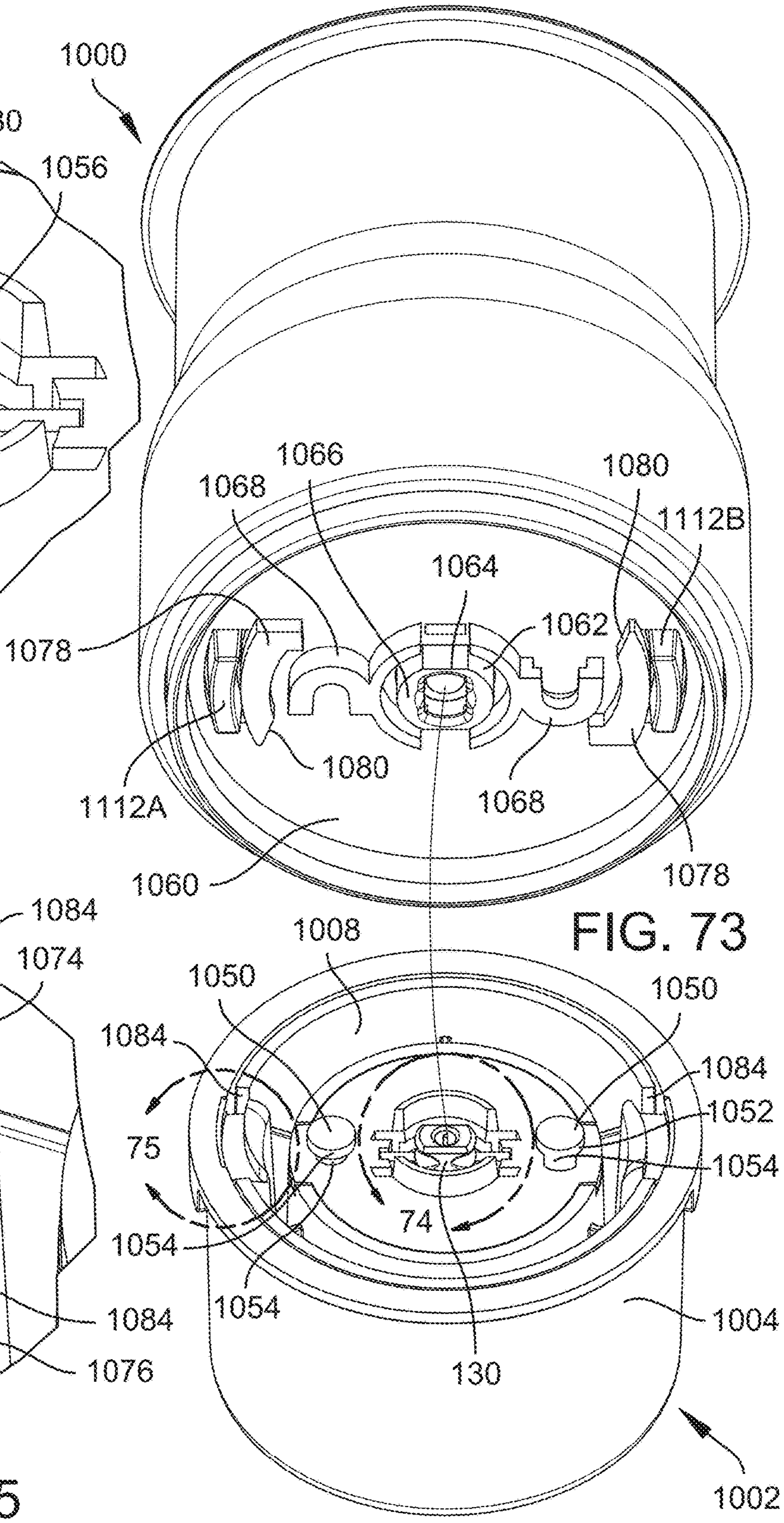
FIG. 73 depicts a view of an example inserter assembly exploded away from an example cartridge.

Referring now to FIGS. 73, a view of an example cartridge 1002 exploded away from an exemplary inserter assembly 1000 is depicted. As shown, the end plate 1028 of infusion base retainer 1014 (see, e.g. FIG. 66) may include at least one mating pin 1050. In the example embodiment two mating pins 1050 are included. The mating pins 1050 may be disposed opposite one another on the top plate 1028 and in the example are shown 180° apart from one another. The mating pins 1050 may include an enlarged head portion 1052 which is connected to the end plate 1028 via a pin body 1054. A portion of the sharp holder 130 is also visible in FIG. 73. As best shown in the detailed view in FIG. 74, the sharp holder 130 may include a mating section 1056. The mating section 1056 may include a thinned region 1058 which is adjacent a terminal flange 1059 that forms an end of the sharp holder 130. The terminal flange 1059 may have a length dimension which is longer than its width dimension. In the example embodiment, the top flange 1059 is obround in shape.

To couple the cartridge 1002 to the inserter assembly 1000, the cartridge 1002 may be placed against a receptacle body 1060 included within the inserter assembly 1000. A sharp driver 1062 including a port 1064 for the mating section 1056 of the sharp holder 130 may be accessible through the receptacle body 1060. In an initial coupling state, the mating section 1056 may be oriented in an aligned position with the port 1064 such that the mating section 1056 may pass into the port 1064. The mating pins 1050 may act as standoffs which limit the amount that the mating section 1056 may be displaced into the port 1064. In the example embodiment, the mating pins 1050 may limit displacement of the mating section 1056 into the port 1064 such that the thinned section 1058 is in line with a rim 1066 surrounding the port 1064. The cartridge 1002 may then be rotated from the initial coupling state to a fully coupled state. As the thinned section 1058 is in line with the rim 1066, the mating section 1056 may be free to rotate. During coupling, the terminal flange 1059 may be swept over an interior face of the rim 1066 into an orientation in which it may no longer pass through the port 1064. The top flange 1059 may be biased against the interior face of the rim 1066 by at least one bias member 1108 (see, e.g. FIG. 77). This may aid in inhibiting additional rotation of the terminal flange 1059. The mating pins 1050 may also be displaced into a mating interface such as retention shoes 1068 included on the receptacle body 1060. The retention shoes 1068 may be formed as "U" shaped bodies which are raised proud of the receptacle body 1060. The "U" shaped bodies may vary in width in a stepwise fashion as distance from the receptacle body 1060 increases. Adjacent the receptacle body 1060, the width may be sized to accept the heads 1052 of the mating pins 1050. The portion of the shoes 1068 most distal to the receptacle body 1060 may have a width sized to accept the pin body 1054 of the mating pins 1050. Thus, when the cartridge 1002 is rotated to the fully coupled state, the heads 1052 of the mating pins 1050 may be overhung by a portion of the shoes 1068 such that the mating pins 1050 may not be translationally displaced out of the shoes 1068 in a direction parallel to the longitudinal axis of the inserter assembly 1000. In alternative embodiments, the mating pins 1050 (or another mating projection) may be included on the receptacle body 1060. Retention shoes 1068 (or another mating interface) may be included as part of the cartridge 1002.

Figure 75:
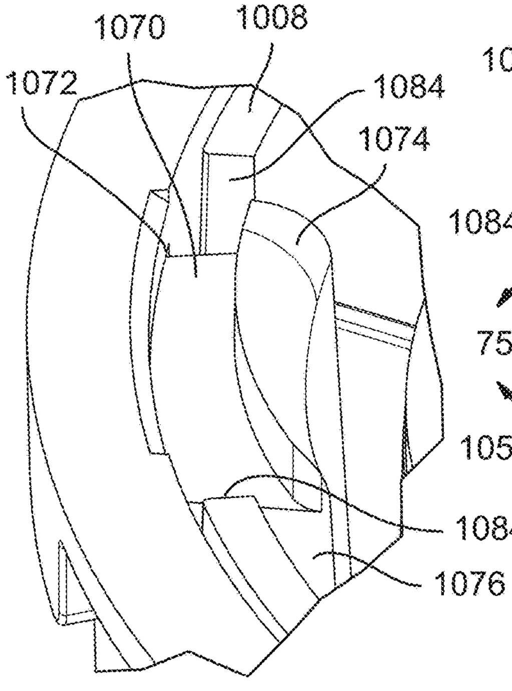
FIG. 75 depicts a detailed view of the indicated region of FIG. 73.

Referring now also to FIG. 75, in some embodiments, rotation of the cartridge 1002 to the fully coupled state may actuate housing tabs 1070 of the interior housing 1008 out of engagement with receiving slots 1072 (see also, e.g., FIG. 69B) of the exterior housing 1004. In the example embodiment, the housing tabs 1070 each include a ramped projection 1074 which may be disposed on a medial portion of the of housing tabs 1070. As best shown in FIG. 67, each housing tab 1070 may be disposed on a cantilevered arm 1076. During coupling of the cartridge 1002 to the inserter assembly 1000, a portion of the receptacle body 1060 may interact with the housing tab 1070 and deflect the cantilevered arm 1076 toward the center of the cartridge 1002. This deflection may cause the housing tab 1070 to be displaced out of the receiving slot 1072 (best shown in FIG. 69B) of the exterior housing 1004. In the example embodiment, the receptacle body 1060 includes a set of deflector members 1078 which are raised from the receptacle body 1060. The deflector members 1078 may include a ramped portion 1080. As the cartridge 1002 is rotated to the fully coupled state, the ramped portions 1080 of the deflector members 1078 may be displaced into abutment with the ramped projections 1074 of the housing tabs 1070. As further rotation occurs the deflector members 1078 may push the ramped projections 1074 out of the displacement path of the deflector members 1078 by bending the cantilevered arms 1076. In turn, this may actuate the housing tabs 1070 out of the receiving slots 1072. The exterior housing 1004 may then be separated from the set cartridge 1002.

Still referring primarily to FIG. 73, the inserter assembly 1000 may include one or more lock members 1112A, B. In the example embodiment, two lock members 1112A, B which are diametrically opposed or spaced 180° from one another are included on the inserter assembly 1000. Other embodiments may include a greater or lesser number of lock members 1112A, B. When a cartridge 1002 is coupled to the inserter assembly 1000 and the exterior housing 1004 is removed, the lock members 1112A, B may be in a state in which they project from the receptacle body 1060. When in the projecting state, the lock members 1112A, B may be positioned between a portion of the edge walls 1084 on either side of the cantilevered arms 1076. This may inhibit rotation of the interior housing 1008 of the cartridge 1002 relative to the inserter assembly 1000 as the edge walls 1084 may act as stop surfaces which present a mechanical interference blocking displacement of the lock members 1112A, B. Thus, the inserter assembly 1000 and interior housing 1008 may be locked together in the fully coupled orientation as rotational displacement of the mating pins 1050 out of the retention shoes 1068 is prevented. Sensor cartridges or lancet cartridges may similarly couple to an inserter assembly 1000.

Figure 76:
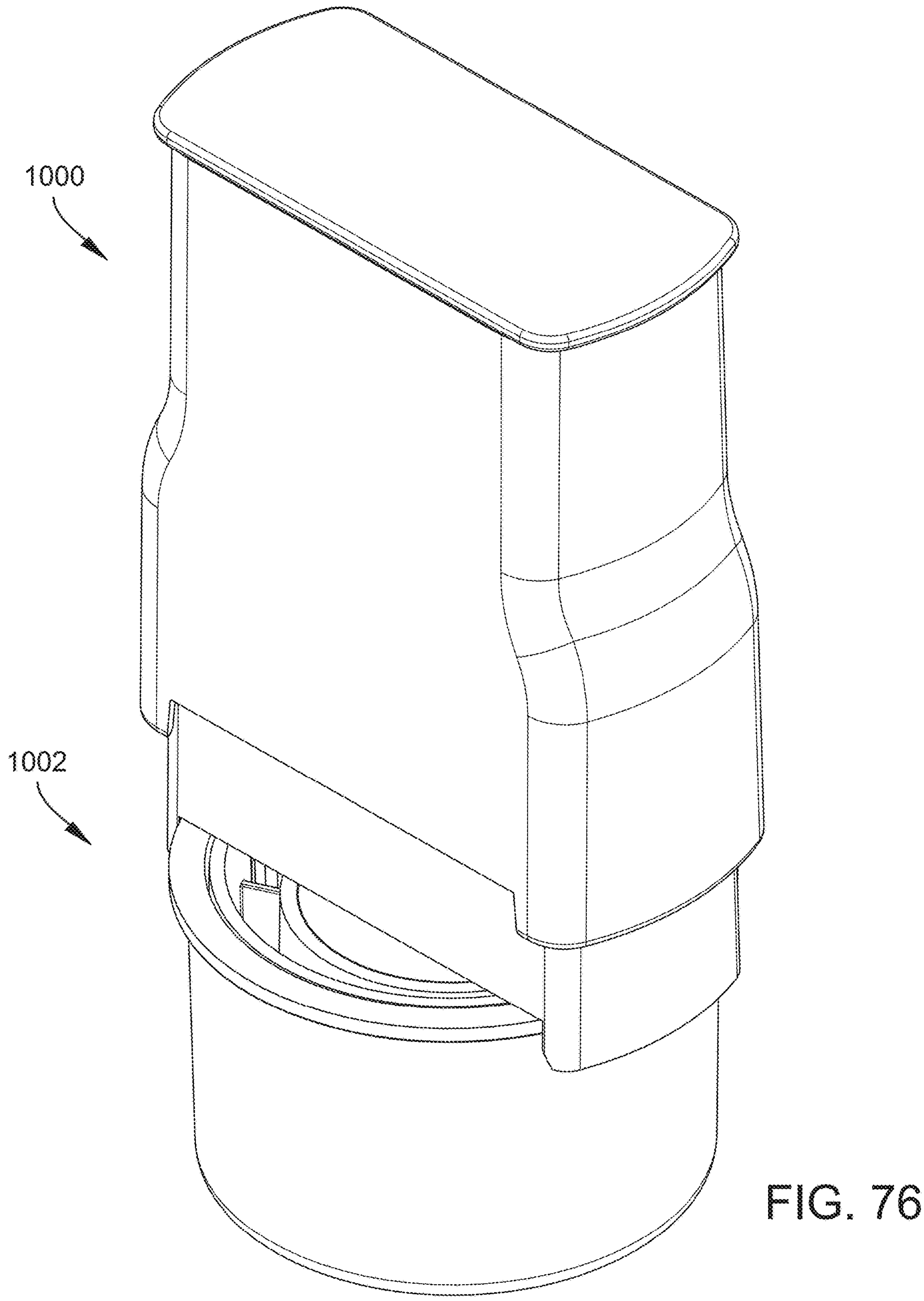
FIG. 76 depicts a perspective view of an example inserter assembly with a cartridge coupled thereto.

Referring now to FIG. 76, in certain embodiments, the cartridge 1002 (or other cartridge) may couple to an inserter assembly 1000 in the same manner, but may not have the same cross sectional shape as the inserter assembly 1000. In the example shown in FIG. 76, the inserter assembly 1000 as a roughly obround cross sectional shape while the set cartridge 1002 has a substantially circular shape. In some examples, various different types of a cartridges may have differing cross sectional shapes so that they are readily differentiable upon visual inspection. Different types of cartridges may also be different colors or have different textures, surface finishes, indicia, labeling, etc.

Figure 77:
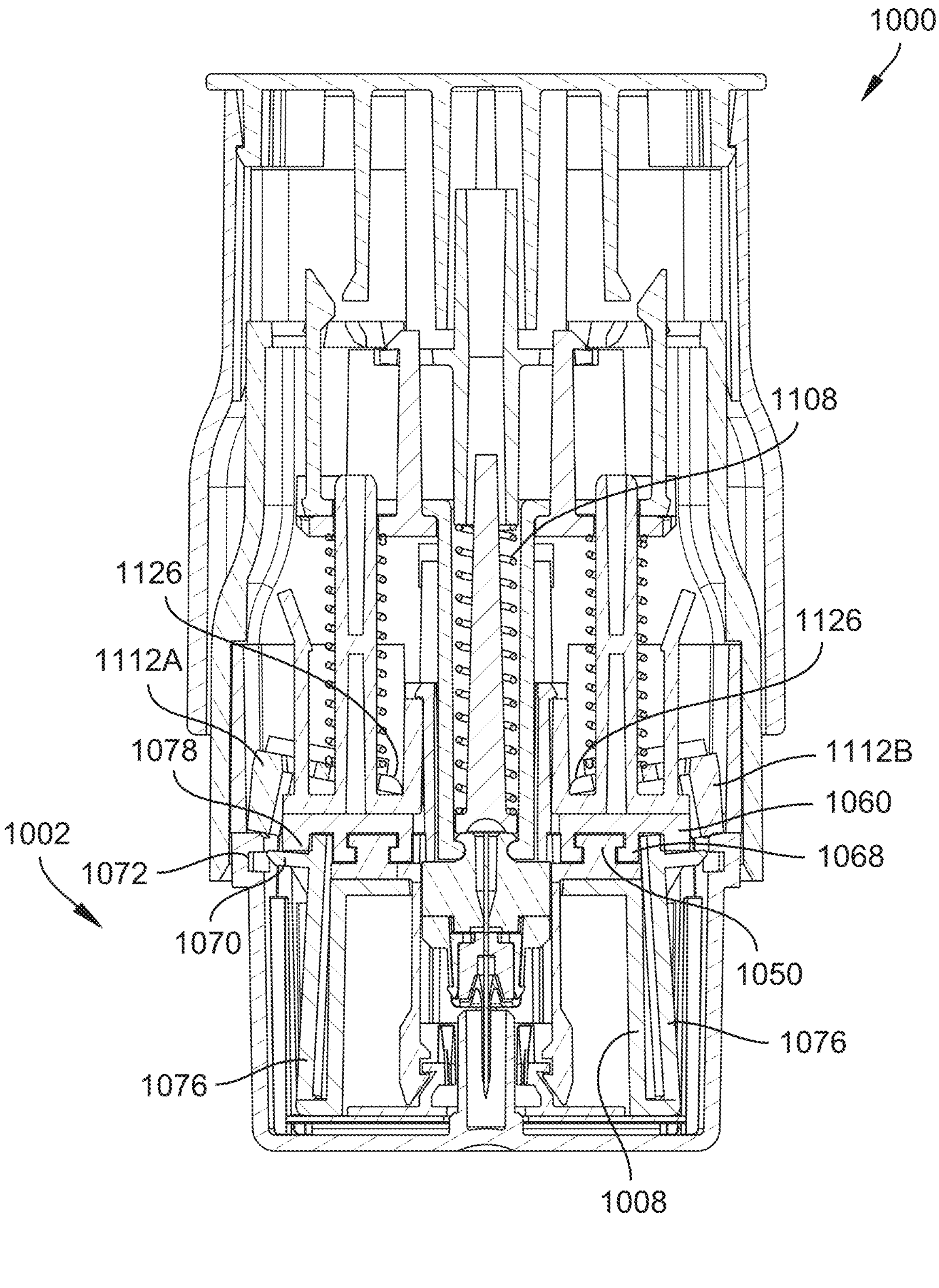
FIG. 77 depicts a cross sectional view of an example inserter assembly.

Referring now to FIG. 77, another cross-sectional view of the inserter assembly 1000 of FIGS. 71A-71B is depicted. The inserter assembly 1000 is coupled to an example set cartridge 1002 in FIG. 77. Mating pins 1050 of the set cartridge 1002 may be retained within the retention shoes 1068 of the receptacle body 1060 of the inserter assembly 1000. The deflector members 1078 of the receptacle body 1060 have deflected the cantilevered arms 1076 of the interior housing 1008. This in turn has pushed the housing tabs 1070 out of engagement with the receiving slots 1072 of the exterior housing 1004. Thus, the exterior housing 1004 of the set cartridge 1002 may be disassociated with the set cartridge 1002 to expose the infusion set base 106.

Still referring to FIG. 77, during coupling of a set cartridge 1002 to an inserter assembly 1000, a portion of the set cartridge 1002 may displace the lock members 1112A, B from a projecting state to a retracted state. As shown in FIG. 77, the exterior housing 1004 of the set cartridge 1002 may force the lock members 1112A, B into the retracted state when the set cartridge 1002 is docked against the inserter assembly 1000. When in the retracted state, the lock members 1112A, B may permit rotation of the set cartridge 1002.

Figure 78:
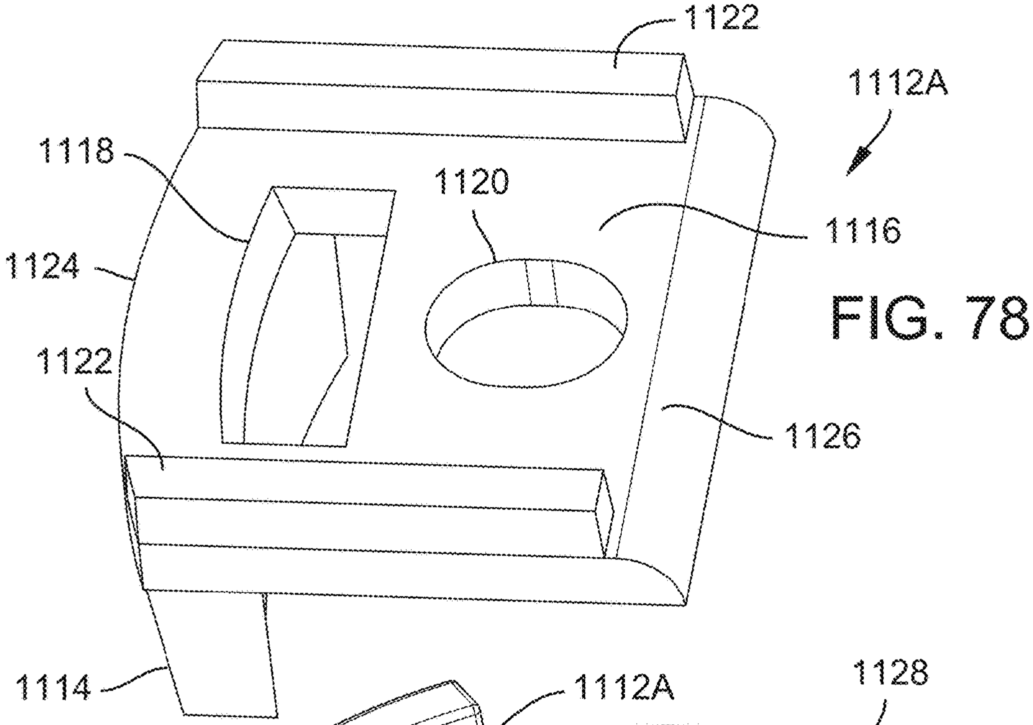
FIG. 78 depicts a perspective view of an example lock member.

Referring now to FIG. 78, a lock member 1112A of the inserter assembly 1000 of FIG. 77 is depicted in isolation. As shown, the lock member 1112A may include a lock projection 1114 which may be the portion of the lock member 1112A which extends out of the receptacle body 1060. The lock projection 1114 may extend from a first end 1124 of a locating plate 1116 at a substantially perpendicular angle to the locating plate 1116. The locating plate 1116 may include one or more orifices 1118, 1120 which may allow the locating plate 1116 to be slid over portions of another component of the inserter assembly 1000 to hold the locating plate 1116 in a prescribed location within the inserter assembly 1000. The locating plate 1116 may slide over portions of the retraction latch body 1100 as, for example, shown in FIG. 77. A second end 1126 of the locating plate 1116 opposite the attachment point of the lock projection 1114 may be rounded.

As shown, the locating plate 1116 may include ridges 1122 which may be disposed on the sides of the locating plate 1116. Other components of the inserter assembly 1000 may also include ridges along their side edges (see e.g. the exploded views in FIGS. 71A-B). These ridges 1122 may be provided as stiffeners which add rigidity to the lock members 1112A, B and any other components on which they are included. In some embodiments, the ridges 1122 may also help to guide or locate other components as they are displaced within an inserter assembly 1000.

As shown in FIG. 77, the lock members 1112A, B may be biased towards the projecting state. In the example, the lock members 1112A, B are disposed between a respective bias member 1104A, B and a face of the retraction latch body 1100. The rounded end 1126 of each lock member 1112A, B may allow the lock member 1112A, B to pivot as they are actuated to the retracted state. The orifices 1118, 1120 may also be dimensioned so as to allow such pivoting. When pivoted, the lock members 1112A, B may stress their associated bias member 1104A, B. Thus, when the exterior housing 1004 of the set cartridge 1002 is doffed, the lock members 1112A, B may automatically displace back to the projecting state as the bias members 1104A, B restore to their unstressed state (see, e.g. FIG. 80). This may, for example, lock an interior housing 1008 of a set cartridge 1002 in place on the inserter assembly 1000.

Figure 79:
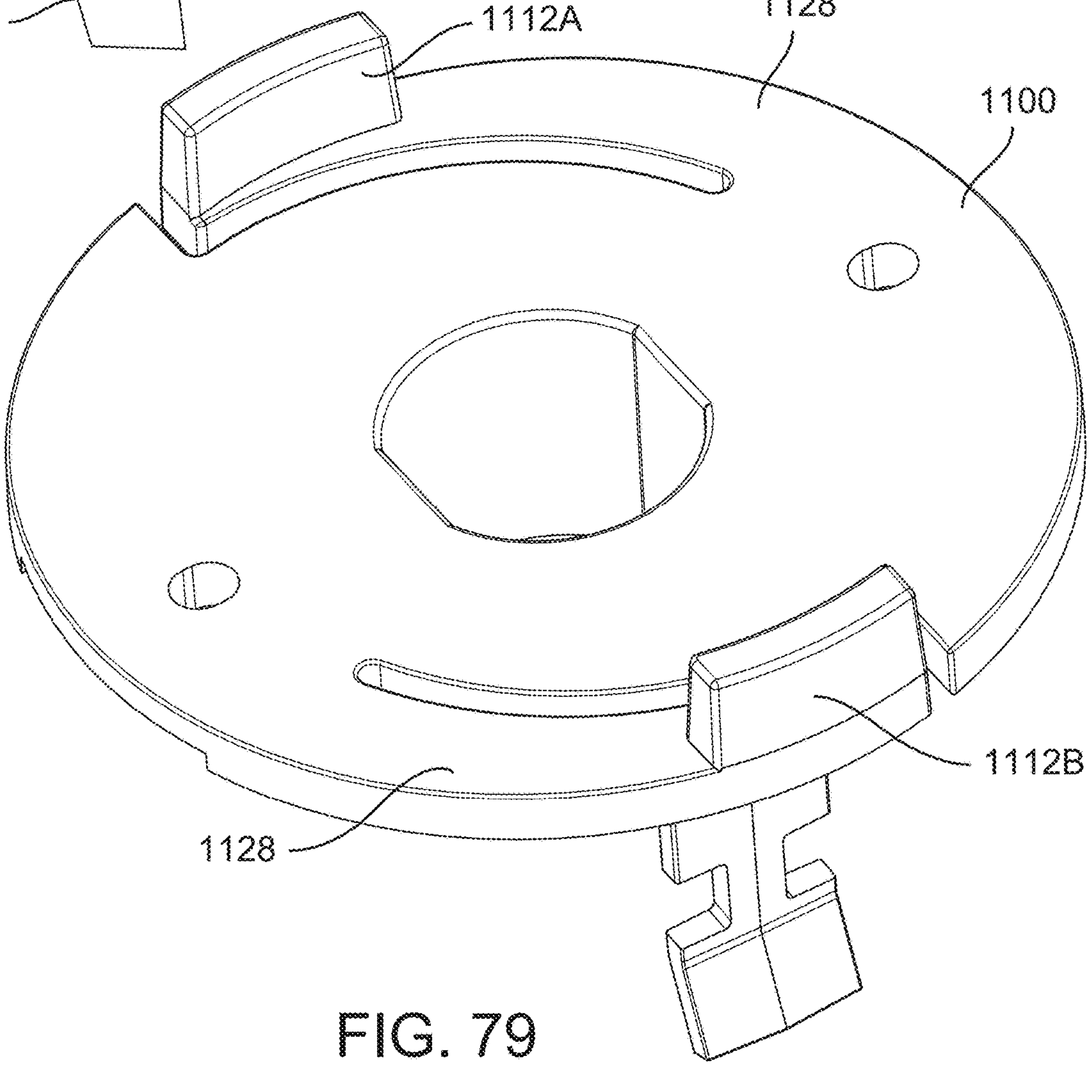
FIG. 79 depicts a perspective view of a retraction latch body.

Referring now to FIG. 79, in certain alternative embodiments (see, e.g. FIGS. 70A-70B) the lock members 1112A, B may be integrated into another component. As shown, the lock members 1112A, B are formed as projections which extend from an arcuate member 1128 which may, for example, be cantilevered to the retraction latch body 1100. When an inserter assembly 1000 including such lock members 1112A, B is assembled, the lock members 1112A, B may extend out of the receptacle body 1060 as shown in FIG. 73. When the lock members 1112A, B are displaced to the retracted state, the cantilevered arcuate members 1128 may resiliently deflect. The cantilevered arcuate members 1128 may resiliently restore to their unstressed state when, for example, the exterior housing 1004 is removed. This may cause the lock members 1112A, B to return to the projecting state and lock the interior housing 1008 in place on the inserter assembly 1000.

Figure 80:
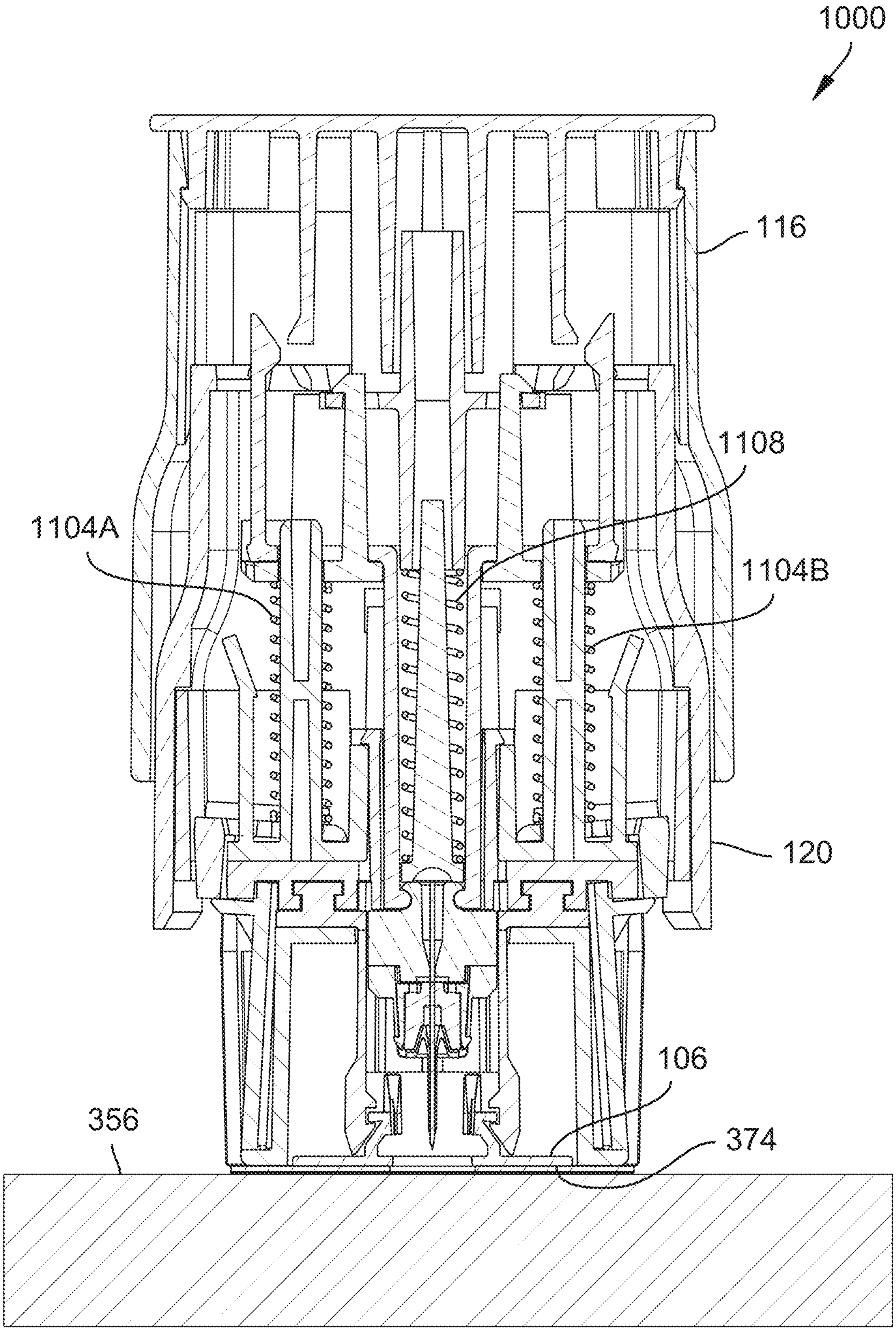
FIG. 80 depicts a cross sectional view of an example inserter assembly.

Referring now to FIG. 80, after removal of the adhesive backing 111 (see, e.g. FIG. 65A) by pulling on pull tabs 410, the set cartridge 1002 may be placed against the skin 356. The inserter assembly 1000 may then be actuated to a ready state. As the storage state of the example inserter assembly 1000 is a state in which all bias members 1104A, B, 1108 are in a relaxed or unstressed state, the inserter assembly 1000 may be actuated through a setting stage in order to place the inserter assembly 1000 in the ready state. In the setting stage, the bias members 1104A, B, 1108 of the inserter assembly 1000 may be transitioned (e.g. compressed) into a stressed state. To accomplish this, a user may press a first unit (e.g. exterior housing 116 and retainer cap 406) of the inserter assembly 1000 toward the remainder of the inserter assembly 1000 (or second unit of the inserter assembly 1000) and the skin 356. In addition to actuating the inserter assembly 1000 to the ready state, the pressure exerted by the user may help to ensure that the adhesive 374 on the infusion set base 106 is soundly adhered to the skin 356. Though FIG. 80 depicts the inserter assembly 1000 illustrated in FIGS. 71A-71B, the example inserter assembly 1000 of FIGS. 70A-70B may also be progressed through a setting stage by pressing on its exterior housing 116 and retainer cap 406. The inserter assembly 1000 may be considered to have progressed through the setting stage and into a ready state once the first unit of the inserter assembly 1000 has been displaced at least a threshold distance to a ready position. Once progressed through the setting stage, and as described in greater detail elsewhere herein, a retainer may engage with a latch to hold the bias members 1104A, B, 1108 in a stressed state.

Figure 81:
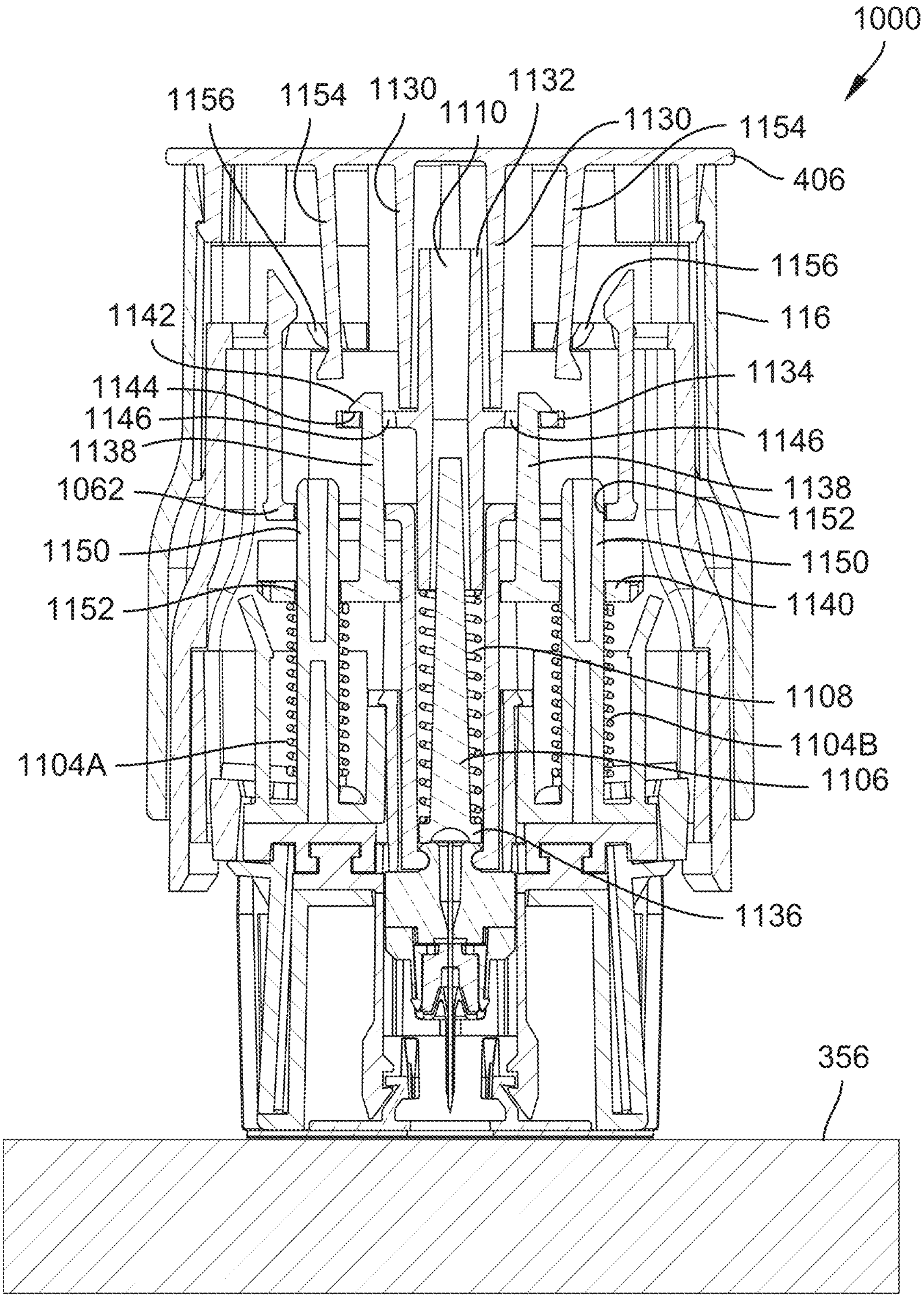
FIG. 81 depicts a cross sectional view of an example inserter assembly.

Referring now to FIG. 81, in the example embodiment, as the user displaces the exterior housing 116 toward the skin 356, the bias members 1108, 1104A, B (or bias member 1104 of the example shown in FIGS. 70A-70B) may begin to compress. As shown, the retainer cap 406 may include a set of standoffs 1130. The standoffs 1130 may surround a barrel 1132 of a reset body 1110 of the inserter assembly 1000. As the exterior housing 116 is displaced, the standoffs 1130 may be driven into contact with a flange 1134 of the reset body 1110. In the example embodiment, the flange 1134 is disposed in a central region of the barrel 1132 and extends substantially perpendicularly thereto. Further displacement of the exterior housing 116 may cause the standoffs 1130 to push against the flange 1134 such that the reset body 1110 moves together with the exterior housing 116. This may cause the barrel 1132 to advance along the plunger 1106 such that an increasing amount of the plunger 1106 is disposed within the bore of the barrel 1132. As bias member 1108 is captured between an end of the barrel 1132 and a flange 1136 of the plunger 1106, the advancement of the barrel 1132 over the plunger 1106 may cause the bias member 1108 to be compressed.

Figure 82:
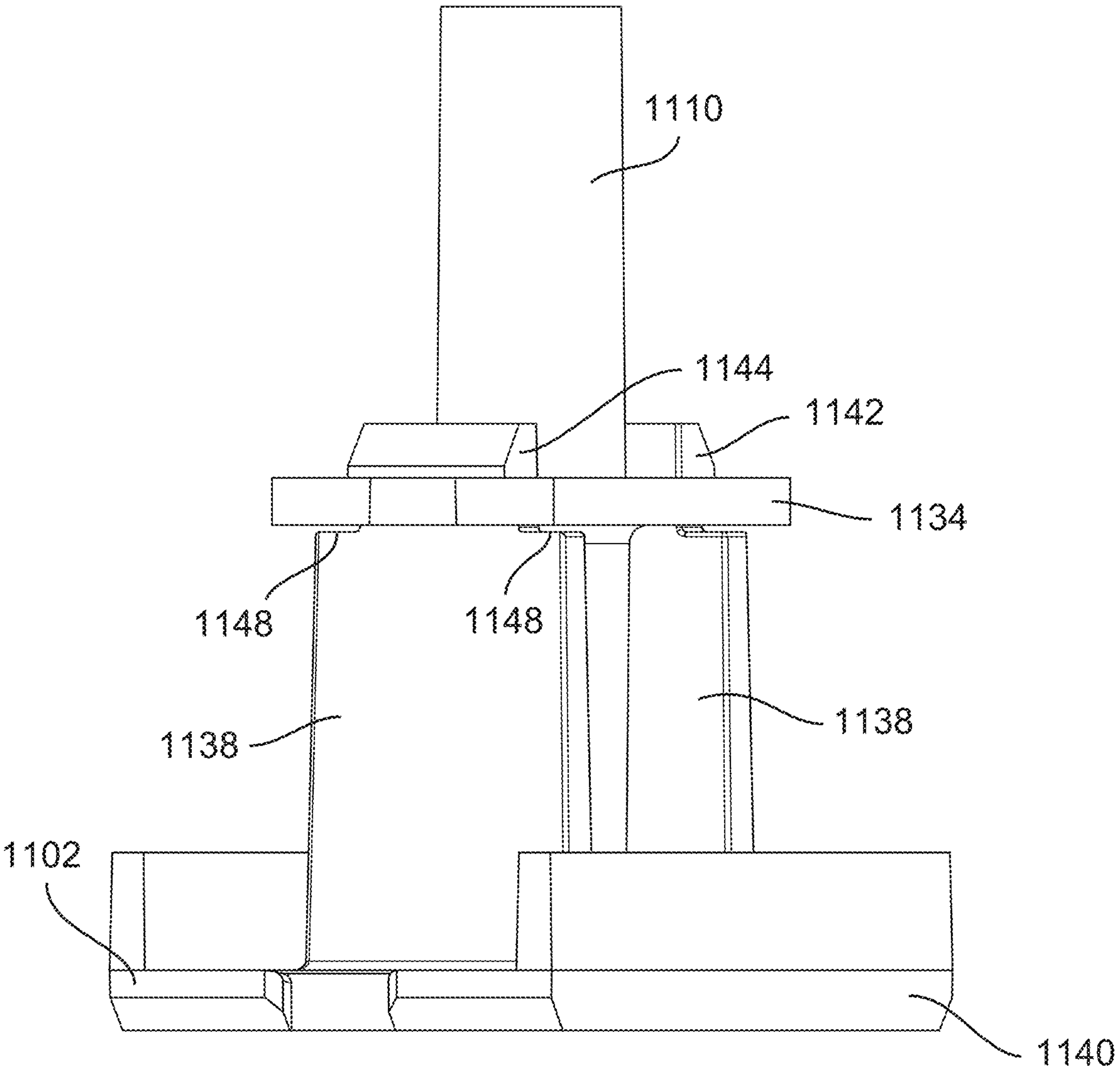
FIG. 82 depicts a view of an example resetting body coupled to an example retraction spring retainer.

As the reset body 1110 is displaced, bias members 1104A, B (or bias member 1104 of the example shown in FIGS. 70A-70B) may also be compressed. In example embodiments, the retraction spring retainer 1102 may be coupled to the reset body 1110 such that the reset body 1110 and retraction spring retainer 1102 displace together as a unit. To illustrate this, an example reset body 1110 and retraction spring retainer 1102 are depicted coupled together and isolated from a remainder of the inserter assembly 1000 in FIG. 82. Referring to both FIGS. 81 and 82, in the example embodiment, the retraction spring retainer 1102 includes a set of retainer arms 1138. The retainer arms 1138 may be cantilevered to a base 1140 of the retraction spring retainer 1102 which in the example embodiment is depicted as a planar body. Each of the retainer arms 1138 may include a protuberance 1142 disposed at an unsupported or terminal end thereof. A ledge section 1144 may be defined by a portion of each of the protuberances 1142. The flange 1134 of the reset body 1110 may include passages 1146 through which the protuberances 1142 may be displaced to couple the reset body 1110 and retainer arms 1138 via a snap fit engagement. The protuberances 1142 may include ramped portions to facilitate deflection of the retainer arms 1138 as the reset body 1110 and the retraction spring retainer 1102 are coupled to one another. When coupled together, a bottom face of the flange 1134 may rest against at least one step 1148 included on each retainer arm 1138. The retainer arm 1138 widths may change at the step 1148. The portion of the retainer arms 1138 proximal to the base 1140 with respect to the step 1148 may have a width which is greater than the width of the passages 1146. Thus, the flange 1136 may be captured between the ledge 1144 and step 1148 of each retainer arm 1138 and be unable to substantially displace relative to the ledge 1144 and step 1148. With the reset body 1110 and retraction spring retainer 1102 coupled together they may be displaced as a unit.

Referring primarily to FIG. 81, bias members 1104A, B may be captured between the retraction spring retainer 1102 and the retraction latch body 1100. One end of the bias members 1104A, B may contact the retraction spring retainer 1102 and the other may contact the lock members 1112A, B. In the example embodiment, the bias members 1104A, B are disposed surrounding guide projections 1150 included on the retraction latch body 1100. The guide projections 1150 may thus serve as locator projections which hold the bias members 1104A, B in place within the inserter assembly 1000. The retraction spring retainer 1102 and the insertion driver 1062 may include guide apertures 1152 through which the guide projections 1150 may extend. As the user pushes down on the exterior housing 116, the retraction spring retainer 1102 may displace toward the retraction latch body 1100 along the guide projections 1150. Since the bias members 1104A, B are captured between the retraction spring retainer 1102 and the retraction latch body 1100, the advancement of retraction spring retainer 1102 may cause the bias members 1104A, B to be compressed.

Figure 83:
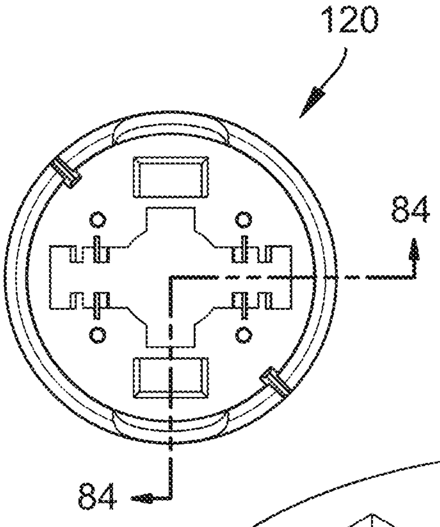
FIG. 83 depicts a top plan view of an example interior housing of an example inserter assembly.
Figure 84:
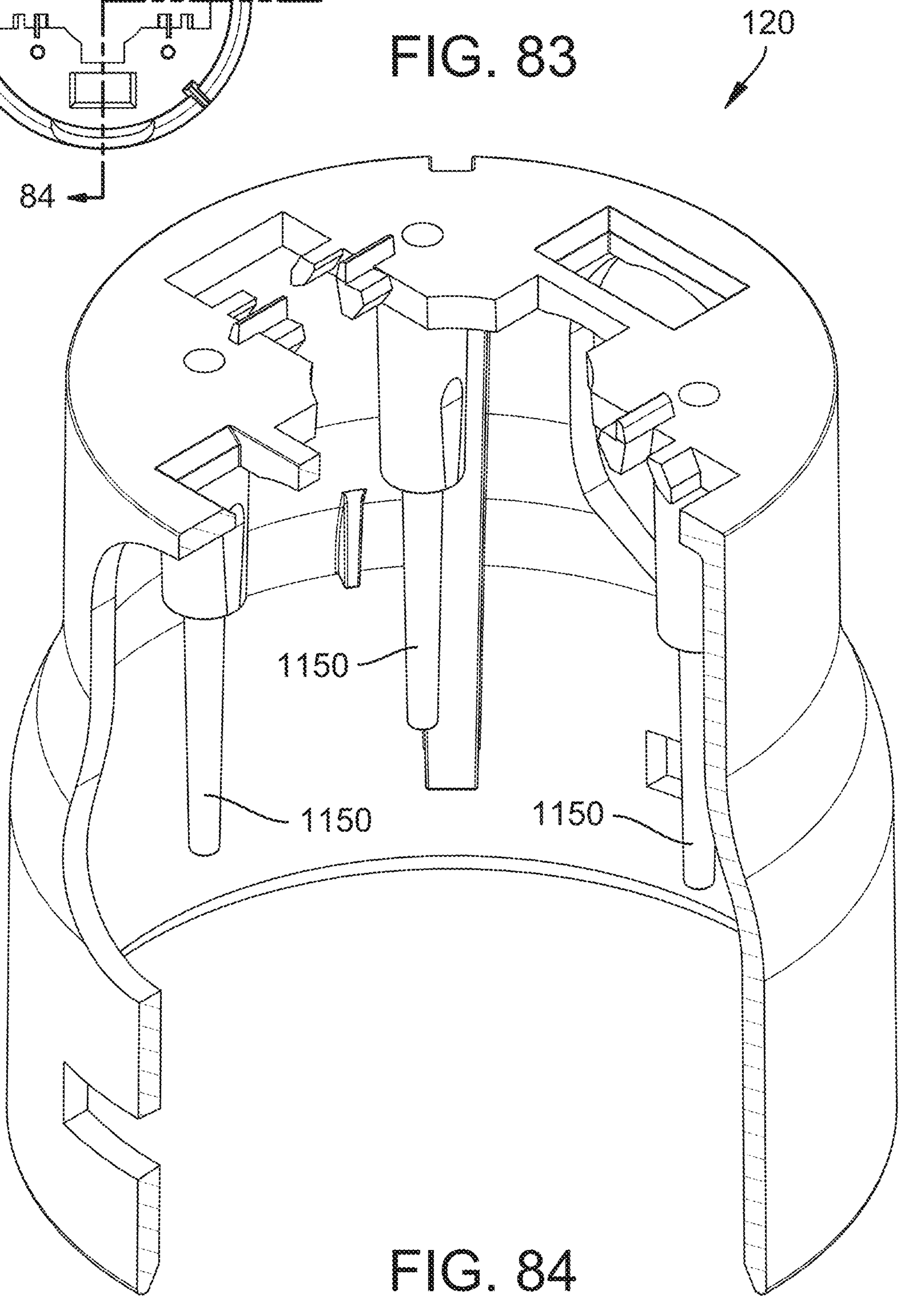
FIG. 84 depicts a cross sectional view taken along 84-84 of FIG. 83.

Referring now to FIGS. 83-84, in some embodiments, additional guide projections 1150 may be included, or guide projections 1150 may be included on another component of the inserter assembly 1000. FIG. 84 depicts a three-quarter section view (taken along line 84-84 of FIG. 83) of the example interior housing 120 of the inserter assembly 1000 shown in FIGS. 70A-70B. As shown, the interior housing 120 may include four guide projections 1150 (one is cut away) which extend from the top of the interior housing 120. The guide projections 1150 may be spaced at even angular intervals from one another though the spacing and number of guide projections 1150 may differ in alternative embodiments. The retraction spring retainer 1102 and insertion driver 1062 may have cooperating guide apertures 1152 (see, FIGS. 70A-70B) and may displace along the guide projections 1150.

Figure 85:
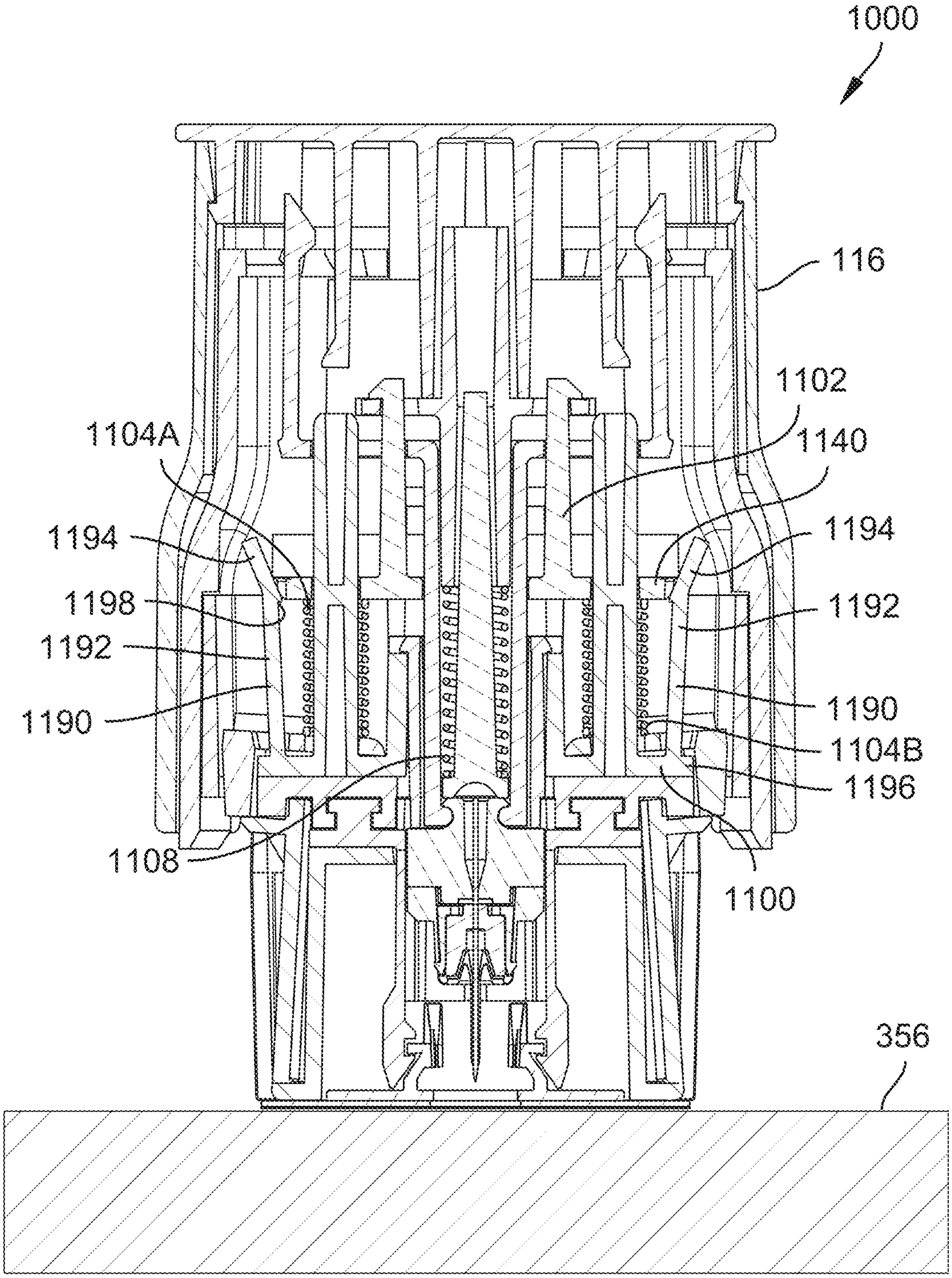
FIG. 85 depicts a cross sectional view of an example inserter assembly.

Referring now to FIG. 85, as the exterior housing 116 of an inserter assembly 1000 continues to displace and the bias members 1104A, B, 1108 continue to compress, the base 1140 of the retraction spring retainer 1102 may contact latch arms 1190 of the retraction latch body 1100. As shown, the latch arms 1190 may be cantilevered from a base 1196 of the retraction latch body 1100. The latch arms 1190 may each include a first portion 1192 which is proximal to the base 1196. The first portions 1192 may, when unstressed, extend substantially perpendicular from the base 1196 and parallel to one another. Each latch arm 1190 may also include a second portion 1194 distal to the base 1196 which may be angled with respect to the first portion 1192. In the example, the second portions 1194 are angled such that distance between the latch arms 1190 increases with distance from the base 1196. A catch 1198 may be included where the second portion 1194 meets the first portion 1192 of each latch arm 1190. As the retraction spring retainer 1102 is driven into contact with the second portion 1194 of each latch arm 1190, the latch arms 1190 may be spread apart from one another as shown in FIG. 85.

Figure 86:
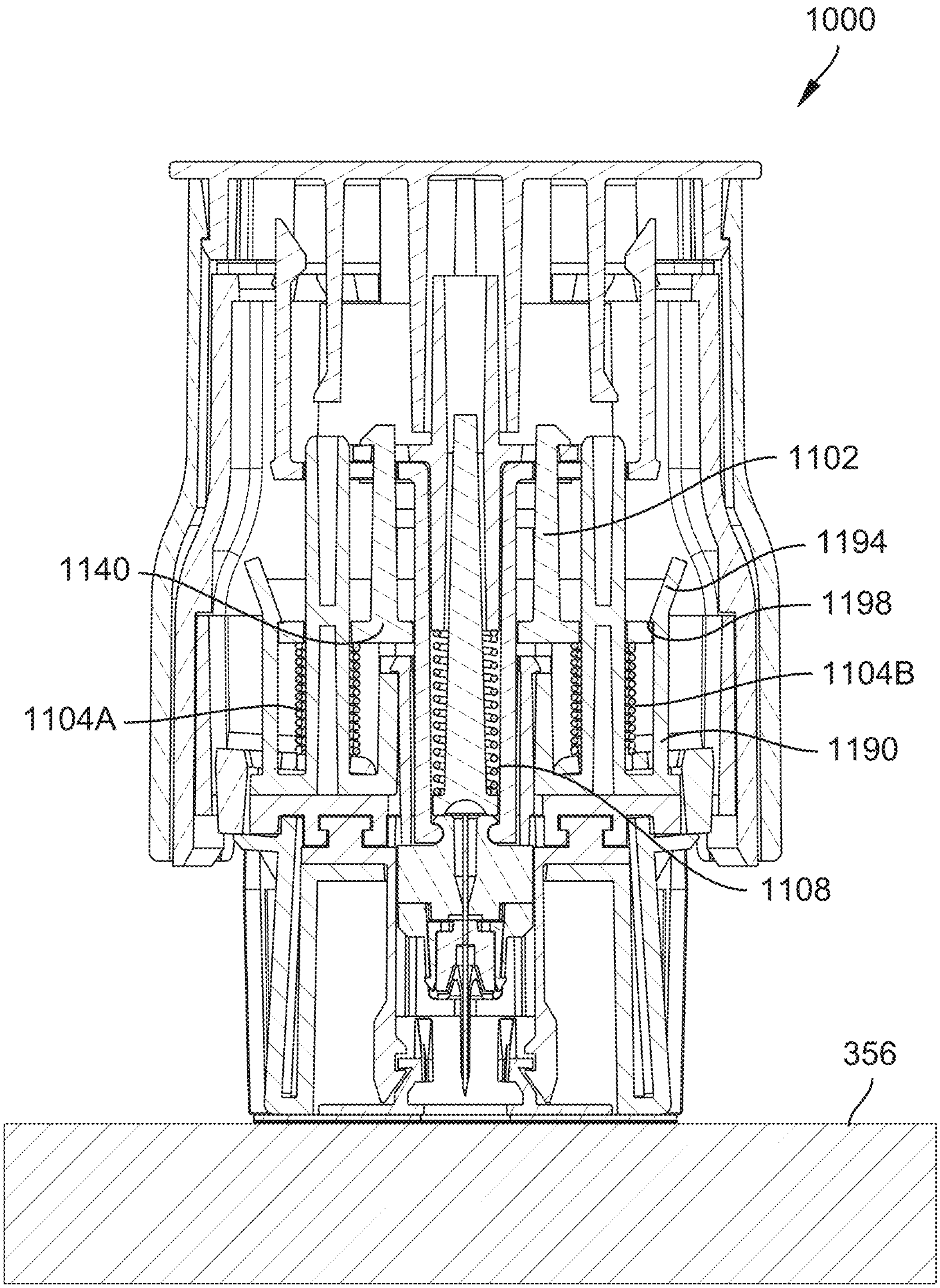
FIG. 86 depicts a cross sectional view of an example inserter assembly.
Figure 87:
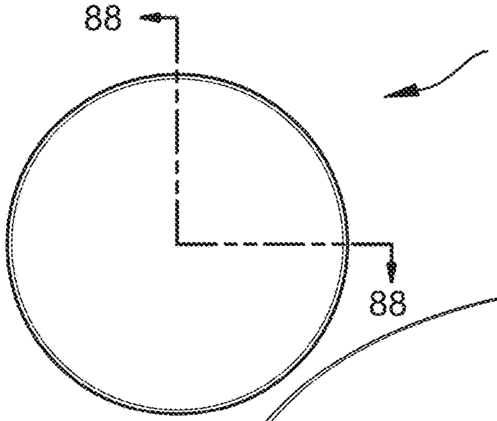
FIG. 87 depicts a top plan view of an example inserter assembly.
Figure 88:
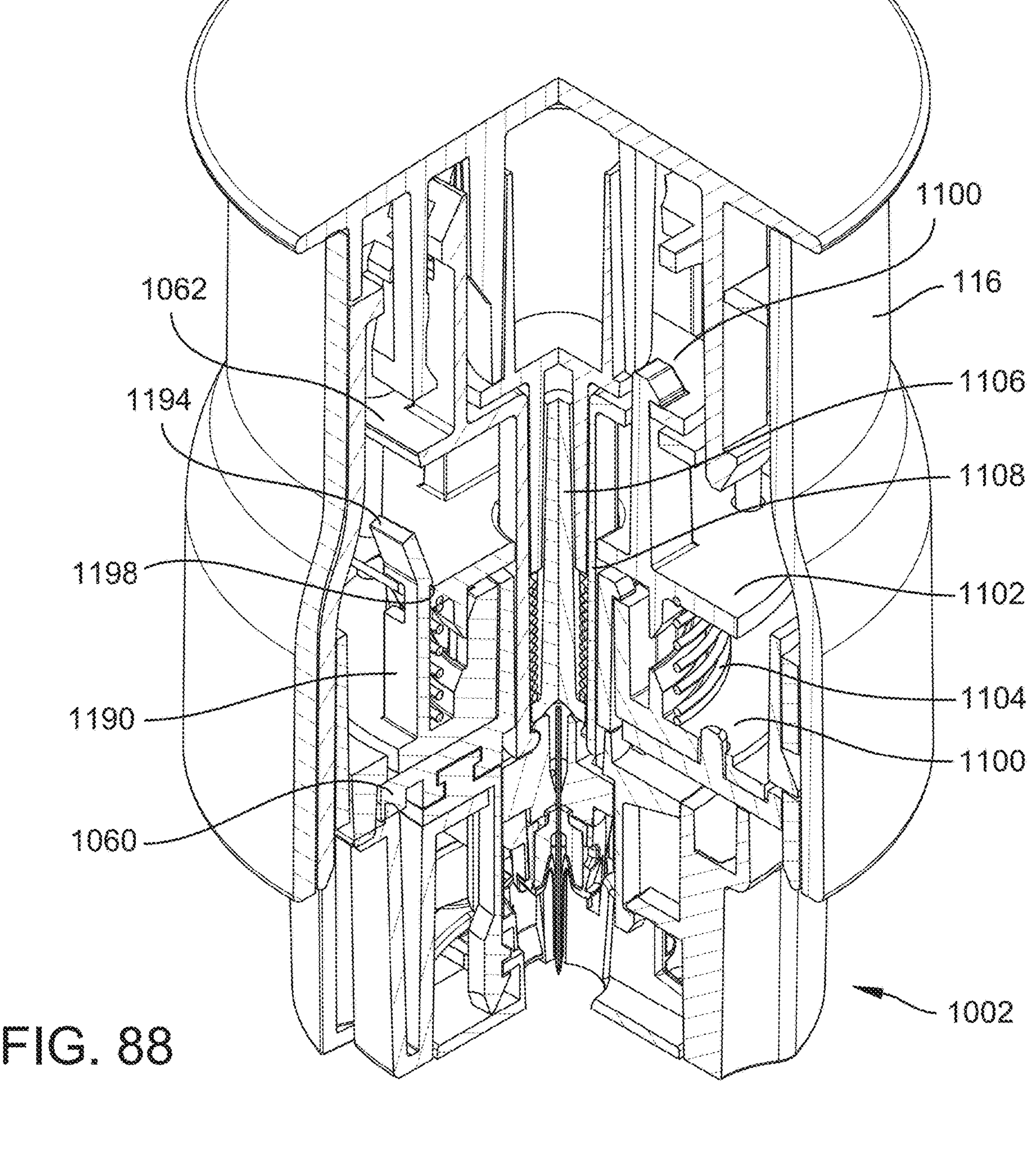

Referring now to FIGS. 86-88, views of the example inserter assemblies 1000 of FIGS. 70A-70B and 71A-71B in a ready state are depicted. Once the retraction spring retainer 1102 has been displaced below the second portion 1194 of each latch arm 1190, the latch arms 1190 may resiliently restore from their spread state. When the latch arms 1190 restore to their unstressed state, the catch 1198 may overhang the base 1140 of the retraction spring retainer 1102. Thus, the catch 1198 may hold the retraction spring retainer 1102 in place with the bias members 1104A, B, 1108 compressed. The inserter assembly 1000 may then be ready to be actuated in order to drive installation of the infusion set 102 to the chosen infusion site on the patient. The exterior housing 116 and retainer cap 406 may be considered in a ready position in FIGS. 86-88.

Figure 89:
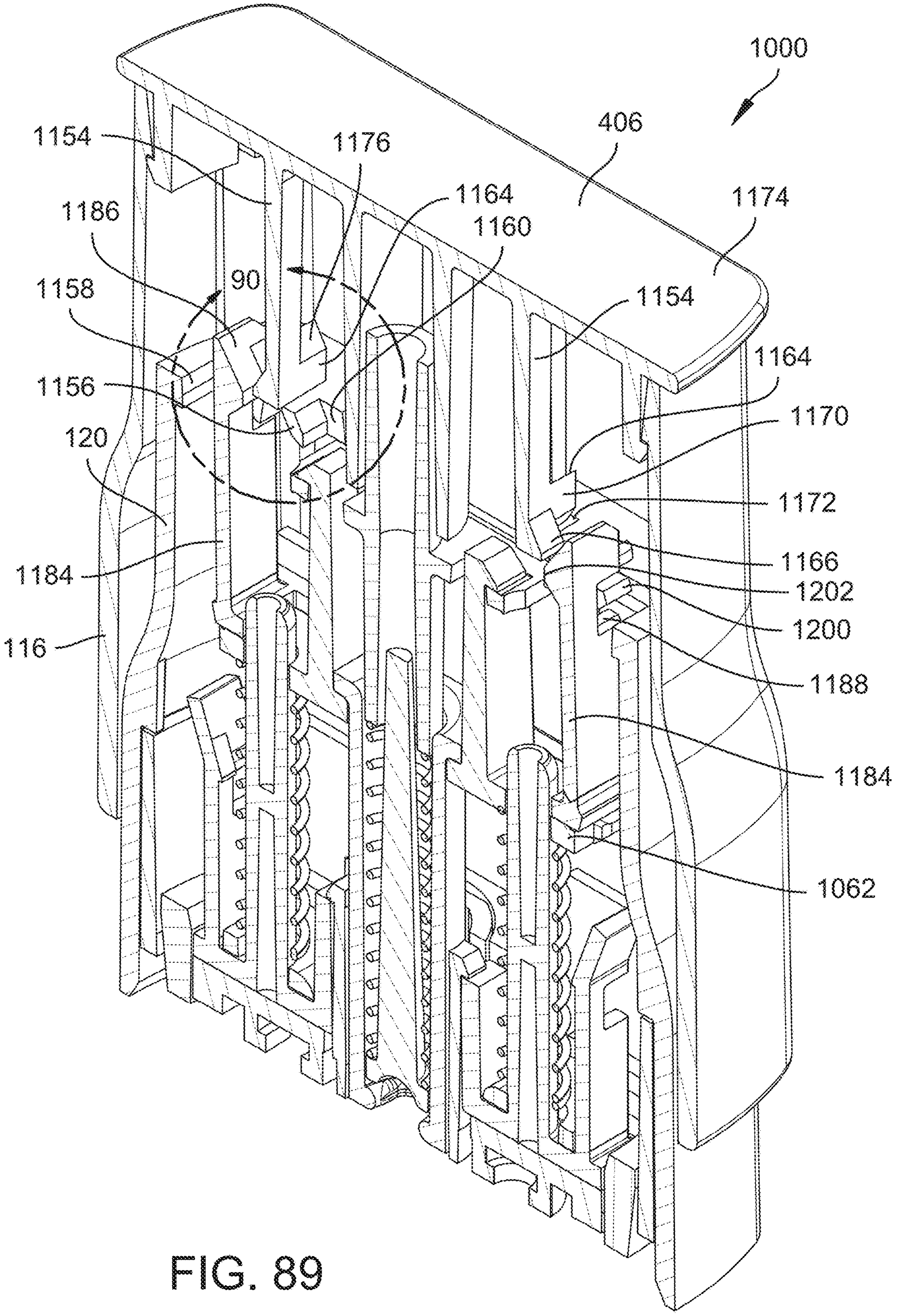
Figure 90:
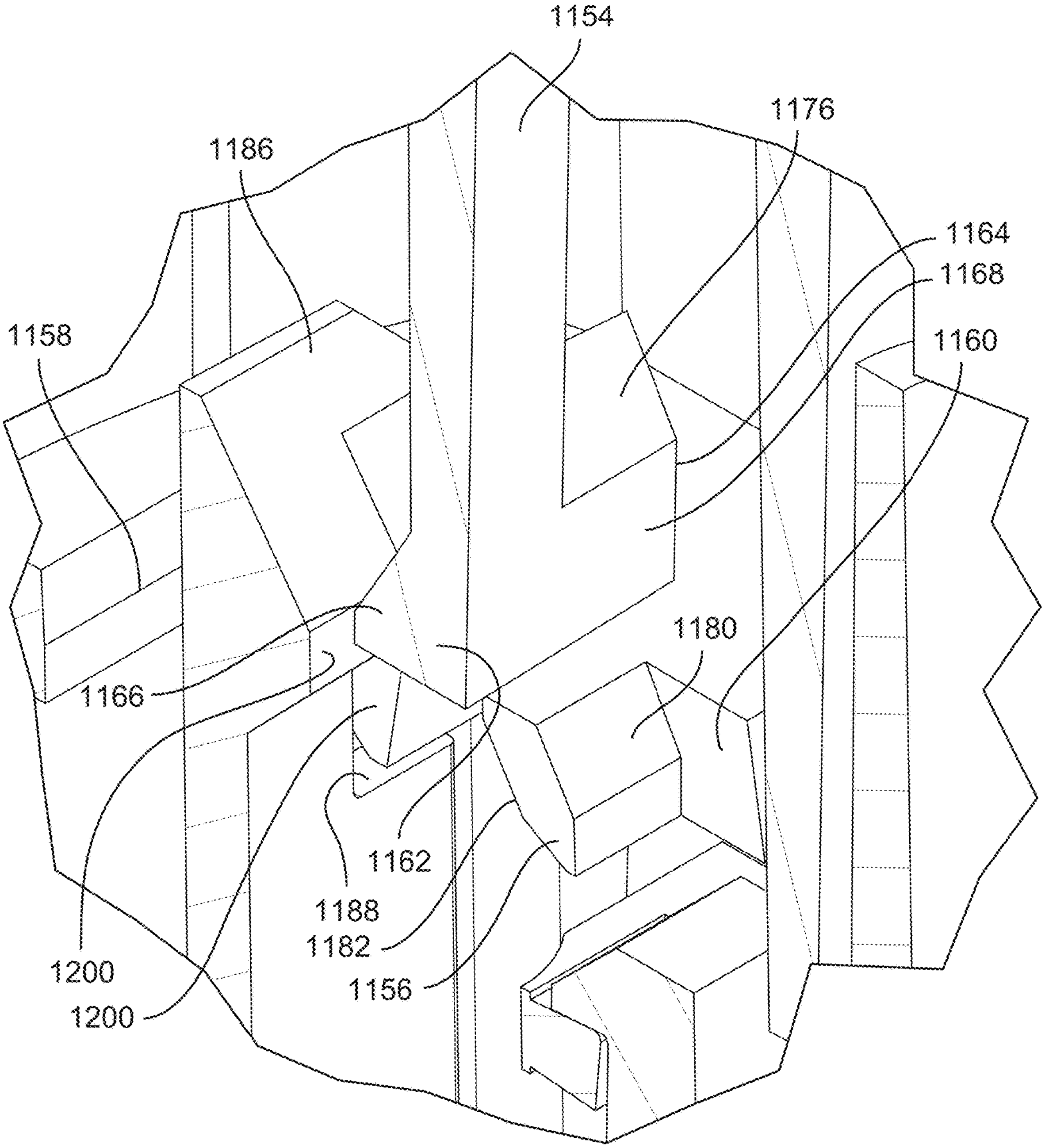

Referring now to FIGS. 89 and 90, a cross-sectional view (FIG. 89) of an example inserter assembly 1000 and a detailed view (FIG. 90) of an indicated region thereof are shown. As the exterior housing 116 of the exemplary inserter assembly 1000 is pressed toward the skin 356 (see, e.g. FIG. 81) during the setting stage, release fingers 1154 extending from the retainer cap 406 may deflect around director wedges 1156 included on the interior housing 120. Each of the release fingers 1154 may be connected to a base portion 1174 of the retainer cap 406 in a cantilevered manner. At an unsupported end 1162 of each release finger 1154, a paddle body 1164 having a projection 1166 may be included. The paddle bodies 1164 may have a width greater than the remainder of the release fingers 1154. In some embodiments, the width may be 2-3 times (e.g. 2.15-2.30 or in some examples 2.25 times) the width of the rest of the release finger 1154. The paddle body 1164 may be disposed such that a center region of the paddle body 1164 is connected to the rest of the associated release finger 1154. Thus, the paddle body 1164 may include two evenly sized portions (only one is visible in the FIG. 89 cross-section) which flank the release finger 1154.

Each paddle body 1164 may include a medial face 1168 proximal to the longitudinal axis or midplane of the inserter assembly 1000 and a lateral face 1170 on a side of the paddle body 1164 opposite the medial face 1168. The projection 1166 may be disposed on the lateral face 1170 of each paddle body 1164. The projection 1166 may be centrally disposed on each paddle body 1164 such that the projection 1166 may be displaced without contacting the director wedges 1156 during actuation. The lateral face 1170 of each paddle body 1164 may include a lateral ramp portion 1172 on the flanking portions of the paddle body 1164. The lateral ramp portions 1172 may be included on a section of the paddle body 1164 most distal to the base portion 1174 of the retainer cap 406. The lateral ramp portions 1172 may slope toward the medial face 1168 as distance from the base portion 1174 of the retainer cap 406 increases. The medial face 1168 of the paddle body 1164 may also include a medial ramp portion 1176 on the flanking portions of the paddle body 1164. The medial ramp portions 1176 may be included on a portion of the paddle body 1164 most proximal to the base portion 1174 of the retainer cap 406. The medial ramp portions 1176 may slope toward the lateral face 1170 as distance to the base portion 1174 of the retainer cap 406 decreases.

Figure 91:
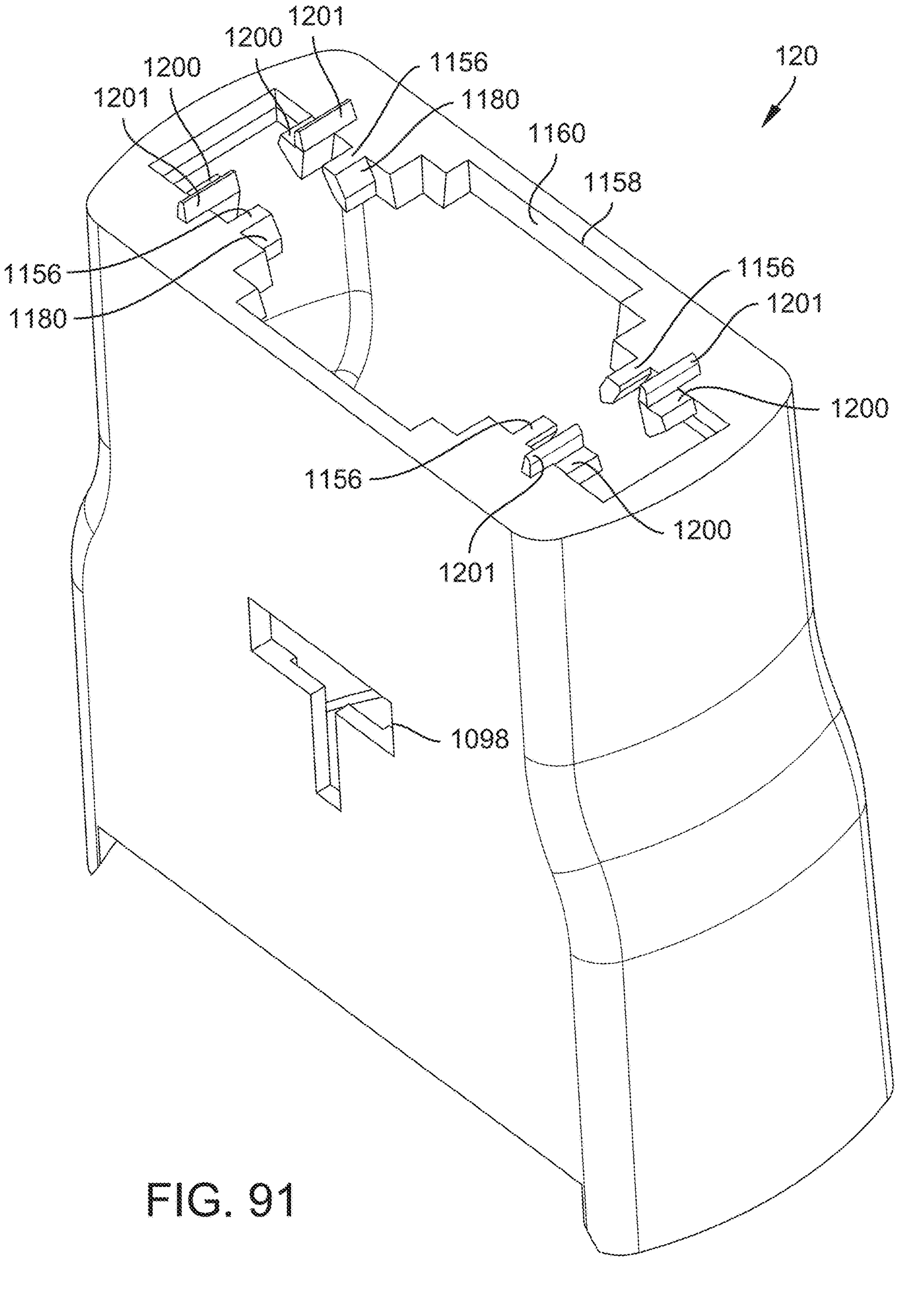

Referring now also to FIG. 91, in the example embodiment, the director wedges 1156 extend from the side wall 1160 of a passage 1158 through the top of the interior housing 120 (shown in isolation in FIG. 91). The director wedges 1156 are included in pairs. The director wedges 1156 of each pair extend from opposing side walls 1160 of the passage toward one another. The director wedges 1156 include a top face 1180 which slopes toward the midplane of the inserter assembly 1000 as distance from the top of the interior housing 120 increases. The director wedges 1156 also include a bottom face 1182 which is parallel to the top face 1180. The ends of the top and bottom faces 1180, 1182 most distal to the top of the interior housing 120 may be rounded or chamfered to form a point (as shown in FIGS. 89-91). As the exterior housing 116 is displaced toward the body during the setting phase, the release fingers 1154 and paddle bodies 1164 may displace along displacement paths into which the director wedges 1156 extend. The lateral ramp portions 1172 of the paddle body 1164 of each release finger 1154 may contact the top faces 1180 of a pair director wedges 1156 during this displacement. Further displacement may cause the lateral ramp portions 1172 to slide along the top faces 1180 of the director wedges 1156. This may generate deflection of the associated release finger 1154 and movement of the projection 1166 of the paddle body 1164 toward the midplane (see, e.g., FIG. 81) of the inserter assembly 1000. The projection 1166 of the paddle body 1164 may pass through the gap between the associated pair of director wedges 1156 as this displacement occurs. Once the paddle body 1164 has been displaced below the director wedges 1156, the release finger 1154 may be free to resiliently restore to its undeflected state (see, e.g., FIG. 85).

As will be described in greater depth later in the specification, the exterior housing 116 may be displaced relative to the interior housing 120 in the opposite direction to fire the inserter assembly 1000. As this occurs, the medial ramp portions 1176 of the paddle body 1164 of each release finger 1154 may contact the bottom face or underside 1182 of the associated director wedges 1156. Further displacement may cause the medial ramp portion 1176 to slide along the underside 1182 of the director wedges 1156. This may generate deflection of the release finger 1154 and projection 1166 of the paddle body 1164 away from the midplane of the inserter assembly 1000. The projection 1166 of the paddle body 1164 may pass through the gap between the associated pair of director wedges 1156 as the exterior housing 116 is displaced.

As the release fingers 1154 are deflected away from the midplane of the inserter assembly 1000, the projections 1166 may deflect toward cantilevered arms 1184 on the insertion driver 1062. The arms 1184 may form resilient projections which may deflect if sufficient force is exerted against them. The unsupported end of the arms 1184 may include a curved or ramped section. A notch or pair of notches 1188 may also be present on each of the cantilevered arms 1184. In the example, each arm 1184 includes a pair of notches 1188 located near the unsupported ends of the arms 1184. The notches 1188 may be disposed similarly to the notches 342 shown in FIG. 36 for example. Each of the one or more notches 1188 may engage with a cooperating projection 1200. The cooperating projection 1200 may be included on the interior housing 120 and may project from the side wall 1160 of the passage 1158 through the top of the interior housing 120. The interaction of the notch(es) 1188 and cooperating projection(s) 1200 may maintain the bias member 1108 under compression and serve as an insertion prevention latch or insertion driver latch.

With the release fingers 1154 deflected toward the arms 1184, further displacement of the exterior housing 116 away from the skin 356 may cause the projections 1166 on the paddle bodies 1164 to collide with protrusions 1202 on the cantilevered arms 1184. This may dislodge the notches 1188 of the cantilevered arms 1184 from cooperating projections 1200 of the interior housing 120. Thus, once the first unit of the inserter assembly 1000 (e.g. exterior housing 116 and retainer cap 406) has been pulled away from the remainder of the inserter assembly 1000 (second unit of the inserter assembly 1000) beyond a threshold distance (which may be measured from the ready position), the insertion driver 1062 may be dislodged from the insertion driver latch. This may free the spring 1108 to transition to its unstressed state and displace the insertion driver 1062 toward the skin 356. As the spring 1108 transitions from its stressed state to a relaxed state, the inserter driver 1062 may displace from its stowed state to an extended position in which at least a portion of the insertion driver 1062 projects out of the inserter assembly 1000 and into the cartridge 1002. As shown in best in FIG. 91, a ridge 1201 which blocks displacement of the cantilevered arms 1184 may be included medial to each of the cooperating projections 1200. This may help to ensure that the cantilevered arms 1184 may only be released from the cooperating projections 1200 when intended by the user.

Figure 92:
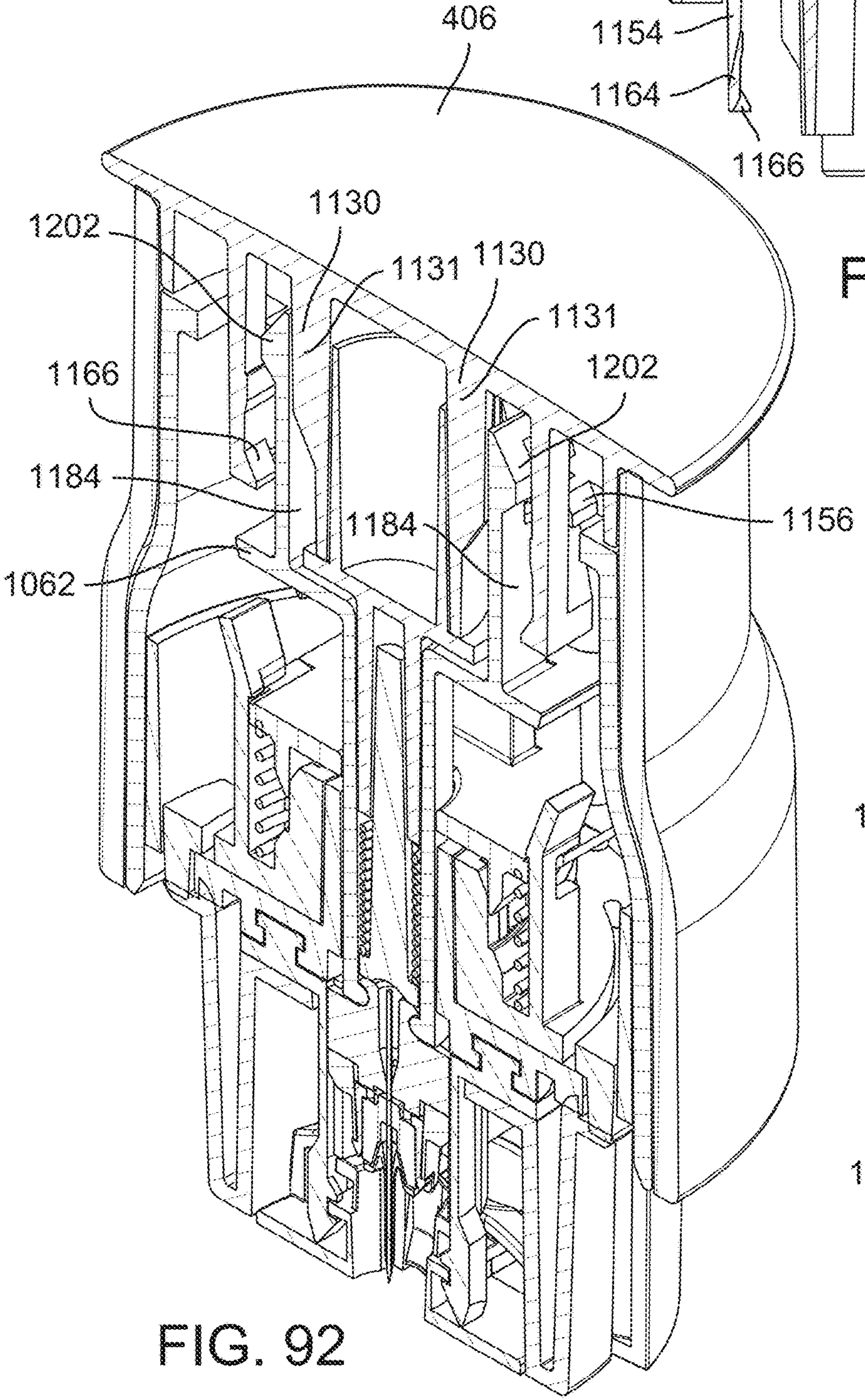

Referring now to FIG. 92, a cross section of the inserter assembly 1000 shown in FIGS. 70A-70B is depicted. In some embodiments, and as shown in FIG. 92, the release fingers 1154 may be disposed outboard (with respect to the midplane) as opposed to inboard (see e.g. embodiment of FIGS. 71A-71B) of the cantilevered arms 1184 of the insertion driver 1062. In such embodiments, to be displaced off their respective cooperating projections 1200 of the interior housing 120, they may be displaced toward the midplane of the inserter assembly 1000. In such embodiments, the standoffs 1130 included on the retainer cap 406 may include an enlarged section 1131. The enlarged sections 1131 may block the cantilevered arms 1184 from being dislodged until the inserter assembly 1000 has been withdrawn from the skin 356 more than a certain amount.

Figure 93:
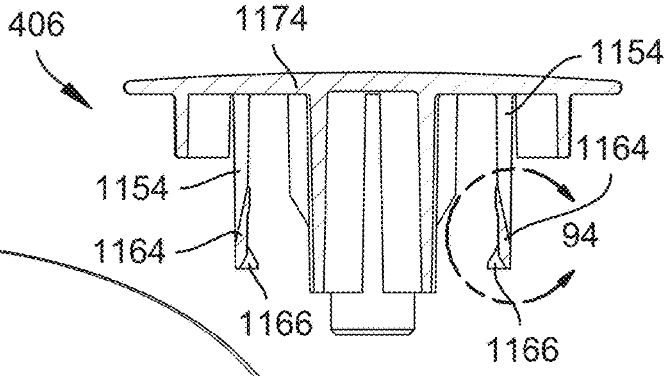
Figure 94:
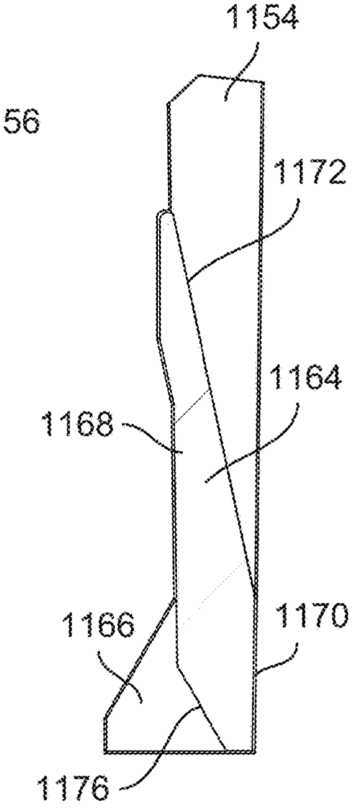

Referring also to FIG. 94, a detailed view of the indicated region of FIG. 93, the release fingers 1154 may have paddle bodies 1164 configured to deflect the release fingers 1154 in opposite directions to those described in relation to FIGS. 89-91. Each paddle body 1164 may include a medial face 1168 proximal to the longitudinal axis or midplane of the inserter assembly 1000 and a lateral face 1170 on a side of the paddle body 1164 opposite the medial face 1168. A projection 1166 may be disposed on the medial face 1170 of each paddle body 1164. The projection 1166 may be centrally disposed on each paddle body 1164 such that the projection 1166 may be displaced without contacting the director wedges 1156 during actuation. The lateral face 1170 of each paddle body 1164 may include a lateral ramp portion 1172 on the flanking portions of the paddle body 1164. The lateral ramp portions 1172 may be included on a section of the paddle body 1164 most proximal to the base portion 1174 (see, e.g., FIG. 93) of the retainer cap 406. The lateral ramp portions 1172 may slope toward the medial face 1168 as distance from the base portion 1174 of the retainer cap 406 decreases. The medical face 1168 of the paddle body 1164 may also include a medial ramp portion 1176 on the flanking portions of the paddle body 1164. The medial ramp portions 1176 may be included on a portion of the paddle body 1164 most distal from the base portion 1174 of the retainer cap 406. The medial ramp portions 1176 may slope toward the lateral face 1170 as distance to the base portion 1174 of the retainer cap 406 increases.

As the exterior housing 116 is pressed toward the skin 356 during the setting stage, the medial ramped portions 1176 may deflect the paddle bodies 1164 of the release fingers 1154 outwardly around the director wedges 1156. As the inserter assembly 1000 is lifted from the skin 356 to trigger insertion, the lateral ramped portions 1172 may deflect the release fingers 1154 inwardly around the director wedges 1156 and towards the cantilevered arms 1184. With the release fingers 1154 deflected toward the arms 1184, further displacement of the exterior housing 116 away from the skin 356 may cause the projections 1166 on the paddle bodies 1164 to collide with protrusions 1202 on the cantilevered arms 1184. This may dislodge the notches 1188 (described above) of the cantilevered arms 1184 from cooperating projections 1200 (described above) of the interior housing 120. This may free the spring 1108 to transition to its unstressed state and displace the insertion driver 1062 toward the skin 356.

Figure 95:
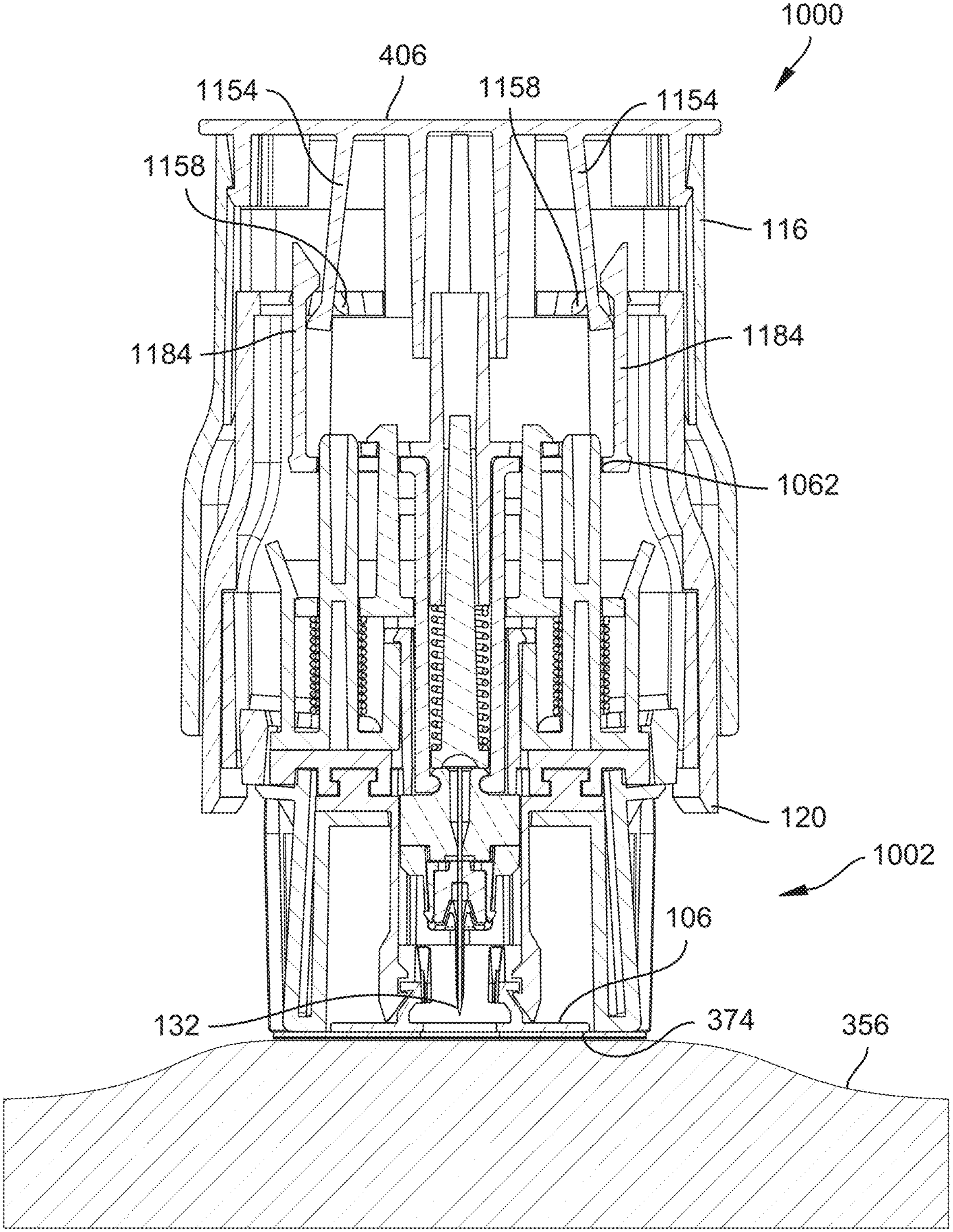

As shown in FIG. 95, actuation of an inserter assembly 1000 may be triggered as the inserter assembly 1000 is lifted up from the skin 356 so as to be removed from the patient. No other depression, twisting, squeezing, etc. of a trigger, button, housing sleeve or other portion of an inserter assembly 100 by a user may be needed to provoke the actuation, however, the actuation may still be under the control of the user. In alternative embodiments, and as discussed elsewhere herein, a discrete manual triggering action may be employed to trigger actuation of an inserter assembly 1000. Where triggering occurs automatically as the inserter assembly 1000 is withdrawn from the skin 356, relative movement of the free component(s) of the inserter assembly 1000 with respect to the restricted component(s) may trigger actuation. As described above, actuation may be triggered by, for example, displacing or dislodging a latch and freeing one or more bias members to begin driving actuation. Thus, one or more trigger internal to the inserter assembly 1000 may be actuated as a result of the removal action of the inserter assembly 1000 from the body. From the perspective of a user, such an inserter assembly 1000 may simply be placed on the skin 356 and then withdrawn to execute placement of the infusion set 102. This may be advantageous for a number of reasons which are detailed elsewhere in the specification.

FIG. 95 depicts the example inserter assembly 1000 of FIGS. 71A-71B coupled set cartridge 1002 and as it is being withdrawn from the skin 356. As shown, the adhesive 374 on the infusion set base 106 may adhere to the skin 356 resulting in the skin 356 being tugged upward as the inserter assembly 1000 and set cartridge 1002 are withdrawn. The exterior housing 116 and retainer cap 406 may displace together as a unit with the hand of the user as the user removes the inserter assembly 1000 from their body. This may also be true of the exterior housing 116 and retainer cap 406 of the example inserter assembly 1000 shown in FIGS. 70A-70B. The other components of the example inserter assemblies 1000 and set cartridges 1002 may not be constrained to displace as a unit with the exterior housing 116 and retainer cap 406. These components may form a second unit which maybe held behind, unable to displace relative to the patch of skin 356 adhered to the adhesive 374.

During removal of the inserter assembly 1000 and set cartridge 1002, the exterior housing 116 and retainer cap 406 may displace away from the skin 356 substantially along the axis of the insertion sharp 132. This displacement relative to the other components may cause the release fingers 1154 to deflect towards the cantilevered arms 1184 of the insertion drive 1062 as described above. The resiliency of release fingers 1154 may cause the entire inserter assembly 1000 and set cartridge 1002 to move together for at least a portion of the inserter assembly 1000 withdrawal motion from the skin 356. During this portion of the removal action of the inserter assembly 1000, the skin 356 may be lifted off underlying body structures. Portions of the inserter assembly 1000 may again displace relative to one another once the force exerted by the elasticity of the skin exceeds a force threshold and the release fingers 1154 fully deflect around the deflector wedges 1158.

Figure 96:
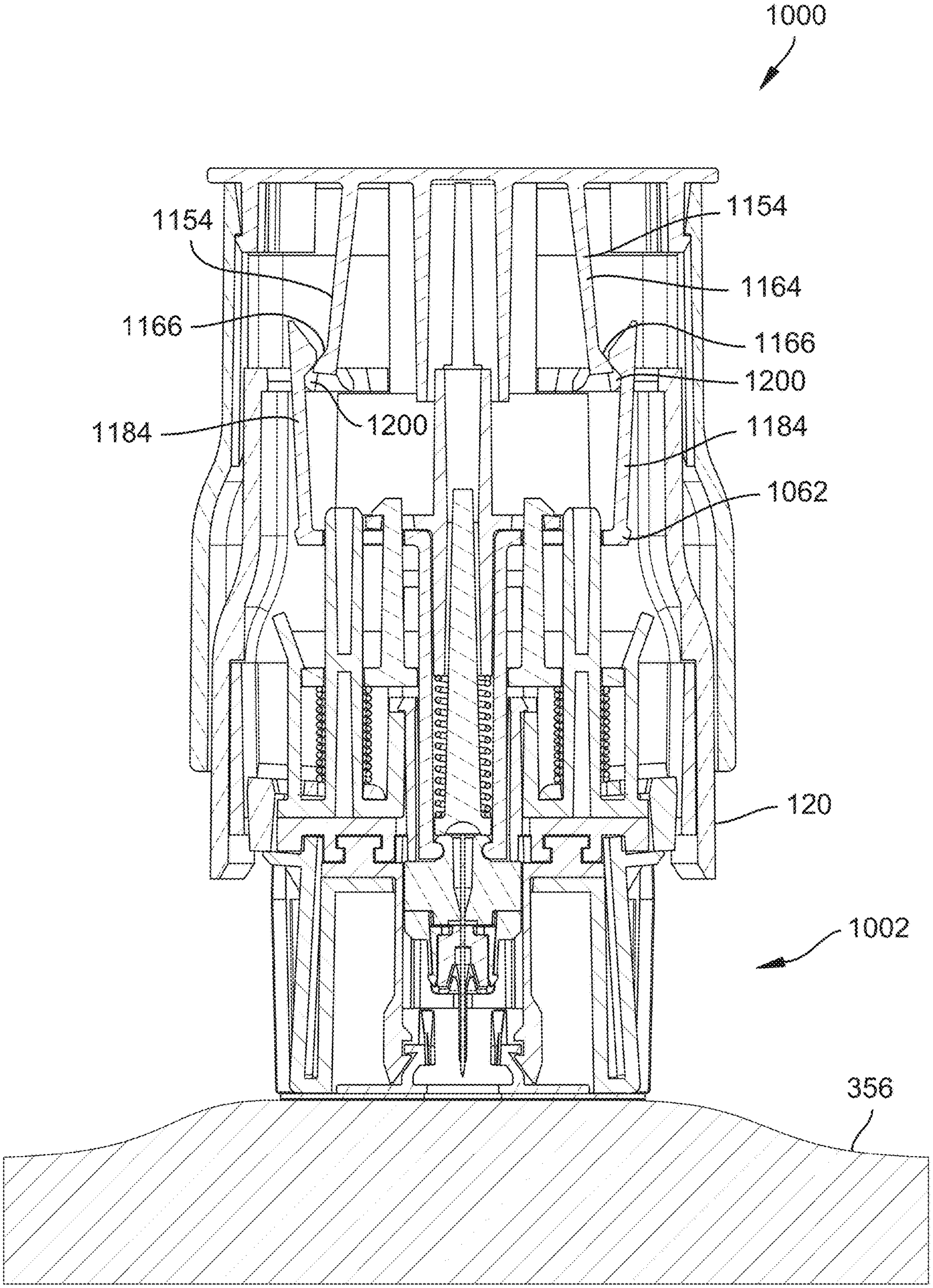

Referring now to FIG. 96, as the exterior housing 116 and retainer cap 406 continue to displace relative to the rest of the inserter assembly 1000 and set cartridge 1002, the cantilevered arms 1184 of the insertion driver 1062 may be dislodged off the associated cooperating projections 1200 of the interior housing 120. As described above with respect to FIGS. 89-91 or FIGS. 92-94, this may be caused by the projections 1166 of the paddle bodies 1164 on the release fingers 1154 colliding with protrusions 1202 at the unsupported ends of the cantilevered arms 1184.

Figure 97:
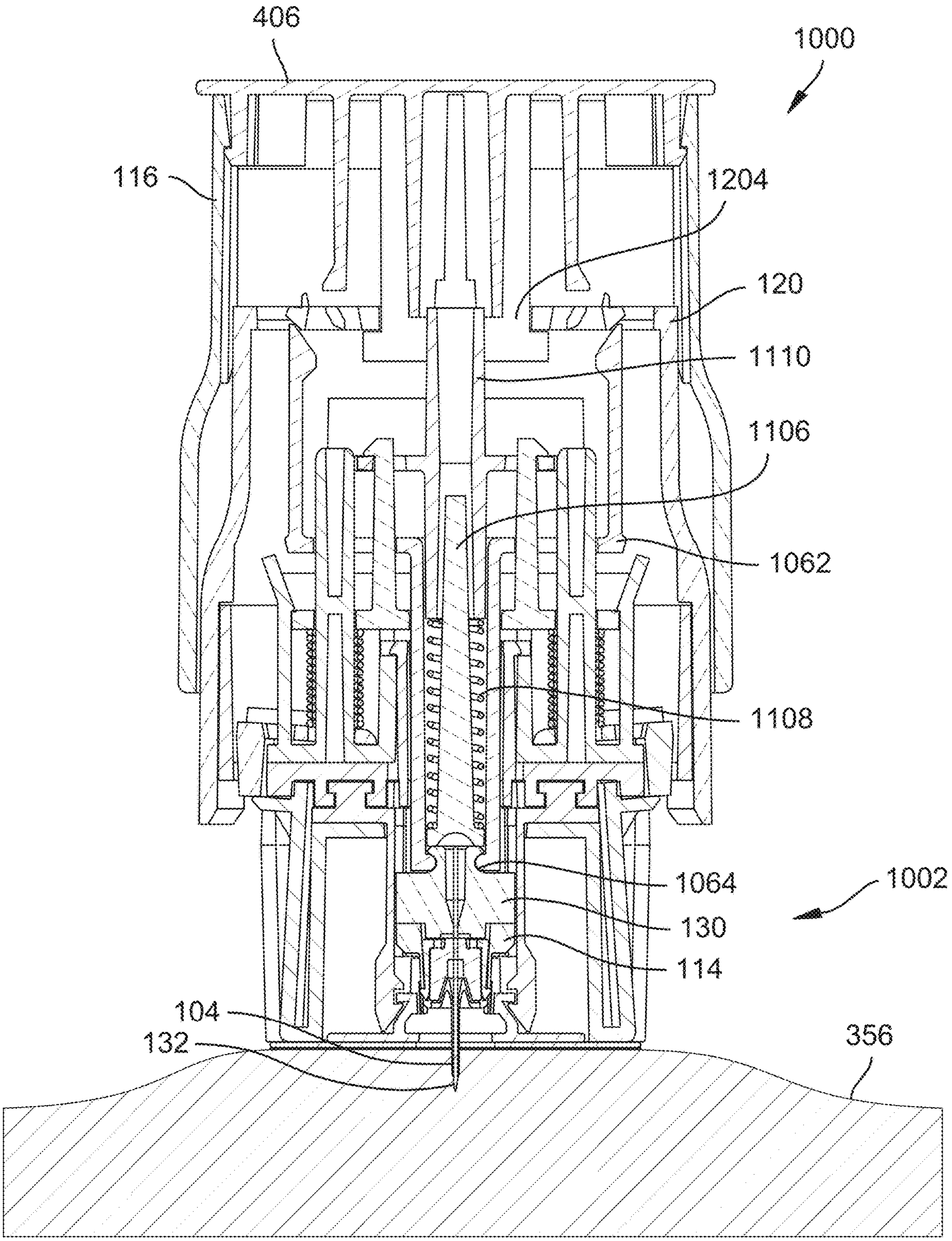

Referring now to FIG. 97, this may allow the bias member 1108 between the reset body 1110 and the plunger 1106 to transition to its uncompressed state. As the bias member 1108 transitions to its relaxed state, the plunger 1106 and insertion driver 1062 may be propelled towards the skin 356. As the sharp holder 130 is coupled into the port 1064 of the insertion driver 1062, the sharp holder 130 and cannula sub assembly 114 coupled thereto may also be shot towards the skin 356 along an insertion path. As shown in FIG. 97, which depicts the inserter assembly 1000 of FIGS. 71A-71B for sake of example, the insertion sharp 132 and cannula 104 have just punctured through the skin 356. During puncture, the skin 356 may still be in a state in which it is tugged up away from muscle and other underlying body structures. The cannula subassembly 114 has begun to be advanced toward the infusion set base 106 as well. Also as shown, the retainer cap 406 of the inserter assembly 1000 may include one or more stop arms 1204 which prevent relative movement beyond a certain point between the interior housing 120 and the casing formed by the exterior housing 116 and retainer cap 406. The stop arms 1204 may catch on a portion of the top of the interior housing 120 inhibiting further relative displacement. The stop arms 1204 may be engaged as the insertion of the cannula 104 begins or is in progress. Thus, additional lifting of the skin 356 may occur during the cannula 104 insertion movement.

In some embodiments, a bias member may be included such that the stop arms 1204 must compress the bias member prior to the cantilevered arms 1184 of the insertion driver 1062 being dislodged from the cooperating projections 1200. This may aid in further lifting the skin 356 before insertion is triggered. In some embodiments, the portions of the interior housing 120 which the stop arms 1204 contact may be resiliently cantilevered in the path of the stop arms 1204. Thus, as the inserter assembly 1000 is withdrawn, the cantilevered portions of the interior housing 120 may be deflected by the stop arms 1204 before the cantilevered arms 1184 are dislodged from the cooperating projections 1200. The resiliency of these cantilevered portions may be chosen to ensure that the skin is lifted at least a certain amount. In other embodiments, springs (e.g. compression springs, leaf type springs, etc.) may be placed in the path of the stop arms 1204. These springs may need to be brought to a stressed state via displacement of the stop arms 1204 before the cantilevered arms 1184 are released. Again, the springs may be chosen such that at least a desired amount of skin lifting occurs prior to the cantilevered arms 1184 being freed from the cooperating projections 1200.

Figure 98:
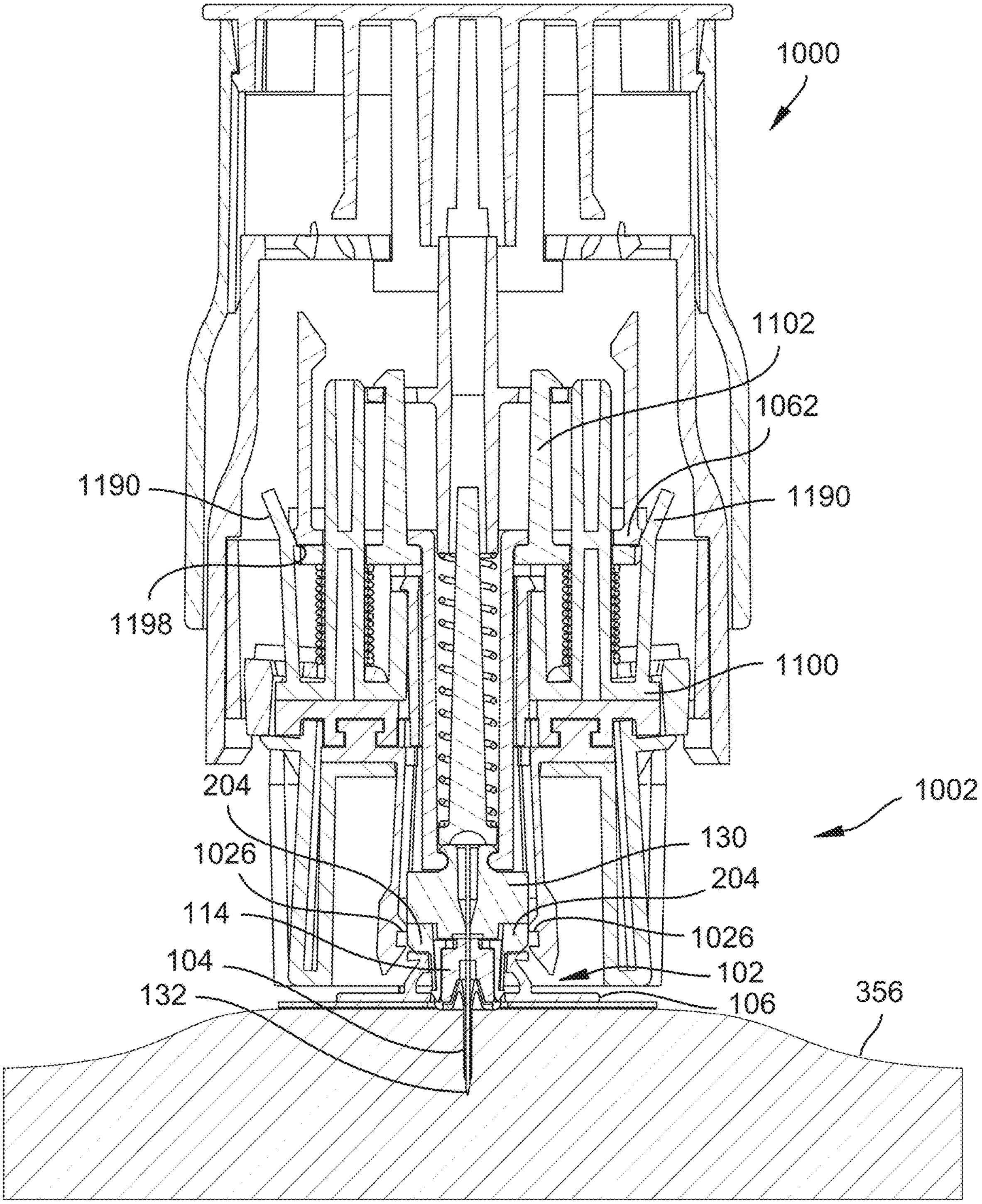

Referring now to FIG. 98, another cross sectional view of an example inserter assembly 1000 and set cartridge 1002 are shown. As shown, the spring 1108 has restored to a relaxed state and completed the insertion movement of the sharp holder 130, insertion sharp 132, and cannula subassembly 114 toward the skin 356. The relaxed state may be a completely relaxed state or a comparatively relaxed state where the spring 1108 is still exerting some pressure against the sharp holder 130 to prevent it from jostling about. Similarly to as shown in FIG. 42B, a notch 184 of the cannula subassembly 114 may be in engagement with a protuberance 182 of the infusion set base 106 locking the cannula subassembly 114 in place and completing assembly of the infusion set 102. As shown, when the cannula subassembly 114 latches into the base 106, the ears 204 on the cannula subassembly 114 may press against the nubs 1026 included on the retainer arms 1016. This may cause the retainer arms 1016 to be splayed apart resulting in disengagement of the retainer arms 1016 from the infusion set base 106. Thus, the assembled infusion set 102 may be installed at the infusion site and released from the set cartridge 1002.

As also shown in FIG. 98, the insertion driver 1062 may collide with the latch arms 1190 of the retraction latch body 1100 as the now assembled infusion set 102 is released. This collision may cause the latch arms 1190 to spread apart freeing the retraction spring retainer 1102 from engagement with the catch 1198 of the latch arms 1190. Thus, FIG. 98 depicts the inserter assembly 1000 at a retraction release state. The example inserter assembly 1000 of FIGS. 70A-70B is shown in the retraction release state in FIGS. 99A-99B.

Referring now to FIG. 100, with the retraction spring retainer 1102 freed from the catches 1198, the bias members 1104A, B (or bias member 1104 for the inserter assembly 1000 of FIGS. 70A-70B) may transition to their unstressed state driving the retraction spring retainer 1102 toward the retainer cap 406 of the exterior housing 116. As a portion of the insertion driver 1062 is between the retraction spring retainer 1102 and the retainer cap 406, the insertion driver 1062 may also be displaced along with the retraction spring retainer 1102 as the bias members 1104A, B relax. Since the sharp holder 130 is coupled to the insertion driver 1062, displacement of the insertion driver 1062 may cause the insertion sharp 132 to be removed from the skin 356 and retracted back into the set cartridge 1002.

In certain alternative embodiments, retraction of the insertion sharp 132 may not be automatic and/or may not be spring biased. For example, the insertion sharp 132 may remain in the advanced position and the removal action of the user may manually pull the insertion sharp 132 out of the cannula 104. In such embodiments, bias members 1104A, B may be omitted. In some embodiments, a button press or similar interaction may be required to trigger a spring biased retraction of the insertion sharp 132.

Referring now to FIG. 101, the exterior housing 1004 is shown separated from the remainder of a spent set cartridge 1002 which is installed on an inserter assembly 1000. Once the infusion set 102 is installed at the desired infusion site, the exterior housing 1004 may be used as a removal and containment tool for the spent set cartridge 1002. As shown, the cantilevered arms 1076 of the interior housing 1008 may be recessed with respect to the external face 1082 of the interior housing 1008. A recess edge wall 1084 may be present on each side of the cantilevered arms 1076. The exterior housing 1004 may include a set of stops 1086 which may fit within the recesses formed in the interior housing 1008. After insertion of the infusion set 102, the exterior housing 1004 may be slid over the interior housing 1008 and the spent set cartridge 1002 may be rotated to an uncoupled state. The stops 1086 may catch against the recess edge walls 1084 and ensure that the interior housing 1008 rotates in tandem with the exterior housing 1004. Referring now also to FIG. 73, this may displace the ramped projections 1074 of the housing tabs 1070 out of abutment with the deflector members 1078 of the receptacle body 1060. Due to the resiliency of the cantilevered arms 1076, the housing tabs 1070 may restore back into engagement with the receiver slots 1072 in the exterior housing 1004. The spent set cartridge 1002 may then be removed from the inserter assembly 1000.

After use, the exterior housing 1004 may serve as a containment for the remaining components of the spent set cartridge 1002. This may ensure that the used insertion sharp 132 is enclosed within the set cartridge 1002. Thus, the point of the insertion sharp 132 may be inaccessible to the user. The engagement of the housing tabs 1070 with the receiver slots 1072 may lock the insertion sharp 132 within the spent set cartridge 1002. In certain embodiments, placement of the infusion set 102 on the infusion site via the inserter assembly 1000 may be performed with one hand. Thus, after removing the exterior housing 1004, the user may be encouraged to hold the exterior housing 1004 in their free hand as the infusion set 102 is applied with the inserter assembly 1000. The user may then remove the spent set cartridge 1002 by reattaching the exterior housing 1004 to the interior housing 1008 and separating the set cartridge 1002 from the inserter 1000. Occupying both hands of the user during the process may aid in limiting opportunity for a user to inadvertently come into contact with the insertion sharp 132.

Referring now to FIGS. 102-106, an example tubing connector 368 (FIG. 102-103B) and a fixture 480 (FIG. 104-105) for assembling a tubing connector 368 are depicted. The fixture 480 may aid in assembly of a sharp 482 and infusion tubing 366 (see, e.g. FIG. 6) into a tubing connector 368. The fixture 480 may ensure that the sharp 482 is positioned so as to have an exposed portion 484 of a prescribed length. In various embodiments, this may aid in ensuring that the sharp 482 extends a desired distance into a septum 110 (see e.g. FIG. 5B) when the tubing connector 368 is coupled to an infusion set 102 (see, e.g. FIG. 6). For example, the length of the exposed portion 484 may be sized so as to extend into a fluid introduction volume of the cannula sub assembly 114 as described elsewhere herein.

In the example, the sharp 482 is depicted with a lancet tip though other types of sharps may be used. For example, a sharp 482 with a back bevel may be used in certain embodiments. The exemplary sharp 482 (see FIG. 103B) includes a primary grind region 487 which is at an angle (e.g. an angle between 10-20° such as 15.5°) with respect to the longitudinal axis of the sharp 482. A set of secondary grinds 489 are also included and form the point 485 of the sharp 482.

Additionally, the fixture 480 may ensure that the sharp 482 is brought into a prescribed rotational orientation. This may be achieved through the use of magnetism. Thus, tips 486 of sharps 482 of tubing connectors 368 may be uniformly oriented across tubing connectors 368. This may be desirable for a variety of reasons. For example, during the typical usage life of an infusion set 102, the tubing connector 368 may be disconnected and reconnected a number of times. As the tip 486 is ramped, there may be a tendency for the sharp 482 to veer from the axis of insertion as the tubing connector 368 is advanced into engagement with the infusion set base 106. This tendency may be exaggerated with repeated connection and disconnection. By ensuring the tip 486 is always oriented in a particular orientation any veering of the sharp 482 may occur in a predictable direction and the septum 110 may be designed to accommodate such veering. This may allow for the septum 110 to be made smaller in portions where veering of the sharp 482 is not expected to occur. The septum 110 may be made smaller in footprint or height and with less material. Additionally, the fluid introduction volume formed by the septum recess 196 (see, e.g. FIG. 5B) may be made smaller. This would minimize any hold up volume in the infusion set 102 and minimize an amount of drug or agent expended filling this volume. Such rotational alignment of the sharp 482 may allow for a wider variety of tip 486 bevels to be used. It may also minimize any potential for occlusion due to the tip 486 being entirely surround by septum 110 material after a connection is made. Alternatively, it may allow for connection between the infusion set 102 and tubing connector 368 to be made in a more forgiving manner. As a result, the range of acceptable tolerances on various features of the infusion set 102 and tubing connector 368 may be greater. Likewise, the amount of material needed to form guides 172 (see, e.g. FIG. 6) or flanking projection 372 of the tubing connector 368 may be lessened.

As best shown in FIG. 106, the fixture 480 may include a dock 490 for a tubing connector 368. The dock 490 may mimic the mating interface of an infusion set base 106 (see, e.g. FIG. 6) and may, for example, include guides 172' and connector receivers 170'. Thus, the tubing connector 368 may engage the fixture 480 and be retained in fixture 480. The dock 490 may also position the tubing connector 368 in a desired location and orientation on the fixture 480.

The fixture 480 may include an adhesive port 510 (best shown in FIG. 105) which may allow glue, epoxy, or adhesive to be introduced into the tubing connector 368 such that the sharp 482 may be retained in the tubing connector 368 once properly positioned therein. A UV cure adhesive may be used in certain embodiments.

Referring now to FIGS. 107-108, two cross-sectional views of a tubing connector 368 installed on a dock 490 are shown. A sharp 482 is shown being installed into the tubing connector 368 in FIG. 107. The sharp 482 is in place within the tubing connector 368 and rotationally clocked such that the point 485 of the sharp 482 is in a specified position which in the example embodiment is a 12 o'clock position. In the example embodiment, the point 485 of the tip 486 of the sharp 482 is positioned to be substantially in line with and perpendicular to the axis of a lumen 202 of a cannula 104 of the infusion set 102 when the tubing connector 368 is connected thereto. The primary grind 487 and secondary grinds 489 on the tip 486 are also in a downward facing position.

As shown, the fixture 480 includes a first body 498 and a second body 500. The bodies 498, 500 may be coupled together via any suitable method including bonding, welding, adhesive, fasteners, etc. In the example, screws 502 are used to couple the first body 498 and second body 500. The second body 500 may fit within a cavity or slot 504 in the first body 498 which may serve to position the second body 500 with respect to the first body 498. As shown, the second body 500 may include a sloped face 506. The sloped face 506 may have an angle with respect to the axis of the sharp 482 which is substantially equal to the angle of one of the grinds 487, 489 on the sharp 482. In the example, the angle is about 15.5° which is the angle of the primary grind 487 of the sharp 482. The sloped face 506 may include a portion which is in line with a sharp receiving bore 508 of the first body 498. This portion may act as a support surface for a primary grind 487 of a sharp 482. The second body 500 may be constructed of a hard, non-metallic material.

As shown, the fixture 480 may include a first magnet 492 and a second magnet 494. The first magnet 492 may be larger than the second magnet 494. The dimensions of each edge of the second magnet 494 may be half the size of the dimensions of the respective sides of the first magnet 492. In some embodiments, the first magnet 492 may be a ⅛ in×⅛ in×½ in NdFeB magnet. The second magnet 494 may be a 1/16 in×1/16 in×¼ in NdFeB magnet. In alternative embodiments electromagnets which may, for example, be equivalent to the permanent magnets just described may be used. The first magnet 492 and second magnet 494 may be located in channels 496 included in the fixture 480. The channel 496 for the second magnet 494 may be at an angle with respect to the channel 496 for the first magnet 492. In the example embodiment the angle is about 15.5°. The angle may reflect the angle of one of the grinds 487, 489 of the sharp 482. The angle may be the same as that of the sloped face 506 of the second body 500. The first magnet 492 may be oriented such that each of its poles are respectively most proximal to the opposing pole of the second magnet 494. The ends of the magnets 492, 494 are set back from the support surface portion of the sloped face 506. In the example embodiment, the ends of the magnets 492, 494 are set back about 0.060 inches.

As a sharp 482 is introduced into the tubing connector 368, the magnetic fields generated by the magnets 492, 494 may rotate and guide the sharp 482 into the desired rotational orientation. The magnetic fields may also draw the sharp 482 into contact with the sloped face 506 setting the length of the exposed portion 484 of the sharp 482. During introduction of the sharp 482, the sharp 482 may be displaced into the desired position and orientation with no or minimal contact of the point 485 or secondary grinds 489 with any material of the tubing connector 368 or the fixture 480. Only the primary grind 487 of the sharp 482 may rest against the sloped face 506. The beveled sections formed by the secondary grinds 489 as well as the point 485 may not be in contact with the sloped face 506. This may help to ensure that the tip 486 remains sharp and may help prevent any attenuation of the piercing capabilities of the tip 486.

With the sharp 482 in place, infusion tubing 366 may be coupled to the tubing connector 368. The tubing 366 may be introduced into a tubing receptacle 512 of the tubing connector 368. The lumen 514 of the tubing 336 may be placed into fluid communication with the lumen 516 of the sharp 482. The tubing receptacle 512 of the tubing connector 368 may include at least one tapered region 518 which may aid in funneling the tubing 366 into the tubing receptacle 512. Any force exerted on the sharp 482 as the tubing 366 is slid into place may be transmitted into the sloped face 506 through the primary grind 487 of the sharp 482. This may help to ensure the tip 486 of the sharp 482 is protected as the tubing 366 is assembled onto the tubing connector 368.

Once the tubing 366 is in place, an applicator may be advanced into the port 510. Glue or adhesive may be dispensed into an aperture 520 of the tubing connector 368. In some embodiments a UV curing adhesive may be used. UV light may be emitted toward the tubing connector 368 to cure the adhesive and fixedly retain the sharp 482 and tubing 366 onto the tubing connector 368. In some embodiments, UV emitting LEDS (no shown) may be included in the fixture 480 for this purpose, though an external light source may also be utilized. The tubing connector 368 may then be removed from the fixture 480.

Referring now also to FIG. 109, a flowchart 530 depicting a number of example actions which may be executed to assemble a tubing connector 368 is shown. In block 532, a tubing connector 368 may be coupled to a fixture 480. A sharp 482 may be introduced into the tubing connector 368 in block 534. The fixture 480 may be oriented such that the sharp 482 is introduced into the tubing connector 368 along the direction of acceleration due to gravity to allow gravity to assist in the introduction. Magnets 492, 494 in the fixture 480 may orient the sharp 482 in a desired position as the sharp 482 is introduced. In block 536, infusion tubing 366 may be inserted into a tubing receptacle 512 of the tubing connector 368. Adhesive may be applied into the tubing connector 540 in block 538. The adhesive may be cured in block 540. In block 542, the completed tubing connector 368 may be removed from the fixture 480.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. The drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A cannulated housing for an infusion set comprising:
a continuous monolithic body comprising:
a cannula; and
a septum housing having a septum receptacle defined by a side wall and bottom wall with a raised region, a lumen of the cannula being enclosed by a surface continuous with the raised region, the side wall having at least one septum retainer guide extending the length of the septum receptacle and aligned with an aperture extending through a bottom of the septum housing, the septum housing including a pair of ears each extending outwardly from the side wall.

2. The cannulated housing of claim 1, wherein the septum housing includes a salient on the exterior face of the side wall arranged to engage a latch of an infusion set base to retain the cannulated housing within the infusion set base.

3. The cannulated housing of claim 1, wherein a top face of a wall of the septum receptacle has slots recessed therein.

4. The cannulated housing of claim 3, wherein the slots include two slots which are disposed opposite one another.

5. The cannulated housing of claim 3, wherein the slots are configured to accept a set of projection included in a septum retainer so as to leave a bottom segment of each of the slots open and providing a path to an interior volume of the septum receptacle.

6. The cannulated housing of claim 1, wherein the raised region of the septum receptacle has a frusto-conic outer wall.

7. The cannulated housing of claim 1, wherein the septum housing includes a notch in an exterior face of the side wall configured to engage a latch of an infusion set base to retain the cannulated housing assembly within the infusion set base.

8. The cannulated housing of claim 1, wherein monolithic body is formed via straight pull molding.

9. The cannulated housing of claim 1, wherein the monolithic body is devoid of undercut features.

10. The cannulated housing of claim 1, wherein the monolithic body is polypropylene.

11. The cannulated housing of claim 1, wherein the monolithic body is PTFE.

12. The cannulated housing of claim 1, wherein the cannula includes a sharp guide encompassed by a substantially flat peripheral edge at an uppermost part of the raised section.

13. The cannulated housing of claim 1, wherein a ledge is positioned adjacent the aperture on an exterior face of the bottom wall.

14. The cannulated housing of claim 1, wherein a wall of the aperture forms a catch configured to engage a protuberance of a projection of a portion of a septum retainer.

15. The cannulated housing of claim 1, wherein the septum retainer guides are recessed into the side wall.

16. The cannulated housing of claim 1, wherein a portion of the cannula extends in a direction away from an exterior face of the bottom wall of the septum housing.

17. The cannulated housing of claim 1, wherein a portion of the cannula is at least partially surrounded by a recess in the exterior face of the bottom wall of the septum housing.

18. The cannulated housing of claim 1, wherein each of the pair of ears are disposed at an end region of the septum housing opposite the bottom wall.

19. The cannulated housing of claim 1, wherein each of the pair of ears includes a ramped face at an end thereof which is most proximate the bottom wall.

20. A cannulated housing for an infusion set comprising:

a continuous monolithic body comprising:

a cannula; and a septum housing having a septum receptacle defined by a side wall and bottom wall with a raised region, a lumen of the cannula being enclosed by a surface continuous with the raised region, the side wall having at least one septum retainer guide extending the length of the septum receptacle and aligned with an aperture extending through a bottom of the septum housing, the septum housing including a pair of ears each extending outwardly from the side wall, the ears being disposed opposite one another.

* * * * *